United States Patent
Kotin et al.

(10) Patent No.: US 10,335,466 B2
(45) Date of Patent: Jul. 2, 2019

(54) AADC POLYNUCLEOTIDES FOR THE TREATMENT OF PARKINSON'S DISEASE

(71) Applicant: VOYAGER THERAPEUTICS, INC., Cambridge, MA (US)

(72) Inventors: Robert Kotin, Boston, MA (US); Adrian Philip Kells, Arlington, MA (US); Bernard Ravina, Cambridge, MA (US)

(73) Assignee: VOYAGER THERAPEUTICS, INC., Cambridge, MA (US)

( * ) Notice: Subject to any disclaimer, the term of this patent is extended or adjusted under 35 U.S.C. 154(b) by 104 days.

(21) Appl. No.: 15/524,986

(22) PCT Filed: Nov. 5, 2015

(86) PCT No.: PCT/US2015/059201
§ 371 (c)(1),
(2) Date: May 5, 2017

(87) PCT Pub. No.: WO2016/073693
PCT Pub. Date: May 12, 2016

(65) Prior Publication Data
US 2017/0333538 A1   Nov. 23, 2017

Related U.S. Application Data

(60) Provisional application No. 62/075,298, filed on Nov. 5, 2014, provisional application No. 62/155,692, filed on May 1, 2015, provisional application No. 62/199,578, filed on Jul. 31, 2015, provisional application No. 62/243,537, filed on Oct. 19, 2015.

(51) Int. Cl.
| | |
|---|---|
| A61K 35/76 | (2015.01) |
| A61P 25/14 | (2006.01) |
| A61P 25/16 | (2006.01) |
| C12N 15/86 | (2006.01) |
| C12N 9/00 | (2006.01) |
| C12N 9/88 | (2006.01) |
| A61K 38/51 | (2006.01) |
| A61K 48/00 | (2006.01) |
| C12N 7/00 | (2006.01) |

(52) U.S. Cl.
CPC ............ *A61K 38/51* (2013.01); *A61K 35/76* (2013.01); *A61K 48/005* (2013.01); *A61P 25/14* (2018.01); *C12N 7/00* (2013.01); *C12N 9/88* (2013.01); *C12N 15/86* (2013.01); *C12Y 401/01028* (2013.01); *C12N 2750/14121* (2013.01); *C12N 2750/14143* (2013.01); *C12N 2800/22* (2013.01); *C12N 2830/42* (2013.01); *C12N 2830/50* (2013.01)

(58) Field of Classification Search
CPC ...... A61K 35/76; A61K 38/51; A61K 48/005; A61K 48/0066; A61P 25/14; A61P 25/16; C12N 9/00; C12N 9/88; C12N 15/86; C12N 15/8645; C12N 2800/22; C12N 2830/42; C12N 2830/50; C12Y 401/01028

See application file for complete search history.

(56) References Cited

U.S. PATENT DOCUMENTS

| | | |
|---|---|---|
| 5,064,764 A | 11/1991 | Besnainon |
| 5,474,935 A | 12/1995 | Chatterjee |
| 5,538,885 A | 7/1996 | Hollis et al. |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | O'Riordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |

(Continued)

FOREIGN PATENT DOCUMENTS

| | | |
|---|---|---|
| EP | 1015619 A1 | 7/2000 |
| EP | 1078096 A1 | 2/2001 |

(Continued)

OTHER PUBLICATIONS

Grimm et al, Gene Therapy 6: 1322-1330, 1999.*

(Continued)

*Primary Examiner* — Kevin K Hill

(74) *Attorney, Agent, or Firm* — DT Ward, PC; Donna T. Ward; Mark J. Hanson

(57) ABSTRACT

The invention relates to compositions and methods for the preparation, manufacture and therapeutic use of polynucleotides encoding AADC for the treatment of Parkinson's Disease.

14 Claims, No Drawings

Specification includes a Sequence Listing.

(56) References Cited

U.S. PATENT DOCUMENTS

| | | |
|---|---|---|
| 6,194,191 B1 | 2/2001 | Zhang |
| 6,200,560 B1 | 3/2001 | Couto |
| 6,204,059 B1 | 3/2001 | Samulski |
| 6,211,163 B1 | 4/2001 | Podsakoff |
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,309,634 B1 | 10/2001 | Bankiewicz |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,841,357 B1 | 1/2005 | Vaillancourt |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,943,019 B2 | 9/2005 | Wilson |
| 6,953,575 B2 | 10/2005 | Bankiewicz |
| 6,953,690 B2 | 10/2005 | Gao |
| 6,984,517 B1 | 1/2006 | Chiorini |
| 6,995,006 B2 | 2/2006 | Atkinson |
| 7,015,026 B2 | 3/2006 | O'Riordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,169,612 B2 | 1/2007 | Kostenis |
| 7,182,944 B2 | 2/2007 | Bankiewicz |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,259,015 B2 * | 8/2007 | Kingsman ............ C12N 9/0071 435/320.1 |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,319,002 B2 | 1/2008 | Wilson |
| 7,326,555 B2 | 2/2008 | Konz |
| 7,344,872 B2 | 3/2008 | Gao |
| 7,419,817 B2 | 9/2008 | Chiorini |
| 7,419,956 B2 | 9/2008 | Ohtaki |
| 7,445,930 B2 | 11/2008 | Zhang |
| 7,479,554 B2 | 1/2009 | Chiorini |
| 7,491,508 B2 | 2/2009 | Roy |
| 7,510,872 B2 | 3/2009 | Clark |
| 7,510,875 B2 | 3/2009 | Zhang |
| 7,534,613 B2 | 5/2009 | Bankiewicz |
| 7,579,181 B2 | 8/2009 | O'Riordan |
| 7,588,757 B2 | 9/2009 | Ozawa |
| 7,588,772 B2 | 9/2009 | Kay et al. |
| 7,625,570 B1 | 12/2009 | Schaffer |
| 7,638,120 B2 | 12/2009 | Liu |
| 7,662,627 B2 | 2/2010 | Johnson |
| 7,704,492 B2 | 4/2010 | Podsakoff |
| 7,704,721 B2 | 4/2010 | Wright |
| 7,732,129 B1 | 6/2010 | Zhang |
| 7,790,449 B2 | 9/2010 | Gao |
| 7,803,622 B2 | 9/2010 | Engelhardt |
| 7,838,277 B2 | 11/2010 | Gao |
| 7,888,096 B2 | 2/2011 | Wu |
| 7,901,921 B2 | 3/2011 | Coffey |
| 7,906,111 B2 | 3/2011 | Wilson et al. |
| 7,968,333 B2 | 6/2011 | Yu |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,309,355 B2 | 11/2012 | Bankiewicz |
| 8,318,480 B2 | 11/2012 | Gao |
| 8,318,687 B2 | 11/2012 | Tabira |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Herm |
| 8,524,219 B2 | 9/2013 | Roy |
| 8,524,446 B2 | 9/2013 | Gao |
| 8,603,459 B2 | 12/2013 | Wilson |
| 8,614,101 B2 | 12/2013 | VanDine |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Fontanellas Roma et al. |
| 8,834,863 B2 | 9/2014 | Roy |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,034,836 B2 | 5/2015 | Dodge |
| 9,050,299 B2 | 6/2015 | Bankiewicz |
| 9,051,542 B2 | 6/2015 | Wright |
| 9,056,892 B2 | 6/2015 | Pun |
| 9,066,966 B2 | 6/2015 | Puccio |
| 9,080,183 B2 | 7/2015 | Klein |
| 9,089,667 B2 | 7/2015 | Bankiewicz |
| 9,102,943 B2 | 8/2015 | Shinmura |
| 9,102,949 B2 | 8/2015 | Gao |
| 9,107,884 B2 | 8/2015 | Chedotal |

(56) References Cited

U.S. PATENT DOCUMENTS

| | | |
|---|---|---|
| 9,115,373 B2 | 8/2015 | Herm |
| 9,116,157 B2 | 8/2015 | Ringe |
| 9,163,260 B2 | 10/2015 | Wilson |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,283,357 B2 | 3/2016 | Stedman |
| 9,415,119 B2 | 8/2016 | Passini |
| 9,415,121 B2 | 8/2016 | Kaspar |
| 9,434,776 B2 | 9/2016 | Ando |
| 9,434,928 B2 | 9/2016 | Mendell |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,486,541 B2 | 11/2016 | Hutton |
| 9,492,415 B2 | 11/2016 | Bankiewicz |
| 9,493,788 B2 | 11/2016 | Gao |
| 9,504,762 B2 | 11/2016 | Colosi |
| 9,506,052 B2 | 11/2016 | Samulski |
| 9,506,083 B2 | 11/2016 | Arbetman |
| 9,528,126 B2 | 12/2016 | Qu |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,719,070 B2 | 2/2017 | Vandenberghe |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,803,218 B2 | 3/2017 | Chatterjee |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,629,930 B2 | 4/2017 | Gregory |
| 9,636,370 B2 | 5/2017 | McCown |
| 9,670,507 B2 | 6/2017 | Xiao |
| 9,677,088 B2 | 6/2017 | Nakai |
| 9,677,089 B2 | 6/2017 | Gao |
| 9,682,193 B2 | 6/2017 | Anand |
| 9,695,220 B2 | 7/2017 | Vandenberghe |
| 9,701,984 B2 | 7/2017 | Gao |
| 9,708,627 B2 | 7/2017 | Hermens |
| 9,777,291 B2 | 7/2017 | Chatterjee |
| 9,783,825 B2 | 7/2017 | Chatterjee |
| 9,719,106 B2 | 8/2017 | Wilson |
| 9,725,485 B2 | 8/2017 | Srivastava |
| 9,732,345 B2 | 8/2017 | Martin |
| 9,737,618 B2 | 8/2017 | Wilson |
| 9,745,590 B2 | 8/2017 | Kay |
| 9,775,918 B2 | 10/2017 | Zhong |
| 9,783,824 B2 | 10/2017 | Kay |
| 9,790,472 B2 | 10/2017 | Gao |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0096264 A1 | 5/2003 | Altar et al. |
| 2003/0100115 A1 | 5/2003 | Raj |
| 2003/0119191 A1 | 6/2003 | Gao |
| 2003/0138772 A1 | 7/2003 | Gao |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0261218 A1 | 11/2005 | Esau |
| 2006/0003451 A1 | 1/2006 | Gao |
| 2006/0204479 A1 | 9/2006 | Wilson |
| 2007/0004042 A1 | 1/2007 | Gao et al. |
| 2008/0008684 A1 | 1/2008 | Wilson |
| 2008/0050343 A1 | 2/2008 | Wilson |
| 2008/0050345 A1 | 2/2008 | Wilson |
| 2008/0075737 A1 | 3/2008 | Gao |
| 2009/0215871 A1 | 8/2009 | Wilson |
| 2009/0275107 A1 | 11/2009 | Lock |
| 2009/0317417 A1 | 12/2009 | Vandenberghe |
| 2010/0247490 A1 | 9/2010 | Roy |
| 2010/0278791 A1 | 11/2010 | Wilson |
| 2011/0136227 A1 | 6/2011 | Bakker |
| 2011/0171262 A1 | 7/2011 | Bakker |
| 2011/0206616 A1 | 8/2011 | Ichtchenko |
| 2011/0223135 A1 | 9/2011 | Roy |
| 2011/0229971 A1 | 9/2011 | Knop |
| 2011/0263001 A1 | 10/2011 | Lakshmipathy |
| 2012/0046349 A1 | 2/2012 | Bell |
| 2012/0058102 A1 | 3/2012 | Wilson |
| 2012/0064115 A1 | 3/2012 | John |
| 2012/0093853 A1 | 4/2012 | Wilson |
| 2012/0137379 A1 | 5/2012 | Gao |
| 2012/0220648 A1* | 8/2012 | Hwu .................. A61K 31/7088 514/44 R |
| 2012/0258046 A1 | 10/2012 | Mutzke |
| 2012/0295960 A1* | 11/2012 | Palfi .................. A61K 48/005 514/44 R |
| 2013/0023033 A1 | 1/2013 | Wilson |
| 2013/0045186 A1 | 2/2013 | Gao |
| 2013/0101558 A1 | 4/2013 | Gao |
| 2013/0195801 A1 | 8/2013 | Gao et al. |
| 2013/0296532 A1 | 11/2013 | Herm |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0336245 A1 | 11/2014 | Mingozzi |
| 2014/0341852 A1 | 11/2014 | Srivastava |
| 2014/0342434 A1 | 11/2014 | Herm |
| 2015/0005369 A1 | 1/2015 | Muzyczka |
| 2015/0023924 A1 | 1/2015 | High |
| 2015/0065562 A1 | 3/2015 | Yazicioglu |
| 2015/0118287 A1 | 4/2015 | Hammond |
| 2015/0139952 A1 | 5/2015 | Webster |
| 2015/0151007 A1 | 6/2015 | Dodge |
| 2015/0152127 A1 | 6/2015 | Selnick |
| 2015/0159173 A1 | 6/2015 | Vandenberghe |
| 2015/0184197 A1 | 7/2015 | Davidson |
| 2015/0196671 A1 | 7/2015 | Byrne |
| 2015/0203553 A1 | 7/2015 | Chiorini |
| 2015/0238610 A1 | 8/2015 | Sista |
| 2015/0307898 A2 | 10/2015 | Herm |
| 2015/0315610 A1 | 11/2015 | Nishie |
| 2015/0374803 A1 | 12/2015 | Wolfe |
| 2016/0032319 A1 | 2/2016 | Wright |
| 2016/0108373 A1 | 4/2016 | Bennett |
| 2016/0153992 A1 | 6/2016 | Buening |
| 2016/0166709 A1 | 6/2016 | Davidson |
| 2016/0256534 A1 | 9/2016 | Bankiewicz |
| 2016/0271192 A1 | 9/2016 | Roy |
| 2016/0273058 A1 | 9/2016 | Akashika |

(56) References Cited

U.S. PATENT DOCUMENTS

| | | |
|---|---|---|
| 2016/0289275 A1 | 10/2016 | Chiorini |
| 2016/0296694 A1 | 10/2016 | Bankiewicz |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0334417 A1 | 11/2016 | Rouillon |
| 2016/0340393 A1 | 11/2016 | Schaffer |
| 2016/0340692 A1 | 11/2016 | Wang |
| 2016/0346359 A1 | 12/2016 | Buchlis |
| 2016/0347822 A1 | 12/2016 | Crystal |
| 2016/0354487 A1 | 12/2016 | Zhang |
| 2016/0355577 A1 | 12/2016 | Kelley |
| 2016/0355796 A1 | 12/2016 | Davidson |
| 2016/0361439 A1 | 12/2016 | Agbandje-McKenna |
| 2016/0367661 A1 | 12/2016 | Flavell |
| 2016/0369297 A1 | 12/2016 | Byrne |
| 2016/0369298 A1 | 12/2016 | Marsic |
| 2016/0369299 A1 | 12/2016 | Boye |
| 2016/0375110 A1 | 12/2016 | High |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007645 A1 | 1/2017 | Handa |
| 2017/0007669 A1 | 1/2017 | Sarkar |
| 2017/0007720 A1 | 1/2017 | Boye |
| 2017/0008939 A1 | 1/2017 | Khanna |
| 2017/0021037 A1 | 1/2017 | Wang |
| 2017/0028082 A1 | 2/2017 | Wilson |
| 2017/0043037 A1 | 2/2017 | Kariko |
| 2017/0044504 A1 | 2/2017 | Schaffer |
| 2017/0051259 A1 | 2/2017 | Wang |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0087219 A1 | 3/2017 | Bunting |
| 2017/0088819 A1 | 3/2017 | Vandendriessche |
| 2017/0088858 A1 | 3/2017 | Gao |
| 2017/0095538 A1 | 4/2017 | Colosi |
| 2017/0096646 A1 | 4/2017 | Roy |
| 2017/0105927 A1 | 4/2017 | Thorne |
| 2017/0107536 A1 | 4/2017 | Zhang |
| 2017/0112946 A1 | 4/2017 | Ikeda |
| 2017/0121734 A1 | 5/2017 | Cairns |
| 2017/0128581 A1 | 5/2017 | Freskgard |
| 2017/0128594 A1 | 5/2017 | Wright |
| 2017/0130208 A1 | 5/2017 | Potter |
| 2017/0130245 A1 | 5/2017 | Kotin |
| 2017/0145440 A1 | 5/2017 | Herm |
| 2017/0151348 A1 | 6/2017 | Kasper |
| 2017/0151416 A1 | 6/2017 | Kutikov |
| 2017/0152525 A1 | 6/2017 | Herm |
| 2017/0157213 A1 | 6/2017 | Dickson |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0183636 A1 | 6/2017 | Roy |
| 2017/0191039 A1 | 7/2017 | Gao |
| 2017/0191079 A1 | 7/2017 | Vandenberghe |
| 2017/0198304 A1 | 7/2017 | Wilson |
| 2017/0204144 A1 | 7/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |
| 2017/0218395 A1 | 8/2017 | Byrne |
| 2017/0226160 A1 | 8/2017 | Sonntag |
| 2017/0232072 A1 | 8/2017 | Ikeda |
| 2017/0232117 A1 | 8/2017 | Arbetman |
| 2017/0240885 A1 | 8/2017 | Deverman |
| 2017/0240921 A1 | 8/2017 | Gao |
| 2017/0246322 A1 | 8/2017 | Mendell |
| 2017/0247664 A1 | 8/2017 | Wright |
| 2017/0258996 A1 | 9/2017 | Anand |
| 2017/0260545 A1 | 9/2017 | Qu |
| 2017/0274024 A1 | 9/2017 | McCown |
| 2017/0275337 A1 | 9/2017 | Srivastava |
| 2017/0298323 A1 | 10/2017 | Vandenberghe |
| 2017/0304464 A1 | 10/2017 | Kügler |
| 2017/0306354 A1 | 10/2017 | Gao |
| 2017/0306355 A1 | 10/2017 | Davidson |
| 2017/0321290 A1 | 11/2017 | Lubelski |
| 2018/0339065 A1 | 11/2018 | Wilson |
| 2019/0000940 A1 | 1/2019 | Kotin |
| 2019/0000991 A1 | 1/2019 | Pykett |
| 2019/0008933 A1 | 1/2019 | Kotin |

FOREIGN PATENT DOCUMENTS

| | | |
|---|---|---|
| EP | 1183380 A1 | 3/2002 |
| EP | 1218035 A2 | 7/2002 |
| EP | 1240345 A2 | 9/2002 |
| EP | 1279740 A1 | 1/2003 |
| EP | 1621625 | 2/2006 |
| EP | 1621625 A2 | 2/2006 |
| EP | 1046711 B1 | 12/2006 |
| EP | 1847614 A1 | 10/2007 |
| EP | 1849872 A1 | 10/2007 |
| EP | 1857552 A1 | 11/2007 |
| EP | 1944043 A1 | 7/2008 |
| EP | 1696036 B1 | 4/2010 |
| EP | 2186283 | 5/2010 |
| EP | 1164195 B1 | 10/2010 |
| EP | 2250256 B1 | 11/2010 |
| EP | 2292780 B1 | 3/2011 |
| EP | 2301582 B1 | 3/2011 |
| EP | 2311967 B1 | 4/2011 |
| EP | 2524037 A1 | 11/2012 |
| EP | 2359866 B1 | 7/2013 |
| EP | 2660325 A3 | 2/2014 |
| EP | 2699270 B1 | 2/2014 |
| EP | 2383346 B1 | 10/2014 |
| EP | 2814958 A1 | 12/2014 |
| EP | 2198016 B1 | 5/2015 |
| EP | 2871239 A9 | 6/2015 |
| EP | 2879719 A1 | 6/2015 |
| EP | 2212348 B1 | 7/2015 |
| EP | 1578253 B1 | 8/2015 |
| EP | 2943567 B1 | 11/2015 |
| EP | 3058959 A1 | 8/2016 |
| EP | 1453547 B1 | 9/2016 |
| EP | 2220241 B1 | 9/2016 |
| EP | 2325298 B1 | 10/2016 |
| EP | 2007795 B1 | 11/2016 |
| EP | 2176283 | 11/2016 |
| EP | 2292779 B1 | 11/2016 |
| EP | 3067417 A3 | 11/2016 |
| EP | 2220242 B1 | 12/2016 |
| EP | 3108000 | 12/2016 |
| EP | 3117005 A1 | 1/2017 |
| EP | 2737071 B1 | 3/2017 |
| EP | 2933336 B1 | 3/2017 |
| EP | 3134431 A1 | 3/2017 |
| EP | 2348119 B1 | 4/2017 |
| EP | 2531604 B1 | 4/2017 |
| EP | 2771471 B1 | 5/2017 |
| EP | 3168298 A1 | 5/2017 |
| EP | 3209311 A1 | 8/2017 |
| EP | 3215191 A2 | 9/2017 |
| EP | 3215602 A1 | 9/2017 |
| EP | 3219801 A1 | 9/2017 |
| EP | 3221453 A1 | 9/2017 |
| EP | 3221456 A2 | 9/2017 |
| EP | 3224376 A1 | 10/2017 |
| EP | 3230441 A1 | 10/2017 |
| EP | 3235827 A2 | 10/2017 |

(56) References Cited

FOREIGN PATENT DOCUMENTS

| | | |
|---|---|---|
| WO | 1993009239 | 5/1993 |
| WO | 1995034670 | 12/1995 |
| WO | 1996023810 A1 | 8/1996 |
| WO | 1996030540 A2 | 10/1996 |
| WO | 1998010088 | 3/1998 |
| WO | 1999027110 A1 | 6/1999 |
| WO | 1999043360 A1 | 9/1999 |
| WO | 1999058700 A1 | 11/1999 |
| WO | 1999061066 A2 | 12/1999 |
| WO | 1999061595 A2 | 12/1999 |
| WO | 200023116 | 4/2000 |
| WO | 2000023116 A1 | 4/2000 |
| WO | 1999060146 | 5/2000 |
| WO | 2000024916 | 5/2000 |
| WO | 2000066780 A2 | 11/2000 |
| WO | 2000075353 A1 | 12/2000 |
| WO | 2001014539 A2 | 3/2001 |
| WO | 2001023001 | 4/2001 |
| WO | 2001025465 A1 | 4/2001 |
| WO | 2001036623 A2 | 5/2001 |
| WO | 2001068888 A2 | 9/2001 |
| WO | 2001089583 A2 | 11/2001 |
| WO | 2001096587 A2 | 12/2001 |
| WO | 2001032711 B1 | 1/2002 |
| WO | 2001042444 A3 | 1/2002 |
| WO | 2002012525 A2 | 2/2002 |
| WO | 2002014487 A2 | 2/2002 |
| WO | 2002020748 A2 | 3/2002 |
| WO | 2002070719 A2 | 9/2002 |
| WO | 2002071843 A1 | 9/2002 |
| WO | 2003010320 A2 | 2/2003 |
| WO | 2003024502 | 3/2003 |
| WO | 2003042397 A2 | 5/2003 |
| WO | 2003087382 A1 | 10/2003 |
| WO | 2003087383 A1 | 10/2003 |
| WO | 2004044003 | 5/2004 |
| WO | 2004083441 A2 | 9/2004 |
| WO | 2004108922 A2 | 12/2004 |
| WO | 2004111248 A2 | 12/2004 |
| WO | 2004112727 A2 | 12/2004 |
| WO | 2005005610 | 1/2005 |
| WO | 2005012537 | 2/2005 |
| WO | 2005111220 A2 | 11/2005 |
| WO | 2006063247 | 6/2006 |
| WO | 2006102072 | 9/2006 |
| WO | 2007130519 | 11/2007 |
| WO | 2007148971 | 7/2009 |
| WO | 2009134681 | 11/2009 |
| WO | 2011038187 | 3/2011 |
| WO | 2011054976 A2 | 5/2011 |
| WO | 2011122950 | 10/2011 |
| WO | 2010109053 | 11/2011 |
| WO | 2012007458 | 1/2012 |
| WO | 2012007458 A1 | 1/2012 |
| WO | WO 12/007458 * | 1/2012 |
| WO | 2012057363 | 5/2012 |
| WO | 2012109570 | 8/2012 |
| WO | 2012109570 A1 | 8/2012 |
| WO | 2012114090 | 8/2012 |
| WO | 2012144446 | 10/2012 |
| WO | 2013078199 | 5/2013 |
| WO | 2013164793 | 11/2013 |
| WO | 2013170078 A1 | 11/2013 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013148 A2 | 1/2015 |
| WO | 2015018503 | 2/2015 |
| WO | 2014186746 | 3/2015 |
| WO | 2015038625 A1 | 3/2015 |
| WO | 2015031686 | 4/2015 |
| WO | 2015044292 | 4/2015 |
| WO | 2015060722 | 4/2015 |
| WO | 2015106273 A2 | 7/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015127128 | 11/2015 |
| WO | 2015196179 | 12/2015 |
| WO | 2016019364 | 2/2016 |
| WO | 2016054554 | 4/2016 |
| WO | 2016054557 | 4/2016 |
| WO | 2016065001 | 4/2016 |
| WO | 2016073693 | 5/2016 |
| WO | 2016081811 | 5/2016 |
| WO | 2016081927 | 5/2016 |
| WO | 2016115382 | 7/2016 |
| WO | 2016122791 | 8/2016 |
| WO | 2016126857 | 8/2016 |
| WO | 2016130591 | 8/2016 |
| WO | 2016145217 A1 | 9/2016 |
| WO | 2016154055 | 9/2016 |
| WO | 2016154344 | 9/2016 |
| WO | 2016137949 A1 | 10/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 A1 | 11/2016 |
| WO | 2016191418 | 12/2016 |
| WO | 2016196328 A1 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017023724 A1 | 2/2017 |
| WO | 2017024198 A1 | 2/2017 |
| WO | 2017058892 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017079768 A1 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017106236 A1 | 6/2017 |
| WO | 2017112948 A1 | 6/2017 |
| WO | 2017122789 A1 | 7/2017 |
| WO | 2017123934 A1 | 7/2017 |
| WO | 2017136202 A1 | 8/2017 |
| WO | 2017136536 A1 | 8/2017 |
| WO | 2017139381 A1 | 8/2017 |
| WO | 2017143100 A1 | 8/2017 |
| WO | 2017147477 A1 | 8/2017 |
| WO | 2017151884 A1 | 9/2017 |
| WO | 2017152149 A1 | 9/2017 |
| WO | 2017155973 A1 | 9/2017 |
| WO | 2017160360 A2 | 9/2017 |
| WO | 2017165167 A1 | 9/2017 |
| WO | 2017165859 A1 | 9/2017 |
| WO | 2017172733 A1 | 10/2017 |
| WO | 2017172772 A1 | 10/2017 |
| WO | 2017173043 A1 | 10/2017 |
| WO | 2017173283 A1 | 10/2017 |
| WO | 2017180854 A1 | 10/2017 |
| WO | 2017181162 A1 | 10/2017 |
| WO | 2017184879 A1 | 10/2017 |

(56) References Cited

FOREIGN PATENT DOCUMENTS

| WO | 2017190031 A1 | 11/2017 |
|---|---|---|
| WO | 2017192699 A1 | 11/2017 |
| WO | 2017192750 A1 | 11/2017 |
| WO | 2018191450 | 10/2018 |

OTHER PUBLICATIONS

Lu et al, Brain Res. Protocols 15:46-51, 2005.*
Cell Biolabs, https://www.cellbiolabs.com/sites/default/files/VPK-410-aav-expression-vector.pdf, 2010; last accessed Oct. 23, 2018.*
Yamada et al, Human Gene Therapy 16:262-270, 2005.*
GenBank Accession AF396260.1, dated Aug. 2001.*
Matsuura, M et al., Human Herpesvirus 6 Major Immediate Early Promoter Has Strong Activity in T Cells and is Useful for Heterologous Gene Expression. Virology Journal. 2011, vol. 8, No. 9, p. 1-9; Figures 1-2.
Brun, L et al., Clinical and Biochemical Features of Aromatic L-amino Acid Decarboxylase Deficiency. Neurology. Jul. 6, 2010, vol. 75, No. 1, pp. 64-71; abstract; Table 1; p. 66, first column, first paragraph.
Quattrochi, JJ et al., Dose-Related Suppression of REM Sleep and PGO Waves by the Serotonin-1 Agonist Eltopraxine. Neuropsychopharmacology. 1993, vol. 8, No. 1, pp. 7-13.
International Search Report dated Apr. 21, 2016 received in corresponding PCT Application No. PCT/US2015/059201.
Bosch ME et al. Self-Complementary AAV9 Gene Delivery Partially Corrects Pathology Associated with Juvenile Neuronal Ceroid Lipofuscinosis (CLN3). J Neurosci. Sep. 14, 2016;36(37):9669-82.
Hocquemiller M et al. Adeno-Associated Virus-Based Gene Therapy for CNS Diseases. Hum Gene Ther. Jul. 2016;27(7):478-96.
Chali F, et al. Inhibiting cholesterol degradation induces neuronal sclerosis and epileptic activity in mouse hippocampus. Eur J Neurosci. May 2015, 41(10):1345-55.
Bassil F, et al. Viral-mediated oligodendroglial alpha-synuclein expression models multiple system atrophy. Mov Disord. May 29, 2017. Epub ahead of print Movement Disorders Aug. 2017 32(8)1230-1239.
Kao JH, et al. Effect of naltrexone on neuropathic pain in mice locally transfected with the mutant mu-opioid receptor gene in spinal cord. Br J Pharmacol. Jan. 2015, 172(2):630-41.
Blits B, et al. Perspective on the Road toward Gene Therapy for Parkinson's Disease. Front Neuroanat. Jan. 2017;10:128.
Daher JPL, et al. Leucine-rich Repeat Kinase 2 (LRRK2) Pharmacological Inhibition Abates alpha-Synuclein Gene-induced Neurodegeneration. J Biol Chem. Aug. 2015, 290(32):19433-44.
Kirik D et al. Gene Therapy for Parkinson's Disease: Disease Modification by GDNF Family of Ligands. Neurobiol Dis. Jan. 2017 97(Part B)179-188.
Singh A et al. Therapeutic Value of Adeno Associated Virus as a Gene Therapy Vector for Parkinson's Disease—A Focused Review. Curr Gene Ther. Jul. 29, 2016 16(4)278-286.
Van Rompuy AS, et al. Nigral overexpression of alpha-synuclein in the absence of parkin enhances alpha-synuclein phosphorylation but does not modulate dopaminergic neurodegeneration. Mol Neurodegener. Jun. 2015, 10:23.
Sehara Y, et al. Persistent Expression of Dopamine-Synthesizing Enzymes 15 years after Gene Transfer in a Primate Model of Parkinson's Disease. Hum Gene Ther Clin Dev. Mar. 9, 2017 Epub ahead of print. Jun. 2017 28(2):74-79.
Ciesielska A, et al. Carbidopa-Based Modulation of the Functional Effect of the AAV2-hAADC Gene Therapy in 6-OHDA Lesioned Rats. PLoS One. Apr. 2015, 10(4):e0122708.
Hadaczek P, et al. GDNF signaling implemented by GM1 ganglioside; failure in Parkinson's disease and GM1-deficient murine model. Exp Neurol. Jan. 2015, 263:177-89.
Rocha EM, et al. Glucocerebrosidase gene therapy prevents alpha-synucleinopathy of midbrain dopamine neurons. Neurobiol Dis. Oct. 2015;82:495-503.

Thome AD et al. Fractalkine Signaling Regulates the Inflammatory Response in an α-Synuclein Model of Parkinson Disease. PLoS One. Oct. 15, 2015;10(10):e0140566.
Marks WJ et al. Long-Term Safety of Patients with Parkinson's Disease Receiving rAAV2-Neurturin (CERE-120) Gene Transfer. Hum Gene Ther. Jul. 2016;27(7):522-7.
Olanow CW, et al. Gene delivery of neurturin to putamen and substantia nigra in Parkinson disease: A double-blind randomized controlled trial. Ann Neurol.Aug. 2015, 78(2):248-57.
Paul G, et al. Safety and tolerability of intracerebroventricular PDGF-BB in Parkinson's disease patients. J Clin Invest. Mar. 2, 2015;125(3):1339-46.
Kim YC, et al. RNA Interference of Human α-Synuclein in Mouse. Front Neurol. Jan. 2017;8:13.
Marongiu R et al. Gene Therapy Blockade of Dorsal Striatal p11 Improves Motor Function and Dyskinesia in Parkinsonian Mice. Proc Natl Acad Sci USA. Feb. 2, 2016;113(5):1423-8.
Stavarache MA, et al. The tumor suppressor PTEN regulates motor responses to striatal dopamine in normal and Parkinsonian animals. Neurobiol Dis. Oct. 2015;82:487-94.
Zharikov AD, et al. shRNA targeting α-synuclein prevents neurodegeneration in a Parkinson's disease model. J Clin Invest. Jul. 1, 2015;125(7):2721-35.
Extended European Search Report received in corresponding EP Application No. 15857231.3 dated Jun. 29, 2018.
Doroudchi MM, et al. AAV Gene Transfer of AADC protects dopaminergic and striatal neurons from toxicity of L-DOPA in a primary cultur model (Abstract). 33rd Annual Meeting of the Society of Neuroscience: New Orleans, LA, USA. Nov. 8, 2003.
Kotin RM, et al. Manufacturing clinical grade recombinant adeno-associated virus using invertebrate cell lines. Hum Gene Ther. Mar. 28, 2017. Epub ahead of print.
Kotterman MA, et al. Enhanced cellular secretion of AAV2 by expression of foreign viral envelope proteins. Biochemical Engineering Journal, vol. 93, Jan. 15, 2015, pp. 108-114.
Methods in Molecular Biology, ed. Richard, Humana Press, NJ (1995).
Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. Oct. 26, 2015(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.
Pacouret S, et al. AAV-ID: A Rapid and Robust Assay for Batch-to-Batch Consistency Evaluation of AAV Preparations. Mol Ther. Apr. 17, 2017. Epub ahead of print.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Ruffing M, et al. Assembly of viruslike particles by recombinant structural proteins of adeno-associated virus type 2 in insect cells. J Virol Dec. 1992;66(12):6922-30.
Samulski RJ, et al. Helper-free stocks of recombinant adeno-associated viruses: normal integration does not require viral gene expression. J Virol. Sep. 1989;63(9):3822-8.
Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1): R42-52.
Wasilko DJ, et al. The titerless infected-cells preservation and scale-up (TIPS) method for large-scale production of NO-sensitive human soluble guanylate cyclase (sGC) from insect cells infected

(56) References Cited

OTHER PUBLICATIONS with recombinant baculovirus. Protein Expr Purif. Jun. 2009;65(2):122-32. doi: 10.1016/j.pep.2009.01.002. Epub Jan. 11, 2009.
Zhao KN, et al. BPV1 E2 protein enhances packaging of full-length plasmid DNA in BPV1 pseudovirions. Virology. Jul. 5, 2000;272(2):382-93.
Pierson EE, et al. Resolving adeno-associated viral particle diversity with charge detection mass spectrometry. Anal Chem. Jul. 2016;88(13):6718-25.
Rashnonejad A, et al. Large-Scale Production of Adeno-Associated Viral Vector Serotype-9 Carrying the Human Survival Motor Neuron Gene. Mol Biotechnol. Jan. 2016;58(1):30-6.
Ling C, et al. Strategies to generate high-titer, high-potency recombinant AAV3 serotype vectors. Mol Ther Methods Clin Dev. May 2016;3:16029.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Mao Y, et al. Single point mutation in adeno-associated viral vectors—DJ capsid leads to improvement for gene delivery in vivo. BMC Biotechnol. Jan. 2016;16:1.
Tu MY, et al. Role of capsid proteins in parvoviruses infection. Virol J. Aug. 2015, 4;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Pillay S, et al. An essential receptor for adeno-associated virus infection. Nature. Feb. 2016;530(7588):108-12.
Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1(14):e88728.
Bensky MJ, et al. Targeted gene delivery to the enteric nervous system using AAV: a comparison across serotypes and capsid mutants.Mol Ther. Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vetors. Mol Ther. Apr. 2016;24(4):726-35.
Davis AS, et al. Rational design and engineering of a modified adeno-associated virus (AAV1)-based vector system for enhanced retrograde gene delivery. Neurosurgery. Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther. Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016:35495. ene Ther Methods. Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Bankiewicz KS, et al. Convection-enhanced delivery of AAV vector in Parkinsonian monkeys; in vivo detection of gene expression and restoration of dopaminergic function using pro-drug approach. Exp. Neurol. 2000 164;2-14.
Bankiewicz KS, et al. Long-term clinical improvement in MPTP-lesioned primates after gene therapy with AAV-hAADC. Mol Ther. Oct. 2006;14(4):564-570.
Bartus RT, et al. Parkinson's disease gene therapy: success by design meets failure by efficacy. Mol Ther. Mar. 2014;22(3):487-497.
Brodsky MA, et al. Effects fo a dopamine agonist on the pharmacodynamics of levodopa in Parkinson Disease. Arch Neurol. Jan. 2010;67(1):27-32.
Chan PLS, et al. Modeling the short- and long-duration responses to exogenous levodopa and to endogenous levodopa production in Parkinson's Disease. J Pharmacokinetics and Pharmacodynamics. Jun. 2004;31(3):243-268.
Chan PLS, et al. Pharmacokinetic and pharmacodynamic changes during the first four years of levodopa treatment in Parkinson's Disease. J Pharmacokinetics and Pharmacodynamics. Aug. 2005;32(3-4):459.
Christine CW, et al. Safety and tolerability of putaminal AADC gene therapy for Parkinson disease. Neurology 2009;73:1662-1669.
Ciesielska A, et al. Depletion of AADC activity in caudate nucleus and putamen of Parkinson's disease patients; Implications for ongoing AAV2-AADC gene therapy trial. PLoS One 12(2):e0169965, Feb. 6, 2017, pp. 1-13.
Dhawan V, et al. Comparative analysis of striatal FDOPA uptake in Parkinson's disease: ratio method versus graphical approach. J Nucl Med 2002;43:1324-1330.
Espay AJ, et al. Optimizing extended-release carbidopa/levodopa in Parkinson disease. Neurol Clin Pract 2017;7:86-93.
Fahn S, et al. Levodopa and the progression of Parkinson's disease. N Engl J Med. Dec. 9, 2004;351(24):2498-508.

(56) References Cited

OTHER PUBLICATIONS

Forsayeth J, et al. A Dose-Ranging Study of AAV-hAADC Therapy in Parkinsonian Monkeys. Mol Ther. Oct. 2006;14(4):571-577.
Forsayeth J and Bankiewicz KS. Transduction of antigen-presenting cells in the brain by AAV9 warrants caution in preclinical studies. Mol Ther. 2015;23(4):612.
PD Med Collaborative Group, et al. Long-term effectiveness of dopamine agonists and monoamine oxidase B inhibitors compared with levodopa as initial treatment for Parkinson's disease (PD MED): a large, open-label, pragmatic randomised trial. Lancet Sep. 27, 2014;384(9949):1196-205.
Hadaczek P, et al. Eight Years of Clinical Improvement in MPTP-Lesioned Primates After Gene Therapy With AAV2-hAADC. Molecular Therapy. Aug. 2010;vol. 18 No. 8, 1458-1461.
Hauser RA, et al. A home diary to assess functional status in patients with Parkinson's disease with motor fluctuations and dyskinesia. Clin Neuropharm. 2000; 23(2):75-81.
Kordower JH, et al. Disease duration and the integrity of the nigrostriatal system in Parkinson's disease. Brain 2013; 136:2419-2431.
Lidstone SC. Great expectations: the placebo effect in Parkinson's disease. Handb Exp Pharmacol. 2014;225:139-47.
Mittermeyer G, et al. Long-term evaluation of a phase I study of AADC gene therapy for Parkinson's disease. Hum Gene Ther. Apr. 23, 2012;377-381.
Muramatsu S, et al. A Phase I Study of Aromatic I-Amino Acid Decarboxylase Gene Therapy for Parkinson's Disease. Mol Ther. Sep. 2010;18(9):1731-5.
Richardson RM, et al. Novel platform for MRI-guided convection enhanced delivery of therapeutics: preclinical validation in nonhuman primate brain. Stereotact Funct Neurosurg 2011;89:141-151.
Sanchez-Pernaute R, et al. Functional Effect of Adeno-associated Virus Mediated Gene Transfer of Aromatic L-Amino Acid Decarboxylase into the Striatum of 6-OHDA-Lesioned Rats. Mol Ther Oct. 4, 2001(4):324-330.
Sehara Y, et al. Persistent Expression of Dopamine-Synthesizing Enzymes 15 years after Gene Transfer in a Primate Model of Parkinson's Disease. Hum Gene Ther Clin Dev. Mar. 9, 2017 Epub ahead of print.
Shulman LM, et al. The clinically important difference on the Unified Parkinson's Disease Rating Scale, Arch Neurol, vol. 67, No. 1, Jan. 2010, 64-70.
Su X, et al. Real-time MR imaging with gadoteridol predicts distribution of transgenes after convection-enhanced delivery of AAV2 vectors. Mol Ther Aug. 2010; 18(8):1490-1495.
Tomlinson CL, et al. Systematic review of levodopa dose equivalency reporting in Parkinson's disease. Movement Disorders. 2010;25(15):2649-2685.
Voon V, et al. Impulse control disorders and levodopa-induced dyskinesias in Parkinson's disease: an update. Lancet Neurol. Mar. 2017;16(3):238-250.
Examination Report No. 1 received in corresponding Australian Patent Application No. 2015343037 dated Jan. 25, 2018.
Japanese Office Action received in corresponding Japanese Patent Application No. 2017-544285 dated Apr. 24, 2018.
Examiner's Report received in corresponding Canadian Patent Application No. 2,966,620 dated Feb. 28, 2018.
Xie J, et al. Short DNA Hairpins Compromise Recombinant Adeno-Associated Virus Genome Homogeneity. Mol Ther. Apr. 24, 2017. Epub ahead of print.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP.B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al., miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.
Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated trough the DNA damage and repair pathways. PLoS Pathog. Jan. 2016;12(1):e1005399.
Kailasan S, et al. Structure of an Enteric Pathogen, Bovine Parvovirus. J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med. Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Lee NC, et al. Mutation-adapted U1 snRNA corrects a splicing error of the dopa decarboxylase gene. Hum Mol Genet. Dec. 2016;25(23):5142-5147.
Lee NC, et al. Benefits of Neuronal Preferential Systemic Gene Therapy for Neurotransmitter Deficiency. Mol Ther. Oct. 2015;23(10):1572-81.
Bradbury AM, et al. Biomarkers for disease progression and AAV therapeutic efficacy in feline Sandhoff disease. Exp Neurol. Jan. 2015, 263:102-12.

(56) References Cited

OTHER PUBLICATIONS

Hemphill DD, et al. Adeno-associated virus gene therapy vector scAAVIGF-1 for transduction of equine articular chondrocytes and RNA-seq analysis. Osteoarthritis Cartilage. May 2016;24(5):902-11.
Ito H, et al. HMGB1 facilitates repair of mitochondrial DNA damage and extends the lifespan of mutant ataxin-1 knock-in mice. EMBO Mol Med. Dec. 2015;7(1):78-101.
Ito H, et al. In utero gene therapy rescues microcephaly caused by Pqbp1-hypofunction in neural stem progenitor cells. Mol Psychiatry. Apr. 2015, 20(4):459-71.
Ko AR, et al. AAV8-mediated expression of N-acetylglucosamine-1-phosphate transferase attenuates bone loss in a mouse model of mucolipidosis II. Mol Genet Metab. Apr. 2016;117(4):447-55.
Lai Z, et al. Aquaporin gene therapy corrects Sjögren's syndrome phenotype in mice. PNAS. May 2016;113(20):5694-9.
Meadows AS, et al. A GLP-compliant toxicology and biodistribution study: systemic delivery of an rAAV9 vector for the treatment of mucopolysaccharidosis IIIB. Hum Gene Ther Clin Dev. Dec. 2015;26(4):228-42.
Osmon KJ, et al. Systemic Gene Transfer of a Hexosaminidase Variant Using a scAAV9.47 Vector Corrects GM2 Gangliosidosis in Sandhoff Mice. Hum Gene Ther. Jul. 2016;27(7):497-508.
Ramos J, et al. Gene therapy for Duchenne muscular dystrophy. Exp Opin Orphan Drugs. 2015;3(11):1255-1266.
Rockwell HE, et al. AAV-Mediated Gene Delivery in a Feline Model of Sandhoff Disease Corrects Lysosomal Storage in the Central Nervous System. ASN Neuro. Apr. 2015, 7(2).
Rosenberg JB et al. Gene Therapy for Metachromatic Leukodystrophy. J Neurosci Res. Nov. 2016;94(11):1169-79.
Sun BD, et al. Preclinical Development of New Therapy for Glycogen Storage Diseases. Curr Gene Ther. Jan. 2015, 15(4):338-47.
Talla V, et al. Complex I Subunit Gene Therapy with NDUFA6 Ameliorates Neurodegeneration in EAE. Invest Ophthalmol Vis Sci. Jan. 2015, 22;56(2):1129-40.
Wang L, et al. AAV gene therapy corrects OTC deficiency and prevents liver fibrosis in aged OTC-knock out heterozygous mice. Mol Genet Metab. Apr. 2017;120(4):299-305.
Wilson JM, et al. Adeno-associated virus vector-mediated gene therapy can effectively treat CNS and cardiac lesions and induce immune tolerance to the therapeutic enzyme in large animal models of mucopolysaccharidosis type. Feb. 2015, 114(2): 126-127.
Yi H, et al. Systemic correction of murine glycogen storage disease type IV by an AAV-mediated gene therapy. Hum Gene Ther. Mar. 2017;28(3):286-294.
Zolotukhin I, et al. Potential for cellular stress response to hepatic factor VIII expression from AAV vector. Mol Ther Methods Clin Dev. Sep. 2016;3:16063.
Arruda VR, et al. Obstacles and future of gene therapy for hemophilia. Expert Opin Orphan Drugs. 2015;3(9):997-1010.
George LA, et al. Gene therapy for hemophilia: past, present and future. Semin Hematol. Jan. 2016;53(1):46-54.
Francis JS et al. N-Acetylaspartate supports the Energetic Demands of Developmental Myelination via Oligodendroglial Aspartoacyclase. Neurobiol Dis. Oct. 4, 2016;96:323-334.
Loring HS, et al. Development of rAAV2-CFTR: History of the First rAAV Vector Product to be Used in Humans. Hum Gene Ther Methods. Apr. 2016;27(2):49-58.
Doerfler PA, et al. Copackaged AAV9 Vectors Promote Simultaneous Immune Tolerance and Phenotypic Correction of Pompe Disease. Hum Gene Ther. Jan. 2016;27(1):43-59.
Fu H, et al. Functional correction of neurological and somatic disorders at later stages of disease in MPS IIIa mice by systemic scAAV9-hSGSH gene delivery. Mol Ther Methods Clin Dev. Jun. 2016;3:16036.
Gessler DJ, et al. Redirecting N-acetylaspartate metabolism in the central nervous system normalizes myelination and rescues Canavan disease. JCI Insight. Feb. 2017;2(3):e90807.
Gilkes JA, et al. Mucopolysaccharidosis IIIb confers enhanced neonatal intracranial transduction by AAV8 but not by 5, 9 or rh10. Gene Ther. Mar. 2016;23(3):263-71.
Golebiowski D, et al. Direct intracranial injection of AAVrh8 encoding monkey β-N-acetylhexosaminidase causes neurotoxicity in primate brain. Hum Gene Ther. Jan. 26, 2017 Epub ahead of print.
Iwayama H, et al. Adeno associated virus 9-based gene therapy delivers a functional monocarboxylate transporter 8 which improves thyroid hormone availability to the brain of Mct8 deficient mice. Thyroid. Sep. 2016;26(9):1311-9.
Meyer K, et al. Improving Single Injection CSF Delivery of AAV9-mediated Gene Therapy for SMA: A Dose-response Study in Mice and Nonhuman Primates. Mol Ther. Mar. 2015,23(3):477-87.
Zerah M, et al. Intracerebral Gene therapy using AAV rh.10-hARSA recombinant vector to treat patients with early-onset forms of metachromatic leukodystrophy: preclinical feasibility and safety assessments in NHP. Hum Gene Ther Clin Dev. Jun. 2015;26(2):113-24.
Gadalla KKE, et al. Development of a Novel AAV Gene Therapy Cassette with Improved Safety Features and Efficacy in a Mouse Model of Rett Syndrome. Mol Ther Methods Clin Dev. Apr. 22, 2017;5:180-190.
Sinnett SE, et al. Improved MECP2 Gene Therapy Extends the Survival of MeCP2-Null Mice without Apparent Toxicity after Intracisternal Delivery. Mol Ther Methods Clin Dev. Apr. 19, 2017;5:106-115.
Armbruster N, et al. Efficacy and biodistribution analysis of intracerebroventricular administration of an optimized scAAV9-SMN1 vector in a mouse model of spinal muscular atrophy. Mol Ther Methods Clin Dev. Sep. 2016;3:16060.
Pan B, et al. Gene therapy restores auditory and vestibular function in a mouse model of Usher syndrome type 1c. Nat Biotechnol. Mar. 2017;35(3):264-272.
Dinculescu A, et al. AAV-mediated clarin-1 expression in the mouse retina: Implications for USH3A gene therapy. PLoS One. Feb. 2016;11(2):e0148874.
Conlon TJ, et al. Transfer of Therapeutic Genes into Fetal Rhesus Monkeys using Recombinant Adeno-Associated Type I Viral Vectors. Hum Gene Ther Clin Dev. Dec. 2016;27(4):152-159.
Marcos-Contreras OA, et al. Sustained correction of FVII deficiency in dogs using AAV-mediated expression of zymogen FVII. Blood. Feb. 2016;127(5):565-71.
Chiuchiolo MJ, et al. Gene therapy for alpha-1 antitrypsin deficiency lung disease. Ann Am Thorac Soc. Aug. 2016;13 Suppl 4:S352-69.
Griesenbach, Uta et al. Cystic Fibrosis Gene Therapy in the UK and Elsewhere. Hum Gene Ther. May 1, 2015; 26(5):266-275.
Corti M, et al. Evaluation of Readministration of a Recombinant Adeno-Associated Virus Vector Expressing Acid Alpha-Glucosidase in Pompe Disease: Preclinical to Clinical Planning. Human Gene Therapy Clin Dev Sep. 2015;26(3):185-193.
Mack DL, et al. Minimally Effective Dose of Systemic AAV8-MTM1 Needed to Prolong Survival and Correct Severe Muscle Pathology in a Canine Model of X-Linked Myotubular Myopathy. Molecular Therapy, vol. 23, Supplement 1, pS201, May 2015.
Mack DL, et al. Systemic AAV8-Mediated Gene Therapy Drives Whole-Body Correction of Myotubular Myopathy in Dogs. Mol Ther. Apr. 2017;25(4):839-854.
Pozsgai ER, et al. β-sarcoglycan gene transfer decreases fibrosis and restores force in LGMD2E mice. Gene Ther. Jan. 2016;23(1):57-66.
Todd A.G., et al. Correcting Neuromuscular Deficits With Gene Therapy in Pompe Disease. Ann Neurol. Aug. 2015, 78(2):222-34.
Han So, et al. Enhanced Efficacy from Gene Therapy in Pompe Disease Using Coreceptor Blockade. Hum Gene Ther.Jan. 2015, 26(1):26-35.
Pierce EA, et al. The status of RPE65 Gene Therapy Trials: Safety and Efficacy. Cold Spring Harb Perspect Med. Sep. 2015;5(9):a017285.
Landau DJ, et al. In vivo zinc finger nuclease mediated targeted integration of a glucose-6-phosphatase transgene promotes survival in mice with glycogen storage disease type 1a. Mol Ther. Apr. 2016;24(4):697-706.

(56) References Cited

OTHER PUBLICATIONS

Valdmanis P, et al. Future of rAAV gene therapy: Platform for RNAi, Gene Editing and Beyond. Hum Gene Ther. Apr. 2017;28(4):361-372.
Ronzitti G, et al. A translationally optimized AAV-UGT1A1 vector drives safe and long-lasting correction of Crigler-Najjar syndrome. Mol Ther Methods Clin Dev. Jul. 2016;3:16049.
Sun J, et al. Gene delivery of activated Factor VII Using Alternative AAV Serotype Improves Hemostasis in Hemophiliac Mice with FVIII Inhibitors and AAV Neutralizing antibodies. Hum Gene Ther. May 6, 2017. Epub ahead of print.
Tse LV, et al. Structure-guided evolution of antigenically distinct adeno-associated virus variants for immune evasion. Proc Natl Acad Sci U S A. May 30, 2017. Epub ahead of print.
Vandamme C, et al. Unraveling the complex story of immune responses to AAV vectors trial after trial. Hum Gene Ther. Aug. 23, 2017.
Fu H, et al. Differential prevalence of antibodies against adeno-associated virus in healthy children and patients with mucopolysaccharidosis III: perspective for AAV-mediated gene therapy. Human Gene Ther Clin Dev Sep. 19, 2017 Epub ahead of print.
Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.
Majowicz A, et al. Successful Repeated Hepatic Gene Delivery in Mice and Non-human Primates Achieved by Sequential Administration of AAV5ch and AAV1. Mol Ther. Jun. 5, 2017. Epub ahead of print.
Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.
Gil-Farina I, et al. Recombinant AAV Integration Is Not Associated With Hepatic Genotoxicity in Nonhuman Primates and Patients. Mol Ther. Jun. 2016;24(6):1100-5.
Logan GJ, et al. Identification of liver-specific enhancer-promoter activity in the 3' untranslated region of the wild-type AAV2 genome. Nat Genet. Jun. 19, 2017. Epub ahead of print.
Pillay S, et al. AAV serotypes have distinctive interactions with domains of the cellular receptor AAVR. J Virol. Jul. 5, 2017. Epub ahead of print.
Wang M, Sun J, Crosby A, Woodard K, Hirsch ML, Samulski RJ, Li C. Direct interaction of human serum proteins with AAV virions to enhance AAV transduction: immediate impact on clinical applications. Gene Ther. Jan. 2017;24(1):49-59. doi: 10.1038/gt.2016.75. Epub Nov. 11, 2016.
Bennett A, et al. Thermal Stability as a Determinant of AAV Serotype Identity. Mol Ther Methods Clin Dev. Jul. 24, 2017;6:171-182. doi: 10.1016/j.omtm.2017.07.003.
Gray-Edwards H, et al. AAV gene therapy in a sheep model of Tay-Sachs disease. Human Gene Therapy. Sep. 19, 2017 Epub ahead of print.
Guggino W, et al. A Preclinical Study in Rhesus Macaques for Cystic Fibrosis to Assess Gene Transfer and Transduction by AAV1 and AAV5 With a Dual-Luciferase Reporter System. Hum Gene Ther Clin Dev. Jul. 20, 2017.
Eichler F, et al. Hematopoietic Stem-Cell Gene Therapy for Cerebral Adrenoleukodystrophy. N Engl J Med Oct. 4, 2017 Epub ahead of print.
Bennett A, et al. Understanding capsid assembly and genome packaging for adeno-associated viruses. Future Virology Jun. 2017; 12(6): 283-297.
Grimm D, et al. Small but increasingly mightly—latest advances in AAV vector research, design and evolution. Hum Gene Ther. Aug. 23 Epub ahead of print.
Pillay S, et al. Host determinants of adeno-associated viral vector entry. Curr Opin Virol. Jun. 30, 2017;24:124-131. Epub ahead of print.

Smith LJ, et al. Gene transfer properties and structural modeling of human stem cell-derived AAV. Molecular Therapy. Sep. 2014;22(9):1625-1634.
Wooley DP, et al. A directed evolution approach to select for novel Adeno-associated virus capsids on an HIV-1 producer T cell line. J Virol. Methods. Sep. 13, 2017 Epub ahead of print.
Eichler K, et al. The complete connectome of a learning and memory centre in an insect brain. Nature. Aug. 9, 2017;548(7666):175-182.
Le Pichon CE, et al. Loss of dual leucine zipper kinase signaling is protective in animal models of neurodegenerative disease. Sci Transl Med. Aug. 16, 2017;9(403).
Durost P, et al. Gene therapy with an AAV vector expressing human IL-2 alters immune system homeostasis in humanized mice. Hum Gene Ther. Aug. 21, 2017 Epub ahead of print.
Ahmad M, et al. Engineered Expression of Broadly Neutralizing Antibodies Against Human Immunodeficiency Virus. Annu Rev Virol. Jun. 23, 2017. Epub ahead of print.
Brady JM, et al. Antibody gene transfer with adeno-associated viral vectors as a method for HIV prevention. Immunol Rev. Jan. 2017;275(1):324-333. doi: 10.1111/imr.12478.
Magnani DM et al., Dengue virus evades AAV-mediated neutralizing antibody prophylaxis in rhesus monkeys. Mol Ther Jun. 24, 2017 Epub ahead of print.
Zhu Z, et al. Zika virus has oncolytic activity against glioblastoma stem cells. J Exp Med. Sep. 5, 2017 Epub ahead of print.
Liu Z et al. Single cell transcriptomics reconstructs fate conversion from fibroblast to cardiomyocyte. Nature. Oct. 25, 2017 Epub ahead of print.
Kurosaki F, et al. Optimization of adeno-associated virus vector-mediated gene transfer to the respiratory tract. Gene Ther. May 2017;24(5):290-297.
Tadokoro T, et al. Subpial Adeno-associated Virus 9 (AAV9) Vector Delivery in Adult Mice. J Vis Exp. Jul. 13, 2017; (125). doi: 10.3791/55770.
Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc.13861.
Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.
Gombash SE, et al. Systemic gene delivery transduces the enteric nervous system of guinea pigs and cynomolgus macaques. Gene Ther. Aug. 3, 2017. doi: 10.1038/gt.2017.72.
Hinderer C, et al. Evaluation of intrathecal routes of administration for adeno-associated virus vectors in large animals. Hum Gene Ther . Aug. 15, 2017. doi: 10.1089/hum.2017.026.
Hordeaux J, et al. Long-term neurologic and cardiac correction by intrathecal gene therapy in Pompe disease. Acta Neuropathol Commun Sep. 6, 2017(5):66.
Tardieu M, et al. Intracerebral gene therapy in children with mucopolysaccharidosis type IIIb syndrome: an uncontrolled phase 1/2 clinical trial. Lancet Neurol. Sep. 2017;16(9):712-720.
Yazdan-Shahmorad A, et al. Widespread Optogenetic Expression in Macaque Cortex Obtained with MR-Guided, Convection Enhanced Delivery (CED) of AAV vector to the Thalamus. J Neurosci Methods. Oct. 14, 2017 Epub ahead of print.
Lee NC, et al. A neuron-specific gene therapy relieves motor deficits in pompe disease mice. Mol Neurobiol. Sep. 11, 2017 Epub ahead of print.
Carvalho LS, et al. Evaluating efficiencies of dual AAV approaches for retinal targeting. Front Neursci. Sep. 8, 2017;11:503.
Reichel FF, et al. AAV8 can induce innate and adaptive immune response in the primate eye. Mol Ther. Aug. 31, 2017 Epub ahead of print.
De Silva SR, Charbel Issa P, Singh MS, Lipinski DM, Barnea-Cramer AO, Walker NJ, Barnard AR, Hankins MW, MacLaren RE. Single residue AAV capsid mutation improves transduction of photoreceptors in the Abca4$^{-/-}$ mouse and bipolar cells

(56) References Cited

OTHER PUBLICATIONS in the rd1 mouse and human retina ex vivo. Gene Ther. Nov. 2016;23(11):767-774. doi: 10.1038/gt.2016.54. Epub Jul. 14, 2016.
Katz MG, et al. Use of Adeno-Associated Virus Vector for Cardiac Gene Delivery in Large Animal Surgical Models of Heart Failure. Hum Gene Ther Clin Dev. Jul. 20, 2017.
Watanabe S, et al. Protein Phosphatase Inhibitor-1 Gene Therapy in a Swine Model of Nonischemic Heart Failure. Journal of the American College of Cardiology 2017.
Mandel RJ, et al. Novel oligodendroglial alpha synuclein viral vector models of multiple system atrophy: studies in rodents and nonhuman primates. Acta Neuropathol Commun. Jun. 16, 2017;5(1):47.
Landeck N, et al. Toxic effects of human and rodent variants of alpha-synuclein in vivo. Eur J Neurosci. Feb. 2017;45(4):536-547.
Arrigo A, et al. Visual System Involvement in Patients with Newly Diagnosed Parkinson Disease. Radiology. Jul. 11, 2017:161732.
Athauda D, et al. Exenatide once weekly versus placebo in Parkinson's disease: a randomised, double-blind, placebo-controlled trial. The Lancet. Aug. 3, 2017.
Mital S, et al. β2-Adrenoreceptor is a regulator of the α-synuclein gene driving risk of Parkinson's disease. Science Sep. 1, 2017.
Burbulla LF, et al. Dopamine oxidation mediates mitochondrial and lysosomal dysfunction in Parkinson's disease. Science. Sep. 22;357(6357):1255-1261.
Deyaert E, et al. A homologue of the Parkinson's disease-associated protein LRRK2 undergoes a monomer-dimer transition during GTP turnover. Nat Commun. Oct. 18, 2017;8(1):1008.
Brown N, et al. Adeno-Associated Virus Vectors and Stem Cells: Friends or Foes? Hum Gene Ther. Jun. 2017;28(6):450-463.
Kikuchi T, et al. Human iPS cell-derived dopaminergic neurons function in a primate Parkinson's disease model. Nature. Aug. 30, 2017;548(7669):592-596.
Morizane A, et al. MHC matching improves engraftment of iPSC-derived neurons in non-human primates. Nat. Commun. Aug. 30, 2017;8(1):385.
Chansel-Debordeaux, et al. In utero delivery of rAAV2/9 induces neuronal expression of the transgene in the brain: towards new models of Parkinson's disease. Gene Ther. Aug. 30, 2017. doi: 10.1038/gt.2017.84.
Delenclos M, et al. Neonatal AAV delivery of alpha-synuclein induces pathology in the adult mouse brain. Acta Neuropathol Commun. Jun. 23, 2017;5(1):51.
Morabito G, et al. Global-scale control of gene expression in the adult mouse nervous system by a single AAV-PHP.B systemic injection enables GBA1 gene therapy for complete protection from synucleinopathy Aug. 10, 2017.
Piguet F, et al. Clinical gene therapy for neurodegenerative diseases: past, present, and future. Hum Gene Ther. Nov. 2017;28(11):988-1003.
Jin X, et al. Direct LC/MS Analysis for Complete Characterization of Recombinant Adeno-Associated Virus Capsid Proteins. Hum Gene Ther Methods. Jun. 18, 2017. Epub ahead of print.
Galli A, et al. Strategies to optimize capsid protein expression and single stranded DNA formation of Adeno-associated virus in *Saccharomyces cerevisiae*. J Appl Microbiol. Jun. 13, 2017. Epub ahead of print.
Wang Z, et al. Human Bocavirus 1 Is a Novel Helper for Adeno-Associated Virus Replication. J Virol. Jun. 28, 2017. Epub ahead of print.
Grobe S, et al. Relevance of assembly-activating protein for Adeno-associated virus vector production and capsid protein stability in mammalian and insect cells. J Virol. Aug. 2, 2017. pii: JVI.01198-17. doi: 10.1128/JVI.01198-17.
Kondratov O, et al. Direct head-to-head evaluation of recombinant Adeno-associated viral (rAAV) vectors manufactured in human vs insect cells. Molecular Therapy. Aug. 10, 2017.
Jungmann A, et al. Protocol for efficient generation and characterization of adeno-associated viral (AAV) vectors. Hum Gene Ther Methods Sep. 21, 2017 Epub ahead of print.
Luo Y, et al. AAVS1-Targeted Plasmid Integration in AAV Producer Cell Lines. Hum Gene Ther Methods. Jun. 2017;28(3):124-138.
Savy A, et al. Impact of ITR integrity on rAAV8 production using baculovirus/Sf9 cells system. Hum Gene Ther Methods. Oct. 1, 2017 Epub ahead of print.
GTEx Consortium et al. Genetic effects on gene expression across human tissues. Nature. Oct. 11, 2017;550(7675):204-213.
Li X, et al. The impact of rare variation on gene expression across tissues. Nature. Oct. 11, 2017;550(7675):239-243.
Ojala DS, et al. In Vivo Selection of a Computationally Designed SCHEMA AAV Library Yields a Novel Variant for Infection of Adult Neural Stem Cells in the SVZ. Mol Ther. Sep. 8, 2017 Epub ahead of print.
Chandran JS, et al. Site Specific Modification of Adeno-Associated Virus Enables Both Fluorescent Imaging of Viral Particles and Characterization of the Capsid Interactome. Sci Rep. Nov. 7, 2017;7(1):14766.
Chai Z, et al. Application of polyploid adeno-associated virus vectors for transduction enhancement and neutralizing antibody evasion. J Control Release. Aug. 5, 2017. pii: S0168-3659(17)30772-1. doi: 10.1016/j.conrel.2017.08.005.
Hickey DG, et al. Tropism of engineered and evolved recombinant AAV serotypes in the rd1 mouse and ex vivo primate retina. Gene Ther. Sep. 5, 2017 Epub ahead of print.
Yan Z, et al. Human Bocavirus Type-1 Capsid Facilitates the Transduction of Ferret Airways by Adeno-Associated Virus Genomes. Hum Gene Ther. May 10, 2017. Epub ahead of print.
Kanaan NM, et al. Rationally Engineered AAV Capsids Improve Transduction and Volumetric Spread in the CNS. Molecular Therapy—Nucleic Acids 8: 184-197 Sep. 15, 2017.
Powell SK, Khan N, Parker CL, Samulski RJ, Matsushima G, Gray SJ, McCown TJ. Characterization of a novel adeno-associated viral vector with preferential oligodendrocyte tropism. Gene Ther. Nov. 2016;23(11):807-814. doi: 10.1038/gt.2016.62. Epub Sep. 15, 2016.
Chan KY, et al. Engineered AAVs for efficient noninvasive gene delivery to the central and peripheral nervous systems. Nat Neurosci. Jun. 26, 2017. Epub ahead of print.
Paulk NK, et al. Bioengineered AAV Capsids with Combined High Human Liver Transduction In Vivo and Unique Humoral Seroreactivity. Mol Ther. Sep. 25, 2017 Epub ahead of print.
Hagedorn C, et al. S/MAR element facilitates episomal long-term persistence of Adeno-associated viral (AAV) vector genomes in proliferating cells. Hum Gene Ther. Jun. 30, 2017. Epub ahead of print.
Ziegler T, et al. Steerable induction of the Thymosin β14/MRTF—A pathway via AAV-based overexpression induces therapeutic neovascularization. Hum Gene Ther. Jul. 20, 2017.
Potter RA, et al. Systemic Delivery of Dysferlin Overlap Vectors Provides Long-Term Functional Improvement for Dysferlinopathy. Hum Gene Ther. Jul. 14, 2017. Epub ahead of print.
Huang W, et al. Targeting Visceral Fat by Intraperitoneal Delivery of Novel AAV Serotype Vector Restricting Off-Target Transduction in Liver. Mol Ther Methods Clin Dev. Jun. 19, 2017;6:68-78.
Herrera-Carrillo E, et al. Improving miRNA delivery by optimizing miRNA expression cassettes in viral vectors. Hum Gene Ther Methods. Jul. 16, 2017.
Krhac Levacic A, et al. Minicircle versus plasmid DNA delivery by receptor-targeted polyplexes. Hum Gene Ther. Aug. 21, 2017 Epub ahead of print.
Moffett HF, et al. Hit-and-run programming of therapeutic cytoreagents using mRNA nanocarriers. Nat Commun. Aug. 30, 2017;8(1):389.
Adachi K, et al. Drawing a high-resolution functional map of adeno-associated virus capsid by massively parallel sequencing. Nat Commun. 2014;5:3075. doi: 10.1038/ncomms4075.
Ahmed SS, et al. rAAV gene therapy in a Canavan's disease mouse model reveals immune impairments and an extended pathology beyond the central nervous system. Mol Ther. Jun. 2016;24(6):1030-41.
Al J, et al. Adeno-associated virus serotype rh.10 displays strong muscle tropism following intraperitoneal delivery. Sci Rep. Jan. 2017;7:40336.
Altschul SF, et al. Basic local alignment search tool. J Mol Biol. Oct. 5, 1990;215(3):403-10.

(56) References Cited

OTHER PUBLICATIONS

Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Aubourg P. Gene therapy for rare central nervous system diseases comes to age. Endocr Dev. 2016;30:141-6.
Aydemir F, et al. Mutants at the 2-fold interface of AAV2 structural proteins suggest a role in viral transcription for AAV capsids. J Virol. Jul. 2016;90(16):7196-204.
Bankiewicz KS et al. AAV Viral Vector Delivery to the Brain by Shape-conforming MR-guided Infusions. J Control Release. Oct. 28, 2016;240:434-442.
Bantel-Schaal U, et al. Human adeno-associated virus type 5 is only distantly related to other known primate helper-dependent parvoviruses. J Virol. Feb. 1999;73(2):939-47.
Baum BJ, et al. Advances in salivary gland gene therapy—oral and systemic implications. Expert Opinion on Biological Therapy. 2015;15(10):1443-54.
Bell P, et al. Effects of self-complementarity, codon optimization, transgene, and dose on liver transduction with AAV8. Hum Gene Ther Methods. Dec. 2016;27(6):228-237.
Berge SM Pharmaceutical salts. J Pharm Sci. Jan. 1977;66(1):1-19.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Bey K, et al. Efficient CNS targeting in adult mice by intrathecal infusion of single-stranded AAV9-GFP for gene therapy of neurological disorders. Gene Ther. Apr. 20, 2017. Epub ahead of print.
Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Carillo H, et al. The Multiple Sequence Alignment Problem in Biology. SIAM J. Appl. Math. 48-5 (1988), pp. 1073-1082.
Carter BJ. Adeno-associated virus and the development of adeno-associated virus vectors: a historical perspective. Mol Ther. Dec. 2004;10(6):981-9.
Chandler RJ, et al. Systemic AAV9 gene therapy improves the lifespan of mice with Niemann-Pick disease, type C1. Hum Mol Genet. Jan. 2017;26(1):52-64.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Dang CH, et al. In vivo dynamics of AAV-mediated gene delivery to sensory neurons of the trigeminal ganglia. Sci Rep. Apr. 19, 2017;7(1):927.
Dashkoff J, et al. Tailored transgene expression to specific cell types in the central nervous system after peripheral injection with AAV9. Mol Ther Methods Clin Dev. Dec. 2016;3:16081.
Devereux J A comprehensive set of sequence analysis programs for the VAX. Nucleic Acids Res. Jan. 11, 1984;12(1Pt 1):387-95.
Dimidsciastein J, et al. A viral strategy for targeting and manipulating interneurons across vertebrate species. Nat Neurosci. Dec. 2016;19(12):1743-1749.
Ding C, et al., Biochemical Characterization of Junonia Coenia Densovirus Nonstructural Protein NS-1. J. Virol., 76(1):338-345 2002.
Donsante A et al. Intracerebroventricular delivery of self-complementary adeno-associated virus serotype 9 to the adult rat brain. Gene Ther. May 2016;23(5):401-7.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
El-Shamayleh Y, et al. Strategies for targeting primate neural circuits with viral vectors. J Neurophysiol. Jul. 2016;116(1):122-34.
Fargnoli AS, et al. Liquid jet delivery method featuring S100A1 gene therapy in the rodent model following acute myocardial infarction. Gene Ther. Feb. 2016;23(2):151-7.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler DJ et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Greig JA, et al. Impact of intravenous infusion time on AAV8 vector pharmacokinetics, safety, and liver transduction in cynomolgus macaGruntman AM, et al. Delivery of Adeno-associated virus gene therapy by intravascular limb infusion methods. Hum Gene Ther Clin Dev Sep. 2015;26(3):159-64. ques. Mol Ther Methods Clin Dev. Dec. 2016;3:16079.
Greig JA, et al. Intramuscular administration of AAV overcomes pre-existing neutralizing antibodies in rhesus macaques. Vaccine. Dec. 2016;34(50):6323-6329.
Gribskov M, et al. Sequence Analysis Primer. M Stockton Press, New York, 1991.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 5, 2007;27(1):91-105.
Gruntman AM, et al. Delivery of Adeno-associated virus gene therapy by intravascular limb infusion methods. Hum Gene Ther Clin Dev Sep. 2015;26(3):159-64.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Gurda BL, et al. Evaluation of AAV-mediated gene therapy for central nervous system disease in canine mucopolysaccharidosis VII. Mol Ther. Feb. 2016;24(2):206-16.
Hagg A, et al. Using AAV vectors expressing the beta 2-adrenoceptor or associated G alpha proteins to modulate skeletal muscle mass and muscle fiber size. Sci Rep. Mar. 2016;6:23042.
Hai B, et al. Long-term transduction of miniature pig parotid glands using serotype 2 adeno-associated viral vectors. J Gene Med. Jun. 2009;11(6):506-14.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Hastie E, et al. Recombinant adeno-associated virus vectors in the treatment of rare diseases. Expert Opin Orphan Drugs. 2015;3(6):675-689.
Heim et al., Wavelength mutations and posttranslational autoxidation of green fluorescent protein. Proc. Natl. Acad. Sci. USA (1994).
Merten OW, et al. Viral vectors for gene therapy and gene modification approaches. Biochem Eng J. Apr. 2016;108:98-115.
Muzyczka N, et al. AAV's Golden Jubilee. Mol Ther. May 2015;23(5):807-8.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.

(56) References Cited

OTHER PUBLICATIONS

Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Moser, et al. Computational Molecular Biology. Oxford University Press, New York, 1988.
Kozak M. Interpreting cDNA sequences: some insights from studies on translation. Mamm Genome. Aug. 1996;7(8):563-74.
Kozak M. Point mutations define a sequence flanking the AUG initiator codon that modulates translation by eukaryotic ribosomes. Cell. Jan. 31, 1986;44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
Heim R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8(342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice. Hum Gene Ther. Aug. 10, 2016.
Hordeaux J., et al. Efficient central nervous system AAVrh10-mediated intrathecal gene transfers in adult and neonate rats. Gene Ther.Apr. 2015, 22(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G, et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.
Hinderer C, et al. Neonatal Systemic AAV Induces Tolerance to CNS Gene Therapy in MPS I Dogs and Nonhuman Primates. Mol Ther. 201-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deticient canine model of the late infantile form of Batten Disease. Sci Transl Med. Nov. 2015;7(313):313ra180.
Landegger LD, et al. A synthetic AAV vector enables safe and efficient gene transfer to the mammalian inner ear. Nat Biotechnol. Mar. 2017;35(3):280-284.
Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li Sy, et al. Efficient and targeted transduction of nonhuman primate liver with systemically delivered optimized AAV3B vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(1):647-56.
Mendell JR, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther. Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger EWI, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther. Apr. 2016;27(4):309-24.
Hudry EM, et al. Exosome-associated AAV vector as a robust and convenient neurosocience tool. Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate In Vivo Non-Invasive Tracking of Adeno-Associated Gene Transfer Vectors. Sci Rep. Jan. 2017;7:39594.

(56) References Cited

OTHER PUBLICATIONS

Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.

Srivastava A. Adeno-Associated Virus: The Naturally Occurring Virus Versus the Recombinant Vector. Hum Gene Ther. Jan. 2016;27(1):1-6.

Tratschin JD, et al. Adeno-associated virus vector for high-frequency integration, expression, and rescue of genes in mammalian cells. Mol Cell Biol. Nov. 1985;5(11):3251-60.

Srivastava A, et al. Nucleotide sequence and organization of the adeno-associated virus 2 genome. J Virol. Feb. 1983;45(2):555-64.

Summerford C, et al. AAVR: A multi-serotype receptor for AAV. Mol Ther. Apr. 2016;24(4):663-6.

Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.

Wu P, et al. Mutational analysis of the adeno-associated virus type 2 (AAV2) capsid gene and construction of AAV2 vectors with altered tropism. J Virol. Sep. 2000;74(18):8635-47.

Yang C, et al. Sequential adeno-associated viral vector serotype 9-green fluorescent protein gene transfer causes massive inflammation and intense immune response in rat striatum. Hum Gene Ther. Jul. 2016;27(7):528-43.

Chandler RJ, et al. rAAV integration and genotoxicity: insights from animal models. Hum Gene Ther. Apr. 2017;28(4):314-322.

Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.

Wang S, et al. Direct brain infusion can be enhanced with focused ultrasound and microbubbles. J Cereb Blood Flow Metab. Feb. 2016;37(2):706-714.

Wang et al., Noninvasive, neuron-specific gene therapy can be facilitated by focused ultrasound and recombinant adeno-associated virus. Gene Therapy. Nov. 22, 2014. 104-110.

Weber-Adrian D, et al. Gene delivery to the spinal cord using MRI-guided focused ultrasound. Gene Ther. Jul. 2015, 22(7):568-77.

Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.

Zhu W, et al. Soluble FLT1 Gene Therapy Alleviates Brain Arteriovenous Malformation Severity. Stroke. May 2017;48(5):1420-1423.

Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.

Suzuki J, et al. Cochlear gene therapy with ancestral AAV in adult mice: complete transduction of inner hair cells without cochlear dysfunction. Apr. 3, 2017;7:45524.

Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90(21):9878-9888.

Wang LL, et al. Comparative study of liver gene transfer with AAV vectors based on endogenous and engineered AAV capsids. Mol Ther Dec. 2015;23(12):1877-87.

Sondhi D, et al. Genetic Modification of the Lung Directed Toward Treatment of Human Disease. Hum Gene Ther. Jan. 2017;28(1):3-84.

Yalvac ME, et al. AAV1.NT-3 gene therapy attenuates spontaneous autoimmune peripheral polyneuropathy. Gene Ther. Jan. 2016;23(1):95-102.

Srivastava A. In Vivo Tissue-tropism of Adeno-associated Viral Vectors. Curr Opin Virol. Sep. 2, 2016;21:75-80.

Adamson-Small L, et al. Sodium chloride enhances rAAV production in a serum-free suspension manufacturing platform using the Herpes Simplex Virus System. Hum Gene Ther Methods. Feb. 2017;28(1):1-14.

Al J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.

Buclez PO, et al. Rapid, scalable, and low-cost purification of recombinant adeno-associated virus produced by baculovirus expression vector system. Mol Ther Methods Clin Dev. May 2016;3:16035.

Burnham B, et al. Analytical ultracentrifugation as an approach to characterize recombinant adeno-associated viral vectors. Hum Gene Ther Methods. Dec. 2015;26(6):228-42.

Clement N, et al. Manufacturing of recombinant adeno-associated viral vectors for clinical trials. Mol Ther Methods Clin Dev. Mar. 2016;3:16002.

D'Costa S, et al. Practical utilization of recombinant AAV vector reference standards: focus on vector genome titration by free ITR qPCR. Mol Ther Methods Clin Dev. Mar. 2016;5:16019.

Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.

Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.

Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.

Kirnbauer R, et al. Virus-like particles of bovine papillomavirus type 4 in prophylactic and therapeutic immunization. Virology. May 1, 1996;219(1):37-44.

Kohlbrenner E, et al. Production and Characterization of Vectors Based on the Cardiotropic AAV Serotype 9. Methods Mol Biol. 2017;1521:91-107.

Kotin RM, et al. Large-scale recombinant adeno-associated virus production. Hum Mol Genet. Apr. 15, 2011;20(R1):R2-6. doi: 10.1093/hmg/ddr141. Epub Apr. 29, 2011.

Douglas, M.R. Gene therapy for Parkinson's disease: state-of-the-art treatments for neurodegenerative disease. Expert Rev Neurother. Jun. 2013; 13(6):695-705.

Grimm et al. Small But Increasingly Mighty: Latest Advances in AAV Vector Research, Design, and Evolution. Hum Gene Ther. Nov. 2017 (Epub Aug. 23, 2017); 28(11):1075-1086.

Examination Report No. 2 received in corresponding AU Application No. 2015343037 dated Oct. 12, 2018.

Matsushita, T. et al. 1998 "Adeno-associated virus vectors can be efficienty produced without helper virus", Gene Ther. vol. 5, pp. 938-945.

Fluri, D. et al. 2007 "Adeno-associated viral vectors engineered for macrolide-adjustable transgene expression in mammalian cells and mice". BMC Biotechnology, vol. 7, art. 75, pp. 1-15.

Official Action and its English translation received in corresponding Russian Patent Application No. 2017115477 dated Mar. 25, 2019.

Search Report and its English translation received in corresponding Russian Patent Application No. 2017115477 dated Mar. 25, 2019.

Li Rebekah Feng et al: "Gene Therapy in Parkinson's Disease: Rationale and CurrentStatus", CNS Drugs, Mar. 1, 2010; 24(3): 177-192.

Stoker TB, et al. Regenerative therapies for Parkinson's Disease: An Update. BioDrugs (2018) 32:357-366. Published online Jul. 19, 2018.

Latourelle JC, et al. Large-scale identification of clinical and genetic predictors of motor progression in patients with newly diagnosed Parkinson's disease: a longitudinal cohort study and validation. Lancet Neurology. Sep. 25, 2017.

Morabito G, Giannelli SG, Ordazzo G, Bido S, Castoldi V, Indrigo M, Cabassi T, Cattaneo S, Luoni M, Cancellieri C, Sessa A, Bacigaluppi M, Taverna S, Leocani L, Lanciego JL, Broccoli V. Mol Ther. Dec. 6, 2017;25(12):2727-2742. Epub Aug. 10, 2017.

(56) References Cited

OTHER PUBLICATIONS

Naidoo J, et al. Extensive Transduction and Enhanced Spread of a Modified AAV2 Capsid in the Non-human Primate CNS. Mol Ther. Jul. 12, 2018 Epub ahead of print.

Man JHK, et al. Cell reprogramming approaches in gene- and cell-based therapies for Parkinson's disease. J Control Release Jul. 17, 2018;286:114-124 Epub ahead of print.

Chandran JS, et al. Gene therapy in the nervous system: failures and successes. Adv Exp Med Biol. 2017;1007:241-257.

Lee NC, et al. Regulation of the dopaminergic system in a murine model of aromatic L-amino acid decarboxylase deficiency. Neurobiology of Disease (2013). 52:177-190.

Hwu WL, et al. Gene Therapy for Aromatic L-Amino Acid Decarboxylase Deficiency. Science Translational Medicine (May 16, 2012). 4:134.

Kojima K et al., Gene therapy improves motor and mental function of aromatic I-amino acid decarboxylase deficiency. Brain. Jan. 23, 2019. [Epub ahead of print].

Dorsey ER, et al. The Emerging Evidence of the Parkinson Pandemic, .J Parkinsons Dis. 2018;8(s1):S3-S8.

Wang D, et al. Adeno-associated virus vector as a platform for gene therapy delivery. Nat Rev Drug Discov. Feb. 1, 2019. doi: 10.1038/s41573-019-0012-9. [Epub ahead of print] Review.

Chen YH etl a., Viral Vectors for Gene Transfer. Curr Protoc Mouse Biol. Dec. 2018;8(4):e58.

Hudry E, Vandenberghe LH. Therapeutic AAV Gene Transfer to the Nervous System: A Clinical Reality. Neuron. Mar. 6, 2019;101(5):839-862.

Cell Biolabs. Product Data Sheet: pAAVS-MCS Expression Vector. 2010.

Yan et al., Inverted terminal repeat sequences are important for intermolecular recombination and circularization of adeno-associated virus genomes. J Virol. Jan. 2005;79(1):364-79.

San Sebastian et al., Safety and tolerability of magnetic resonance imaging-guided convection-enhanced delivery of AAV2-hAADC with a novel delivery platform in nonhuman primate striatum. Hum Gene Ther. Feb. 2012;23(2):210-7. Epub Jan. 26, 2012.

San Sebastian et al., Safety and tolerability of MRI-guided infusion of AAV2-hAADC into the mid-brain of nonhuman primate. Mol Ther Methods Clin Dev. 2014; 3: 14049. Published online Oct. 15, 2014.

Sehara et al., Persistent Expression of Dopamine-Synthesizing Enzymes 15 Years After Gene Transfer in a Primate Model of Parkinson's Disease. Hum Gene Ther Clin Dev. Jun. 2017;28(2):74-79. Epub Mar. 9, 2017.

Nutt et al., The response to levodopa in Parkinson's disease: imposing pharmacological law and order. Ann Neurol. May 1996;39(5):561-73.

De la Manza et al., Molecular Structure of Adeno-associated Virus Variant DNA. The Journal of Biological Chemistry (1980), 255, 3194-3203.

Ossig et al., Treatment of Parkinson's disease in the advanced stage. J Neural Transm. Apr. 2013; 120(4): 523-529. Published online Mar. 10, 2013.

Varanese et al., Treatment of Advanced Parkinson's Disease. Parkinsons Dis. Feb. 7, 2011;2010:480260.

Dewey RB Jr. Autonomic dysfunction in Parkinson's disease. Neurol Clin. Oct. 2004;22(3 Suppl):S127-39.

Fahn S. The medical treatment of Parkinson disease from James Parkinson to George Cotzias. Mov Disord. Jan. 2015;30(1):4-18. doi: 10.1002/mds.26102.

Tysnes OB and Storstein A., Epidemiology of Parkinson's disease. J Neural Transm (Vienna). Aug. 2017;124 (8):901-905.

\* cited by examiner

SEQUENCE LISTING

<160> NUMBER OF SEQ ID NOS: 23

<210> SEQ ID NO 1
<211> LENGTH: 480
<212> TYPE: PRT
<213> ORGANISM: Homo sapiens

<400> SEQUENCE: 1

Met Asn Ala Ser Glu Phe Arg Arg Gly Lys Glu Met Val Asp Tyr
1               5                   10                  15

Val Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Pro Gln
            35                  40                  45

Glu Pro Asp Thr Phe Glu Asp Ile Ile Asn Asp Val Glu Lys Ile Ile
        50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
                100                 105                 110

Glu Leu Glu Thr Val Met Met Asp Trp Leu Gly Lys Met Leu Glu Leu
                115                 120                 125

Pro Lys Ala Phe Leu Asn Glu Lys Ala Gly Glu Gly Gly Gly Val Ile
        130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
                180                 185                 190

Ser Ser Val Glu Arg Ala Gly Leu Ile Gly Gly Val Lys Leu Lys Ala
        195                 200                 205

Ile Pro Ser Asp Gly Asn Phe Ala Met Arg Ala Ser Ala Leu Gln Glu
    210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
                260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
        290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
                340                 345                 350

Leu Gly Arg Arg Phe Arg Ser Leu Lys Met Trp Phe Val Phe Arg Met
        355                 360                 365

```
Tyr Gly Val Lys Gly Leu Gln Ala Tyr Ile Arg Lys His Val Gln Leu
370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
                420                 425                 430

Ile His Leu Val Pro Cys His Leu Arg Asp Lys Phe Val Leu Arg Phe
                435                 440                 445

Ala Ile Cys Ser Arg Thr Val Glu Ser Ala His Val Gln Arg Ala Trp
450                 455                 460

Glu His Ile Lys Glu Leu Ala Ala Asp Val Leu Arg Ala Glu Arg Glu
465                 470                 475                 480

<210> SEQ ID NO 2
<211> LENGTH: 8150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cattcgccat tcaggctgca aataagcgtt gatattcagt caattacaaa cattaataac      60
gaagagatga cagaaaaatt ttcattctgt gacagagaaa aagtagccga agatgacggt     120
ttgtcacatg gagttggcag gatgtttgat taaaaacata acaggaagaa aaatgccccg     180
ctgtgggcgg acaaaatagt tgggaactgg gaggggtgga aatggagttt ttaaggatta     240 tttaggaag agtgacaaaa tagatgggaa ctgggtgtag cgtcgtaagc taatacgaaa     300
attaaaaatg acaaaatagt ttggaactag atttcactta tctggttcgg atctcctagg     360
cgatatcagt gatcagatcc agacatgata agatacattg atgagtttgg acaaaccaca     420
actagaatgc agtgaaaaaa atgctttatt tgtgaaattt gtgatgctat tgctttattt     480
gtaaccatta taagctgcaa taaacaagtt aacaacaaca attgcattca ttttatgttt     540
caggttcagg gggaggtgtg ggaggttttt taaagcaagt aaaacctcta caaatgtggt     600
atggctgatt atgatcctct agtacttctc gacaagctta cattattgaa gcatttatca     660
gggttattgt ctcagacctg caggcagctg cgcgctcgct cgctcactga ggccgcccgg     720
gcaaagcccg ggcgtcgggc gacctttggt cgcccggcct cagtgagcga gcgagcgcgc     780
agagagggag tggccaactc catcactagg ggttccttgt agttaatgat taacccgcca     840
tgctacttat ctacgtagcc atgctctaga gcggccgcac gcgtggagct agttattaat     900
agtaatcaat tacggggtca ttagttcata gcccatatat ggagttccgc gttacataac     960
ttacggtaaa tggcccgcct ggctgaccgc ccaacgaccc ccgcccattg acgtcaataa    1020
tgacgtatgt tcccatagta acgtcaatag ggactttcca ttgacgtcaa tgggtggagt    1080
atttacggta aactgcccac ttggcagtac atcaagtgta tcatatgcca agtacgcccc    1140
ctattgacgt caatgacggt aaatggcccg cctggcatta tgcccagtac atgaccttat    1200
gggactttcc tacttggcag tacatctacg tattagtcat cgctattacc atggtgatgc    1260
ggttttggca gtacatcaat gggcgtggat agcggtttga ctcacgggga tttccaagtc    1320
tccaccccat tgacgtcaat gggagtttgt tttgcaccaa aatcaacggg actttccaaa    1380
atgtcgtaac aactccgccc cattgacgca aatgggcggt aggcgtgtac ggtgggaggt    1440
```

```
ctatataagc agagctcgtt tagtgaaccg tcagatcgcc tggagacgcc atccacgctg    1500
ttttgacctc catagaagac accgggaccg atccagcctc cgcggattcg aatcccggcc    1560
gggaacggtg cattggaacg cggattcccc gtgccaagag tgacgtaagt accgcctata    1620
gagtctatag gcccacaaaa aatgcttcct tcttttaata tacttttttg tttatcttat    1680
ttctaatact ttccctaatc tctttctttc agggcaataa tgatacaatg tatcatgcct    1740 cttttgcacca ttctaaagaa taacagtgat aatttctggg ttaaggcaat agcaatattt   1800
ctgcatataa atatttctgc atataaattg taactgatgt aagaggtttc atattgctaa    1860
tagcagctac aatccagcta ccattctgct tttattttat ggttgggata aggctggatt    1920
attctgagtc caagctaggc cctttttgcta atcatgttca tacctcttat cttcctccca   1980
cagctcctgg gcaacgtgct ggtctgtgtg ctggcccatc actttggcaa agaattggga    2040
ttcgaacatc ggccgccacc atgaacgcaa gtgaattccg aaggagaggg aaggagatgg    2100
tggattacgt ggccaactac atggaaggca ttgagggacg ccaggtctac cctgacgtgg    2160
agcccgggta cctgcggccg ctgatccctg ccgctgcccc tcaggagcca gacacgtttg    2220
aggacatcat caacgacgtt gagaagataa tcatgcctgg ggtgacgcac tggcacagcc    2280
cctacttctt cgcctacttc cccactgcca gctcgtaccc ggccatgctt gcggacatgc    2340
tgtgcggggc cattggctgc atcggcttct cctgggcggc aagcccagca tgcacagagc    2400
tggagactgt gatgatggac tggctcggga agatgctgga actaccaaag gcattttga    2460 atgagaaagc tggagaaggg ggaggagtga tccaggaaag tgccagtgaa gccaccctgg    2520
tggccctgct ggccgctcgg accaaagtga tccatcggct gcaggcagcg tccccagagc    2580
tcacacaggc cgctatcatg gagaagctgg tggcttactc atccgatcag gcacactcct    2640
cagtggaaag agctgggtta attggtggag tgaaattaaa agccatcccc tcagatggca    2700
acttcgccat gcgtgcgtct gccctgcagg aagccctgga gagagacaaa gcggctggcc    2760
tgattccttt ctttatggtt gccaccctgg ggaccacaac atgctgctcc tttgacaatc    2820
tcttagaagt cggtcctatc tgcaacaagg aagacatatg gctgcacgtt gatgcagcct    2880
acgcaggcag tgcattcatc tgccctgagt tccggcacct tctgaatgga gtggagtttg    2940
cagattcatt caactttaat ccccacaaat ggctattggt gaattttgac tgttctgcca    3000
tgtgggtgaa aaagagaaca gacttaacgg gagcctttag actggacccc acttacctga    3060
agcacagcca tcaggattca gggcttatca ctgactaccg gcattggcag ataccactgg    3120
gcagaagatt tcgctctttg aaaatgtggt ttgtatttag gatgtatgga gtcaaaggac    3180
tgcaggctta tatccgcaag catgtccagc tgtcccatga gtttgagtca ctggtgcgcc    3240 aggatcccg ctttgaaatc tgtgtggaag tcattctggg gcttgtctgc tttcggctaa     3300
agggttccaa caaagtgaat gaagctcttc tgcaaagaat aaacagtgcc aaaaaaatcc    3360
acttggttcc atgtcacctc agggacaagt ttgtcctgcg ctttgccatc tgttctcgca    3420
cggtggaatc tgcccatgtg cagcgggcct gggaacacat caaagagctg gcggccgacg    3480
tgctgcgagc agagagggag taggagtgag ctgctcgaga gatctacggg tggcatccct    3540
gtgacccctc cccagtgcct ctcctggccc tggaagttgc cactccagtg cccaccagcc    3600
ttgtcctaat aaaattaagt tgcatcattt tgtctgacta ggtgtccttc tataatatta    3660
tggggtggag gggggtggta tggagcaagg ggcaagttgg gaagacaacc tgtagggcct    3720
gcggggtcta ttgggaacca agctggagtg cagtggcaca atcttggctc actgcaatct    3780
```

```
ccgcctcctg ggttcaagcg attctcctgc ctcagcctcc cgagttgttg ggattccagg      3840
catgcatgac caggctcagc taattttttgt tttttggta gagacggggt ttcaccatat      3900
tggccaggct ggtctccaac tcctaatctc aggtgatcta cccaccttgg cctcccaaat      3960
tgctgggatt acaggcgtga accactgctc ccttccctgt ccttctgatt ttgtaggtaa      4020
ccccggacca cgtgcggacc gagcggccgc tctagagcat ggctacgtag ataagtagca      4080
tggcgggtta atcattaact acaaggaacc cctagtgatg gagttggcca ctccctctct      4140
gcgcgctcgc tcgctcactg aggccgggcg accaaaggtc gcccgacgcc cgggcggcct      4200
cagtgagcga gcgagcgcgc agctgcctgc aggtctgaga caataaccct gataaatgct      4260
tcaataatgt agccaaccac tagaactata gctagagtcc tgggcgaaca aacgatgctc      4320
gccttccaga aaaccgagga tgcgaaccac ttcatccggg gtcagcacca ccggcaagcg      4380
ccgcgacggc cgaggtcttc cgatctcctg aagccagggc agatccgtgc acagcacctt      4440
gccgtagaag aacagcaagg ccgccaatgc ctgacgatgc gtggagaccg aaaccttgcg      4500
ctcgttcgcc agccaggaca gaaatgcctc gacttcgctg ctgcccaagg ttgccgggtg      4560
acgcacaccg tggaaacgga tgaaggcacg aacccagttg acataagcct gttcggttcg      4620
taaactgtaa tgcaagtagc gtatgcgctc acgcaactgg tccagaacct tgaccgaacg      4680
cagcggtggt aacggcgcag tggcggtttt catggcttgt tatgactgtt tttttgtaca      4740
gtctatgcct cgggcatcca agcagcaagc gcgttacgcc gtgggtcgat gtttgatgtt      4800
atggagcagc aacgatgtta cgcagcagca acgatgttac gcagcagggc agtcgcccta      4860
aaacaaagtt aggtggctca agtatgggca tcattcgcac atgtaggctc ggccctgacc      4920
aagtcaaatc catgcgggct gctcttgatc ttttcggtcg tgagttcgga cgtagcca       4980 cctactccca acatcagccg gactccgatt acctcgggaa cttgctccgt agtaagacat      5040
tcatcgcgct tgctgccttc gaccaagaag cggttgttgg cgctctcgcg gcttacgttc      5100
tgcccaagtt tgagcagccg cgtagtgaga tctatatcta tgatctcgca gtctccggcg      5160
agcaccggag gcagggcatt gccaccgcgc tcatcaatct cctcaagcat gaggccaacg      5220
cgcttggtgc ttatgtgatc tacgtgcaag cagattacgg tgacgatccc gcagtggctc      5280
tctatacaaa gttgggcata cgggaagaag tgatgcactt tgatatcgac ccaagtaccg      5340
ccacctaaca attcgttcaa gccgagatcg gcttcccggc cgcggagttg ttcggtaaat      5400
tgtcacaacg ccgcgaatat agtctttacc atgcccttgg ccacgcccct ctttaatacg      5460
acgggcaatt tgcacttcag aaaatgaaga gtttgcttta gccataacaa agtccagta      5520 tgcttttca cagcataact ggactgattt cagtttacaa ctattctgtc tagtttaaga      5580
ctttattgtc atagtttaga tctatttttgt tcagttaag actttattgt ccgcccacac      5640
ccgcttacgc agggcatcca tttattactc aaccgtaacc gattttgcca ggttacgcgg      5700
ctggtctatg cggtgtgaaa taccgcacag atgcgtaagg agaaaatacc gcatcaggcg      5760
ctcttccgct tcctcgctca ctgactcgct gcgctcggtc gttcggctgc ggcgagcggt      5820
atcagctcac tcaaaggcgg taatacggtt atccacagaa tcagggata acgcaggaaa      5880 gaacatgtga gcaaaaggcc agcaaaaggc caggaaccgt aaaaaggccg cgttgctggc      5940 gttttttccat aggctccgcc ccctgacga gcatcacaaa aatcgacgct caagtcagag      6000
gtggcgaaac ccgacaggac tataaagata ccaggcgttt ccccctggaa gctccctcgt      6060
gcgctctcct gttccgaccc tgccgcttac cggatacctg tccgcctttc tcccttcggg      6120
aagcgtggcg ctttctcata gctcacgctg taggtatctc agttcggtgt aggtcgttcg      6180
```

```
ctccaagctg ggctgtgtgc acgaaccccc cgttcagccc gaccgctgcg ccttatccgg      6240
taactatcgt cttgagtcca acccggtaag acacgactta tcgccactgg cagcagccac      6300
tggtaacagg attagcagag cgaggtatgt aggcggtgct acagagttct tgaagtggtg      6360
gcctaactac ggctacacta aagaacagt atttggtatc tgcgctctgc tgaagccagt       6420
taccttcgga aaagagttg gtagctcttg atccggcaaa caaaccaccg ctggtagcgg       6480
tggttttttt gtttgcaagc agcagattac gcgcagaaaa aaggatctc aagaagatcc       6540
tttgatcttt tctacggggt ctgacgctca gtggaacgaa aactcacgtt aagggatttt      6600
ggtcatgaga ttatcaaaaa ggatcttcac ctagatcctt taaattaaa aatgaagttt       6660
taaatcaatc taaagtatat atgagtaaac ttggtctgac agttaccaat gcttaatcag      6720
tgaggcacct atctcagcga tctgtctatt tcgttcatcc atagttgcct gactccccgt      6780
cgtgtagata actacgatac gggagggctt accatctggc cccagtgctg caatgatacc      6840
gcgagaccca cgctcaccgg ctccagattt atcagcaata aaccagccag ccggaagggc      6900
cgagcgcaga agtggtcctg caactttatc cgcctccatc cagtctatta attgttgccg      6960
ggaagctaga gtaagtagtt cgccagttaa tagtttgcgc aacgttgttg ccattgctac      7020
aggcatcgtg gtgtcacgct cgtcgtttgg tatggcttca ttcagctccg gttcccaacg      7080
atcaaggcga gttacatgat cccccatgtt gtgcaaaaaa gcggttagct ccttcggtcc      7140
tccgatcgtt gtcagaagta agttggccgc agtgttatca ctcatggtta tggcagcact      7200
gcataattct cttactgtca tgccatccgt aagatgcttt tctgtgactg gtgagtactc      7260
aaccaagtca ttctgagaat agtgtatgcg gcgaccgagt tgctcttgcc cggcgtcaat      7320
acgggataat accgcgccac atagcagaac tttaaaagtg ctcatcattg gaaaacgttc      7380
ttcggggcga aaactctcaa ggatcttacc gctgttgaga tccagttcga tgtaacccac      7440
tcgtgcaccc aactgatctt cagcatcttt tactttcacc agcgtttctg ggtgagcaaa      7500
aacaggaagg caaaatgccg caaaaaaggg aataagggcg acacggaaat gttgaatact      7560
catactcttc ctttttcaat attattgaag catttatcag ggttattgtc tcatgagcgg      7620
atacatattt gaatgtattt agaaaaataa acaaataggg gttccgcgca catttccccg      7680
aaaagtgcca cctaaattgt aagcgttaat attttgttaa aattcgcgtt aaattttgt       7740
taaatcagct cattttttaa ccaataggcc gaaatcggca aaatccctta taaatcaaaa      7800
gaatagaccg agatagggtt gagtgttgtt ccagtttgga acaagagtcc actattaaag      7860
aacgtggact ccaacgtcaa agggcgaaaa accgtctatc agggcgatgg cccactacgt      7920
gaaccatcac cctaatcaag ttttttgggg tcgaggtgcc gtaaagcact aaatcggaac      7980
cctaaaggga gcccccgatt tagagcttga cggggaaagc cggcgaacgt ggcgagaaag      8040
gaagggaaga agcgaaagg agcgggcgct agggcgctgg caagtgtagc ggtcacgctg       8100
cgcgtaacca ccacacccgc cgcgcttaat gcgccgctac agggcgcgtc                 8150
```

<210> SEQ ID NO 3
<211> LENGTH: 8149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
cattcgccat tcaggctgca aataagcgtt gatattcagt caattacaaa cattaataac       60
```

```
gaagagatga cagaaaaatt ttcattctgt gacagagaaa aagtagccga agatgacggt    120
ttgtcacatg gagttggcag gatgtttgat taaaaacata acaggaagaa aaatgccccg    180
ctgtgggcgg acaaaatagt tgggaactgg gaggggtgga aatggagttt ttaaggatta    240
tttagggaag agtgacaaaa tagatgggaa ctgggtgtag cgtcgtaagc taatacgaaa    300
attaaaaatg acaaaatagt ttggaactag atttcactta tctggttcgg atctcctagg    360
cgatatcagt gatcagatcc agacatgata agatacattg atgagtttgg acaaaccaca    420
actagaatgc agtgaaaaaa atgctttatt tgtgaaattt gtgatgctat tgctttattt    480
gtaaccatta taagctgcaa taaacaagtt aacaacaaca attgcattca ttttatgttt    540
caggttcagg gggaggtgtg ggaggttttt taaagcaagt aaaacctcta caaatgtggt    600
atggctgatt atgatcctct agtacttctc gacaagctta cattattgaa gcatttatca    660
gggttattgt ctcagacctg caggcagctg cgcgctcgct cgctcactga ggccgcccgg    720
gcaaagcccg ggcgtcgggc gacctttggt cgcccggcct cagtgagcga gcgagcgcgc    780
agagagggag tggccaactc catcactagg ggttccttgt agttaatgat taacccgcca    840
tgctacttat ctacgtagcc atgctctaga gcggccgcac gcgtggagct agttattaat    900
agtaatcaat tacggggtca ttagttcata gcccatatat ggagttccgc gttacataac    960
ttacggtaaa tggcccgcct ggctgaccgc ccaacgaccc ccgcccattg acgtcaataa   1020
tgacgtatgt tcccatagta acgtcaatag ggactttcca ttgacgtcaa tgggtggagt   1080
atttacggta aactgcccac ttggcagtac atcaagtgta tcatatgcca agtacgcccc   1140
ctattgacgt caatgacggt aaatggcccg cctggcatta tgcccagtac atgaccttat   1200
gggactttcc tacttggcag tacatctacg tattagtcat cgctattacc atggtgatgc   1260
ggttttggca gtacatcaat gggcgtggat agcggtttga ctcacgggga tttccaagtc   1320
tccaccccat tgacgtcaat gggagtttgt tttgcaccaa aatcaacggg actttccaaa   1380
atgtcgtaac aactccgccc cattgacgca aatgggcggt aggcgtgtac ggtgggaggt   1440
ctatataagc agagctcgtt tagtgaaccg tcagatcgcc tggagacgcc atccacgctg   1500
ttttgacctc catagaagac accgggaccg atccagcctc cgcggattcg aatcccggcc   1560
gggaacggtg cattggaacg cggattcccc gtgccaagag tgacgtaagt accgcctata   1620
gagtctatag gcccacaaaa aatgctttct tcttttaata tacttttttg tttatcttat   1680
ttctaatact ttccctaatc tctttctttc agggcaataa tgatacaatg tatcatgcct   1740
ctttgcacca ttctaaagaa taacagtgat aatttctggg ttaaggcaat agcaatattt   1800
ctgcatataa atatttctgc atataaattg taactgatgt aagaggtttc atattgctaa   1860
tagcagctac aatccagcta ccattctgct tttattttat ggttgggata aggctggatt   1920
attctgagtc caagctaggc ccttttgcta atcatgttca tacctcttat cttcctccca   1980
cagctcctgg gcaacgtgct ggtctgtgtg ctggcccatc actttggcaa gaattggga    2040 ttcgaacatc ggccgccacc atgaacgcca gcgagttcag gaggaggggc aaggagatgg   2100
tggactacgt ggccaactac atggagggca tcgagggcag gcaggtgtac cccgacgtgg   2160
agcccggcta cctgaggccc ctgatccccg ccgccgcccc caggagccca gacaccttcg   2220
aggacatcat caacgacgtg gagaagatca tcatgcccgg cgtgacccac tggcacagcc   2280
cctacttctt cgcctacttc cccaccgcca gcagctaccc cgccatgctg gccgacatgc   2340
tgtgcggcgc catcggctgc atcggcttca gctgggccgc cagccccgcc tgcaccgagc   2400
```

```
tggagaccgt gatgatggac tggctgggca agatgctgga gctgcccaag gccttcctga    2460
acgagaaggc cggcgagggc ggcggcgtga tccagggcag cgccagcgag ccaccctgg     2520 tggccctgct ggccgccagg accaaggtga tccacaggct gcaggccgcc agccccgagc    2580
tgacccaggc cgccatcatg gagaagctgg tggcctacag cagcgaccag gcccacagca    2640
gcgtggagag ggccggcctg atcggcggcg tgaagctgaa ggccatcccc agcgacggca    2700
acttcgccat gagggccagc gccctgcagg aggccctgga gagggacaag gccgccggcc    2760
tgatccccct cttcatggtg gccaccctgg gcaccaccac ctgctgcagc ttcgacaacc    2820
tgctggaggt gggccccatc tgcaacaagg aggacatctg gctgcacgtg gacgccgcct    2880
acgccggcag cgccttcatc tgccccgagt tcaggcacct gctgaacggc gtggagttcg    2940
ccgacagctt caacttcaac ccccacaagt ggctgctggt gaacttcgac tgcagcgcca    3000
tgtgggtgaa gaagaggacc gacctgaccg gcgccttcag gctggacccc acctacctga    3060
agcacagcca ccaggacagc ggcctgatca ccgactacag gcactggcag atccccctgg    3120
gcaggaggtt caggagcctg aagatgtggt tcgtgttcag gatgtacggc gtgaagggcc    3180
tgcaggccta catcaggaag cacgtgcagc tgagccacga gttcgagagc ctggtgaggc    3240
aggaccccag gttcgagatc tgcgtggagg tgatcctggg cctggtgtgc ttcaggctga    3300
agggcagcaa caaggtgaac gaggccctgc tgcagaggat caacagcgcc aagaagatcc    3360
acctggtgcc ctgccacctg agggacaagt tcgtgctgag gttcgccatc tgcagcagga    3420
ccgtggagag cgcccacgtg cagagggcct gggagcacat caaggagctg gccgccgacg    3480
tgctgagggc cgagagggag tgagctgctc gagagatcta cgggtggcat ccctgtgacc    3540
cctccccagt gcctctcctg gccctggaag ttgccactcc agtgcccacc agccttgtcc    3600
taataaaatt aagttgcatc attttgtctg actaggtgtc cttctataat attatggggt    3660
ggaggggggt ggtatggagc aagggggcaag ttgggaagac aacctgtagg gcctgcgggg   3720
tctattggga accaagctgg agtgcagtgg cacaatcttg gctcactgca atctccgcct    3780
cctgggttca agcgattctc ctgcctcagc ctcccgagtt gttgggattc caggcatgca    3840
tgaccaggct cagctaattt ttgttttttt ggtagagacg gggtttcacc atattggcca    3900
ggctggtctc caactcctaa tctcaggtga tctacccacc ttggcctccc aaattgctgg    3960
gattacaggc gtgaaccact gctcccttcc ctgtccttct gattttgtag gtaacgtaac    4020
cccggaccac gtgcggaccg agcggccgct ctagagcatg gctacgtaga taagtagcat    4080
ggcgggttaa tcattaacta caaggaaccc ctagtgatgg agttggccac tccctctctg    4140
cgcgctcgct cgctcactga ggccgggcga ccaaaggtcg cccgacgccc gggcggcctc    4200
agtgagcgag cgagcgcgca gctgcctgca ggtctgagac aataaccctg ataaatgctt    4260
caataatgta gccaaccact agaactatag ctagagtcct gggcgaacaa acgatgctcg    4320
ccttccagaa aaccgaggat gcgaaccact tcatccgggg tcagcaccac cggcaagcgc    4380
cgcgacggcc gaggtcttcc gatctcctga agccagggca gatccgtgca cagcaccttg    4440
ccgtagaaga acagcaaggc cgccaatgcc tgacgatgcg tggagaccga accttgcgc    4500 tcgttcgcca gccaggacag aaatgcctcg acttcgctgc tgcccaaggt tgccgggtga    4560
cgcacaccgt ggaaacggat gaaggcacga acccagttga cataagcctg ttcggttcgt    4620
aaactgtaat gcaagtagcg tatgcgctca cgcaactggt ccagaacctt gaccgaacgc    4680
agcggtggta acgcgcagt ggcggttttc atggcttgtt atgactgttt ttttgtacag    4740
tctatgcctc gggcatccaa gcagcaagcg cgttacgccg tgggtcgatg tttgatgtta    4800
```

```
tggagcagca acgatgttac gcagcagcaa cgatgttacg cagcagggca gtcgccctaa    4860
aacaaagtta ggtggctcaa gtatgggcat cattcgcaca tgtaggctcg ccctgacca     4920 agtcaaatcc atgcgggctg ctcttgatct tttcggtcgt gagttcggag acgtagccac    4980
ctactcccaa catcagccgg actccgatta cctcgggaac ttgctccgta gtaagacatt    5040
catcgcgctt gctgccttcg accaagaagc ggttgttggc gctctcgcgg cttacgttct    5100
gcccaagttt gagcagccgc gtagtgagat ctatatctat gatctcgcag tctccggcga    5160
gcaccggagg cagggcattg ccaccgcgct catcaatctc ctcaagcatg aggccaacgc    5220
gcttggtgct tatgtgatct acgtgcaagc agattacggt gacgatcccg cagtggctct    5280
ctatacaaag ttgggcatac gggaagaagt gatgcacttt gatatcgacc caagtaccgc    5340
cacctaacaa ttcgttcaag ccgagatcgg cttcccggcc gcggagttgt tcggtaaatt    5400
gtcacaacgc cgcgaatata gtctttacca tgcccttggc cacgcccctc tttaatacga    5460
cgggcaattt gcacttcaga aaatgaagag tttgctttag ccataacaaa gtccagtat     5520 gcttttcac agcataactg gactgatttc agtttacaac tattctgtct agtttaagac     5580
tttattgtca tagtttagat ctattttgtt cagtttaaga ctttattgtc cgcccacacc    5640
cgcttacgca gggcatccat ttattactca accgtaaccg attttgccag gttacgcggc    5700
tggtctatgc ggtgtgaaat accgcacaga tgcgtaagga gaaataccg catcaggcgc     5760 tcttccgctt cctcgctcac tgactcgctg cgctcggtcg ttcggctgcg gcgagcggta    5820
tcagctcact caaaggcggt aatacggtta tccacagaat cagggataa cgcaggaaag     5880 aacatgtgag caaaaggcca gcaaaaggcc aggaaccgta aaaaggccgc gttgctggcg    5940
tttttccata ggctccgccc ccctgacgag catcacaaaa atcgacgctc aagtcagagg    6000
tggcgaaacc cgacaggact ataaagatac caggcgtttc cccctggaag ctccctcgtg    6060
cgctctcctg ttccgaccct gccgcttacc ggatacctgt ccgcctttct cccttcggga    6120
agcgtggcgc tttctcatag ctcacgctgt aggtatctca gttcggtgta ggtcgttcgc    6180
tccaagctgg gctgtgtgca cgaaccccc gttcagcccg accgctgcgc cttatccggt     6240
aactatcgtc ttgagtccaa cccggtaaga cacgacttat cgccactggc agcagccact    6300
ggtaacagga ttagcagagc gaggtatgta ggcggtgcta cagagttctt gaagtggtgg    6360
cctaactacg gctacactag aagaacagta tttggtatct gcgctctgct gaagccagtt    6420
accttcggaa aaagagttgg tagctcttga tccggcaaac aaaccaccgc tggtagcggt    6480
ggtttttttg tttgcaagca gcagattacg cgcagaaaaa aaggatctca agaagatcct    6540
ttgatctttt ctacggggtc tgacgctcag tggaacgaaa actcacgtta agggattttg    6600
gtcatgagat tatcaaaaag gatcttcacc tagatccttt taaattaaaa atgaagtttt    6660
aaatcaatct aaagtatata tgagtaaact tggtctgaca gttaccaatg cttaatcagt    6720
gaggcaccta tctcagcgat ctgtctattt cgttcatcca tagttgcctg actccccgtc    6780
gtgtagataa ctacgatacg ggagggctta ccatctggcc ccagtgctgc aatgataccg    6840
cgagacccac gctcaccggc tccagattta tcagcaataa accagccagc cggaagggcc    6900
gagcgcagaa gtggtcctgc aactttatcc gcctccatcc agtctattaa ttgttgccgg    6960
gaagctagag taagtagttc gccagttaat agtttgcgca acgttgttgc cattgctaca    7020
ggcatcgtgg tgtcacgctc gtcgtttggt atggcttcat tcagctccgg ttcccaacga    7080
tcaaggcgag ttacatgatc ccccatgttg tgcaaaaaag cggttagctc cttcggtcct    7140
```

```
ccgatcgttg tcagaagtaa gttggccgca gtgttatcac tcatggttat ggcagcactg    7200
cataattctc ttactgtcat gccatccgta agatgctttt ctgtgactgg tgagtactca    7260
accaagtcat tctgagaata gtgtatgcgg cgaccgagtt gctcttgccc ggcgtcaata    7320
cgggataata ccgcgccaca tagcagaact ttaaaagtgc tcatcattgg aaaacgttct    7380
tcggggcgaa aactctcaag gatcttaccg ctgttgagat ccagttcgat gtaacccact    7440
cgtgcaccca actgatcttc agcatctttt actttcacca gcgtttctgg gtgagcaaaa    7500
acaggaaggc aaaatgccgc aaaaaaggga ataagggcga cacggaaatg ttgaatactc    7560
atactcttcc ttttcaata ttattgaagc atttatcagg gttattgtct catgagcgga    7620
tacatatttg aatgtattta gaaaaataaa caaatagggg ttccgcgcac atttccccga    7680
aaagtgccac ctaaattgta agcgttaata ttttgttaaa attcgcgtta aattttgtt     7740 aaatcagctc attttttaac caataggccg aaatcggcaa aatcccttat aaatcaaaag    7800
aatagaccga datagggttg agtgttgttc cagtttggaa caagagtcca ctattaaaga    7860
acgtggactc caacgtcaaa gggcgaaaaa ccgtctatca gggcgatggc ccactacgtg    7920
aaccatcacc ctaatcaagt tttttggggt cgaggtgccg taaagcacta atcggaacc    7980 ctaaagggag cccccgattt agagcttgac ggggaaagcc ggcgaacgtg gcgagaaagg    8040
aagggaagaa agcgaaagga gcgggcgcta gggcgctggc aagtgtagcg gtcacgctgc    8100
gcgtaaccac cacacccgcc gcgcttaatg cgccgctaca gggcgcgtc                8149
```

<210> SEQ ID NO 4
<211> LENGTH: 8555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
cattcgccat tcaggctgca aataagcgtt gatattcagt caattacaaa cattaataac     60
gaagagatga cagaaaaatt ttcattctgt gacagagaaa aagtagccga agatgacggt    120
ttgtcacatg gagttggcag gatgtttgat taaaaacata acaggaagaa aaatgccccg    180
ctgtgggcgg acaaaatagt tgggaactgg gaggggtgga aatggagttt ttaaggatta    240
tttagggaag agtgacaaaa tagatgggaa ctgggtgtag cgtcgtaagc taatacgaaa    300
attaaaaatg acaaaatagt ttggaactag atttcactta tctggttcgg atctcctagg    360
cgatatcagt gatcagatcc agacatgata agatacattg atgagtttgg acaaaccaca    420
actagaatgc agtgaaaaaa atgctttatt tgtgaaattt gtgatgctat tgctttattt    480
gtaaccatta taagctgcaa taaacaagtt aacaacaaca attgcattca ttttatgttt    540
caggttcagg gggaggtgtg ggaggttttt taaagcaagt aaaacctcta caaatgtggt    600
atggctgatt atgatcctct agtacttctc gacaagctta cattattgaa gcatttatca    660
gggttattgt ctcagacctg caggcagctg cgcgctcgct cgctcactga ggccgcccgg    720
gcaaagcccg ggcgtcgggc gacctttggt cgcccggcct cagtgagcga gcgagcgcgc    780 agagaggag tggccaactc catcactagg ggttccttgt agttaatgat taacccgcca    840
tgctacttat ctacgtagcc atgctctaga gcggccgcac gcgtggagct agttattaat    900
agtaatcaat tacggggtca ttagttcata gcccatatat ggagttccgc gttacataac    960
ttacggtaaa tggcccgcct ggctgaccgc ccaacgaccc ccgcccattg acgtcaataa   1020
```

```
tgacgtatgt tcccatagta acgtcaatag ggactttcca ttgacgtcaa tgggtggagt    1080
atttacggta aactgcccac ttggcagtac atcaagtgta tcatatgcca agtacgcccc    1140
ctattgacgt caatgacggt aaatggcccg cctggcatta tgcccagtac atgaccttat    1200
gggactttcc tacttggcag tacatctacg tattagtcat cgctattacc atggtgatgc    1260
ggttttggca gtacatcaat gggcgtggat agcggtttga ctcacgggga tttccaagtc    1320 tccacccat tgacgtcaat gggagtttgt tttgcaccaa atcaacggg actttccaaa      1380 atgtcgtaac aactccgccc cattgacgca atgggcggt aggcgtgtac ggtgggaggt     1440
ctatataagc agagctcgtt tagtgaaccg tcagatcgcc tggagacgcc atccacgctg    1500
ttttgacctc catagaagac accgggaccg atccagcctc cgcggattcg aatcccggcc    1560
gggaacggtg cattggaacg cggattcccc gtgccaagag tgacgtaagt accgcctata    1620
gagtctatag gcccacaaaa aatgctttct tcttttaata tactttttg tttatcttat     1680 ttctaatact ttccctaatc tctttctttc agggcaataa tgatacaatg tatcatgcct    1740
ctttgcacca ttctaaagaa taacagtgat aatttctggg ttaaggcaat agcaatattt    1800
ctgcatataa atatttctgc atataaattg taactgatgt aagaggtttc atattgctaa    1860
tagcagctac aatccagcta ccattctgct tttatttat ggttgggata aggctggatt     1920
attctgagtc caagctaggc cctttgcta atcatgttca tacctcttat cttcctccca     1980
cagctcctgg gcaacgtgct ggtctgtgtg ctggcccatc actttggcaa gaattggga    2040 ttcgaacatc ggccgccacc atgaacgcaa gtgaattccg aaggagaggg aaggagatgg    2100
tggattacgt ggccaactac atggaaggca ttgagggacg ccagtctac cctgacgtgg     2160 agcccgggta cctgcggccg ctgatccctg ccgctgcccc tcaggagcca gacacgtttg    2220
aggacatcat caacgacgtt gagaagataa tcatgcctgg ggtgacgcac tggcacagcc    2280
cctacttctt cgcctacttc cccactgcca gctcgtaccc ggccatgctt gcggacatgc    2340
tgtgcggggc cattggctgc atcggcttct cctgggcgc aagcccagca tgcacagagc     2400
tggagactgt gatgatggac tggctcggga agatgctgga actaccaaag gcattttga     2460 atgagaaagc tggagaaggg ggaggagtga tccagggaag tgccagtgaa gccaccctgg    2520
tggccctgct ggccgctcgg accaaagtga tccatcggct gcaggcagcg tccccagagc    2580
tcacacaggc cgctatcatg gagaagctgg tggcttactc atccgatcag gcacactcct    2640
cagtggaaag agctgggtta attggtggag tgaaattaaa agccatcccc tcagatggca    2700
acttcgccat gcgtgcgtct gccctgcagg aagccctgga gagagacaaa gcggctggcc    2760
tgattccttt ctttatggtt gccaccctgg ggaccacaac atgctgctcc tttgacaatc    2820
tcttagaagt cggtcctatc tgcaacaagg aagacatatg gctgcacgtt gatgcagcct    2880
acgcaggcag tgcattcatc tgccctgagt tccggcacct tctgaatgga gtggagtttg    2940
cagattcatt caactttaat ccccacaaat ggctattggt gaattttgac tgttctgcca    3000
tgtgggtgaa aaagagaaca gacttaacgg gagcctttag actggacccc acttacctga    3060
agcacagcca tcaggattca gggcttatca ctgactaccg gcattggcag ataccactgg    3120
gcagaagatt tcgctctttg aaaatgtggt ttgtatttag gatgtatgga gtcaaaggac    3180
tgcaggctta tatccgcaag catgtccagc tgtcccatga gtttgagtca ctggtgcgcc    3240
aggatccccg ctttgaaatc tgtgtggaag tcattctggg gcttgtctgc tttcggctaa    3300
agggttccaa caaagtgaat gaagctcttc tgcaaagaat aaacagtgcc aaaaaaatcc    3360
acttggttcc atgtcacctc aggacaagt ttgtcctgcg cttttgccatc tgttctcgca    3420
```

```
cggtggaatc tgcccatgtg cagcgggcct gggaacacat caaagagctg gcggccgacg   3480
tgctgcgagc agagagggag taggagtgaa gccagctgca ggaatcaaaa attgaagaga   3540
gatatatctg aaaactggaa taagaagcaa ataaatatca tcctgccttc atggaactca   3600
gctgtctgtg gcttcccatg tctttctcca aagttatcca gagggttgtg attttgtctg   3660
cttagtatct catcaacaaa gaaatattat ttgctaatta aaaagttaat cttcatggcc   3720
atagctttta ttcattagct gtgattttg ttgattaaaa cattatagat tttcatgttc   3780
ttgcagtcat cagaagtggt aggaaagcct cactgatata ttttccaggg caatcaatgt   3840
tcacgcaact tgaaattata tctgtggtct tcaaattgtc ttttgtcatg tggctaaatg   3900
cctaataagc tgctcgagag atctacgggt ggcatccctg tgacccctcc ccagtgcctc   3960
tcctggccct ggaagttgcc actccagtgc ccaccagcct tgtcctaata aaattaagtt   4020
gcatcatttt gtctgactag gtgtccttct ataatattat ggggtggagg ggggtggtat   4080
ggagcaaggg gcaagttggg aagacaacct gtagggcctg cggggtctat tgggaaccaa   4140
gctggagtgc agtggcacaa tcttggctca ctgcaatctc cgcctcctgg gttcaagcga   4200
ttctcctgcc tcagcctccc gagttgttgg gattccaggc atgcatgacc aggctcagct   4260
aatttttgtt tttttggtag agacggggtt tcaccatatt ggccaggctg gtctccaact   4320
cctaatctca ggtgatctac ccaccttggc ctcccaaatt gctgggatta caggcgtgaa   4380
ccactgctcc cttccctgtc cttctgattt tgtaggtaac cgtaacccg gaccacgtgc   4440 ggaccgagcg gccgctctag agcatggcta cgtagataag tagcatggcg ggttaatcat   4500
taactacaag gaaccctag tgatggagtt ggccactccc tctctgcgcg ctcgctcgct   4560
cactgaggcc gggcgaccaa aggtcgcccg acgcccgggc ggcctcagtg agcgagcgag   4620
cgcgcagctg cctgcaggtc tgagacaata accctgataa atgcttcaat aatgtagcca   4680
accactagaa ctatagctag agtcctgggc gaacaaacga tgctcgcctt ccagaaaacc   4740
gaggatgcga accacttcat ccggggtcag caccaccggc aagcgccgcg acggccgagg   4800
tcttccgatc tcctgaagcc agggcagatc cgtgcacagc accttgccgt agaagaacag   4860
caaggccgcc aatgcctgac gatgcgtgga gaccgaaacc ttgcgctcgt tcgccagcca   4920
ggacagaaat gcctcgactt cgctgctgcc caaggttgcc gggtgacgca ccgtggaa    4980 acggatgaag gcacgaaccc agttgacata agcctgttcg gttcgtaaac tgtaatgcaa   5040
gtagcgtatg cgctcacgca actggtccag aaccttgacc gaacgcagcg gtggtaacgg   5100
cgcagtggcg gttttcatgg cttgttatga ctgtttttt gtacagtcta tgcctcgggc   5160
atccaagcag caagcgcgtt acgccgtggg tcgatgtttg atgttatgga gcagcaacga   5220
tgttacgcag cagcaacgat gttacgcagc agggcagtcg ccctaaaaca agttaggtg    5280 gctcaagtat gggcatcatt cgcacatgta ggctcggccc tgaccaagtc aaatccatgc   5340
gggctgctct tgatcttttc ggtcgtgagt tcggagacgt agccacctac tcccaacatc   5400
agccggactc cgattacctc gggaacttgc tccgtagtaa gacattcatc gcgcttgctg   5460
ccttcgacca agaagcggtt gttggcgctc tcgcggctta cgttctgccc aagtttgagc   5520
agccgcgtag tgagatctat atctatgatc tcgcagtctc cggcgagcac cggaggcagg   5580
gcattgccac cgcgctcatc aatctcctca agcatgaggc caacgcgctt ggtgcttatg   5640
tgatctacgt gcaagcagat tacggtgacg atcccgcagt ggctctctat acaaagttgg   5700
gcatacggga agaagtgatg cactttgata tcgacccaag taccgccacc taacaattcg   5760
```

-continued

```
ttcaagccga gatcggcttc ccggccgcgg agttgttcgg taaattgtca caacgccgcg    5820
aatatagtct ttaccatgcc cttggccacg cccctcttta atacgacggg caatttgcac    5880
ttcagaaaat gaagagtttg ctttagccat aacaaaagtc cagtatgctt tttcacagca    5940
taactggact gatttcagtt tacaactatt ctgtctagtt taagacttta ttgtcatagt    6000
ttagatctat tttgttcagt ttaagacttt attgtccgcc cacacccgct tacgcagggc    6060
atccatttat tactcaaccg taaccgattt tgccaggtta cgcggctggt ctatgcggtg    6120
tgaaataccg cacagatgcg taaggagaaa ataccgcatc aggcgctctt ccgcttcctc    6180
gctcactgac tcgctgcgct cggtcgttcg gctgcggcga gcggtatcag ctcactcaaa    6240
ggcggtaata cggttatcca cagaatcagg ggataacgca ggaaagaaca tgtgagcaaa    6300
aggccagcaa aaggccagga accgtaaaaa ggccgcgttg ctggcgtttt tccataggct    6360 ccgccccct gacgagcatc acaaaaatcg acgctcaagt cagaggtggc gaaacccgac    6420
aggactataa agataccagg cgtttccccc tggaagctcc ctcgtgcgct ctcctgttcc    6480
gaccctgccg cttaccggat acctgtccgc ctttctccct tcgggaagcg tggcgctttc    6540
tcatagctca cgctgtaggt atctcagttc ggtgtaggtc gttcgctcca agctgggctg    6600
tgtgcacgaa ccccccgttc agcccgaccg ctgcgcctta ccggtaact atcgtcttga    6660 gtccaacccg gtaagacacg acttatcgcc actggcagca gccactggta acaggattag    6720
cagagcgagg tatgtaggcg gtgctacaga gttcttgaag tggtggccta actacggcta    6780
cactagaaga acagtatttg gtatctgcgc tctgctgaag ccagttacct tcggaaaaag    6840
agttggtagc tcttgatccg gcaaacaaac caccgctggt agcggtggtt tttttgtttg    6900
caagcagcag attacgcgca gaaaaaagg atctcaagaa gatcctttga tcttttctac    6960
ggggtctgac gctcagtgga acgaaaactc acgttaaggg attttggtca tgagattatc    7020
aaaaaggatc ttcacctaga tccttttaaa ttaaaaatga agttttaaat caatctaaag    7080
tatatatgag taaacttggt ctgacagtta ccaatgctta atcagtgagg cacctatctc    7140
agcgatctgt ctatttcgtt catccatagt tgcctgactc cccgtcgtgt agataactac    7200
gatacgggag ggcttaccat ctggccccag tgctgcaatg ataccgcgag acccacgctc    7260
accggctcca gatttatcag caataaacca gccagccgga agggccgagc gcagaagtgg    7320
tcctgcaact ttatccgcct ccatccagtc tattaattgt tgccgggaag ctagagtaag    7380
tagttcgcca gttaatagtt tgcgcaacgt tgttgccatt gctacaggca tcgtggtgtc    7440
acgctcgtcg tttggtatgg cttcattcag ctccggttcc caacgatcaa ggcgagttac    7500
atgatccccc atgttgtgca aaaaagcggt tagctccttc ggtcctccga tcgttgtcag    7560
aagtaagttg gccgcagtgt tatcactcat ggttatggca gcactgcata attctcttac    7620
tgtcatgcca tccgtaagat gcttttctgt gactggtgag tactcaacca agtcattctg    7680
agaatagtgt atgcggcgac cgagttgctc ttgcccggcg tcaatacggg ataataccgc    7740
gccacatagc agaactttaa aagtgctcat cattggaaaa cgttcttcgg ggcgaaaact    7800
ctcaaggatc ttaccgctgt tgagatccag ttcgatgtaa cccactcgtg cacccaactg    7860
atcttcagca tcttttactt tcaccagcgt ttctgggtga gcaaaaacag gaaggcaaaa    7920
tgccgcaaaa aagggaataa gggcgacacg gaaatgttga atactcatac tcttcctttt    7980
tcaatattat tgaagcattt atcagggtta ttgtctcatg agcggataca tatttgaatg    8040
tatttagaaa aataaacaaa tagggggttcc gcgcacattt ccccgaaaag tgccacctaa    8100
attgtaagcg ttaatatttt gttaaaattc gcgttaaatt tttgttaaat cagctcattt    8160
```

```
tttaaccaat aggccgaaat cggcaaaatc ccttataaat caaaagaata gaccgagata    8220
gggttgagtg ttgttccagt ttggaacaag agtccactat taaagaacgt ggactccaac    8280
gtcaaagggc gaaaaaccgt ctatcagggc gatggcccac tacgtgaacc atcaccctaa    8340
tcaagttttt tggggtcgag gtgccgtaaa gcactaaatc ggaaccctaa agggagcccc    8400
cgatttagag cttgacgggg aaagccggcg aacgtggcga aaaggaagg gaagaaagcg     8460
aaaggagcgg gcgctagggc gctggcaagt gtagcggtca cgctgcgcgt aaccaccaca    8520
cccgccgcgc ttaatgcgcc gctacagggc gcgtc                              8555
```

```
<210> SEQ ID NO 5
<211> LENGTH: 8694
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cattcgccat tcaggctgca aataagcgtt gatattcagt caattacaaa cattaataac      60
gaagagatga cagaaaaatt ttcattctgt gacagagaaa agtagccga agatgacggt      120
ttgtcacatg gagttggcag gatgtttgat taaaaacata acaggaagaa aaatgccccg    180
ctgtgggcgg acaaaatagt tgggaactgg gaggggtgga aatggagttt ttaaggatta    240
tttagggaag agtgacaaaa tagatgggaa ctgggtgtag cgtcgtaagc taatacgaaa    300
attaaaaatg acaaaatagt ttggaactag atttcactta tctggttcgg atctcctagg    360
cgatatcagt gatcagatcc agacatgata agatacattg atgagtttgg acaaaccaca    420
actgaatgc agtgaaaaaa atgctttatt tgtgaaattt gtgatgctat tgctttattt      480
gtaaccatta taagctgcaa taaacaagtt aacaacaaca attgcattca ttttatgttt    540
caggttcagg gggaggtgtg ggaggttttt taaagcaagt aaaacctcta caaatgtggt    600
atggctgatt atgatcctct agtacttctc gacaagctta cattattgaa gcatttatca    660
gggttattgt ctcagacctg caggcagctg cgcgctcgct cgctcactga ggccgcccgg    720
gcaaagcccg ggcgtcgggc gacctttggt cgcccggcct cagtgagcga gcgagcgcgc    780
agagagggag tggccaactc catcactagg ggttccttgt agttaatgat taacccgcca    840
tgctacttat ctacgtagcc atgctctaga gcggccgcaa cgcgtaaact cgtcgacga    900
tctgcggccg cacgcgtgga gctagttatt aatagtaatc aattacgggg tcattagttc    960
atagcccata tatggagttc cgcgttacat aacttacggt aaatggcccg cctggctgac    1020
cgcccaacga cccccgccca ttgacgtcaa taatgacgta tgttcccata gtaacgtcaa    1080
tagggacttt ccattgacgt caatgggtgg agtatttacg gtaaactgcc cacttggcag    1140
tacatcaagt gtatcatatg ccaagtacgc ccctattga cgtcaatgac ggtaaatggc     1200
ccgcctggca ttatgcccag tacatgacct tatgggactt tcctacttgg cagtacatct    1260
acgtattagt catcgctatt accatggtga tgcggttttg gcagtacatc aatgggcgtg    1320
gatagcggtt tgactcacgg ggatttccaa gtctccaccc cattgacgtc aatgggagtt    1380
tgttttgcac caaaatcaac gggactttcc aaaatgtcgt aacaactccg ccccattgac    1440
gcaaatgggc ggtaggcgtg tacggtggga ggtctatata agcagagctc gtttagtgaa    1500
ccgtcagatc gcctggagac gccatccacg ctgttttgac ctccatagaa gacaccggga    1560
ccgatccagc ctccgcggat tcgaatcccg gccgggaacg gtgcattgga acgcggattc    1620
```

```
cccgtgccaa gagtgacgta agtaccgcct atagagtcta taggcccaca aaaaatgctt    1680
tcttctttta atatactttt ttgtttatct tatttctaat actttcccta atctctttct    1740
ttcagggcaa taatgataca atgtatcatg cctctttgca ccattctaaa gaataacagt    1800
gataatttct gggttaaggc aatagcaata tttctgcata taaatatttc tgcatataaa    1860
ttgtaactga tgtaagaggt ttcatattgc taatagcagc tacaatccag ctaccattct    1920
gcttttattt tatggttggg ataaggctgg attattctga gtccaagcta ggccttttg     1980 ctaatcatgt tcatacctct tatcttcctc ccacagctcc tgggcaacgt gctggtctgt    2040
gtgctggccc atcactttgg caaagaattg ggattcgaac atcgaattcg ggcacgaggg    2100
aggacagaga gcaagtcact cccggctgcc tttttcacct ctgacagagc cagacacca     2160 tgaacgcaag tgaattccga aggagaggga aggagatggt ggattacgtg ccaactaca     2220 tggaaggcat tgagggacgc caggtctacc ctgacgtgga gcccgggtac ctgcggccgc    2280
tgatccctgc cgctgcccct caggagccag acacgtttga ggacatcatc aacgacgttg    2340
agaagataat catgcctggg gtgacgcact ggcacagccc ctacttcttc gcctacttcc    2400
ccactgccag ctcgtacccg gccatgcttg cggacatgct gtgcgggcc attggctgca     2460 tcggcttctc ctgggcggca agcccagcat gcacagagct ggagactgtg atgatggact    2520
ggctcgggaa gatgctggaa ctaccaaagg cattttgaa tgagaaagct ggagaagggg     2580
gaggagtgat ccagggaagt gccagtgaag ccaccctggt ggccctgctg gccgctcgga    2640
ccaaagtgat ccatcggctg caggcagcgt ccccagagct cacacaggcc gctatcatgg    2700
agaagctggt ggcttactca tccgatcagg cacactcctc agtggaaaga gctgggttaa    2760
ttggtggagt gaaattaaaa gccatcccct cagatggcaa cttcgccatg cgtgcgtctg    2820
ccctgcagga agccctggag agagacaaag cggctggcct gattcctttc tttatggttg    2880
ccaccctggg gaccacaaca tgctgctcct ttgacaatct cttagaagtc ggtcctatct    2940
gcaacaagga agacatatgg ctgcacgttg atgcagccta cgcaggcagt gcattcatct    3000
gccctgagtt ccggcacctt ctgaatggag tggagtttgc agattcattc aactttaatc    3060
cccacaaatg gctattggtg aattttgact gttctgccat gtgggtgaaa aagagaacag    3120
acttaacggg agcctttaga ctggaccoca cttacctgaa gcacagccat caggattcag    3180
ggcttatcac tgactaccgg cattggcaga taccactggg cagaagattt cgctctttga    3240
aaatgtggtt tgtatttagg atgtatggag tcaaaggact gcaggcttat atccgcaagc    3300
atgtccagct gtcccatgag tttgagtcac tggtgcgcca ggatcccgc tttgaaatct     3360 gtgtggaagt cattctgggg cttgtctgct ttcggctaaa gggttccaac aaagtgaatg    3420
aagctcttct gcaaagaata aacagtgcca aaaaaatcca cttggttcca tgtcacctca    3480
gggacaagtt tgtcctgcgc tttgccatct gttctcgcac ggtggaatct gcccatgtgc    3540
agcgggcctg gaacacatc aaagagctgg cggccgacgt gctgcgagca gagagggagt     3600
aggagtgaag ccagctgcag gaatcaaaaa ttgaagagag atatatctga aaactggaat    3660
aagaagcaaa taaatatcat cctgccttca tggaactcag ctgtctgtgg cttcccatgt    3720 cttctccaa agttatccag agggttgtga ttttgtctgc ttagtatctc atcaacaaag     3780
aaatattatt tgctaattaa aaagttaatc ttcatggcca tagcttttat tcattagctg    3840 tgattttgt tgattaaaac attatagatt ttcatgttct tgcagtcatc agaagtggta     3900
ggaaagcctc actgatatat tttccagggc aatcaatgtt cacgcaactt gaaattatat    3960
```

```
ctgtggtctt caaattgtct tttgtcatgt ggctaaatgc ctaataaaca attcaagtga      4020
aatactaaaa aaaaaaaaaa aaaaaaaagc tgctcgagag atctacgggt ggcatccctg      4080 tgaccccctcc ccagtgcctc tcctggccct ggaagttgcc actccagtgc ccaccagcct     4140
tgtcctaata aaattaagtt gcatcatttt gtctgactag gtgtccttct ataatattat      4200
ggggtggagg ggggtggtat ggagcaaggg gcaagttggg aagacaacct gtagggcctg      4260
cggggtctat tgggaaccaa gctggagtgc agtggcacaa tcttggctca ctgcaatctc      4320
cgcctcctgg gttcaagcga ttctcctgcc tcagcctccc gagttgttgg gattccaggc      4380
atgcatgacc aggctcagct aattttttgtt tttttggtag agacggggtt tcaccatatt     4440
ggccaggctg gtctccaact cctaatctca ggtgatctac ccaccttggc ctcccaaatt      4500
gctgggatta caggcgtgaa ccactgctcc cttccctgtc cttctgattt tgtaggtaac      4560
gtaaccccgg accacgtgcg gaccgagcgg ccgctctaga gcatggctac gtagataagt      4620
agcatggcgg gttaatcatt aactacaagg aaccccctagt gatggagttg gccactccct     4680
ctctgcgcgc tcgctcgctc actgaggccg ggcgaccaaa ggtcgcccga cgcccgggcg      4740
gcctcagtga gcgagcgagc gcgcagctgc ctgcaggtct gagacaataa ccctgataaa      4800
tgcttcaata atgtagccaa ccactagaac tatagctaga gtcctgggcg aacaaacgat      4860
gctcgccttc cagaaaaccg aggatgcgaa ccacttcatc cggggtcagc accaccggca      4920
agcgccgcga cggccgaggt cttccgatct cctgaagcca gggcagatcc gtgcacagca      4980
ccttgccgta gaagaacagc aaggccgcca atgcctgacg atgcgtggag accgaaacct      5040
tgcgctcgtt cgccagccag gacagaaatg cctcgacttc gctgctgccc aaggttgccg      5100
ggtgacgcac accgtggaaa cggatgaagg cacgaaccca gttgacataa gcctgttcgg      5160
ttcgtaaact gtaatgcaag tagcgtatgc gctcacgcaa ctggtccaga accttgaccg      5220
aacgcagcgg tggtaacggc gcagtggcgg ttttcatggc ttgttatgac tgtttttttg      5280
tacagtctat gcctcgggca tccaagcagc aagcgcgtta cgccgtgggt cgatgtttga      5340
tgttatggag cagcaacgat gttacgcagc agcaacgatg ttacgcagca gggcagtcgc      5400
cctaaaacaa agttaggtgg ctcaagtatg gcatcattc gcacatgtag gctcggccct      5460
gaccaagtca atccatgcg ggctgctctt gatcttttcg gtcgtgagtt cggagacgta      5520
gccacctact cccaacatca gccggactcc gattacctcg gaacttgct ccgtagtaag      5580 acattcatcg cgcttgctgc cttcgaccaa gaagcggttg ttggcgctct cgcggcttac      5640
gttctgccca gtttgagca gccgcgtagt gagatctata tctatgatct cgcagtctcc       5700
ggcgagcacc ggaggcaggg cattgccacc gcgctcatca atctcctcaa gcatgaggcc      5760
aacgcgcttg gtgcttatgt gatctacgtg caagcagatt acggtgacga tcccgcagtg      5820
gctctctata caaagttggg catacgggaa gaagtgatgc actttgatat cgacccaagt      5880
accgccacct aacaattcgt tcaagccgag atcggcttcc cggccgcgga gttgttcggt      5940
aaattgtcac aacgccgcga atatagtctt taccatgccc ttggccacgc ccctctttaa      6000
tacgacgggc aatttgcact tcagaaaatg aagagtttgc tttagccata acaaaagtcc      6060
agtatgcttt tcacagcat aactggactg atttcagttt acaactattc tgtcagtttt       6120
aagactttat tgtcatagtt tagatctatt ttgttcagtt taagacttta ttgtccgccc      6180
acacccgctt acgcagggca tccatttatt actcaaccgt aaccgatttt gccaggttac      6240
gcggctggtc tatgcggtgt gaaataccgc acagatgcgt aaggagaaaa taccgcatca      6300
ggcgctcttc cgcttcctcg ctcactgact cgctgcgctc ggtcgttcgg ctgcggcgag      6360
```

```
cggtatcagc tcactcaaag gcggtaatac ggttatccac agaatcaggg gataacgcag    6420
gaaagaacat gtgagcaaaa ggccagcaaa aggccaggaa ccgtaaaaag gccgcgttgc    6480
tggcgttttt ccataggctc cgcccccctg acgagcatca caaaaatcga cgctcaagtc    6540
agaggtggcg aaacccgaca ggactataaa gataccaggc gtttccccct ggaagctccc    6600
tcgtgcgctc tcctgttccg accctgccgc ttaccggata cctgtccgcc tttctccctt    6660
cgggaagcgt ggcgctttct catagctcac gctgtaggta tctcagttcg gtgtaggtcg    6720
ttcgctccaa gctgggctgt gtgcacgaac cccccgttca gcccgaccgc tgcgccttat    6780
ccggtaacta tcgtcttgag tccaacccgg taagacacga cttatcgcca ctggcagcag    6840
ccactggtaa caggattagc agagcgaggt atgtaggcgg tgctacagag ttcttgaagt    6900
ggtggcctaa ctacggctac actagaagaa cagtatttgg tatctgcgct ctgctgaagc    6960
cagttacctt cggaaaaaga gttggtagct cttgatccgg caaacaaacc accgctggta    7020
gcggtggttt ttttgtttgc aagcagcaga ttacgcgcag aaaaaaagga tctcaagaag    7080
atcctttgat cttttctacg gggtctgacg ctcagtggaa cgaaaactca cgttaaggga    7140
ttttggtcat gagattatca aaaaggatct tcacctagat ccttttaaat taaaaatgaa    7200
gttttaaatc aatctaaagt atatatgagt aaacttggtc tgacagttac caatgcttaa    7260
tcagtgaggc acctatctca gcgatctgtc tatttcgttc atccatagtt gcctgactcc    7320
ccgtcgtgta gataactacg atacgggagg gcttaccatc tggccccagt gctgcaatga    7380
taccgcgaga cccacgctca ccggctccag atttatcagc aataaaccag ccagccggaa    7440
gggccgagcg cagaagtggt cctgcaactt tatccgcctc catccagtct attaattgtt    7500
gccgggaagc tagagtaagt agttcgccag ttaatagttt cgcaacgtt gttgccattg    7560 ctacaggcat cgtggtgtca cgctcgtcgt ttggtatggc ttcattcagc tccggttccc    7620
aacgatcaag gcgagttaca tgatccccca tgttgtgcaa aaaagcggtt agctccttcg    7680
gtcctccgat cgttgtcaga agtaagttgg ccgcagtgtt atcactcatg gttatggcag    7740
cactgcataa ttctcttact gtcatgccat ccgtaagatg cttttctgtg actggtgagt    7800
actcaaccaa gtcattctga gaatagtgta tgcggcgacc gagttgctct tgcccggcgt    7860
caatacggga taataccgcg ccacatagca gaactttaaa agtgctcatc attggaaaac    7920
gttcttcggg gcgaaaactc tcaaggatct taccgctgtt gagatccagt tcgatgtaac    7980
ccactcgtgc acccaactga tcttcagcat cttttacttt caccagcgtt tctgggtgag    8040
caaaaacagg aaggcaaaat gccgcaaaaa agggaataag ggcgacacgg aaatgttgaa    8100
tactcatact cttccttttt caatattatt gaagcattta tcagggttat tgtctcatga    8160
gcggatacat atttgaatgt atttagaaaa ataaacaaat aggggttccg cgcacatttc    8220
cccgaaaagt gccacctaaa ttgtaagcgt taatattttg ttaaaattcg cgttaaattt    8280
ttgttaaatc agctcatttt ttaaccaata ggccgaaatc ggcaaaatcc cttataaatc    8340
aaaagaatag accgagatag ggttgagtgt tgttccagtt tggaacaaga gtccactatt    8400
aaagaacgtg gactccaacg tcaaagggcg aaaaaccgtc tatcagggcg atggcccact    8460
acgtgaacca tcaccctaat caagtttttt ggggtcgagg tgccgtaaag cactaaatcg    8520
gaaccctaaa gggagccccc gatttagagc ttgacgggga aagccggcga acgtggcgag    8580
aaaggaaggg aagaaagcga aaggagcggg cgctagggcg ctggcaagtg tagcggtcac    8640
gctgcgcgta accaccacac ccgccgcgct taatgcgccg ctacagggcg cgtc          8694
```

<210> SEQ ID NO 6
<211> LENGTH: 3535
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

| | | | | | | |
|---|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctacgta | gccatgctct | 180 |
| agagcggccg | cacgcgtgga | gctagttatt | aatagtaatc | aattacgggg | tcattagttc | 240 |
| atagcccata | tatggagttc | cgcgttacat | aacttacggt | aaatggcccg | cctggctgac | 300 |
| cgcccaacga | cccccgccca | ttgacgtcaa | taatgacgta | tgttcccata | gtaacgtcaa | 360 |
| tagggacttt | ccattgacgt | caatgggtgg | agtatttacg | gtaaactgcc | cacttggcag | 420 |
| tacatcaagt | gtatcatatg | ccaagtacgc | cccctattga | cgtcaatgac | ggtaaatggc | 480 |
| ccgcctggca | ttatgcccag | tacatgacct | tatgggactt | tcctacttgg | cagtacatct | 540 |
| acgtattagt | catcgctatt | accatggtga | tgcggttttg | gcagtacatc | aatgggcgtg | 600 |
| gatagcggtt | tgactcacgg | ggatttccaa | gtctccaccc | cattgacgtc | aatgggagtt | 660 |
| tgttttgcac | caaaatcaac | gggactttcc | aaaatgtcgt | aacaactccg | ccccattgac | 720 |
| gcaaatgggc | ggtaggcgtg | tacggtggga | ggtctatata | agcagagctc | gtttagtgaa | 780 |
| ccgtcagatc | gcctggagac | gccatccacg | ctgttttgac | ctccatagaa | gacaccggga | 840 |
| ccgatccagc | ctccgcggat | tcgaatcccg | gccgggaacg | gtgcattgga | acgcggattc | 900 |
| cccgtgccaa | gagtgacgta | agtaccgcct | atagagtcta | taggcccaca | aaaaatgctt | 960 |
| tcttctttta | atatactttt | ttgtttatct | tatttctaat | actttcccta | atctctttct | 1020 |
| ttcagggcaa | taatgataca | atgtatcatg | cctctttgca | ccattctaaa | gaataacagt | 1080 |
| gataatttct | gggttaaggc | aatagcaata | tttctgcata | taaatatttc | tgcatataaa | 1140 |
| ttgtaactga | tgtaagaggt | ttcatattgc | taatagcagc | tacaatccag | ctaccattct | 1200 |
| gcttttattt | tatggttggg | ataaggctgg | attattctga | gtccaagcta | ggcccttttg | 1260 |
| ctaatcatgt | tcatacctct | tatcttcctc | ccacagctcc | tgggcaacgt | gctggtctgt | 1320 |
| gtgctggccc | atcactttgg | caaagaattg | ggattcgaac | atcggccgcc | accatgaacg | 1380 |
| caagtgaatt | ccgaaggaga | gggaaggaga | tggtggatta | cgtggccaac | tacatggaag | 1440 |
| gcattgaggg | acgccaggtc | taccctgacg | tggagcccgg | gtacctgcgg | ccgctgatcc | 1500 |
| ctgccgctgc | ccctcaggag | ccagacacgt | tgaggacat | catcaacgac | gttgagaaga | 1560 |
| taatcatgcc | tgggtgacg | cactggcaca | gcccctactt | cttcgcctac | ttccccactg | 1620 |
| ccagctcgta | cccggccatg | cttgcggaca | tgctgtgcgg | ggccattggc | tgcatcggct | 1680 |
| tctcctgggc | ggcaagccca | gcatgcacag | agctggagac | tgtgatgatg | gactggctcg | 1740 |
| ggaagatgct | ggaactacca | aaggcatttt | tgaatgagaa | agctggagaa | ggggaggag | 1800 |
| tgatccaggg | aagtgccagt | gaagccaccc | tggtggccct | gctggccgct | cggaccaaag | 1860 |
| tgatccatcg | gctgcaggca | gcgtccccag | agctcacaca | ggccgctatc | atggagaagc | 1920 |
| tggtggctta | ctcatccgat | caggcacact | cctcagtgga | aagagctggg | ttaattggtg | 1980 |
| gagtgaaatt | aaaagccatc | ccctcagatg | gcaacttcgc | catgcgtgcg | tctgccctgc | 2040 |

| | |
|---|---|
| aggaagccct ggagagagac aaagcggctg gcctgattcc tttctttatg gttgccaccc | 2100 |
| tggggaccac aacatgctgc tcctttgaca atctcttaga agtcggtcct atctgcaaca | 2160 |
| aggaagacat atggctgcac gttgatgcag cctacgcagg cagtgcattc atctgccctg | 2220 |
| agttccggca ccttctgaat ggagtggagt ttgcagattc attcaacttt aatccccaca | 2280 |
| aatggctatt ggtgaatttt gactgttctg ccatgtgggt gaaaaagaga acagacttaa | 2340 |
| cgggagcctt tagactggac cccacttacc tgaagcacag ccatcaggat tcagggctta | 2400 |
| tcactgacta ccggcattgg cagataccac tgggcagaag atttcgctct ttgaaaatgt | 2460 |
| ggtttgtatt taggatgtat ggagtcaaag gactgcaggc ttatatccgc aagcatgtcc | 2520 |
| agctgtccca tgagtttgag tcactggtgc gccaggatcc ccgctttgaa atctgtgtgg | 2580 |
| aagtcattct ggggcttgtc tgctttcggc taaagggttc caacaaagtg aatgaagctc | 2640 |
| ttctgcaaag aataaacagt gccaaaaaaa tccacttggt tccatgtcac ctcagggaca | 2700 |
| agtttgtcct gcgctttgcc atctgttctc gcacggtgga atctgcccat gtgcagcggg | 2760 |
| cctgggaaca catcaaagag ctggcggccg acgtgctgcg agcagagagg gagtaggagt | 2820 |
| gagctgctcg agagatctac gggtggcatc cctgtgaccc ctccccagtg cctctcctgg | 2880 |
| ccctggaagt tgccactcca gtgcccacca gccttgtcct aataaaatta agttgcatca | 2940 |
| ttttgtctga ctaggtgtcc ttctataata ttatggggtg agggggggtg gtatggagca | 3000 |
| aggggcaagt tgggaagaca acctgtaggg cctgcgggt ctattgggaa ccaagctgga | 3060 |
| gtgcagtggc acaatcttgg ctcactgcaa tctccgcctc ctgggttcaa gcgattctcc | 3120 |
| tgcctcagcc tcccgagttg ttgggattcc aggcatgcat gaccaggctc agctaatttt | 3180 |
| tgttttttg gtagagacgg ggtttcacca tattggccag gctggtctcc aactcctaat | 3240 |
| ctcaggtgat ctacccacct tggcctccca aattgctggg attacaggcg tgaaccactg | 3300 |
| ctcccttccc tgtccttctg attttgtagg taaccccgga ccacgtgcgg accgagcggc | 3360 |
| cgctctagag catggctacg tagataagta gcatggcggg ttaatcatta actacaagga | 3420 |
| accccctagtg atggagttgg ccactccctc tctgcgcgct cgctcgctca ctgaggccgg | 3480 |
| gcgaccaaag gtcgcccgac gcccgggcgg cctcagtgag cgagcgagcg cgcag | 3535 |

<210> SEQ ID NO 7
<211> LENGTH: 3534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| agggggttcct tgtagttaat gattaacccg ccatgctact tatctacgta gccatgctct | 180 |
| agagcggccg cacgcgtgga gctagttatt aatagtaatc aattacgggg tcattagttc | 240 |
| atagcccata tatggagttc cgcgttacat aacttacggt aaatggcccg cctggctgac | 300 |
| cgcccaacga ccccgcccca ttgacgtcaa taatgacgta tgttcccata gtaacgtcaa | 360 |
| tagggacttt ccattgacgt caatgggtgg agtatttacg gtaaactgcc cacttggcag | 420 |
| tacatcaagt gtatcatatg ccaagtacgc cccctattga cgtcaatgac ggtaaatggc | 480 |
| ccgcctggca ttatgcccag tacatgacct tatgggactt tcctacttgg cagtacatct | 540 |

```
acgtattagt catcgctatt accatggtga tgcggttttg gcagtacatc aatgggcgtg   600
gatagcggtt tgactcacgg ggatttccaa gtctccaccc cattgacgtc aatgggagtt   660
tgttttgcac caaaatcaac gggactttcc aaaatgtcgt aacaactccg ccccattgac   720
gcaaatgggc ggtaggcgtg tacggtggga ggtctatata agcagagctc gtttagtgaa   780
ccgtcagatc gcctggagac gccatccacg ctgttttgac ctccatagaa gacaccggga   840
ccgatccagc ctccgcggat tcgaatcccg gccgggaacg gtgcattgga acgcggattc   900
cccgtgccaa gagtgacgta agtaccgcct atagagtcta taggcccaca aaaaatgctt   960
tcttctttta atatactttt ttgtttatct tatttctaat actttcccta atctcttttct  1020
ttcagggcaa taatgataca atgtatcatg cctctttgca ccattctaaa gaataacagt  1080
gataatttct gggttaaggc aatagcaata tttctgcata taaatatttc tgcatataaa  1140
ttgtaactga tgtaagaggt ttcatattgc taatagcagc tacaatccag ctaccattct  1200
gcttttattt tatggttggg ataaggctgg attattctga gtccaagcta ggccctttg   1260
ctaatcatgt tcatacctct tatcttcctc ccacagctcc tgggcaacgt gctggtctgt  1320
gtgctggccc atcactttgg caaagaattg ggattcgaac atcggccgcc accatgaacg  1380
ccagcgagtt caggaggagg ggcaaggaga tggtggacta cgtggccaac tacatggagg  1440
gcatcgaggg caggcaggtg taccccgacg tggagcccgg ctacctgagg cccctgatcc  1500
ccgccgccgc cccccaggag cccgacacct tcgaggacat catcaacgac gtggagaaga  1560
tcatcatgcc cggcgtgacc cactggcaca gcccctactt cttcgcctac ttccccaccg  1620
ccagcagcta ccccgccatg ctggccgaca tgctgtgcgg cgccatcggc tgcatcggct  1680
tcagctgggc cgccagcccc gcctgcaccg agctggagac cgtgatgatg gactggctgg  1740
gcaagatgct ggagctgccc aaggccttcc tgaacgagaa ggccggcgag ggcggcggcg  1800
tgatccaggg cagcgccagc gaggccaccc tggtggccct gctggccgcc aggaccaagg  1860
tgatccacag gctgcaggcc gccagccccg agctgaccca ggccgccatc atggagaagc  1920
tggtggccta cagcagcgac caggcccaca gcagcgtgga gagggccggc ctgatcggcg  1980
gcgtgaagct gaaggccatc cccagcgacg caacttcgc catgagggcc agcgccctgc  2040
aggaggccct ggagagggac aaggccgccg gcctgatccc cttcttcatg gtggccaccc  2100
tgggcaccac cacctgctgc agcttcgaca acctgctgga ggtggccccc atctgcaaca  2160
aggaggacat ctggctgcac gtggacgccg cctacgccgg cagcgccttc atctgccccg  2220
agttcaggca cctgctgaac ggcgtggagt tcgccgacag cttcaacttc aaccccaca   2280
agtggctgct ggtgaacttc gactgcagcg ccatgtgggt gaagaagagg accgacctga  2340
ccggcgcctt caggctggac cccacctacc tgaagcacag ccaccaggac agcggcctga  2400
tcaccgacta caggcactgg cagatccccc tgggcaggag gttcaggagc ctgaagatgt  2460
ggttcgtgtt caggatgtac ggcgtgaagg gcctgcaggc ctacatcagg aagcacgtgc  2520
agctgagcca cgagttcgag agcctggtga ggcaggaccc caggttcgag atctgcgtgg  2580
aggtgatcct gggcctggtg tgcttcaggc tgaagggcag caacaaggtg aacgaggccc  2640
tgctgcagag gatcaacagc gccaagaaga tccacctggt gccctgccac ctgagggaca  2700
agttcgtgct gaggttcgcc atctgcagca ggaccgtgga gagcgcccac gtgcagaggg  2760
cctgggagca catcaaggag ctggccgccg acgtgctgag ggccgagagg gagtgagctg  2820
ctcgagagat ctacgggtgg catccctgtg acccctcccc agtgcctctc ctggccctgg  2880
aagttgccac tccagtgccc accagccttg tcctaataaa attaagttgc atcattttgt  2940
```

```
ctgactaggt gtccttctat aatattatgg ggtggagggg ggtggtatgg agcaaggggc    3000
aagttgggaa gacaacctgt agggcctgcg gggtctattg ggaaccaagc tggagtgcag    3060
tggcacaatc ttggctcact gcaatctccg cctcctgggt tcaagcgatt ctcctgcctc    3120
agcctcccga gttgttggga ttccaggcat gcatgaccag gctcagctaa ttttttgtttt   3180 tttggtagag acggggtttc accatattgg ccaggctggt ctccaactcc taatctcagg    3240
tgatctaccc accttggcct cccaaattgc tgggattaca ggcgtgaacc actgctccct    3300
tccctgtcct tctgattttg taggtaacgt aaccccggac cacgtgcgga ccgagcggcc    3360
gctctagagc atggctacgt agataagtag catggcgggt taatcattaa ctacaaggaa    3420
cccctagtga tggagttggc cactccctct ctgcgcgctc gctcgctcac tgaggccggg    3480
cgaccaaagg tcgcccgacg cccgggcggc ctcagtgagc gagcgagcgc gcag          3534
```

<210> SEQ ID NO 8
<211> LENGTH: 3940
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
agagcggccg cacgcgtgga gctagttatt aatagtaatc aattacgggg tcattagttc    240
atagcccata tatggagttc cgcgttacat aacttacggt aaatggcccg cctggctgac    300
cgcccaacga cccccgccca ttgacgtcaa taatgacgta tgttcccata gtaacgtcaa    360
tagggacttt ccattgacgt caatgggtgg agtatttacg gtaaactgcc cacttggcag    420
tacatcaagt gtatcatatg ccaagtacgc cccctattga cgtcaatgac ggtaaatggc    480
ccgcctggca ttatgcccag tacatgacct tatgggactt tcctacttgg cagtacatct    540
acgtattagt catcgctatt accatggtga tgcggttttg gcagtacatc aatgggcgtg    600
gatagcggtt tgactcacgg ggatttccaa gtctccaccc cattgacgtc aatgggagtt    660
tgttttgcac caaaatcaac gggactttcc aaaatgtcgt aacaactccg ccccattgac    720
gcaaatgggc ggtaggcgtg tacggtggga ggtctatata agcagagctc gtttagtgaa    780
ccgtcagatc gcctggagac gccatccacg ctgttttgac ctccatagaa gacaccggga    840
ccgatccagc ctccgcggat tcgaatcccg gccgggaacg gtgcattgga acgcggattc    900
cccgtgccaa gagtgacgta agtaccgcct atagagtcta taggcccaca aaaaatgctt    960
tcttctttta atatacttttt tgtttatct tatttctaat actttcccta atctctttct    1020
ttcagggcaa taatgataca atgtatcatg cctctttgca ccattctaaa gaataacagt    1080
gataatttct gggttaaggc aatagcaata tttctgcata taaatatttc tgcatataaa    1140
ttgtaactga tgtaagaggt ttcatattgc taatagcagc tacaatccag ctaccattct    1200
gcttttattt tatggttggg ataaggctgg attattctga gtccaagcta ggcccttttg    1260
ctaatcatgt tcatacctct tatcttcctc ccacagctcc tgggcaacgt gctggtctgt    1320 gtgctgccc atcactttgg caaagaattg ggattcgaac atcggccgcc accatgaacg    1380
caagtgaatt ccgaaggaga gggaaggaga tggtggatta cgtggccaac tacatggaag    1440
```

```
gcattgaggg acgccaggtc taccctgacg tggagcccgg gtacctgcgg ccgctgatcc    1500
ctgccgctgc ccctcaggag ccagacacgt ttgaggacat catcaacgac gttgagaaga    1560
taatcatgcc tggggtgacg cactggcaca gcccctactt cttcgcctac ttccccactg    1620
ccagctcgta cccggccatg cttgcggaca tgctgtgcgg ggccattggc tgcatcggct    1680
tctcctgggc ggcaagccca gcatgcacag agctggagac tgtgatgatg gactggctcg    1740
ggaagatgct ggaactacca aaggcatttt tgaatgagaa agctggagaa ggggaggag    1800 tgatccaggg aagtgccagt gaagccaccc tggtggccct gctggccgct cggaccaaag    1860
tgatccatcg gctgcaggca gcgtccccag agctcacaca ggccgctatc atggagaagc    1920
tggtggctta ctcatccgat caggcacact cctcagtgga aagagctggg ttaattggtg    1980
gagtgaaatt aaaagccatc ccctcagatg gcaacttcgc catgcgtgcg tctgccctgc    2040
aggaagccct ggagagagac aaagcggctg gcctgattcc tttctttatg gttgccaccc    2100
tggggaccac aacatgctgc tcctttgaca atctcttaga agtcggtcct atctgcaaca    2160
aggaagacat atggctgcac gttgatgcag cctacgcagg cagtgcattc atctgccctg    2220
agttccggca ccttctgaat ggagtggagt ttgcagattc attcaacttt aatccccaca    2280
aatggctatt ggtgaatttt gactgttctg ccatgtgggt gaaaaagaga acagacttaa    2340
cgggagcctt tagactggac cccacttacc tgaagcacag ccatcaggat tcagggctta    2400
tcactgacta ccggcattgg cagataccac tgggcagaag atttcgctct ttgaaaatgt    2460
ggtttgtatt taggatgtat ggagtcaaag gactgcaggc ttatatccgc aagcatgtcc    2520
agctgtccca tgagtttgag tcactggtgc gccaggatcc ccgctttgaa atctgtgtgg    2580
aagtcattct ggggcttgtc tgctttcggc taaagggttc caacaaagtg aatgaagctc    2640
ttctgcaaag aataaacagt gccaaaaaaa tccacttggt tccatgtcac ctcagggaca    2700
agtttgtcct gcgctttgcc atctgttctc gcacggtgga atctgcccat gtgcagcggg    2760
cctgggaaca catcaaagag ctggcggccg acgtgctgcg agcagagagg gagtaggagt    2820
gaagccagct gcaggaatca aaaattgaag agagatatat ctgaaaactg gaataagaag    2880
caaataaata tcatcctgcc ttcatggaac tcagctgtct gtggcttccc atgtcttttct    2940 ccaaagttat ccagagggtt gtgattttgt ctgcttagta tctcatcaac aaagaaatat    3000
tatttgctaa ttaaaaagtt aatcttcatg gccatagctt ttattcatta gctgtgattt    3060
ttgttgatta aaacattata gattttcatg ttcttgcagt catcagaagt ggtaggaaag    3120
cctcactgat atattttcca gggcaatcaa tgttcacgca acttgaaatt atatctgtgg    3180
tcttcaaatt gtcttttgtc atgtggctaa atgcctaata agctgctcga gagatctacg    3240
ggtggcatcc ctgtgacccc tccccagtgc ctctcctggc cctggaagtt gccactccag    3300
tgcccaccag ccttgtccta ataaaattaa gttgcatcat tttgtctgac taggtgtcct    3360
tctataatat tatggggtgg agggggtgg tatgagcaa gggcaagtt gggaagacaa    3420 cctgtagggc ctgcggggtc tattgggaac caagctggag tgcagtggca caatcttggc    3480
tcactgcaat ctccgcctcc tgggttcaag cgattctcct gcctcagcct cccgagttgt    3540
tgggattcca ggcatgcatg accaggctca gctaattttt gttttttgg tagagacggg    3600 gtttcaccat attggccagg ctggtctcca actcctaatc tcaggtgatc tacccacctt    3660
ggcctcccaa attgctggga ttacaggcgt gaaccactgc tcccttccct gtccttctga    3720
ttttgtaggt aaccgtaacc ccggaccacg tgcggaccga gcggccgctc tagagcatgg    3780
```

| | |
|---|---|
| ctacgtagat aagtagcatg cgggttaat cattaactac aaggaacccc tagtgatgga | 3840 |
| gttggccact ccctctctgc gcgctcgctc gctcactgag gccgggcgac caaaggtcgc | 3900 |
| ccgacgcccg ggcggcctca gtgagcgagc gagcgcgcag | 3940 |

<210> SEQ ID NO 9
<211> LENGTH: 4079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| agagcggccg caacgcgtaa acttcgtcga cgatctgcgg ccgcacgcgt ggagctagtt | 240 |
| attaatagta atcaattacg gggtcattag ttcatagccc atatatggag ttccgcgtta | 300 |
| cataacttac ggtaaatggc ccgcctggct gaccgcccaa cgaccccgc ccattgacgt | 360 |
| caataatgac gtatgttccc atagtaacgt caatagggac tttccattga cgtcaatggg | 420 |
| tggagtattt acggtaaact gcccacttgg cagtacatca agtgtatcat atgccaagta | 480 |
| cgccccctat tgacgtcaat gacggtaaat ggcccgcctg gcattatgcc cagtacatga | 540 |
| ccttatggga ctttcctact tggcagtaca tctacgtatt agtcatcgct attaccatgg | 600 |
| tgatgcggtt ttggcagtac atcaatgggc gtggatagcg gtttgactca cggggatttc | 660 |
| caagtctcca ccccattgac gtcaatggga gtttgttttg gcaccaaaatc aacgggactt | 720 |
| tccaaaatgt cgtaacaact ccgccccatt gacgcaaatg ggcggtaggc gtgtacggtg | 780 |
| ggaggtctat ataagcagag ctcgtttagt gaaccgtcag atcgcctgga gacgccatcc | 840 |
| acgctgtttt gacctccata aagacaccg ggaccgatcc agcctccgcg gattcgaatc | 900 |
| ccggccggga acgtgcatt ggaacgcgga ttccccgtgc caagagtgac gtaagtaccg | 960 |
| cctatagagt ctataggccc acaaaaaatg ctttcttctt taatatact tttttgttta | 1020 |
| tcttatttct aatactttcc ctaatctctt tctttcaggg caataatgat acaatgtatc | 1080 |
| atgcctcttt gcaccattct aaagaataac agtgataatt tctgggttaa ggcaatagca | 1140 |
| atatttctgc atataaatat ttctgcatat aaattgtaac tgatgtaaga ggtttcatat | 1200 |
| tgctaatagc agctacaatc cagctaccat tctgctttta ttttatggtt gggataaggc | 1260 |
| tggattattc tgagtccaag ctaggccctt ttgctaatca tgttcatacc tcttatcttc | 1320 |
| ctcccacagc tcctgggcaa cgtgctggtc tgtgtgctgg cccatcactt tggcaaagaa | 1380 |
| ttgggattcg aacatcgaat tcgggcacga gggaggacag agagcaagtc actcccggct | 1440 |
| gccttttca cctctgacag agcccagaca ccatgaacgc aagtgaattc gaaggagag | 1500 |
| ggaaggagat ggtggattac gtggccaact acatggaagg cattgaggga cgccaggtct | 1560 |
| accctgacgt ggagcccggg tacctgcggc cgctgatccc tgccgctgcc cctcaggagc | 1620 |
| cagacacgtt tgaggacatc atcaacgacg ttgagaagat aatcatgcct ggggtgacgc | 1680 |
| actggcacag ccctacttc ttcgcctact tccccactgc cagctcgtac ccggccatgc | 1740 |
| ttgcggacat gctgtgcggg gccattggct gcatcggctt ctcctgggcg gcaagcccag | 1800 |
| catgcacaga gctggagact gtgatgatgg actggctcgg gaagatgctg gaactaccaa | 1860 |

```
aggcattttt gaatgagaaa gctggagaag ggggaggagt gatccaggga agtgccagtg    1920
aagccaccct ggtggccctg ctggccgctc ggaccaaagt gatccatcgg ctgcaggcag    1980
cgtccccaga gctcacacag gccgctatca tggagaagct ggtggcttac tcatccgatc    2040
aggcacactc ctcagtggaa agagctgggt taattggtgg agtgaaatta aaagccatcc    2100
cctcagatgg caacttcgcc atgcgtgcgt ctgccctgca ggaagccctg gagagagaca    2160
aagcggctgg cctgattcct ttctttatgg ttgccaccct ggggaccaca acatgctgct    2220
cctttgacaa tctcttagaa gtcggtccta tctgcaacaa ggaagacata tggctgcacg    2280
ttgatgcagc ctacgcaggc agtgcattca tctgccctga gttccggcac cttctgaatg    2340
gagtggagtt tgcagattca ttcaacttta atccccacaa atggctattg gtgaattttg    2400
actgttctgc catgtgggtg aaaaagagaa cagacttaac gggagccttt agactggacc    2460
ccacttacct gaagcacagc catcaggatt cagggcttat cactgactac cggcattggc    2520
agataccact gggcagaaga tttcgctctt gaaaatgtg gtttgtattt aggatgtatg    2580
gagtcaaagg actgcaggct tatatccgca agcatgtcca gctgtcccat gagtttgagt    2640
cactggtgcg ccaggatccc cgctttgaaa tctgtgtgga agtcattctg gggcttgtct    2700
gctttcggct aaagggttcc aacaaagtga atgaagctct tctgcaaaga ataaacagtg    2760
ccaaaaaaat ccacttggtt ccatgtcacc tcagggacaa gtttgtcctg cgctttgcca    2820
tctgttctcg cacggtggaa tctgcccatg tgcagcgggc ctgggaacac atcaaagagc    2880
tggcggccga cgtgctgcga gcagagaggg agtaggagtg aagccagctg caggaatcaa    2940
aaattgaaga gagatatatc tgaaaactgg aataagaagc aaataaatat catcctgcct    3000
tcatggaact cagctgtctg tggcttccca tgtctttctc caaagttatc cagagggttg    3060
tgattttgtc tgcttagtat ctcatcaaca aagaaatatt atttgctaat taaaagtta    3120 atcttcatgg ccatagcttt tattcattag ctgtgatttt tgttgattaa acattatag    3180 attttcatgt tcttgcagtc atcagaagtg gtaggaaagc ctcactgata tattttccag    3240
ggcaatcaat gttcacgcaa cttgaaatta tatctgtggt cttcaaattg tcttttgtca    3300
tgtggctaaa tgcctaataa acaattcaag tgaaatacta aaaaaaaaaa aaaaaaaaa    3360 agctgctcga gagatctacg ggtggcatcc ctgtgacccc tccccagtgc ctctcctggc    3420
cctggaagtt gccactccag tgcccaccag ccttgtccta ataaaattaa gttgcatcat    3480
tttgtctgac taggtgtcct tctataatat tatggggtgg agggggggtgg tatggagcaa    3540 ggggcaagtt gggaagacaa cctgtagggc ctgcggggtc tattgggaac caagctggag    3600
tgcagtggca caatcttggc tcactgcaat ctccgcctcc tgggttcaag cgattctcct    3660
gcctcagcct cccgagttgt tgggattcca ggcatgcatg accaggctca gctaattttt    3720
gtttttttgg tagagacggg gtttcaccat attggccagg ctggtctcca actcctaatc    3780
tcaggtgatc tacccacctt ggcctcccaa attgctggga ttacaggcgt gaaccactgc    3840
tcccttccct gtccttctga ttttgtaggt aacgtaaccc cggaccacgt gcggaccgag    3900
cggccgctct agagcatggc tacgtagata agtagcatgg cgggttaatc attaactaca    3960 aggaaccccct agtgatggag ttggccactc cctctctgcg cgctcgctcg ctcactgagg    4020
ccgggcgacc aaaggtcgcc cgacgcccgg gcggcctcag tgagcgagcg agcgcgcag    4079
```

<210> SEQ ID NO 10
<211> LENGTH: 9266
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
gagaggcggt tgcgtattg ggcgctcttc cgcttcctcg ctcactgact cgctgcgctc      60
ggtcgttcgg ctgcggcgag cggtatcagc tcactcaaag gcggtaatac ggttatccac    120
agaatcaggg gataacgcag gaaagaacat gtgagcaaaa ggccagcaaa aggccaggaa    180
ccgtaaaaag gccgcgttgc tggcgttttg agatcctttt tttctgcgcg taatctgctg    240
cttgcaaaca aaaaaaccac cgctaccagc ggtggtttgt ttgccggatc aagagctacc    300
aactcttttt ccgaaggtaa ctggcttcag cagagcgcag ataccaaata ctgttcttct    360
agtgtagccg tagttaggcc accacttcaa gaactctgta gcaccgccta catacctcgc    420
tctgctaatc ctgttaccag tggctgctgc cagtggcgat aagtcgtgtc ttaccgggtt    480
ggactcaaga cgatagttac cggataaggc gcagcggtcg ggctgaacgg ggggttcgtg    540
cacacagccc agcttggagc gaacgaccta caccgaactg agatacctac agcgtgagct    600
atgagaaagc gccacgcttc ccgaagggag aaaggcggac aggtatccgg taagcggcag    660
ggtcggaaca ggagagcgca cgagggagct tccaggggga aacgcctggt atctttatag    720
tcctgtcggg tttcgccacc tctgacttga gcgtcgattt ttgtgatgct cgtcaggggg    780
gcggagccta tggaaagaag atcctttgat cttttctacg gggtctgacg ctcagtggaa    840
cgaaaactca cgttaaggga ttttggtcat gagattatca aaaggatct tcacctagat     900
cctttaaat taaaaatgaa gttttaaatc aagcccaatc tgaataatgt tacaaccaat     960
taaccaattc tgaaaacgcg cgatgcagct ctggcccgtg tctcaaaatc tctgatgtta   1020
cattgcacaa gataaaaata tatcatcatg aacaataaaa ctgtctgctt acataaacag   1080
taatacaagg ggtgttatga gccatattca acgggaaacg tcgaggccgc gattaaattc   1140
caacatggat gctgatttat atgggtataa atgggctcgc gataatgtcg ggcaatcagg   1200
tgcgacaatc tatcgcttgt atgggaagcc cgatgcgcca gagttgtttc tgaaacatgg   1260
caaaggtagc gttgccaatg atgttacaga tgagatggtc agactaaact ggctgacgga   1320
atttatgcct cttccgacca tcaagcattt tatccgtact cctgatgatg catggttact   1380
caccactgcg atccccggaa aaacagcatt ccaggtatta gaagaatatc ctgattcagg   1440
tgaaaatatt gttgatgcgc tggcagtgtt cctgcgccgg ttgcattcga ttcctgtttg   1500
taattgtcct tttaacagcg atcgcgtatt tcgtctcgct caggcgcaat cacgaatgaa   1560
taacggtttg gttgatgcga gtgattttga tgacgagcgt aatggctggc ctgttgaaca   1620
agtctggaaa gaaatgcata aacttttgcc attctcaccg gattcagtcg tcactcatgg   1680
tgatttctca cttgataacc ttattttga cgaggggaaa ttaataggtt gtattgatgt   1740
tggacgagtc ggaatcgcag accgatacca ggatcttgcc atcctatgga actgcctcgg   1800
tgagttttct ccttcattac agaaacggct ttttcaaaaa tatggtattg ataatcctga   1860
tatgaataaa ttgcagtttc atttgatgct cgatgagttt ttctaatcag aattggttaa   1920
ttggttgtaa cattattcag attgggcttg atttaaaact tcatttttaa tttaaaagga   1980
tctaggtgaa gatcctttt gataatctca tgaccaaaat cccttaacgt gagttttcgt   2040
tccactgagc gtcagacccc gtagaaaaga tcaaaggatc ttcaacaccc cttgtattac   2100
tgtttatgta agcagacagt tttattgttc atgatgatat ttttatct tgtgcaatgt   2160
aacatcagag attttgagac acgggccaga gctgcatcgc gcgtttcggt gatgacggtg   2220
```

```
aaaacctctg acacatgcag ctcccgtatc tggaggctat aaatgattac gatacttcga    2280
aaacatcctt atcctggaaa actccccgtt catttcccac tctcctgcca ttcgacactc    2340
gtgcgtccat tcaagtctgt gctaatttct acgcatttcc ctctgccatt gactttgctt    2400
gcgtgggata taactatta agccaacttg attcaactca ggcattcaaa aggcattttg     2460
attagtcgaa aagtggcacg gctgacgagt ggagctgcca tttcacgttt atttcgaact    2520
tttgattaca tggtatattt agtaatacac atatttttta gccagcaggt taatacttca    2580
aagttgtttc gattttcaac gaataaaagg aatttggcat ggtgttttt ctggtctttg     2640
gtattgacaa atcagggata tacaatatgt attaacaaaa ttggattgct acatatattt    2700
aatgattttc attattagaa tgggtggaat aaagttttaa attacattat taatttcatt    2760
agggttggct gattgattac tatttcctca ttgaattgca ttcgatatta gcagtattta    2820
tctggcccat tttggaagtt acttaaattt cgaaccttaa gtcattatta gagctaatat    2880
acaacagagt tgtcaacttg gtttgatcag cattgaaatt aaactgatttt cttgttcgtt   2940
cttatttcgt ttggttttgt atctcgtatt ttatatgcag gagggcatat attggcacaa    3000
gacaaataat cacagcaccc attctcaact ttgtcctgtt tctcagttta gtgtaaatag    3060
aatgttgcaa aaaattgaat ataagcatta tcatagtgtc aaattcgaga ggatgagttt    3120
gctgtgggtc ttcgaggttc tttccctgtg tttgccacgg ttcgttgcac gttgccactg    3180
attggacaca tgtccgcagt gaaaaatcta cggtcaggta ccacccaact aaaccggaag    3240
gcggcacgtg tgtgggcgtt gagcggtgtg ggcgtggcag ccatataatg agacatttat    3300
ttaaaagaa cattcgaaca tttttgatgg gccatatctt ggcttgtcaa gctccagggc     3360
agacattttc ctcgactcca ccgccttttt catttgaatg gaggaggtgt agggcacaaa    3420
aaacgtttcc tgccttttta agcagcacaa aggatatgag ccattaaatt agttaatttc    3480
gagtgcattt cattttaaat aagtgttgga aagggaataa aaaagcgact gatagaaaag    3540
ttgcagacac caagagaatg ttaaatattt taataatagc tacattttttc tatctctgtg    3600
acaaggcctg tgtactttaa tgttatatta cttctttgtg tttgatttct gttaaaagtt    3660
tatgattttg gcatgtacaa atcttacaac ccttttttgt catcatgaca aaatcaaaat    3720
cgtgcaatat ttccattctc atcttttagc cgattcataa cattcgtaga aattaatatg    3780
aaatcaatca tgtataattt tcatgcacgt tatgccgatt tggtatcgtc gatttgccgg    3840
ctcatcgtcg ccattgtgtt aatggaaaag ttatgctttt cgcaggaaaa aagagttgaa    3900
aattccaatt tttgtcatgc tcatcaaaat gttatacatt cggtaatttg agctggccaa    3960
acgttaaccc cttatcgccc cgcgcaagca ttcattaact gcccccagag cgtaattaat    4020
ctctttctcg cagaatttcc ttcacagcca cgtcttgggt aaaagtcacc cctcaaagtg    4080
gcagttgcat gttgtaaatt agattttcgt ccgtcatgac aaccctcgtg cgagggttgc    4140
tgcagcattt gaatgcaaaa ctgcttttgg tcattaacct gtctgaggca ctttgctgca    4200
aaacttctat tagaattcgg tttggactcg aattcggatt tcttccccca aaatgcgatg    4260
gctacagcaa aatgctttca gcttccgaag ttttgcaacc ccaaagtcca gagtttccac    4320
gctgtcacga ttccaaagcg gcgccatttt tggctcacgc aaaacttatt aatgaacttt    4380
aagcagacta cgaggaaagg gctataatgg ccacacaaaa gggttaagca agtgttaagg    4440
gctggtggga gggaaaaatc atcaatcata ttttctgcat agctgaatca tttgcgccga    4500
tcagttgggg ttacttaatg ggtttatttc aagaagaaaa ctgtgggaaa ctaactgact    4560
```

```
ctaaacttaa tcagattaaa tgtaacctgg agatgatttt caaaatatta aaagagtttt    4620
atggaggtaa ttttaaagaa aactgaaaaa ctttgaagaa gtctataata gatccagtct    4680
taatcgtagc actgattatt tgttttttaa ttggaaaaaa ttaaatgata catcatgctt    4740
aaatgcgatg tccaacaaat cccaagacgg taatttccgt gcgttccaaa ctcatctgaa    4800
gaatcttaca aatacatttc gtgtatcccc aggctcagcg tgcaaataaa tcttttggat    4860
ctttgcaaat gcgaaatgct tatttttatg cgttttcaat gccaattcga tggcaaaacc    4920
aacaaaatca catggaaata atggaaaagc aatttccatt tctacaaggg aggcagtgag    4980
acacaagagc agcgtataca attccccagc agcgatttga ccattaaaat tatacccaca    5040
ggacgagcag gcataaaaag cagaggatgc gaggtgttca ggggactgtc tatatctcca    5100
acttgaatat atgaaatcgt ttggaaatag ccaagcgacc aaattggcat ttggaaaatt    5160
gcacaacgac agaagaagat gtttgaaaag agaaattgaa ataataaacc aagatatatg    5220
taaacggttg gtcacatttg ggttctgaga cggtcacagc ttgtctgtaa gcggatgccg    5280
ggagcagaca agcccgtcag ggcgcgtcag cgggtgttgg cgggtgtcgg ggctggctta    5340
actatgcggc atcagagcag attgtactga gagtgcacca tatgcggtgt gaaataccgc    5400
acagatgcgt aaggagaaaa taccgcatca ggcgccattc gccattcagg ctgcgcaact    5460
gttgggaagg gcgatcggtg cgggcctctt cgctattacg ccagctggcg aaagggggat    5520
gtgctgcaag gcgattaagt tgggtaacgc cagggttttc ccagtcacga cgttgtaaaa    5580
cgacggccag tgaattcgag ctcggtacca tttaaatcgt cttggccact ccctctctgc    5640
gcgctcgctc gctcactgag gccgcccggg caaagcccgg gcgtcgggcg acctttggtc    5700
gcccggcctc agtgagcgag cgagcgcgca gagaggagt ggccaactcc atcactaggg    5760
gttccttcgc gagcttaatt aactgcggcc gctcggtccg cacgtggtta cctacaaaat    5820
cagaaggaca gggaagggag cagtggttca cgcctgtaat cccagcaatt tgggaggcca    5880
aggtgggtag atcacctgag attaggagtt ggagaccagc ctggccaata tggtgaaacc    5940
ccgtctctac caaaaaaaca aaaattagct gagcctggtc atgcatgcct ggaatcccaa    6000
caactcggga ggctgaggca ggagaatcgc ttgaacccag gaggcggaga ttgcagtgag    6060
ccaagattgt gccactgcac tccagcttgg ttcccaatag accccgcagg ccctacaggt    6120
tgtcttccca acttgcccct tgctccatac caccccctc cacccataa tattatagaa     6180
ggacacctag tcagacaaaa tgatgcaact taattttatt aggacaaggc tggtgggcac    6240
tggagtggca acttccaggg ccaggagagg cactggggag gggtcacagg gatgccaccc    6300
gtagatctct cgagcagctc actcctactc cctctctgct cgcagcacgt cggccgccag    6360
ctctttgatg tgttcccagg cccgctgcac atgggcagat tccaccgtgc gagaacagat    6420
ggcaaagcgc aggacaaact tgtccctgag gtgacatgga accaagtgga tttttttggc    6480
actgtttatt ctttgcagaa gagcttcatt cactttgttg gaacccttta gccgaaagca    6540
gacaagcccc agaatgactt ccacacagat ttcaaagcgg ggatcctggc gcaccagtga    6600
ctcaaactca tgggacagct ggacatgctt gcggatataa gcctgcagtc ctttgactcc    6660
atacatccta aatacaaacc acattttcaa agagcgaaat cttctgccca gtggtatctg    6720
ccaatgccgg tagtcagtga taagccctga atcctgatgg ctgtgcttca ggtaagtggg    6780
gtccagtcta aaggctcccg ttaagtctgt tctcttttc acccacatgg cagaacagtc     6840
aaaattcacc aatagccatt tgtggggatt aaagttgaat gaatctgcaa actccactcc    6900
attcagaagg tgccggaact cagggcagat gaatgcactg cctgcgtagg ctgcatcaac    6960
```

```
gtgcagccat atgtcttcct tgttgcagat aggaccgact tctaagagat tgtcaaagga    7020
gcagcatgtt gtggtcccca gggtggcaac cataaagaaa ggaatcaggc cagccgcttt    7080
gtctctctcc agggcttcct gcagggcaga cgcacgcatg gcgaagttgc catctgaggg    7140
gatggctttt aatttcactc caccaattaa cccagctctt tccactgagg agtgtgcctg    7200
atcggatgag taagccacca gcttctccat gatagcggcc tgtgtgagct ctggggacgc    7260
tgcctgcagc cgatggatca ctttggtccg agcggccagc agggccacca gggtggcttc    7320
actggcactt ccctggatca ctcctccccc ttctccagct ttctcattca aaaatgcctt    7380
tggtagttcc agcatcttcc cgagccagtc catcatcaca gtctccagct ctgtgcatgc    7440
tgggcttgcc gcccaggaga agccgatgca gccaatggcc ccgcacagca tgtccgcaag    7500
catggccggg tacgagctgg cagtggggaa gtaggcgaag aagtaggggc tgtgccagtg    7560 cgtcaccccca ggcatgatta tcttctcaac gtcgttgatg atgtcctcaa acgtgtctgg    7620
ctcctgaggg gcagcggcag ggatcagcgg ccgcaggtac ccgggctcca cgtcagggta    7680
gacctggcgt ccctcaatgc cttccatgta gttggccacg taatccacca tctccttccc    7740
tctccttcgg aattcacttg cgttcatggt ggcggccgat gttcgaatcc caattctttg    7800
ccaaagtgat gggccagcac acagaccagc acgttgccca ggagctgtgg gaggaagata    7860
agaggtatga acatgattag caaaagggcc tagcttggac tcagaataat ccagccttat    7920
cccaaccata aaataaaagc agaatggtag ctggattgta gctgctatta gcaatatgaa    7980
acctcttaca tcagttacaa tttatatgca gaaatattta tatgcagaaa tattgctatt    8040
gccttaaccc agaaattatc actgttattc tttagaatgg tgcaaagagg catgatacat    8100
tgtatcatta ttgccctgaa agaaagagat tagggaaagt attagaaata agataaacaa    8160
aaaagtatat taaaagaaga aagcattttt tgtgggccta tagactctat aggcggtact    8220
tacgtcactc ttggcacggg gaatccgcgt tccaatgcac cgttcccggc cgggattcga    8280
atccgcggag gctggatcgg tcccggtgtc ttctatggag gtcaaaacag cgtggatggc    8340
gtctccaggc gatctgacgg ttcactaaac gagctctgct tatatagacc tcccaccgta    8400
cacgcctacc gcccatttgc gtcaatgggg cggagttgtt acgacatttt ggaaagtccc    8460
gttgattttg gtgcaaaaca aactcccatt gacgtcaatg gggtggagac ttggaaatcc    8520
ccgtgagtca aaccgctatc cacgcccatt gatgtactgc caaaaccgca tcaccatggt    8580
aatagcgatg actaatacgt agatgtactg ccaagtagga aagtcccata aggtcatgta    8640
ctgggcataa tgccaggcgg gccatttacc gtcattgacg tcaatagggg gcgtacttgg    8700
catatgatac acttgatgta ctgccaagtg gcagtttac cgtaaatact ccacccattg    8760
acgtcaatgg aaagtcccta ttgacgttac tatgggaaca tacgtcatta ttgacgtcaa    8820
tgggcggggg tcgttgggcg gtcagccagg cgggccattt accgtaagtt atgtaacgcg    8880
gaactccata tatgggctat gaactaatga ccccgtaatt gattactatt aataactagc    8940
tccacgcgtg cggccgcaga tcgtcgacga agtttaaact caggaacccc tagtgatgga    9000
gttggccact ccctctctgc gcgctcgctc gctcactgag gccgcccggg caaagcccgg    9060
gcgtcgggcg acctttggtc gcccggcctc agtgagcgag cgagcgcgca gagagggagt    9120
ggccaacgtc atttaaatgc atgcaagctt ggcgtaatca tggtcatagc tgtttcctgt    9180
gtgaaaattg cgttgcgctc actgcccgct ttccagtcgg gaaacctgtc gtgccagctg    9240
cattaatgaa tcggccaacg cgcggg                                         9266
```

<210> SEQ ID NO 11
<211> LENGTH: 9236
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
cccgcgcgtt ggccgattca ttaatgcagc tggcacgaca ggtttcccga ctggaaagcg      60
ggcagtgagc gcaacgcaat tttcacacag gaaacagcta tgaccatgat tacgccaagc     120
ttgcatgcat ttaaatgacg cagctgcgcg ctcgctcgct cactgaggcc gcccgggcaa     180
agcccgggcg tcgggcgacc tttggtcgcc cggcctcagt gagcgagcga gcgcgcagag     240
agggagtggc caactccatc actaggggtt gagtttaaac ttcgtcgacg atctgcggcc     300
gcacgcgtgg agctagttat taatagtaat caattacggg gtcattagtt catagcccat     360
atatggagtt ccgcgttaca taacttacgg taaatggccc gcctggctga ccgcccaacg     420
accccgccc attgacgtca ataatgacgt atgttcccat agtaacgtca atagggactt     480
tccattgacg tcaatgggtg gagtatttac ggtaaactgc ccacttggca gtacatcaag     540
tgtatcatat gccaagtacg ccccctattg acgtcaatga cggtaaatgg cccgcctggc     600
attatgccca gtacatgacc ttatgggact ttcctacttg gcagtacatc tacgtattag     660
tcatcgctat taccatggtg atgcggtttt ggcagtacat caatgggcgt ggatagcggt     720
ttgactcacg gggatttcca agtctccacc ccattgacgt caatgggagt ttgttttgca     780
ccaaaatcaa cgggactttc caaaatgtcg taacaactcc gccccattga cgcaaatggg     840
cggtaggcgt gtacggtggg aggtctatat aagcagagct cgtttagtga accgtcagat     900
cgcctggaga cgccatccac gctgttttga cctccataga agacaccggg accgatccag     960
cctccgcgga ttcgaatccc ggccgggaac ggtgcattgg aacgcggatt ccccgtgcca    1020
agagtgacgt aagtaccgcc tatagagtct ataggcccac aaaaaatgct tcttcttttt    1080
aatatacttt tttgtttatc ttatttctaa tactttccct aatctctttc tttcagggca    1140
ataatgatac aatgtatcat gcctctttgc accattctaa agaataacag tgataatttc    1200
tgggttaagg caatagcaat atttctgcat ataaatattt ctgcatataa attgtaactg    1260
atgtaagagg tttcatattg ctaatagcag ctacaatcca gctaccattc tgcttttatt    1320
ttatggttgg gataaggctg gattattctg agtccaagct aggcccttt gctaatcatg    1380
ttcatacctc ttatcttcct cccacagctc ctgggcaacg tgctggtctg tgtgctggcc    1440
catcactttg gcaaagaatt gggattcgaa catcggccgc caccatgaac gcaagtgaat    1500
tccgaaggag agggaaggag atggtggatt acgtggccaa ctacatgaa ggcattgagg    1560
gacgccaggt ctaccctgac gtggagcccg gtacctgcg gccgctgatc cctgccgctg    1620
cccctcagga gccagacacg tttgaggaca tcatcaacga cgttgagaag ataatcatgc    1680
ctgggggtgac gcactggcac agcccctact tcttcgccta cttccccact gccagctcgt    1740
acccggccat gcttgcggac atgctgtgcg gggccattgg ctgcatcggc ttctcctggg    1800
cggcaagccc agcatgcaca gagctggaga ctgtgatgat ggactggctc gggaagatgc    1860
tggaactacc aaaggcattt ttgaatgaga aagctggaga aggggagga gtgatccagg    1920
gaagtgccag tgaagccacc ctggtggccc tgctggccgc tcggaccaaa gtgatccatc    1980
ggctgcaggc agcgtcccca gagctcacac aggccgctat catggagaag ctggtggctt    2040
```

```
actcatccga tcaggcacac tcctcagtgg aaagagctgg gttaattggt ggagtgaaat    2100
taaaagccat cccctcagat ggcaacttcg ccatgcgtgc gtctgccctg caggaagccc    2160
tggagagaga caaagcggct ggcctgattc ctttctttat ggttgccacc ctggggacca    2220
caacatgctg ctcctttgac aatctcttag aagtcggtcc tatctgcaac aaggaagaca    2280
tatggctgca cgttgatgca gcctacgcag gcagtgcatt catctgccct gagttccggc    2340
accttctgaa tggagtggag tttgcagatt cattcaactt taatcccac aaatggctat     2400 tggtgaattt tgactgttct gccatgtggg tgaaaaagag aacagactta acgggagcct    2460
ttagactgga ccccacttac ctgaagcaca gccatcagga ttcagggctt atcactgact    2520
accggcattg gcagatacca ctgggcagaa gatttcgctc tttgaaaatg tggtttgtat    2580
ttaggatgta tggagtcaaa ggactgcagg cttatatccg caagcatgtc cagctgtccc    2640
atgagtttga gtcactggtg cgccaggatc cccgctttga atctgtgtg gaagtcattc     2700 tggggcttgt ctgctttcgg ctaaagggtt ccaacaaagt gaatgaagct cttctgcaaa    2760
gaataaacag tgccaaaaaa atccacttgg ttccatgtca cctcagggac aagtttgtcc    2820
tgcgctttgc catctgttct cgcacggtgg aatctgccca tgtgcagcgg gcctgggaac    2880
acatcaaaga gctggcggcc gacgtgctgc gagcagagag ggagtaggag tgagctgctc    2940
gagagatcta cgggtggcat ccctgtgacc ctccccagt gcctctcctg gccctggaag     3000
ttgccactcc agtgcccacc agccttgtcc taataaaatt aagttgcatc attttgtctg    3060
actaggtgtc cttctataat attatggggt ggaggggggt ggtatggagc aaggggcaag    3120
ttgggaagac aacctgtagg gcctgcgggg tctattggga accaagctgg agtgcagtgg    3180
cacaatcttg gctcactgca atctccgcct cctgggttca agcgattctc ctgcctcagc    3240
ctcccgagtt gttgggattc caggcatgca tgaccaggct cagctaattt ttgtttttt     3300 ggtagagacg gggtttcacc atattggcca ggctggtctc caactcctaa tctcaggtga    3360
tctacccacc ttggcctccc aaattgctgg gattacaggc gtgaaccact gctcccttcc    3420
ctgtccttct gattttgtag gtaaccacgt gcggaccgag cggccgcagt taattaagct    3480
cgcgaaaccc ctagtgatgg agttggccac tccctctctg cgcgctcgct cgctcactga    3540
ggccgggcga ccaaaggtcg cccgacgccc gggctttgcc cggcggcct cagtgagcga    3600 gcgagcgcgc agctgacga tttaaatggt accgagctcg aattcactgg ccgtcgtttt    3660
acaacgtcgt gactgggaaa accctggcgt tacccaactt aatcgccttg cagcacatcc    3720 cccttcgcc agctggcgta atagcgaaga ggcccgcacc gatcgccctt cccaacagtt    3780
gcgcagcctg aatggcgaat ggcgcctgat gcggtatttt ctccttacgc atctgtgcgg    3840
tatttcacac cgcatatggt gcactctcag tacaatctgc tctgatgccg catagttaag    3900
ccagccccga cacccgccaa cacccgctga cgcgccctga cgggcttgtc tgctcccggc    3960
atccgcttac agacaagctg tgaccgtctc agaacccaaa tgtgaccaac cgtttacata    4020
tatcttggtt tattatttca atttctcttt tcaaacatct tcttctgtcg ttgtgcaatt    4080
ttccaaatgc caatttggtc gcttggctat ttccaaacga tttcatatat tcaagttgga    4140
gatatagaca gtcccctgaa cacctcgcat cctctgcttt ttatgcctgc tcgtcctgtg    4200
ggtataattt taatggtcaa atcgctgctg gggaattgta tacgctgctc ttgtgtctca    4260
ctgcctccct tgtagaaatg gaaattgctt tccattatt tccatgtgat tttgttggtt     4320
ttgccatcga attggcattg aaaacgcata aaaataagca tttcgcattt gcaaagatcc    4380
aaaagattta tttgcacgct gagcctgggg atacacgaaa tgtatttgta agattcttca    4440
```

```
gatgagtttg gaacgcacgg aaattaccgt cttgggattt gttggacatc gcatttaagc    4500
atgatgtatc atttaatttt ttccaattta aaaacaaata atcagtgcta cgattaagac    4560
tggatctatt atagacttct tcaaagtttt tcagttttct ttaaaattac ctccataaaa    4620
ctcttttaat attttgaaaa tcatctccag gttacattta atctgattaa gtttagagtc    4680
agttagtttc ccacagtttt cttcttgaaa taaacccatt aagtaacccc aactgatcgg    4740
cgcaaatgat tcagctatgc agaaaatatg attgatgatt tttccctccc accagccctt    4800
aacacttgct taacccttt tgtgtggccat tatagcccct tcctcgtagt ctgcttaaag     4860
ttcattaata agttttgcgt gagccaaaaa tggcgccgct ttggaatcgt gacagcgtgg    4920
aaactctgga ctttggggtt gcaaaacttc ggaagctgaa agcatttttgc tgtagccatc   4980 gcattttggg ggaagaaatc cgaattcgag tccaaaccga attctaatag aagttttgca    5040
gcaaagtgcc tcagacaggt taatgaccaa aagcagtttt gcattcaaat gctgcagcaa    5100
ccctcgcacg agggttgtca tgacggacga aaatctaatt tacaacatgc aactgccact    5160
ttgaggggtg acttttaccc aagacgtggc tgtgaaggaa attctgcgag aaagagatta    5220
attacgctct gggggcagtt aatgaatgct tgcgcggggc gataagggt taacgtttgg     5280 ccagctcaaa ttaccgaatg tataacattt tgatgagcat gacaaaaatt ggaattttca    5340 actcttttt cctgcgaaaa gcataacttt tccattaaca caatggcgac gatgagccgg     5400
caaatcgacg ataccaaatc ggcataacgt gcatgaaaat tatacatgat tgatttcata    5460
ttaatttcta cgaatgttat gaatcggcta aagatgaga atggaaatat tgcacgatt      5520 tgattttgtc atgatgacaa aaaagggttg taagatttgt acatgccaaa atcataaact    5580
tttaacagaa atcaaacaca aagaagtaat ataacattaa agtacacagg ccttgtcaca    5640
gagatagaaa aatgtagcta ttattaaaat atttaacatt ctcttggtgt ctgcaacttt    5700
tctatcagtc gctttttat tccctttcca acacttattt aaaatgaaat gcactcgaaa     5760
ttaactaatt taatggctca tatcctttgt gctgcttaaa aaggcaggaa acgttttttg    5820
tgccctacac ctcctccatt caaatgaaaa aggcggtgga gtcgaggaaa atgtctgccc    5880
tggagcttga caagccaaga tatggcccat caaaaatgtt cgaatgttct ttttaaataa    5940
atgtctcatt atatggctgc cacgcccaca ccgctcaacg cccacacacg tgccgccttc    6000
cggtttagtt gggtggtacc tgaccgtaga ttttcactg cggacatgtg tccaatcagt     6060
ggcaacgtgc aacgaaccgt ggcaaacaca gggaagaac ctcgaagacc cacagcaaac     6120
tcatcctctc gaatttgaca ctatgataat gcttatattc aattttttgc aacattctat    6180
ttacactaaa ctgagaaaca ggacaaagtt gagaatgggt gctgtgatta tttgtcttgt    6240
gccaatatat gccctcctgc atataaaata cgagatacaa aaccaaacga aataagaacg    6300
aacaagaaat cagtttaatt tcaatgctga tcaaaccaag ttgacaactc tgttgtatat    6360
tagctctaat aatgacttaa ggttcgaaat ttaagtaact tccaaaatgg gccagataaa    6420
tactgctaat atcgaatgca attcaatgag gaaatagtaa tcaatcagcc aaccctaatg    6480
aaattaataa tgtaatttaa aactttattc cacccattct aataatgaaa atcattaaat    6540
atatgtagca atccaatttt gttaatacat attgtatatc cctgatttgt caataccaaa    6600
gaccagaaaa aacaccatgc caaattcctt ttattcgttg aaaatcgaaa caactttgaa    6660
gtattaacct gctggctaaa aaatatgtgt attactaaat ataccatgta atcaaaagtt    6720
cgaaataaac gtgaaatggc agctccactc gtcagccgtg ccacttttcg actaatcaaa    6780
```

```
atgccttttg aatgcctgag ttgaatcaag ttggcttaat agttattatc ccacgcaagc    6840
aaagtcaatg gcagagggaa atgcgtagaa attagcacag acttgaatgg acgcacgagt    6900
gtcgaatggc aggagagtgg gaaatgaacg gggagttttc caggataagg atgttttcga    6960
agtatcgtaa tcatttatag cctccagata cgggagctgc atgtgtcaga ggttttcacc    7020
gtcatcaccg aaacgcgcga tgcagctctg gcccgtgtct caaaatctct gatgttacat    7080
tgcacaagat aaaatatat catcatgaac aataaaactg tctgcttaca taaacagtaa    7140
tacaaggggt gttgaagatc ctttgatctt ttctacgggg tctgacgctc agtggaacga    7200
aaactcacgt taagggattt tggtcatgag attatcaaaa aggatcttca cctagatcct    7260
tttaaattaa aaatgaagtt ttaaatcaag cccaatctga ataatgttac aaccaattaa    7320
ccaattctga ttagaaaaac tcatcgagca tcaaatgaaa ctgcaattta ttcatatcag    7380
gattatcaat accatatttt tgaaaaagcc gtttctgtaa tgaaggagaa aactcaccga    7440
ggcagttcca taggatggca agatcctggt atcggtctgc gattccgact cgtccaacat    7500
caatacaacc tattaatttc ccctcgtcaa aaataaggtt atcaagtgag aaatcaccat    7560
gagtgacgac tgaatccggt gagaatggca aaagtttatg catttctttc cagacttgtt    7620
caacaggcca gccattacgc tcgtcatcaa aatcactcgc atcaaccaaa ccgttattca    7680
ttcgtgattg cgcctgagcg agacgaaata cgcgatcgct gttaaaagga caattacaaa    7740
caggaatcga atgcaaccgg cgcaggaaca ctgccagcgc atcaacaata ttttcacctg    7800
aatcaggata ttcttctaat acctggaatg ctgttttttcc ggggatcgca gtggtgagta    7860
accatgcatc atcaggagta cggataaaat gcttgatggt cggaagaggc ataaattccg    7920
tcagccagtt tagtctgacc atctcatctg taacatcatt ggcaacgcta cctttgccat    7980
gtttcagaaa caactctggc gcatcgggct tcccatacaa gcgatagatt gtcgcacctg    8040
attgcccgac attatcgcga gcccatttat acccatataa atcagcatcc atgttggaat    8100
ttaatcgcgg cctcgacgtt tcccgttgaa tatggctcat aacacccctt gtattactgt    8160
ttatgtaagc agacagtttt attgttcatg atgatatatt tttatcttgt gcaatgtaac    8220
atcagagatt tgagacacg ggccagagct gcatcgcgcg ttttcagaat tggttaattg    8280
gttgtaacat tattcagatt gggcttgatt taaaacttca ttttttaattt aaaaggatct    8340 aggtgaagat cctttttgat aatctcatga ccaaaatccc ttaacgtgag ttttcgttcc    8400
actgagcgtc agaccccgta gaaaagatca aggatcttc tttccatagg ctccgccccc    8460
ctgacgagca tcacaaaaat cgacgctcaa gtcagaggtg gcgaaacccg acaggactat    8520
aaagatacca ggcgtttccc cctggaagct ccctcgtgcg ctctcctgtt ccgaccctgc    8580
cgcttaccgg atacctgtcc gcctttctcc cttcgggaag cgtggcgctt tctcatagct    8640
cacgctgtag gtatctcagt tcggtgtagg tcgttcgctc caagctgggc tgtgtgcacg    8700
aaccccccgt tcagcccgac cgctgcgcct tatccggtaa ctatcgtctt gagtccaacc    8760
cggtaagaca cgacttatcg ccactggcag cagccactgg taacaggatt agcagagcga    8820
ggtatgtagg cggtgctaca gagttcttga agtggtggcc taactacggc tacactagaa    8880
gaacagtatt tggtatctgc gctctgctga agccagttac cttcggaaaa agagttggta    8940
gctcttgatc cggcaaacaa accaccgctg gtagcggtgg ttttttgtt tgcaagcagc    9000 agattacgcg cagaaaaaaa ggatctcaaa acgccagcaa gcggcctttt tacggttcc    9060 tggccttttg ctggcctttt gctcacatgt tctttcctgc gttatcccct gattctgtgg    9120
ataaccgtat taccgccttt gagtgagctg ataccgctcg ccgcagccga acgaccgagc    9180
```

<210> SEQ ID NO 12
<211> LENGTH: 6260
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
cccgcgcgtt ggccgattca ttaatgcagc tggcacgaca ggtttcccga ctggaaagcg      60
ggcagtgagc gcaacgcaat tttcacacag gaaacagcta tgaccatgat tacgccaagc     120
ttgcatgcat ttaaatgacg ttggccactc cctctctgcg cgctcgctcg ctcactgagg     180
ccgggcgacc aaaggtcgcc cgacgcccgg gctttgcccg ggcggcctca gtgagcgagc     240
gagcgcgcag agagggagtg gccaactcca tcactagggg ttcctgagtt taaacttcgt     300
cgacgatctg cggccgcacg cgtggagcta gttattaata gtaatcaatt acgggtcat      360
tagttcatag cccatatatg gagttccgcg ttacataact tacggtaaat ggcccgcctg     420
gctgaccgcc caacgacccc cgcccattga cgtcaataat gacgtatgtt cccatagtaa     480
cgtcaatagg gactttccat tgacgtcaat gggtggagta tttacggtaa actgcccact     540
tggcagtaca tcaagtgtat catatgccaa gtacgccccc tattgacgtc aatgacggta     600
aatggcccgc ctggcattat gcccagtaca tgaccttatg ggactttcct acttggcagt     660
acatctacgt attagtcatc gctattacca tggtgatgcg gttttggcag tacatcaatg     720
ggcgtggata gcggtttgac tcacggggat ttccaagtct ccaccccatt gacgtcaatg     780
ggagtttgtt ttgcaccaaa atcaacggga ctttccaaaa tgtcgtaaca actccgcccc     840
attgacgcaa atgggcggta ggcgtgtacg gtgggaggtc tatataagca gagctcgttt     900
agtgaaccgt cagatcgcct ggagacgcca tccacgctgt tttgacctcc atagaagaca     960
ccgggaccga tccagcctcc gcggattcga atcccggccg gaacggtgc attggaacgc     1020
ggattccccg tgccaagagt gacgtaagta ccgcctatag agtctatagg cccacaaaaa    1080
atgctttctt cttttaatat acttttttgt ttatcttatt tctaatactt tccctaatct    1140
ctttctttca gggcaataat gatacaatgt atcatgcctc tttgcaccat tctaaagaat    1200
aacagtgata atttctgggt taaggcaata gcaatatttc tgcatataaa tatttctgca    1260
tataaattgt aactgatgta agaggtttca tattgctaat agcagctaca atccagctac    1320
cattctgctt ttattttatg gttgggataa ggctggatta ttctgagtcc aagctaggcc    1380
cttttgctaa tcatgttcat acctcttatc ttcctcccac agctcctggg caacgtgctg    1440
gtctgtgtgc tggcccatca ctttggcaaa gaattgggat tcgaacatcg ccgccacca    1500
tgaacgccag cgagttcagg aggagggggca aggagatggt ggactacgtg ccaactaca    1560
tggagggcat cgagggcagg caggtgtacc ccgacgtgga gccggctac ctgaggcccc    1620
tgatccccgc cgccgccccc caggagcccg acaccttcga ggacatcatc aacgacgtgg    1680
agaagatcat catgcccggc gtgacccact ggcacagccc ctacttcttc gcctacttcc    1740
ccaccgccag cagctacccc gccatgctgg ccgacatgct gtgcggcgcc atcggctgca    1800
tcggcttcag ctgggccgcc agcccgcct gcaccgagct ggagaccgtg atgatggact    1860
ggctgggcaa gatgctggag ctgcccaagg ccttcctgaa cgagaaggcc ggcgagggcg    1920
gcggcgtgat ccagggcagc gccagcgagg ccaccctggt ggccctgctg gccgccagga    1980
```

```
ccaaggtgat ccacaggctg caggccgcca gccccgagct gacccaggcc gccatcatgg   2040
agaagctggt ggcctacagc agcgaccagg cccacagcag cgtggagagg gccggcctga   2100
tcggcggcgt gaagctgaag gccatcccca gcgacggcaa cttcgccatg agggccagcg   2160
ccctgcagga ggccctggag agggacaagg ccgccggcct gatcccctte ttcatggtgg   2220 ccaccctggg caccaccacc tgctgcagct tcgacaacct gctggaggtg gcccccatct   2280
gcaacaagga ggacatctgg ctgcacgtgg acgccgccta cgccggcagc gccttcatct   2340
gccccgagtt caggcacctg ctgaacggcg tggagttcgc cgacagcttc aacttcaacc   2400
cccacaagtg gctgctggtg aacttcgact gcagcgccat gtgggtgaag aagaggaccg   2460
acctgaccgg cgccttcagg ctggacccca cctacctgaa gcacagccac caggacagcg   2520
gcctgatcac cgactacagg cactggcaga tcccccctggg caggaggttc aggagcctga   2580
agatgtggtt cgtgttcagg atgtacggcg tgaagggcct gcaggcctac atcaggaagc   2640
acgtgcagct gagccacgag ttcgagagcc tggtgaggca ggaccccagg ttcgagatct   2700
gcgtggaggt gatcctgggc ctggtgtgct tcaggctgaa gggcagcaac aaggtgaacg   2760
aggccctgct gcagaggatc aacagcgcca agaagatcca cctggtgccc tgccacctga   2820
gggacaagtt cgtgctgagg ttcgccatct gcagcaggac cgtggagagc gcccacgtgc   2880
agagggcctg ggagcacatc aaggagctgg ccgccgacgt gctgagggcc gagagggagt   2940
gagctgctcg agagatctac gggtggcatc cctgtgaccc ctccccagtg cctctcctgg   3000
ccctggaagt tgccactcca gtgcccacca gccttgtcct aataaaatta agttgcatca   3060
ttttgtctga ctaggtgtcc ttctataata ttatggggtg agggggggtg gtatggagca   3120
aggggcaagt tgggaagaca acctgtaggg cctgcgggt ctattgggaa ccaagctgga   3180
gtgcagtggc acaatcttgg ctcactgcaa tctccgcctc ctgggttcaa gcgattctcc   3240
tgcctcagcc tcccgagttg ttgggattcc aggcatgcat gaccaggctc agctaatttt   3300 tgttttttg gtagagacgg ggtttcacca tattggccag gctggtctcc aactcctaat   3360
ctcaggtgat ctacccacct tggcctccca aattgctggg attacaggcg tgaaccactg   3420
ctcccttccc tgtccttctg attttgtagg taaccacgtg cggaccgagc ggccgcagtt   3480
aattaagctc gcgaaggaac ccctagtgat ggagttggcc actccctctc tgcgcgctcg   3540
ctcgctcact gaggccgggc gaccaaaggt cgcccgacgc ccgggctttg cccgggcggc   3600
ctcagtgagc gagcgagcgc gcagagaggg agtggccaag acgatttaaa tggtaccgag   3660
ctcgaattca ctggccgtcg ttttacaacg tcgtgactgg gaaaaccctg gcgttaccca   3720
acttaatcgc cttgcagcac atccccttt cgccagctgg cgtaatagcg aagaggcccg   3780
caccgatcgc ccttcccaac agttgcgcag cctgaatggc gaatggcgcc tgatgcggta   3840
ttttctcctt acgcatctgt gcggtatttc acaccgcata tggtgcactc tcagtacaat   3900
ctgctctgat gccgcatagt taagccagcc ccgacacccg ccaacacccg ctgacgcgcc   3960
ctgacgggct tgtctgctcc cggcatccgc ttacagacaa gctgtgaccg tctccgggag   4020
ctgcatgtgt cagaggtttt caccgtcatc accgaaacgc gcgatgcagc tctggcccgt   4080
gtctcaaaat ctctgatgtt acattgcaca agataaaaat atatcatcat gaacaataaa   4140
actgtctgct tacataaaca gtaatacaag gggtgttgaa gatcctttga tcttttctac   4200
ggggtctgac gctcagtgga acgaaaactc acgttaaggg attttggtca tgagattatc   4260
aaaaaggatc ttcacctaga tccttttaaa ttaaaaatga agttttaaat caagcccaat   4320
```

```
ctgaataatg ttacaaccaa ttaaccaatt ctgattagaa aaactcatcg agcatcaaat      4380
gaaactgcaa tttattcata tcaggattat caataccata tttttgaaaa agccgtttct      4440
gtaatgaagg agaaaactca ccgaggcagt tccataggat ggcaagatcc tggtatcggt      4500
ctgcgattcc gactcgtcca acatcaatac aacctattaa tttccctcg tcaaaaataa       4560 ggttatcaag tgagaaatca ccatgagtga cgactgaatc cggtgagaat ggcaaaagtt      4620
tatgcatttc tttccagact tgttcaacag gccagccatt acgctcgtca tcaaaatcac      4680
tcgcatcaac caaaccgtta ttcattcgtg attgcgcctg agcgagacga atacgcgat       4740 cgctgttaaa aggacaatta caaacaggaa tcgaatgcaa ccggcgcagg aacactgcca      4800
gcgcatcaac aatattttca cctgaatcag gatattcttc taatacctgg aatgctgttt      4860
ttccggggat cgcagtggtg agtaaccatg catcatcagg agtacggata aaatgcttga      4920
tggtcggaag aggcataaat tccgtcagcc agtttagtct gaccatctca tctgtaacat      4980
cattggcaac gctacctttg ccatgtttca gaaacaactc tggcgcatcg gcttcccat      5040 acaagcgata gattgtcgca cctgattgcc cgacattatc gcgagcccat ttatacccat      5100
ataaatcagc atccatgttg gaatttaatc gcggcctcga cgtttcccgt tgaatatggc      5160
tcataacacc ccttgtatta ctgtttatgt aagcagacag ttttattgtt catgatgata      5220
tatttttatc ttgtgcaatg taacatcaga gattttgaga cacgggccag agctgcatcg      5280
cgcgttttca gaattggtta attggttgta acattattca gattgggctt gatttaaaac      5340 ttcatttta atttaaaagg atctaggtga agatccttt tgataatctc atgaccaaaa       5400
tcccttaacg tgagtttcg ttccactgag cgtcagaccc cgtagaaag atcaaaggat       5460 cttctttcca taggctccgc cccctgacg agcatcacaa aaatcgacgc tcaagtcaga      5520
ggtggcgaaa cccgacagga ctataaagat accaggcgtt tccccctgga agctccctcg      5580
tgcgctctcc tgttccgacc ctgccgctta ccggatacct gtccgccttt ctcccttcgg      5640
gaagcgtggc gctttctcat agctcacgct gtaggtatct cagttcggtg taggtcgttc      5700
gctccaagct gggctgtgtg cacgaaccc ccgttcagcc cgaccgctgc gccttatccg      5760
gtaactatcg tcttgagtcc aacccggtaa gacacgactt atcgccactg gcagcagcca      5820
ctggtaacag gattagcaga gcgaggtatg taggcggtgc tacagagttc ttgaagtggt      5880
ggcctaacta cggctacact agaagaacag tatttggtat ctgcgctctg ctgaagccag      5940
ttaccttcgg aaaagagtt ggtagctctt gatccggcaa acaaaccacc gctggtagcg       6000
gtggtttttt tgtttgcaag cagcagatta cgcgcagaaa aaaaggatct caaaacgcca      6060
gcaacgcggc cttttacgg ttcctggcct tttgctggcc ttttgctcac atgttctttc       6120
ctgcgttatc ccctgattct gtggataacc gtattaccgc ctttgagtga gctgataccg      6180
ctcgccgcag ccgaacgacc gagcgcagcg agtcagtgag cgaggaagcg gaagagcgcc      6240
caatacgcaa accgcctctc                                                  6260
```

<210> SEQ ID NO 13
<211> LENGTH: 6442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
cccgcgcgtt ggccgattca ttaatgcagc tggcacgaca ggtttcccga ctggaaagcg      60
```

```
ggcagtgagc gcaacgcaat tttcacacag gaaacagcta tgaccatgat tacgccaagc    120
ttgcatgcat ttaaatgacg cagctgcgcg ctcgctcgct cactgaggcc gcccgggcaa    180
agcccgggcg tcgggcgacc tttggtcgcc cggcctcagt gagcgagcga gcgcgcagag    240
agggagtggc caactccatc actaggggtt gagtttaaac ttcgtcgacg atctgcggcc    300
gcacgcgtgg agctagttat taatagtaat caattacggg gtcattagtt catagcccat    360
atatggagtt ccgcgttaca taacttacgg taaatggccc gcctggctga ccgcccaacg    420
acccccgccc attgacgtca ataatgacgt atgttcccat agtaacgtca atagggactt    480
tccattgacg tcaatgggtg gagtatttac ggtaaactgc ccacttggca gtacatcaag    540
tgtatcatat gccaagtacg ccccctattg acgtcaatga cggtaaatgg cccgcctggc    600
attatgccca gtacatgacc ttatgggact ttcctacttg gcagtacatc tacgtattag    660
tcatcgctat taccatggtg atgcggtttt ggcagtacat caatgggcgt ggatagcggt    720
ttgactcacg gggatttcca agtctccacc ccattgacgt caatgggagt ttgttttgca    780
ccaaaatcaa cgggactttc caaaatgtcg taacaactcc gccccattga cgcaaatggg    840
cggtaggcgt gtacggtggg aggtctatat aagcagagct cgtttagtga accgtcagat    900
cgcctggaga cgccatccac gctgttttga cctccataga agacaccggg accgatccag    960
cctccgcgga ttcgaatccc ggccgggaac ggtgcattgg aacgcggatt ccccgtgcca    1020
agagtgacgt aagtaccgcc tatagagtct ataggcccac aaaaaatgct tcttcttttt    1080
aatatacttt tttgtttatc ttatttctaa tactttccct aatctctttc tttcagggca    1140
ataatgatac aatgtatcat gcctctttgc accattctaa agaataacag tgataatttc    1200
tgggttaagg caatagcaat atttctgcat ataaatattt ctgcatataa attgtaactg    1260
atgtaagagg tttcatattg ctaatagcag ctacaatcca gctaccattc tgcttttatt    1320
ttatggttgg gataaggctg gattattctg agtccaagct aggcccttt gctaatcatg    1380
ttcatacctc ttatcttcct cccacagctc ctgggcaacg tgctggtctg tgtgctggcc    1440
catcactttg gcaaagaatt gggattcgaa catcgaattc gggcacgagg gaggacagag    1500
agcaagtcac tcccggctgc cttttttcacc tctgacagag cccagacacc atgaacgcaa    1560
gtgaattccg aaggagaggg aaggagatgg tggattacgt ggccaactac atggaaggca    1620
ttgagggacg ccaggtctac cctgacgtgg agcccgggta cctgcggccg ctgatccctg    1680
ccgctgcccc tcaggagcca gacacgtttg aggacatcat caacgacgtt gagaagataa    1740
tcatgcctgg ggtgacgcac tggcacagcc cctacttctt cgcctacttc cccactgcca    1800
gctcgtaccc ggccatgctt gcggacatgc tgtgcggggc cattggctgc atcggcttct    1860
cctgggcggc aagcccagca tgcacagagc tggagactgt gatgatggac tggctcggga    1920
agatgctgga actaccaaag gcattttga atgagaaagc tggagaaggg ggaggagtga    1980
tccagggaag tgccagtgaa gccacccctgg tggccctgct ggccgctcgg accaaagtga    2040
tccatcggct gcaggcagcg tccccagagc tcacacaggc cgctatcatg gagaagctgg    2100
tggcttactc atccgatcag gcacactcct cagtggaaag agctgggtta attggtggag    2160
tgaaattaaa agccatcccc tcagatgcaa acttcgccat gcgtgcgtct gccctgcagg    2220
aagcccctgga gagagacaaa gcggctggcc tgattccttt ctttatggtt gccaccctgg    2280
ggaccacaac atgctgctcc tttgacaatc tcttagaagt cggtcctatc tgcaacaagg    2340
aagacatatg gctgcacgtt gatgcagcct acgcaggcag tgcattcatc tgccctgagt    2400
tccggcacct tctgaatgga gtggagtttg cagattcatt caacttaat ccccacaaat    2460
```

```
ggctattggt gaattttgac tgttctgcca tgtgggtgaa aaagagaaca gacttaacgg   2520
gagcctttag actggacccc acttacctga agcacagcca tcaggattca gggcttatca   2580
ctgactaccg gcattggcag ataccactgg gcagaagatt tcgctctttg aaaatgtggt   2640
ttgtatttag gatgtatgga gtcaaaggac tgcaggctta tatccgcaag catgtccagc   2700
tgtcccatga gtttgagtca ctggtgcgcc aggatccccg ctttgaaatc tgtgtggaag   2760
tcattctggg gcttgtctgc tttcggctaa agggttccaa caaagtgaat gaagctcttc   2820
tgcaaagaat aaacagtgcc aaaaaaatcc acttggttcc atgtcacctc agggacaagt   2880
ttgtcctgcg ctttgccatc tgttctcgca cggtggaatc tgcccatgtg cagcgggcct   2940
gggaacacat caaagagctg gcggccgacg tgctgcgagc agagagggag taggagtgaa   3000
gccagctgca ggaatcaaaa attgaagaga gatatatctg aaaactggaa taagaagcaa   3060
ataaatatca tcctgccttc atggaactca gctgtctgtg gcttcccatg tctttctcca   3120
aagttatcca gagggttgtg attttgtctg cttagtatct catcaacaaa gaaatattat   3180
ttgctaatta aaaagttaat cttcatggcc atagctttta ttcattagct gtgattttg   3240 ttgattaaaa cattatagat tttcatgttc ttgcagtcat cagaagtggt aggaaagcct   3300
cactgatata ttttccaggg caatcaatgt tcacgcaact tgaaattata tctgtggtct   3360
tcaaattgtc ttttgtcatg tggctaaatg cctaataaac aattcaagtg aaatactaaa   3420 aaaaaaaaa aaaaaaaaag ctgctcgaga gatctacggg tggcatccct gtgacccctc   3480
cccagtgcct ctcctggccc tggaagttgc cactccagtg cccaccagcc ttgtcctaat   3540
aaaattaagt tgcatcattt tgtctgacta ggtgtccttc tataatatta tggggtggag   3600
gggggtggta tggagcaagg ggcaagttgg aagacaacc tgtagggcct gcggggtcta   3660
ttgggaacca agctggagtg cagtggcaca atcttggctc actgcaatct ccgcctcctg   3720
ggttcaagcg attctcctgc ctcagcctcc cgagttgttg ggattccagg catgcatgac   3780
caggctcagc taattttttgt tttttggta gagacggggt ttcaccatat tggccaggct   3840
ggtctccaac tcctaatctc aggtgatcta cccaccttgg cctcccaaat tgctgggatt   3900
acaggcgtga accactgctc ccttccctgt ccttctgatt ttgtaggtaa ccacgtgcgg   3960
accgagcggc cgcagttaat taagctcgcg aaacccctag tgatggagtt ggccactccc   4020
tctctgcgcg ctcgctcgct cactgaggcc gggcgaccaa aggtcgcccg acgcccgggc   4080
tttgcccggg cggcctcagt gagcgagcga gcgcgcagct ggacgattta aatggtaccg   4140
agctcgaatt cactggccgt cgttttacaa cgtcgtgact gggaaaaccc tggcgttacc   4200
caacttaatc gccttgcagc acatccccct ttcgccagct ggcgtaatag cgaagaggcc   4260
cgcaccgatc gcccttccca acagttgcgc agcctgaatg gcgaatggcg cctgatgcgg   4320
tattttctcc ttacgcatct gtgcggtatt tcacaccgca tatggtgcac tctcagtaca   4380
atctgctctg atgccgcata gttaagccag ccccgacacc cgccaacacc cgctgacgcg   4440
ccctgacggg cttgtctgct cccggcatcc gcttacagac aagctgtgac cgtctccggg   4500
agctgcatgt gtcagaggtt ttcaccgtca tcaccgaaac gcgcgatgca gctctggccc   4560
gtgtctcaaa atctctgatg ttacattgca caagataaaa atatatcatc atgaacaata   4620
aaactgtctg cttacataaa cagtaataca agggggtgtta tgagccatat tcaacgggaa   4680
acgtcgaggc cgcgattaaa ttccaacatg gatgctgatt tatatgggta taaatgggct   4740
cgcgataatg tcgggcaatc aggtgcgaca atctatcgct tgtatgggaa gcccgatgcg   4800
```

```
ccagagttgt ttctgaaaca tggcaaaggt agcgttgcca atgatgttac agatgagatg    4860
gtcagactaa actggctgac ggaatttatg cctcttccga ccatcaagca ttttatccgt    4920
actcctgatg atgcatggtt actcaccact gcgatcccg gaaaaacagc attccaggta     4980
ttagaagaat atcctgattc aggtgaaaat attgttgatg cgctggcagt gttcctgcgc    5040
cggttgcatt cgattcctgt tgtaattgt ccttttaaca gcgatcgcgt atttcgtctc     5100
gctcaggcgc aatcacgaat gaataacggt ttggttgatg cgagtgattt tgatgacgag    5160
cgtaatggct ggcctgttga acaagtctgg aaagaaatgc ataaactttt gccattctca    5220
ccggattcag tcgtcactca tggtgatttc tcacttgata accttatttt tgacgagggg    5280
aaattaatag gttgtattga tgttggacga gtcggaatcg cagaccgata ccaggatctt    5340
gccatcctat ggaactgcct cggtgagttt tctccttcat acagaaacg gcttttcaa     5400 aaatatggta ttgataatcc tgatatgaat aaattgcagt tcatttgat gctcgatgag     5460 tttttctaat cagaattggt taattggttg taacattatt cagattgggc ttgatttaaa    5520
acttcatttt taatttaaaa ggatctaggt gaagatcctt tttgataatc tcatgaccaa    5580
aatcccttaa cgtgagtttt cgttccactg agcgtcagac cccgtagaaa agatcaaagg    5640
atcttcttga tccttttt ttctgcgcgt aatctgctgc ttgcaaacaa aaaaaccacc      5700
gctaccagcg gtggtttgtt tgccggatca agagctacca actctttttc cgaaggtaac    5760
tggcttcagc agagcgcaga taccaaatac tgttcttcta gtgtagccgt agttaggcca    5820
ccacttcaag aactctgtag caccgcctac atacctcgct ctgctaatcc tgttaccagt    5880
ggctgctgcc agtggcgata gtcgtgtct taccggttg gactcaagac gatagttacc      5940
ggataaggcg cagcggtcgg gctgaacggg gggttcgtgc acacagccca gcttggagcg    6000
aacgacctac accgaactga gatacctaca gcgtgagcta tgagaaagcg ccacgcttcc    6060
cgaagggaga aggcggaca ggtatccggt aagcggcagg gtcggaacag gagagcgcac     6120
gagggagctt ccaggggaa acgcctggta tctttatagt cctgtcgggt ttcgccacct     6180
ctgacttgag cgtcgatttt tgtgatgctc gtcaggggg cggagcctat ggaaaaacgc     6240
cagcaacgcg gcctttttac ggttcctggc cttttgctgg cttttgctc acatgttctt     6300 tcctgcgtta tccctgatt ctgtggataa ccgtattacc gcctttgagt gagctgatac     6360
cgctcgccgc agccgaacga ccgagcgcag cgagtcagtg agcgaggaag cggaagagcg    6420
cccaatacgc aaaccgcctc tc                                              6442
```

<210> SEQ ID NO 14
<211> LENGTH: 9260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
cccgcgcgtt ggccgattca ttaatgcagc tggcacgaca ggtttcccga ctggaaagcg      60
ggcagtgagc gcaacgcaat tttcacacag gaaacagcta tgaccatgat tacgccaagc     120
ttgcatgcat ttaaatgacg ttggccactc cctctctgcg cgctcgctcg ctcactgagg     180
ccgggcgacc aaaggtcgcc cgacgcccgg gctttgcccg gcggcctca gtgagcgagc      240 gagcgcgcag agagggagtg gccaactcca tcactagggg ttcctgagtt taaacttcgt     300
cgacgatctg cggccgcacg cgtggagcta gttattaata gtaatcaatt acggggtcat     360
```

```
tagttcatag cccatatatg gagttccgcg ttacataact tacggtaaat ggcccgcctg    420
gctgaccgcc caacgacccc cgcccattga cgtcaataat gacgtatgtt cccatagtaa    480
cgtcaatagg gactttccat tgacgtcaat gggtggagta tttacggtaa actgcccact    540
tggcagtaca tcaagtgtat catatgccaa gtacgcccc tattgacgtc aatgacggta    600
aatggcccgc ctggcattat gcccagtaca tgaccttatg ggactttcct acttggcagt    660
acatctacgt attagtcatc gctattacca tggtgatgcg gttttggcag tacatcaatg    720
ggcgtggata gcggtttgac tcacggggat ttccaagtct ccaccccatt gacgtcaatg    780
ggagtttgtt ttgcaccaaa atcaacggga ctttccaaaa tgtcgtaaca actccgcccc    840
attgacgcaa atgggcggta ggcgtgtacg gtgggaggtc tatataagca gagctcgttt    900
agtgaaccgt cagatcgcct ggagacgcca tccacgctgt tttgacctcc atagaagaca    960
ccgggaccga tccagcctcc gcggattcga atcccggccg gaacggtgc attggaacgc    1020 ggattccccg tgccaagagt gacgtaagta ccgcctatag agtctatagg cccacaaaaa    1080
atgctttctt ctttaatat actttttgt ttatcttatt tctaatactt tccctaatct    1140
ctttctttca gggcaataat gatacaatgt atcatgcctc tttgcaccat tctaaagaat    1200
aacagtgata atttctgggt taaggcaata gcaatatttc tgcatataaa tatttctgca    1260
tataaattgt aactgatgta agaggtttca tattgctaat agcagctaca atccagctac    1320
cattctgctt ttattttatg gttgggataa ggctggatta ttctgagtcc aagctaggcc    1380
cttttgctaa tcatgttcat acctcttatc ttcctcccac agctcctggg caacgtgctg    1440
gtctgtgtgc tggcccatca ctttggcaaa gaattgggat tcgaacatcg ccgccacca    1500 tgaacgccag cgagttcagg aggaggggca aggagatggt ggactacgtg ccaactaca    1560 tggagggcat cgagggcagg caggtgtacc ccgacgtgga gcccggctac ctgaggcccc    1620
tgatccccgc cgccgccccc caggagcccg acaccttcga ggacatcatc aacgacgtgg    1680
agaagatcat catgcccggc gtgacccact ggcacagccc ctacttcttc gcctacttcc    1740
ccaccgccag cagctacccc gccatgctgg ccgacatgct gtgcggcgcc atcggctgca    1800
tcggcttcag ctgggccgcc agcccgcct gcaccgagct ggagaccgtg atgatggact    1860
ggctgggcaa gatgctggag ctgcccaagg ccttcctgaa cgagaaggcc ggcgagggcg    1920
gcggcgtgat ccagggcagc gccagcgagg ccacccctggt ggccctgctg ccgccagga    1980 ccaaggtgat ccacaggctg caggccgcca gccccgagct gacccaggcc gccatcatgg    2040
agaagctggt ggcctacagc agcgaccagg cccacagcag cgtggagagg gccggcctga    2100
tcggcggcgt gaagctgaag gccatcccca gcgacggcaa cttcgccatg agggccagcg    2160
ccctgcagga ggccctggag agggacaagg ccgccggcct gatcccctc ttcatggtgg    2220 ccaccctggg caccaccacc tgctgcagct tcgacaacct gctggaggtg ggccccatct    2280
gcaacaagga ggacatctgg ctgcacgtgg acgccgccta cgccggcagc gccttcatct    2340
gccccgagtt caggcacctg ctgaacggcg tggagttcgc cgacagcttc aacttcaacc    2400
cccacaagtg gctgctggtg aacttcgact gcagcgccat gtgggtgaag aagaggaccg    2460
acctgaccgg cgccttcagg ctggaccca cctacctgaa gcacagccac caggacagcg    2520
gcctgatcac cgactacagg cactggcaga tccccctggg caggaggttc aggagcctga    2580
agatgtggtt cgtgttcagg atgtacggcg tgaagggcct gcaggcctac atcaggaagc    2640
acgtgcagct gagccacgag ttcgagagcc tggtgaggca ggaccccagg ttcgagatct    2700
gcgtggaggt gatcctgggc ctggtgtgct tcaggctgaa gggcagcaac aaggtgaacg    2760
```

```
aggccctgct gcagaggatc aacagcgcca agaagatcca cctggtgccc tgccacctga    2820
gggacaagtt cgtgctgagg ttcgccatct gcagcaggac cgtggagagc gcccacgtgc    2880
agagggcctg ggagcacatc aaggagctgg ccgccgacgt gctgagggcc gagagggagt    2940
gagctgctcg agagatctac gggtggcatc cctgtgaccc ctccccagtg cctctcctgg    3000
ccctggaagt tgccactcca gtgcccacca gccttgtcct aataaaatta agttgcatca    3060
ttttgtctga ctaggtgtcc ttctataata ttatggggtg aggggggtg gtatggagca     3120 aggggcaagt tgggaagaca acctgtaggg cctgcggggt ctattgggaa ccaagctgga    3180
gtgcagtggc acaatcttgg ctcactgcaa tctccgcctc ctgggttcaa gcgattctcc    3240
tgcctcagcc tcccgagttg ttgggattcc aggcatgcat gaccaggctc agctaatttt    3300 tgttttttg gtagagacgg ggtttcacca tattggccag gctggtctcc aactcctaat     3360
ctcaggtgat ctacccacct tggcctccca aattgctggg attacaggcg tgaaccactg    3420
ctcccttccc tgtccttctg attttgtagg taaccacgtg cggaccgagc ggccgcagtt    3480
aattaagctc gcgaaggaac ccctagtgat ggagttggcc actccctctc tgcgcgctcg    3540
ctcgctcact gaggccgggc gaccaaaggt cgcccgacgc ccgggctttg cccgggcggc    3600
ctcagtgagc gagcgagcgc gcagagaggg agtggccaag acgatttaaa tggtaccgag    3660
ctcgaattca ctggccgtcg ttttacaacg tcgtgactgg gaaaaccctg gcgttaccca    3720
acttaatcgc cttgcagcac atcccccttt cgccagctgg cgtaatagcg aagaggcccg    3780
caccgatcgc ccttcccaac agttgcgcag cctgaatggc gaatggcgcc tgatgcggta    3840
ttttctcctt acgcatctgt gcggtatttc acaccgcata tggtgcactc tcagtacaat    3900
ctgctctgat gccgcatagt taagccagcc ccgacacccg ccaacacccg ctgacgcgcc    3960
ctgacgggct tgtctgctcc cggcatccgc ttacagacaa gctgtgaccg tctcagaacc    4020
caaatgtgac caaccgttta catatatctt ggtttattat ttcaatttct cttttcaaac    4080
atcttcttct gtcgttgtgc aattttccaa atgccaattt ggtcgcttgg ctatttccaa    4140
acgatttcat atattcaagt tggagatata gacagtcccc tgaacacctc gcatcctctg    4200 cttttatgc ctgctcgtcc tgtgggtata attttaatgg tcaaatcgct gctggggaat     4260
tgtatacgct gctcttgtgt ctcactgcct cccttgtaga aatggaaatt gcttttccat    4320
tatttccatg tgattttgtt ggttttgcca tcgaattggc attgaaaacg cataaaaata    4380
agcatttcgc atttgcaaag atccaaaaga tttatttgca cgctgagcct ggggatacac    4440
gaaatgtatt tgtaagattc ttcagatgag tttggaacgc acggaaatta ccgtcttggg    4500
atttgttgga catcgcattt aagcatgatg tatcatttaa tttttttccaa tttaaaaaca   4560 aataatcagt gctacgatta agactggatc tattatagac ttcttcaaag tttttcagtt    4620
ttctttaaaa ttacctccat aaaactcttt taatatttg aaaatcatct ccaggttaca     4680
tttaatctga ttaagtttag agtcagttag ttttcccacag ttttcttctt gaataaaacc   4740
cattaagtaa ccccaactga tcggcgcaaa tgattcagct atgcagaaaa tatgattgat    4800 gattttccc tcccaccagc ccttaacact tgcttaaccc ttttgtgtgg ccattatagc     4860
cctttcctcg tagtctgctt aaagttcatt aataagtttt gcgtgagcca aaaatggcgc    4920
cgctttggaa tcgtgacagc gtggaaactc tggactttgg ggttgcaaaa cttcggaagc    4980
tgaaagcatt ttgctgtagc catcgcattt tgggggaaga aatccgaatt cgagtccaaa    5040
ccgaattcta atagaagttt tgcagcaaag tgcctcagac aggttaatga ccaaaagcag    5100
```

```
ttttgcattc aaatgctgca gcaaccctcg cacgagggtt gtcatgacgg acgaaaatct    5160
aatttacaac atgcaactgc cactttgagg ggtgacttt  acccaagacg tggctgtgaa    5220
ggaaattctg cgagaaagag attaattacg ctctggggc  agttaatgaa tgcttgcgcg    5280
gggcgataag gggttaacgt ttggccagct caaattaccg aatgtataac attttgatga    5340
gcatgacaaa aattggaatt ttcaactctt ttttcctgcg aaaagcataa cttttccatt    5400
aacacaatgg cgacgatgag ccggcaaatc gacgatacca aatcggcata acgtgcatga    5460
aaattataca tgattgattt catattaatt tctacgaatg ttatgaatcg gctaaaagat    5520
gagaatggaa atattgcacg attttgattt tgtcatgatg acaaaaaagg gttgtaagat    5580
ttgtacatgc caaaatcata aacttttaac agaaatcaaa cacaagaag  taatataaca    5640 ttaaagtaca caggccttgt cacagagata gaaaaatgta gctattatta aaatatttaa    5700
cattctcttg gtgtctgcaa cttttctatc agtcgctttt ttattccctt tccaacactt    5760
atttaaaatg aaatgcactc gaaattaact aatttaatgg ctcatatcct ttgtgctgct    5820
taaaaaggca ggaaacgttt tttgtgccct cacctcctc  cattcaaatg aaaaaggcgg    5880
tggagtcgag gaaaatgtct gccctggagc ttgacaagcc aagatatggc ccatcaaaaa    5940
tgttcgaatg ttctttttaa ataaatgtct cattatatgg ctgccacgcc cacaccgctc    6000
aacgcccaca cacgtgccgc cttccggttt agttgggtgg tacctgaccg tagattttc    6060 actgcggaca tgtgtccaat cagtggcaac gtgcaacgaa ccgtggcaaa cagggaaa     6120 gaacctcgaa gacccacagc aaactcatcc tctcgaattt gacactatga taatgcttat    6180 attcaattt  ttgcaacatt ctatttacac taaactgaga acaggacaa  agttgagaat    6240 gggtgctgtg attatttgtc ttgtgccaat atatgccctc ctgcatataa aatacgagat    6300
acaaaaccaa acgaaataag aacgaacaag aaatcagttt aatttcaatg ctgatcaaac    6360
caagttgaca actctgttgt atattagctc taataatgac ttaaggttcg aaatttaagt    6420
aacttccaaa atgggccaga taaatactgc taatatcgaa tgcaattcaa tgaggaaata    6480
gtaatcaatc agccaaccct aatgaaatta ataatgtaat ttaaaacttt attccaccca    6540
ttctaataat gaaaatcatt aaatatatgt agcaatccaa ttttgttaat acatattgta    6600
tatccctgat ttgtcaatac caaagaccag aaaaaacacc atgccaaatt cctttattc    6660 gttgaaaatc gaaacaactt tgaagtatta acctgctggc taaaaatat  gtgtattact    6720 aaatatacca tgtaatcaaa agttcgaaat aaacgtgaaa tggcagctcc actcgtcagc    6780
cgtgccactt ttcgactaat caaaatgcct tttgaatgcc tgagttgaat caagttggct    6840
taatagttat tatcccacgc aagcaaagtc aatggcagag ggaaatgcgt agaaattagc    6900
acagacttga atggacgcac gagtgtcgaa tggcaggaga gtgggaaatg aacgggagt    6960 tttccaggat aaggatgttt tcgaagtatc gtaatcattt atagcctcca gatacgggag    7020
ctgcatgtgt cagaggtttt caccgtcatc accgaaacgc gcgatgcagc tctgccccgt    7080
gtctcaaaat ctctgatgtt acattgcaca agataaaaat atatcatcat gaacaataaa    7140
actgtctgct tacataaaca gtaatacaag gggtgttgaa gatcctttga tcttttctac    7200
ggggtctgac gctcagtgga acgaaaactc acgttaaggg attttggtca tgagattatc    7260
aaaaaggatc ttcacctaga tccttttaaa ttaaaatga  agttttaaat caagcccaat    7320
ctgaataatg ttacaaccaa ttaaccaatt ctgattagaa aaactcatcg agcatcaaat    7380
gaaactgcaa tttattcata tcaggattat caataccata tttttgaaaa agccgtttct    7440
gtaatgaagg agaaaactca ccgaggcagt tccataggat ggcaagatcc tggtatcggt    7500
```

```
ctgcgattcc gactcgtcca acatcaatac aacctattaa tttcccctcg tcaaaataa      7560 ggttatcaag tgagaaatca ccatgagtga cgactgaatc cggtgagaat ggcaaaagtt     7620
tatgcatttc tttccagact tgttcaacag gccagccatt acgctcgtca tcaaaatcac     7680
tcgcatcaac caaaccgtta ttcattcgtg attgcgcctg agcgagacga aatacgcgat     7740
cgctgttaaa aggacaatta caaacaggaa tcgaatgcaa ccggcgcagg aacactgcca     7800
gcgcatcaac aatattttca cctgaatcag gatattcttc taatacctgg aatgctgttt     7860
ttccggggat cgcagtggtg agtaaccatg catcatcagg agtacggata aaatgcttga     7920
tggtcggaag aggcataaat tccgtcagcc agtttagtct gaccatctca tctgtaacat     7980
cattggcaac gctacctttg ccatgtttca gaaacaactc tggcgcatcg gcttcccat     8040 acaagcgata gattgtcgca cctgattgcc cgacattatc gcgagcccat ttatacccat     8100
ataaatcagc atccatgttg gaatttaatc gcggcctcga cgtttcccgt tgaatatggc     8160
tcataacacc cctttgtatta ctgtttatgt aagcagacag ttttattgtt catgatgata    8220
tatttttatc ttgtgcaatg taacatcaga gattttgaga cacgggccag agctgcatcg     8280
cgcgttttca gaattggtta attggttgta acattattca gattgggctt gatttaaaac     8340
ttcattttta atttaaaagg atctaggtga agatccttt tgataatctc atgaccaaaa      8400
tcccttaacg tgagttttcg ttccactgag cgtcagaccc cgtagaaaag atcaaaggat     8460 cttcttttcca taggctccgc cccctgacg agcatcacaa aaatcgacgc tcaagtcaga    8520
ggtggcgaaa cccgacagga ctataaagat accaggcgtt tccccctgga agctccctcg     8580
tgcgctctcc tgttccgacc ctgccgctta ccggatacct gtccgccttt ctcccttcgg     8640
gaagcgtggc gctttctcat agctcacgct gtaggtatct cagttcggtg taggtcgttc     8700
gctccaagct gggctgtgtg cacgaacccc ccgttcagcc cgaccgctgc gccttatccg     8760
gtaactatcg tcttgagtcc aacccggtaa gacacgactt atcgccactg gcagcagcca     8820
ctggtaacag gattagcaga gcgaggtatg taggcggtgc tacagagttc ttgaagtggt     8880
ggcctaacta cggctacact agaagaacag tatttggtat ctgcgctctg ctgaagccag     8940
ttaccttcgg aaaaagagtt ggtagctctt gatccggcaa acaaaccacc gctggtagcg     9000
gtggtttttt tgtttgcaag cagcagatta cgcgcagaaa aaaaggatct caaaacgcca     9060
gcaacgcggc cttttttacgg ttcctggcct tttgctggcc ttttgctcac atgttctttc     9120
ctgcgttatc ccctgattct gtggataacc gtattaccgc ctttgagtga gctgataccg     9180
ctcgccgcag ccgaacgacc gagcgcagcg agtcagtgag cgaggaagcg gaagagcgcc     9240
caatacgcaa accgcctctc                                                9260
```

<210> SEQ ID NO 15
<211> LENGTH: 9665
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
cccgcgcgtt ggccgattca ttaatgcagc tggcacgaca ggtttcccga ctggaaagcg      60
ggcagtgagc gcaacgcaat tttcacacag gaaacagcta tgaccatgat tacgccaagc     120
ttgcatgcat ttaaatgacg ttggccactc cctctctgcg cgctcgctcg ctcactgagg     180
ccgggcgacc aaaggtcgcc cgacgcccgg gctttgcccg gcggcctca gtgagcgagc      240
```

-continued

| | |
|---|---|
| gagcgcgcag agagggagtg gccaactcca tcactagggg ttcctgagtt taaacttcgt | 300 |
| cgacgatctg cggccgcacg cgtggagcta gttattaata gtaatcaatt acggggtcat | 360 |
| tagttcatag cccatatatg gagttccgcg ttacataact tacggtaaat ggcccgcctg | 420 |
| gctgaccgcc caacgacccc cgcccattga cgtcaataat gacgtatgtt cccatagtaa | 480 |
| cgtcaatagg gactttccat tgacgtcaat gggtggagta tttacggtaa actgcccact | 540 |
| tggcagtaca tcaagtgtat catatgccaa gtacgccccc tattgacgtc aatgacggta | 600 |
| aatggcccgc ctggcattat gcccagtaca tgaccttatg ggactttcct acttggcagt | 660 |
| acatctacgt attagtcatc gctattacca tggtgatgcg gttttggcag tacatcaatg | 720 |
| ggcgtggata gcggtttgac tcacggggat ttccaagtct ccaccccatt gacgtcaatg | 780 |
| ggagtttgtt ttgcaccaaa atcaacggga ctttccaaaa tgtcgtaaca actccgcccc | 840 |
| attgacgcaa atgggcggta ggcgtgtacg gtgggaggtc tatataagca gagctcgttt | 900 |
| agtgaaccgt cagatcgcct ggagacgcca tccacgctgt tttgacctcc atagaagaca | 960 |
| ccgggaccga tccagcctcc gcggattcga atcccggccg ggaacggtgc attggaacgc | 1020 |
| ggattccccg tgccaagagt gacgtaagta ccgcctatag agtctatagg cccacaaaaa | 1080 |
| atgctttctt cttttaatat actttttgt ttatcttatt tctaatactt tccctaatct | 1140 |
| ctttctttca gggcaataat gatacaatgt atcatgcctc tttgcaccat tctaaagaat | 1200 |
| aacagtgata atttctgggt taaggcaata gcaatatttc tgcatataaa tatttctgca | 1260 |
| tataaattgt aactgatgta agaggtttca tattgctaat agcagctaca atccagctac | 1320 |
| cattctgctt ttattttatg gttgggataa ggctggatta ttctgagtcc aagctaggcc | 1380 |
| cttttgctaa tcatgttcat acctcttatc ttcctcccac agctcctggg caacgtgctg | 1440 |
| gtctgtgtgc tggcccatca ctttggcaaa gaattgggat tcgaacatcg ccgccacca | 1500 |
| tgaacgcaag tgaattccga aggagaggga aggagatggt ggattacgtg gccaactaca | 1560 |
| tggaaggcat tgagggacgc caggtctacc ctgacgtgga gcccgggtac ctgcggccgc | 1620 |
| tgatccctgc cgctgcccct caggagccag acacgtttga ggacatcatc aacgacgttg | 1680 |
| agaagataat catgcctggg gtgacgcact ggcacagccc ctacttcttc gcctacttcc | 1740 |
| ccactgccag ctcgtacccg gccatgcttg cggacatgct gtgcggggcc attggctgca | 1800 |
| tcggcttctc ctgggcggca agcccagcat gcacagagct ggagactgtg atgatggact | 1860 |
| ggctcgggaa gatgctggaa ctaccaaagg cattttttgaa tgagaaagct ggagaagggg | 1920 |
| gaggagtgat ccagggaagt gccagtgaag ccaccctggt ggccctgctg ccgctcgga | 1980 |
| ccaaagtgat ccatcggctg caggcagcgt ccccagagct cacacaggcc gctatcatgg | 2040 |
| agaagctggt ggcttactca tccgatcagg cacactcctc agtggaaaga gctgggttaa | 2100 |
| ttggtggagt gaaattaaaa gccatcccct cagatggcaa cttcgccatg cgtgcgtctg | 2160 |
| ccctgcagga gccctggag agagacaaag cggctggcct gattcctttc tttatggttg | 2220 |
| ccaccctggg gaccacaaca tgctgctcct ttgacaatct cttagaagtc ggtcctatct | 2280 |
| gcaacaagga agacatatgg ctgcacgttg atgcagccta cgcaggcagt gcattcatct | 2340 |
| gccctgagtt ccggcacctt ctgaatggag tggagtttgc agattcattc aactttaatc | 2400 |
| cccacaaatg gctattggtg aattttgact gttctgccat gtgggtgaaa aagagaacag | 2460 |
| acttaacggg agcctttaga ctggacccca cttacctgaa gcacagccat caggattcag | 2520 |
| ggcttatcac tgactaccgg cattggcaga taccactggg cagaagattt cgctctcttga | 2580 |

```
aaatgtggtt tgtatttagg atgtatggag tcaaaggact gcaggcttat atccgcaagc    2640
atgtccagct gtcccatgag tttgagtcac tggtgcgcca ggatccccgc tttgaaatct    2700
gtgtggaagt cattctgggg cttgtctgct ttcggctaaa gggttccaac aaagtgaatg    2760
aagctcttct gcaaagaata aacagtgcca aaaaaatcca cttggttcca tgtcacctca    2820
gggacaagtt tgtcctgcgc tttgccatct gttctcgcac ggtggaatct gcccatgtgc    2880
agcgggcctg gaacacatc aaagagctgg cggccgacgt gctgcgagca gagagggagt     2940
aggagtgaag ccagctgcag gaatcaaaaa ttgaagagag atatatctga aaactggaat    3000
aagaagcaaa taaatatcat cctgccttca tggaactcag ctgtctgtgg cttcccatgt    3060 cttctccaa agttatccag agggttgtga ttttgtctgc ttagtatctc atcaacaaag     3120
aaatattatt tgctaattaa aaagttaatc ttcatggcca tagcttttat tcattagctg    3180 tgattttgt tgattaaaac attatagatt ttcatgttct tgcagtcatc agaagtggta     3240
ggaaagcctc actgatatat tttccagggc aatcaatgtt cacgcaactt gaaattatat    3300
ctgtggtctt caaattgtct tttgtcatgt ggctaaatgc ctaataagct gctcgagaga    3360
tctacgggtg gcatccctgt gacccctccc cagtgcctct cctggccctg gaagttgcca    3420
ctccagtgcc caccagcctt gtcctaataa aattaagttg catcattttg tctgactagg    3480
tgtccttcta taatattatg gggtggaggg gggtggtatg gagcaagggg caagttggga    3540
agacaacctg tagggcctgc ggggtctatt gggaaccaag ctggagtgca gtggcacaat    3600
cttggctcac tgcaatctcc gcctcctggg ttcaagcgat tctcctgcct cagcctcccg    3660
agttgttggg attccaggca tgcatgacca ggctcagcta attttgttt ttttggtaga     3720 gacggggttt caccatattg gccaggctgg tctccaactc ctaatctcag gtgatctacc    3780
caccttggcc tcccaaattg ctgggattac aggcgtgaac cactgctccc ttccctgtcc    3840
ttctgatttt gtaggtaacc acgtgcggac cgagcggccg cagttaatta agctcgcgaa    3900 ggaacccta gtgatggagt tggccactcc ctctctgcgc gctcgctcgc tcactgaggc     3960
cgggcgacca aaggtcgccc gacgcccggg ctttgcccgg gcggcctcag tgagcgagcg    4020
agcgcgcaga gagggagtgg ccaagacgat ttaaatggta ccgagctcga attcactggc    4080
cgtcgtttta caacgtcgtg actgggaaaa ccctggcgtt acccaactta atcgccttgc    4140
agcacatccc cctttcgcca gctggcgtaa tagcgaagag gcccgcaccg atcgcccttc    4200
ccaacagttg cgcagcctga atggcgaatg gcgcctgatg cggtattttc tccttacgca    4260
tctgtgcggt atttcacacc gcatatggtg cactctcagt acaatctgct ctgatgccgc    4320
atagttaagc cagccccgac acccgccaac acccgctgac gcgccctgac gggcttgtct    4380
gctcccggca tccgcttaca gacaagctgt gaccgtctca gacccaaat gtgaccaacc     4440 gtttacatat atcttggttt attatttcaa tttctctttt caaacatctt cttctgtcgt    4500
tgtgcaattt tccaaatgcc aatttggtcg cttggctatt ccaaacgat ttcatatatt     4560 caagttggag atatagacag tcccctgaac acctcgcatc ctctgctttt tatgcctgct    4620
cgtcctgtgg gtataatttt aatggtcaaa tcgctgctgg ggaattgtat acgctgctct    4680
tgtgtctcac tgcctcccctt gtagaaatgg aaattgcttt tccattattt ccatgtgatt    4740
ttgttggttt tgccatcgaa ttggcattga aaacgcataa aaataagcat ttcgcatttg    4800
caaagatcca aaagatttat ttgcacgctg agcctgggga tacacgaaat gtatttgtaa    4860
gattcttcag atgagtttgg aacgcacgga aattaccgtc ttgggatttg ttggacatcg    4920
catttaagca tgatgtatca tttaattttt tccaatttaa aaacaaataa tcagtgctac    4980
```

```
gattaagact ggatctatta tagacttctt caaagttttt cagttttctt taaaattacc      5040
tccataaaac tcttttaata ttttgaaaat catctccagg ttacatttaa tctgattaag      5100
tttagagtca gttagtttcc cacagttttc ttcttgaaat aaacccatta agtaacccca      5160
actgatcggc gcaaatgatt cagctatgca gaaaatatga ttgatgattt ttccctccca      5220
ccagcccttn acacttgctt aacccttttg tgtggccatt atagcccttt cctcgtagtc      5280
tgcttaaagt tcattaataa gttttgcgtg agccaaaaat ggcgccgctt tggaatcgtg      5340
acagcgtgga aactctggac tttggggttg caaaacttcg gaagctgaaa gcattttgct      5400
gtagccatcg cattttgggg gaagaaatcc gaattcgagt ccaaaccgaa ttctaataga      5460
agttttgcag caaagtgcct cagacaggtt aatgaccaaa agcagttttg cattcaaatg      5520
ctgcagcaac cctcgcacga gggttgtcat gacggacgaa aatctaattt acaacatgca      5580
actgccactt tgaggggtga cttttaccca agacgtggct gtgaaggaaa ttctgcgaga      5640
aagagattaa ttacgctctg ggggcagtta atgaatgctt gcgcggggcg ataagggggtt      5700 aacgtttggc cagctcaaat taccgaatgt ataacatttt gatgagcatg acaaaaattg      5760
gaattttcaa ctcttttttc ctgcgaaaag cataactttt ccattaacac aatggcgacg      5820
atgagccggc aaatcgacga taccaaatcg gcataacgtg catgaaaatt atacatgatt      5880
gatttcatat taatttctac gaatgttatg aatcggctaa aagatgagaa tggaaatatt      5940
gcacgatttt gattttgtca tgatgacaaa aaagggttgt aagatttgta catgccaaaa      6000
tcataaactt ttaacagaaa tcaaacacaa agaagtaata taacattaaa gtacacaggc      6060
cttgtcacag agatagaaaa atgtagctat tattaaaata tttaacattc tcttggtgtc      6120 tgcaacttttt ctatcagtcg cttttttatt cccttttccaa cacttattta aaatgaaatg      6180
cactcgaaat taactaattt aatggctcat atcctttgtg ctgcttaaaa aggcaggaaa      6240
cgttttttgt gccctacacc tcctccattc aaatgaaaaa ggcggtggag tcgaggaaaa      6300
tgtctgccct ggagcttgac aagccaagat atggcccatc aaaaatgttc gaatgttctt      6360
tttaaataaa tgtctcatta tatggctgcc acgcccacac cgctcaacgc ccacacacgt      6420
gccgccttcc ggtttagttg ggtggtacct gaccgtagat ttttcactgc ggacatgtgt      6480
ccaatcagtg gcaacgtgca acgaaccgtg gcaaacacag ggaagaaacc tcgaagaccc      6540
acagcaaact catcctctcg aatttgacac tatgataatg cttatattca atttttgca      6600 acattctatt tacactaaac tgagaaacag gacaaagttg agaatgggtg ctgtgattat      6660
ttgtcttgtg ccaatatatg ccctcctgca tataaaatac gagatacaaa accaaacgaa      6720
ataagaacga acaagaaatc agtttaattt caatgctgat caaaccaagt tgacaactct      6780
gttgtatatt agctctaata atgacttaag gttcgaaatt taagtaactt ccaaaatggg      6840
ccagataaat actgctaata tcgaatgcaa ttcaatgagg aaatagtaat caatcagcca      6900
accctaatga aattaataat gtaatttaaa actttattcc acccattcta ataatgaaaa      6960
tcattaaata tatgtagcaa tccaattttg ttaatacata ttgtatatcc ctgatttgtc      7020
aataccaaag accagaaaaa acaccatgcc aaattccttt tattcgttga aaatcgaaac      7080
aactttgaag tattaacctg ctggctaaaa aatatgtgta ttactaaata taccatgtaa      7140
tcaaaagttc gaaataaacg tgaaatggca gctccactcg tcagccgtgc cacttttcga      7200
ctaatcaaaa tgccttttga atgcctgagt tgaatcaagt tggcttaata gttattatcc      7260
cacgcaagca aagtcaatgg cagagggaaa tgcgtagaaa ttagcacaga cttgaatgga      7320
```

```
cgcacgagtg tcgaatggca ggagagtggg aaatgaacgg ggagttttcc aggataagga    7380
tgttttcgaa gtatcgtaat catttatagc ctccagatac gggagctgca tgtgtcagag    7440
gttttcaccg tcatcaccga aacgcgcgat gcagctctgg cccgtgtctc aaaatctctg    7500
atgttacatt gcacaagata aaatatatc atcatgaaca ataaaactgt ctgcttacat     7560
aaacagtaat acaaggggtg ttgaagatcc tttgatcttt tctacggggt ctgacgctca    7620
gtggaacgaa aactcacgtt aagggatttt ggtcatgaga ttatcaaaaa ggatcttcac    7680
ctagatcctt ttaaattaaa aatgaagttt taaatcaagc ccaatctgaa taatgttaca    7740
accaattaac caattctgat tagaaaaact catcgagcat caaatgaaac tgcaattat    7800 tcatatcagg attatcaata ccatattttt gaaaaagccg tttctgtaat gaaggagaaa    7860
actcaccgag gcagttccat aggatggcaa gatcctggta tcggtctgcg attccgactc    7920
gtccaacatc aatacaacct attaatttcc cctcgtcaaa aataaggtta tcaagtgaga    7980
aatcaccatg agtgacgact gaatccggtg agaatggcaa agtttatgc atttctttcc    8040 agacttgttc aacaggccag ccattacgct cgtcatcaaa atcactcgca tcaaccaaac    8100
cgttattcat tcgtgattgc gcctgagcga gacgaaatac gcgatcgctg ttaaaaggac    8160
aattacaaac aggaatcgaa tgcaaccggc gcaggaacac tgccagcgca tcaacaatat    8220
tttcacctga atcaggatat tcttctaata cctggaatgc tgttttcg gggatcgcag     8280 tggtgagtaa ccatgcatca tcaggagtac ggataaaatg cttgatgtc ggaagaggca    8340 taaattccgt cagccagttt agtctgacca tctcatctgt aacatcattg gcaacgctac    8400
ctttgccatg tttcagaaac aactctggcg catcgggctt cccatacaag cgatagattg    8460
tcgcacctga ttgcccgaca ttatcgcgag cccatttata cccatataaa tcagcatcca    8520
tgttggaatt taatcgcggc ctcgacgttt cccgttgaat atggctcata caccccttg    8580 tattactgtt tatgtaagca gacagttta ttgttcatga tgatatattt ttatcttgtg    8640
caatgtaaca tcagagattt tgagacacgg gccagcagctg catcgcgcgt tttcagaatt    8700
ggttaattgg ttgtaacatt attcagattg ggcttgattt aaaacttcat ttttaattta    8760
aaaggatcta ggtgaagatc ctttttgata atctcatgac caaaatccct taacgtgagt    8820
tttcgttcca ctgagcgtca gaccccgtag aaaagatcaa aggatcttct tccataggc    8880 tccgcccccc tgacgagcat cacaaaaatc gacgctcaag tcagaggtgg cgaaacccga    8940
caggactata aagataccag gcgtttcccc ctggaagctc cctcgtgcgc tctcctgttc    9000
cgaccctgcc gcttaccgga tacctgtccg ccttctccc ttcgggaagc gtggcgcttt    9060
ctcatagctc acgctgtagg tatctcagtt cggtgtaggt cgttcgctcc aagctgggct    9120
gtgtgcacga accccccgtt cagcccgacc gctgcgcctt atccggtaac tatcgtcttg    9180
agtccaaccc ggtaagacac gacttatcgc cactggcagc agccactggt aacaggatta    9240
gcagagcgag gtatgtaggc ggtgctacag agttcttgaa gtggtggcct aactacggct    9300
acactagaag aacagtattt ggtatctgcg ctctgctgaa gccagttacc ttcggaaaaa    9360
gagttggtag ctcttgatcc ggcaaacaaa ccaccgctgg tagcggtggt ttttttgttt    9420
gcaagcagca gattacgcgc agaaaaaaag gatctcaaaa cgccagcaac gcggcctttt    9480
tacggttcct ggccttttgc tggccttttg ctcacatgtt ctttcctgcg ttatcccctg    9540
attctgtgga taaccgtatt accgcctttg agtgagctga taccgctcgc cgcagccgaa    9600
cgaccgagcg cagcgagtca gtgagcgagg aagcggaaga gcgcccaata cgcaaaccgc    9660
ctctc                                                                9665
```

<210> SEQ ID NO 16
<211> LENGTH: 6236
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
cccgcgcgtt ggccgattca ttaatgcagc tggcacgaca ggtttcccga ctggaaagcg     60
ggcagtgagc gcaacgcaat tttcacacag gaaacagcta tgaccatgat tacgccaagc    120
ttgcatgcat ttaaatgacg cagctgcgcg ctcgctcgct cactgaggcc gcccgggcaa    180
agcccgggcg tcgggcgacc tttggtcgcc cggcctcagt gagcgagcga gcgcgcagag    240
agggagtggc caactccatc actaggggtt gagtttaaac ttcgtcgacg atctgcggcc    300
gcacgcgtgg agctagttat taatagtaat caattacggg gtcattagtt catagcccat    360
atatggagtt ccgcgttaca taacttacgg taaatggccc gcctggctga ccgcccaacg    420
acccccgccc attgacgtca ataatgacgt atgttcccat agtaacgtca atagggactt    480
tccattgacg tcaatgggtg gagtatttac ggtaaactgc ccacttggca gtacatcaag    540
tgtatcatat gccaagtacg ccccctattg acgtcaatga cggtaaatgg cccgcctggc    600
attatgccca gtacatgacc ttatgggact ttcctacttg gcagtacatc tacgtattag    660
tcatcgctat taccatggtg atgcggtttt ggcagtacat caatgggcgt ggatagcggt    720
ttgactcacg gggatttcca agtctccacc ccattgacgt caatgggagt tgttttgca    780
ccaaaatcaa cgggactttc caaaatgtcg taacaactcc gccccattga cgcaaatggg    840
cggtaggcgt gtacggtggg aggtctatat aagcagagct cgtttagtga accgtcagat    900
cgcctggaga cgccatccac gctgttttga cctccataga agacaccggg accgatccag    960
cctccgcgga ttcgaatccc ggccgggaac ggtgcattgg aacgcggatt ccccgtgcca   1020
agagtgacgt aagtaccgcc tatagagtct ataggcccac aaaaaatgct tcttcttttt   1080
aatatacttt tttgtttatc ttatttctaa tactttccct aatctctttc tttcagggca   1140
ataatgatac aatgtatcat gcctctttgc accattctaa agaataacag tgataatttc   1200
tgggttaagg caatagcaat atttctgcat ataaatattt ctgcatataa attgtaactg   1260
atgtaagagg tttcatattg ctaatagcag ctacaatcca gctaccattc tgcttttatt   1320
ttatggttgg gataaggctg gattattctg agtccaagct aggcccttt gctaatcatg    1380
ttcataccta ttatcttcct cccacagctc ctgggcaacg tgctggtctg tgtgctggcc    1440
catcactttg gcaaagaatt gggattcgaa catcggccgc accatgaac gcaagtgaat    1500
tccgaaggag agggaaggag atggtggatt acgtggccaa ctacatggaa ggcattgagg    1560
gacgccaggt ctaccctgac gtggagcccg gtacctgcg gccgctgatc cctgccgctg    1620
cccctcagga gccagacacg tttgaggaca tcatcaacga cgttgagaag ataatcatgc    1680
ctggggtgac gcactggcac agcccctact tcttcgccta cttccccact gccagctcgt    1740
acccggccat gcttgcggac atgctgtgcg gggccattgg ctgcatcggc ttctcctggg    1800
cggcaagccc agcatgcaca gagctggaga ctgtgatgat ggactggctc gggaagatgc    1860
tggaactacc aaaggcattt ttgaatgaga aagctggaga aggggagga gtgatccagg    1920
gaagtgccag tgaagccacc ctggtggccc tgctggccgc tcgaccaaa gtgatccatc    1980
ggctgcaggc agcgtcccca gagctcacac aggccgctat catggagaag ctggtggctt   2040
```

-continued

```
actcatccga tcaggcacac tcctcagtgg aaagagctgg gttaattggt ggagtgaaat    2100
taaaagccat cccctcagat ggcaacttcg ccatgcgtgc gtctgccctg caggaagccc    2160
tggagagaga caaagcggct ggcctgattc ctttctttat ggttgccacc ctggggacca    2220
caacatgctg ctcctttgac aatctcttag aagtcggtcc tatctgcaac aaggaagaca    2280
tatggctgca cgttgatgca gcctacgcag gcagtgcatt catctgccct gagttccggc    2340
accttctgaa tggagtggag tttgcagatt cattcaactt taatccccac aaatggctat    2400
tggtgaattt tgactgttct gccatgtggg tgaaaaagag aacagactta acgggagcct    2460
ttagactgga ccccacttac ctgaagcaca gccatcagga ttcagggctt atcactgact    2520
accggcattg gcagatacca ctgggcagaa gatttcgctc tttgaaaatg tggtttgtat    2580
ttaggatgta tggagtcaaa ggactgcagg cttatatccg caagcatgtc cagctgtccc    2640
atgagtttga gtcactggtg cgccaggatc cccgctttga aatctgtgtg gaagtcattc    2700
tggggcttgt ctgctttcgg ctaaagggtt ccaacaaagt gaatgaagct cttctgcaaa    2760
gaataaacag tgccaaaaaa atccacttgg ttccatgtca cctcagggac aagtttgtcc    2820
tgcgctttgc catctgttct cgcacggtgg aatctgccca tgtgcagcgg gcctgggaac    2880
acatcaaaga gctggcggcc gacgtgctgc gagcagagag ggagtaggag tgagctgctc    2940
gagagatcta cggtgggcat ccctgtgacc cctccccagt gcctctcctg gcctggaag    3000 ttgccactcc agtgcccacc agccttgtcc taataaaatt aagttgcatc attttgtctg    3060
actaggtgtc cttctataat attatggggt ggagggggt ggtatggagc aaggggcaag    3120
ttgggaagac aacctgtagg gcctgcgggg tctattggga accaagctgg agtgcagtgg    3180
cacaatcttg gctcactgca atctccgcct cctgggttca agcgattctc ctgcctcagc    3240
ctcccgagtt gttgggattc caggcatgca tgaccaggct cagctaattt ttgttttttt    3300
ggtagagacg gggtttcacc atattggcca ggctggtctc caactcctaa tctcaggtga    3360
tctacccacc ttggcctccc aaattgctgg gattacaggc gtgaaccact gctcccttcc    3420
ctgtccttct gattttgtag gtaaccacgt gcggaccgag cggccgcagt taattaagct    3480
cgcgaaaccc ctagtgatgg agttggccac tccctctctg cgcgctcgct cgctcactga    3540
ggccgggcga ccaaaggtcg cccgacgccc gggctttgcc cgggcggcct cagtgagcga    3600
gcgagcgcgc agctggacga tttaaatggt accgagctcg aattcactgg ccgtcgtttt    3660
acaacgtcgt gactgggaaa accctggcgt tacccaactt aatcgccttg cagcacatcc    3720 cccttcgcc agctggcgta atagcgaaga ggcccgcacc gatcgccctt cccaacagtt    3780
gcgcagcctg aatggcgaat ggcgcctgat gcggtatttt ctccttacgc atctgtgcgg    3840
tatttcacac cgcatatggt gcactctcag tacaatctgc tctgatgccg catagttaag    3900
ccagccccga cacccgccaa cacccgctga cgcgccctga cgggcttgtc tgctcccggc    3960
atccgcttac agacaagctg tgaccgtctc cgggagctgc atgtgtcaga ggttttcacc    4020
gtcatcaccg aaacgcgcga tgcagctctg gcccgtgtct caaaatctct gatgttacat    4080
tgcacaagat aaaaatatat catcatgaac aataaaactg tctgcttaca taaacagtaa    4140 tacaggggt gttgaagatc ctttgatctt ttctacgggg tctgacgctc agtggaacga    4200
aaactcacgt taagggattt tggtcatgag attatcaaaa aggatcttca cctagatcct    4260
tttaaattaa aaatgaagtt ttaaatcaag cccaatctga ataatgttac aaccaattaa    4320
ccaattctga ttagaaaaac tcatcgagca tcaaatgaaa ctgcaattta ttcatatcag    4380
```

```
gattatcaat accatatttt tgaaaaagcc gtttctgtaa tgaaggagaa aactcaccga    4440
ggcagttcca taggatggca agatcctggt atcggtctgc gattccgact cgtccaacat    4500
caatacaacc tattaatttc ccctcgtcaa aaataaggtt atcaagtgag aaatcaccat    4560
gagtgacgac tgaatccggt gagaatggca aaagtttatg catttctttc cagacttgtt    4620
caacaggcca gccattacgc tcgtcatcaa aatcactcgc atcaaccaaa ccgttattca    4680
ttcgtgattg cgcctgagcg agacgaaata cgcgatcgct gttaaaagga caattacaaa    4740
caggaatcga atgcaaccgg cgcaggaaca ctgccagcgc atcaacaata ttttcacctg    4800
aatcaggata ttcttctaat acctggaatg ctgttttttcc ggggatcgca gtggtgagta    4860
accatgcatc atcaggagta cggataaaat gcttgatggt cggaagaggc ataaattccg    4920
tcagccagtt tagtctgacc atctcatctg taacatcatt ggcaacgcta cctttgccat    4980
gtttcagaaa caactctggc gcatcgggct tcccatacaa gcgatagatt gtcgcacctg    5040
attgcccgac attatcgcga gcccatttat acccatataa atcagcatcc atgttggaat    5100
ttaatcgcgg cctcgacgtt tcccgttgaa tatggctcat aacacccctt gtattactgt    5160
ttatgtaagc agacagtttt attgttcatg atgatatatt tttatcttgt gcaatgtaac    5220
atcagagatt ttgagacacg ggccagagct gcatcgcgcg ttttcagaat tggttaattg    5280
gttgtaacat tattcagatt gggcttgatt taaaacttca ttttttaattt aaaaggatct    5340 aggtgaagat cctttttgat aatctcatga ccaaaatccc ttaacgtgag ttttcgttcc    5400
actgagcgtc agaccccgta gaaaagatca aaggatcttc ttttccatagg ctccgccccc    5460 ctgacgagca tcacaaaaat cgacgctcaa gtcagaggtg cgaaacccg acaggactat    5520 aaagatacca ggcgtttccc cctggaagct ccctcgtgcg ctctcctgtt ccgaccctgc    5580
cgcttaccgg atacctgtcc gcctttctcc cttcgggaag cgtggcgctt tctcatagct    5640
cacgctgtag gtatctcagt tcggtgtagg tcgttcgctc caagctgggc tgtgtgcacg    5700
aaccccccgt tcagcccgac cgctgcgcct tatccggtaa ctatcgtctt gagtccaacc    5760
cggtaagaca cgacttatcg ccactggcag cagccactgg taacaggatt agcagagcga    5820
ggtatgtagg cggtgctaca gagttcttga agtggtggcc taactacggc tacactagaa    5880
gaacagtatt tggtatctgc gctctgctga agccagttac cttcggaaaa agagttggta    5940
gctcttgatc cggcaaacaa accaccgctg gtagcggtgg tttttttgtt tgcaagcagc    6000
agattacgcg cagaaaaaaa ggatctcaaa acgccagcaa cgcggccttt ttacggttcc    6060
tggccttttg ctggccttttt gctcacatgt tctttcctgc gttatcccct gattctgtgg    6120
ataaccgtat taccgccttt gagtgagctg ataccgctcg ccgcagccga acgaccgagc    6180
gcagcgagtc agtgagcgag gaagcggaag agcgcccaat acgcaaaccg cctctc        6236
```

<210> SEQ ID NO 17
<211> LENGTH: 3497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgagtttaaa cttcgtcgac gatctgcggc cgcacgcgtg    180
```

```
gagctagtta ttaatagtaa tcaattacgg ggtcattagt tcatagccca tatatggagt    240
tccgcgttac ataacttacg gtaaatggcc cgcctggctg accgcccaac gaccccgcc     300
cattgacgtc aataatgacg tatgttccca tagtaacgtc aatagggact ttccattgac    360
gtcaatgggt ggagtattta cggtaaactg cccacttggc agtacatcaa gtgtatcata    420
tgccaagtac gccccctatt gacgtcaatg acggtaaatg gcccgcctgg cattatgccc    480
agtacatgac cttatgggac tttcctactt ggcagtacat ctacgtatta gtcatcgcta    540
ttaccatggt gatgcggttt tggcagtaca tcaatgggcg tggatagcgg tttgactcac    600
ggggatttcc aagtctccac cccattgacg tcaatgggag tttgttttgc accaaaatca    660
acgggacttt ccaaaatgtc gtaacaactc cgccccattg acgcaaatgg gcggtaggcg    720
tgtacggtgg gaggtctata taagcagagc tcgtttagtg aaccgtcaga tcgcctggag    780
acgccatcca cgctgttttg acctccatag aagacaccgg gaccgatcca gcctccgcgg    840
attcgaatcc cggccgggaa cggtgcattg aacgcggat tccccgtgcc aagagtgacg     900
taagtaccgc ctatagagtc tataggccca caaaaaatgc tttcttcttt taatatactt    960
ttttgtttat cttatttcta atactttccc taatctcttt ctttcagggc aataatgata   1020
caatgtatca tgcctctttg caccattcta aagaataaca gtgataattt ctgggttaag   1080
gcaatagcaa tatttctgca tataaatatt tctgcatata aattgtaact gatgtaagag   1140
gtttcatatt gctaatagca gctacaatcc agctaccatt ctgcttttat tttatggttg   1200
ggataaggct ggattattct gagtccaagc taggcccttt tgctaatcat gttcatacct   1260
cttatcttcc tcccacagct cctgggcaac gtgctggtct gtgtgctggc ccatcacttt   1320
ggcaaagaat tgggattcga acatcggccg ccaccatgaa cgcaagtgaa ttccgaagga   1380
gagggaagga gatggtggat tacgtggcca actacatgga aggcattgag ggacgccagg   1440
tctaccctga cgtggagccc gggtacctgc ggccgctgat ccctgccgct gcccctcagg   1500
agccagacac gtttgaggac atcatcaacg acgttgagaa gataatcatg cctggggtga   1560
cgcactggca cagcccctac ttcttcgcct acttccccac tgccagctcg tacccggcca   1620
tgcttgcgga catgctgtgc ggggccattg gctgcatcgg cttctcctgg gcggcaagcc   1680
cagcatgcac agagctggag actgtgatga tggactggct cgggaagatg ctggaactac   1740
caaaggcatt tttgaatgag aaagctggag aaggggagg agtgatccag ggaagtgcca    1800
gtgaagccac cctggtggcc ctgctggccg ctcggaccaa agtgatccat cggctgcagg   1860
cagcgtcccc agagctcaca caggccgcta tcatggagaa gctggtggct tactcatccg   1920
atcaggcaca ctcctcagtg gaaagagctg ggttaattgg tggagtgaaa ttaaaagcca   1980
tcccctcaga tggcaacttc gccatgcgtg cgtctgccct gcaggaagcc ctggagagag   2040
acaaagcggc tggcctgatt cctttcttta tggttgccac cctgggacc acaacatgct    2100
gctcctttga caatctctta gaagtcggtc ctatctgcaa caaggaagac atatggctgc   2160
acgttgatgc agcctacgca ggcagtgcat tcatctgccc tgagttccgg caccttctga   2220
atggagtgga gtttgcagat tcattcaact ttaatcccca caaatggcta ttggtgaatt   2280
ttgactgttc tgccatgtgg gtgaaaaaga gaacagactt aacggagcc tttagactgg    2340
accccactta cctgaagcac agccatcagg attcagggct tatcactgac taccggcatt   2400
ggcagatacc actgggcaga agatttcgct cttttgaaaat gtggtttgta tttaggatgt   2460
atggagtcaa aggactgcag gcttatatcc gcaagcatgt ccagctgtcc catgagtttg   2520
agtcactggt gcgccaggat ccccgctttg aaatctgtgt ggaagtcatt ctggggcttg   2580
```

```
tctgctttcg gctaaagggt tccaacaaag tgaatgaagc tcttctgcaa agaataaaca    2640
gtgccaaaaa aatccacttg gttccatgtc acctcaggga caagtttgtc ctgcgctttg    2700
ccatctgttc tcgcacggtg gaatctgccc atgtgcagcg ggcctgggaa cacatcaaag    2760
agctggcggc cgacgtgctg cgagcagaga gggagtagga gtgagctgct cgagagatct    2820
acgggtggca tccctgtgac ccctccccag tgcctctcct ggccctggaa gttgccactc    2880
cagtgcccac cagccttgtc ctaataaaat taagttgcat catttgtct gactaggtgt    2940 ccttctataa tattatgggg tggaggggggg tggtatggag caaggggcaa gttgggaaga    3000
caacctgtag ggcctgcggg gtctattggg aaccaagctg gagtgcagtg gcacaatctt    3060
ggctcactgc aatctccgcc tcctgggttc aagcgattct cctgcctcag cctcccgagt    3120
tgttgggatt ccaggcatgc atgaccaggc tcagctaatt tttgtttttt tggtagagac    3180
ggggtttcac catattggcc aggctggtct ccaactccta atctcaggtg atctacccac    3240
cttggcctcc caaattgctg gattacagg cgtgaaccac tgctcccttc cctgtccttc    3300
tgattttgta ggtaaccacg tgcggaccga gcggccgcag ttaattaagc tcgcgaagga    3360 accccctagtg atggagttgg ccactccctc tctgcgcgct cgctcgctca ctgaggccgg    3420
gcgaccaaag gtcgcccgac gcccgggctt tgcccgggcg gcctcagtga gcgagcgagc    3480
gcgcagctgc ctgcagg                                                   3497
```

<210> SEQ ID NO 18
<211> LENGTH: 3497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
cctgcaggca gctgcgcgct cgctcgctca ctgaggccgc cgggcaaag cccgggcgtc      60 gggcgacctt tggtcgcccg gcctcagtga gcgagcgagc gcgcagagag ggagtggcca    120
actccatcac taggggttcc tgagtttaaa cttcgtcgac gatctgcggc cgcacgcgtg    180
gagctagtta ttaatagtaa tcaattacgg ggtcattagt tcatagccca tatatggagt    240
tccgcgttac ataacttacg gtaaatggcc cgcctggctg accgcccaac gaccccccgcc    300 cattgacgtc aataatgacg tatgttccca tagtaacgtc aatagggact ttccattgac    360
gtcaatgggt ggagtattta cggtaaactg cccacttggc agtacatcaa gtgtatcata    420
tgccaagtac gccccctatt gacgtcaatg acggtaaatg gcccgcctgg cattatgccc    480
agtacatgac cttatgggac tttcctactt ggcagtacat ctacgtatta gtcatcgcta    540
ttaccatggt gatgcggttt tggcagtaca tcaatgggcg tggatagcgg tttgactcac    600
ggggatttcc aagtctccac cccattgacg tcaatgggag tttgttttgc accaaaatca    660
acgggacttt ccaaaatgtc gtaacaactc cgccccattg acgcaaatgg gcggtaggcg    720
tgtacggtgg gaggtctata taagcagagc tcgtttagtg aaccgtcaga tcgcctggag    780
acgccatcca cgctgttttg acctccatag aagacaccgg gaccgatcca gcctccgcgg    840
attcgaatcc cggccgggaa cggtgcattg gaacgcggat tccccgtgcc aagagtgacg    900
taagtaccgc ctatagagtc tataggccca caaaaaatgc tttcttcttt taatatactt    960 tttttgtttat cttatttcta atactttccc taatctcttt ctttcagggc aataatgata   1020
caatgtatca tgcctctttg caccattcta aagaataaca gtgataattt ctgggttaag   1080
```

-continued

```
gcaatagcaa tatttctgca tataaatatt tctgcatata aattgtaact gatgtaagag    1140
gtttcatatt gctaatagca gctacaatcc agctaccatt ctgcttttat tttatggttg    1200
ggataaggct ggattattct gagtccaagc taggccctttt tgctaatcat gttcatacct   1260
cttatcttcc tcccacagct cctgggcaac gtgctggtct gtgtgctggc ccatcacttt    1320
ggcaaagaat tgggattcga acatcggccg ccaccatgaa cgcaagtgaa ttccgaagga    1380
gagggaagga gatggtggat tacgtggcca actacatgga aggcattgag gacgccagg     1440
tctaccctga cgtggagccc gggtacctgc ggccgctgat ccctgccgct gcccctcagg    1500
agccagacac gtttgaggac atcatcaacg acgttgagaa gataatcatg cctggggtga    1560
cgcactggca cagcccctac ttcttcgcct acttccccac tgccagctcg tacccggcca    1620
tgcttgcgga catgctgtgc ggggccattg gctgcatcgg cttctcctgg gcggcaagcc    1680
cagcatgcac agagctggag actgtgatga tggactggct cgggaagatg ctggaactac    1740
caaaggcatt tttgaatgag aaagctggag aaggggagg agtgatccag ggaagtgcca     1800
gtgaagccac cctggtggcc ctgctggccg ctcggaccaa agtgatccat cggctgcagg    1860
cagcgtcccc agagctcaca caggccgcta tcatggagaa gctggtggct tactcatccg    1920
atcaggcaca ctcctcagtg gaaagagctg ggttaattgg tggagtgaaa ttaaaagcca    1980
tccccctcaga tggcaacttc gccatgcgtg cgtctgccct gcaggaagcc ctggagagag   2040
acaaagcggc tggcctgatt cctttctttta tggttgccac cctggggacc acaacatgct   2100
gctcctttga caatctctta gaagtcggtc ctatctgcaa caaggaagac atatggctgc    2160
acgttgatgc agcctacgca ggcagtgcat tcatctgccc tgagttccgg caccttctga    2220
atggagtgga gtttgcagat tcattcaact ttaatcccca caaatggcta ttggtgaatt    2280
ttgactgttc tgccatgtgg gtgaaaaaga gaacagactt aacgggagcc tttagactgg    2340
accccactta cctgaagcac agccatcagg attcagggct tatcactgac taccggcatt    2400
ggcagatacc actgggcaga agatttcgct cttttgaaaat gtggtttgta tttaggatgt    2460
atggagtcaa aggactgcag gcttatatcc gcaagcatgt ccagctgtcc catgagtttg    2520
agtcactggt gcgccaggat ccccgctttg aaatctgtgt ggaagtcatt ctggggcttg    2580
tctgctttcg gctaaagggt tccaacaaag tgaatgaagc tcttctgcaa agaataaaca    2640
gtgccaaaaa aatccacttg gttccatgtc acctcaggga caagtttgtc ctgcgctttg    2700
ccatctgttc tcgcacggtg gaatctgccc atgtgcagcg ggcctgggaa cacatcaaag    2760
agctggcggc cgacgtgctg cgagcagaga gggagtagga gtgagctgct cgagagatct    2820
acgggtggca tccctgtgac ccctccccag tgcctctcct ggccctggaa gttgccactc    2880
cagtgcccac cagccttgtc ctaataaaat taagttgcat cattttgtct gactaggtgt    2940
ccttctataa tattatgggg tggagggggg tggtatggag caagggcaa gttgggaaga     3000
caacctgtag ggcctgcggg gtctattggg aaccaagctg gagtgcagtg gcacaatctt    3060
ggctcactgc aatctccgcc tcctgggttc aagcgattct cctgcctcag cctcccgagt    3120
tgttgggatt ccaggcatgc atgaccaggc tcagctaatt tttgtttttt tggtagagac    3180
ggggtttcac catattggcc aggctggtct ccaactccta atctcaggtg atctaccac    3240
cttggcctcc caaattgctg ggattacagg cgtgaaccac tgctcccttc cctgtccttc    3300
tgattttgta ggtaaccacg tgcggaccga gcggccgcag ttaattaagc tcgcgaagga    3360
acccctagtg atggagttgg ccactccctc tctgcgcgct cgctcgctca ctgaggccgg    3420
```

```
gcgaccaaag gtcgcccgac gcccgggctt tgcccgggcg gcctcagtga gcgagcgagc      3480
gcgcagctgc ctgcagg                                                    3497

<210> SEQ ID NO 19
<211> LENGTH: 3491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggttcc tgagtttaaa cttcgtcgac gatctgcggc cgcacgcgtg       180
gagctagtta ttaatagtaa tcaattacgg ggtcattagt tcatagccca tatatggagt       240
tccgcgttac ataacttacg gtaaatggcc cgcctggctg accgcccaac gacccccgcc       300
cattgacgtc aataatgacg tatgttccca tagtaacgtc aatagggact ttccattgac       360
gtcaatgggt ggagtattta cggtaaactg cccacttggc agtacatcaa gtgtatcata       420
tgccaagtac gccccctatt gacgtcaatg acggtaaatg gcccgcctgg cattatgccc       480
agtacatgac cttatgggac tttcctactt ggcagtacat ctacgtatta gtcatcgcta       540
ttaccatggt gatgcggttt tggcagtaca tcaatgggcg tggatagcgg tttgactcac       600
ggggatttcc aagtctccac cccattgacg tcaatgggag tttgttttgc accaaaatca       660
acgggacttt ccaaaatgtc gtaacaactc cgccccattg acgcaaatgg gcggtaggcg       720
tgtacggtgg gaggtctata taagcagagc tcgtttagtg aaccgtcaga tcgcctggag       780
acgccatcca cgctgttttg acctccatag aagacaccgg gaccgatcca gcctccgcgg       840
attcgaatcc cggccgggaa cggtgcattg gaacgcggat tccccgtgcc aagagtgacg       900
taagtaccgc ctatagagtc tataggccca caaaaaatgc tttcttcttt taatatactt       960
ttttgtttat cttatttcta atactttccc taatctcttt ctttcagggc aataatgata      1020
caatgtatca tgcctctttg caccattcta aagaataaca gtgataattt ctgggttaag      1080
gcaatagcaa tatttctgca tataaatatt tctgcatata aattgtaact gatgtaagag      1140
gtttcatatt gctaatagca gctacaatcc agctaccatt ctgcttttat tttatggttg      1200
ggataaggct ggattattct gagtccaagc taggcccttt tgctaatcat gttcatacct      1260
cttatcttcc tcccacagct cctgggcaac gtgctggtct gtgtgctggc ccatcacttt      1320
ggcaaagaat tgggattcga acatcggccg ccaccatgaa cgccagcgag ttcaggagga      1380
ggggcaagga gatggtggac tacgtggcca actacatgga gggcatcgag gcaggcagg      1440 tgtaccccga cgtggagccc ggctacctga ggcccctgat ccccgccgcc gcccccagg      1500 agcccgacac cttcgaggac atcatcaacg acgtggagaa gatcatcatg cccggcgtga      1560
cccactggca cagcccctac ttcttcgcct acttccccac cgccagcagc taccccgcca      1620
tgctggccga catgctgtgc ggcgccatcg gctgcatcgg cttcagctgg gccgccagcc      1680
ccgcctgcac cgagctggag accgtgatga tggactggct gggcaagatg ctggagctgc      1740
ccaaggcctt cctgaacgag aaggccggcg agggcggcgg cgtgatccag ggcagcgcca      1800
gcgaggccac cctggtggcc ctgctggccg ccaggaccaa ggtgatccac aggctgcagg      1860
ccgccagccc cgagctgacc caggccgcca tcatggagaa gctggtggcc tacagcagcg      1920
```

| | |
|---|---|
| accaggccca cagcagcgtg gagagggccg gcctgatcgg cggcgtgaag ctgaaggcca | 1980 |
| tccccagcga cggcaacttc gccatgaggg ccagcgccct gcaggaggcc ctggagaggg | 2040 |
| acaaggccgc cggcctgatc cccttcttca tggtggccac cctgggcacc accacctgct | 2100 |
| gcagcttcga caacctgctg gaggtgggcc ccatctgcaa caaggaggac atctggctgc | 2160 |
| acgtggacgc cgcctacgcc ggcagcgcct tcatctgccc cgagttcagg cacctgctga | 2220 |
| acggcgtgga gttcgccgac agcttcaact tcaaccccca caagtggctg ctggtgaact | 2280 |
| tcgactgcag cgccatgtgg gtgaagaaga ggaccgacct gaccggcgcc ttcaggctgg | 2340 |
| accccaccta cctgaagcac agccaccagg acagcgcc gatcaccgac tacaggcact | 2400 |
| ggcagatccc cctgggcagg aggttcagga gcctgaagat gtggttcgtg ttcaggatgt | 2460 |
| acggcgtgaa gggcctgcag gcctacatca ggaagcacgt gcagctgagc cacgagttcg | 2520 |
| agagcctggt gaggcaggac cccaggttcg agatctgcgt ggaggtgatc ctgggcctgg | 2580 |
| tgtgcttcag gctgaaggc agcaacaagg tgaacgaggc cctgctgcag aggatcaaca | 2640 |
| gcgccaagaa gatccacctg gtgccctgcc acctgaggga caagttcgtg ctgaggttcg | 2700 |
| ccatctgcag caggaccgtg gagagcgccc acgtgcagag ggcctgggag cacatcaagg | 2760 |
| agctggccgc cgacgtgctg agggccgaga gggagtgagc tgctcgagag atctacgggt | 2820 |
| ggcatccctg tgacccctcc ccagtgcctc tcctggccct ggaagttgcc actccagtgc | 2880 |
| ccaccagcct tgtcctaata aaattaagtt gcatcatttt gtctgactag gtgtccttct | 2940 |
| ataatattat ggggtggagg ggggtggtat ggagcaaggg gcaagttggg aagacaacct | 3000 |
| gtagggcctg cggggtctat tgggaaccaa gctggagtgc agtggcacaa tcttggctca | 3060 |
| ctgcaatctc cgcctcctgg gttcaagcga ttctcctgcc tcagcctccc gagttgttgg | 3120 |
| gattccagge atgcatgacc aggctcagct aattttttgtt ttttttggtag agacggggtt | 3180 |
| tcaccatatt ggccaggctg gtctccaact cctaatctca ggtgatctac ccaccttggc | 3240 |
| ctcccaaatt gctgggatta caggcgtgaa ccactgctcc cttccctgtc cttctgattt | 3300 |
| tgtaggtaac cacgtgcgga ccgagcggcc gcagttaatt aagctcgcga aggaacccct | 3360 |
| agtgatggag ttggccactc cctctctgcg cgctcgctcg ctcactgagg ccgggcgacc | 3420 |
| aaaggtcgcc cgacgcccgg gctttgcccg ggcggcctca gtgagcgagc gagcgcgcag | 3480 |
| ctgcctgcag g | 3491 |

<210> SEQ ID NO 20
<211> LENGTH: 4003
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgagtttaaa cttcgtcgac gatctgcggc cgcacgcgtg | 180 |
| gagctagtta ttaatagtaa tcaattacgg ggtcattagt tcatagccca tatatggagt | 240 |
| tccgcgttac ataacttacg gtaaatggcc cgcctggctg accgcccaac gacccccgcc | 300 |
| cattgacgtc aataatgacg tatgttccca tagtaacgtc aatagggact ttccattgac | 360 |
| gtcaatgggt ggagtattta cggtaaactg cccacttggc agtacatcaa gtgtatcata | 420 |

```
tgccaagtac gcccctatt gacgtcaatg acggtaaatg gcccgcctgg cattatgccc      480
agtacatgac cttatgggac tttcctactt ggcagtacat ctacgtatta gtcatcgcta      540
ttaccatggt gatgcggttt tggcagtaca tcaatgggcg tggatagcgg tttgactcac      600
ggggatttcc aagtctccac cccattgacg tcaatgggag tttgttttgc accaaaatca      660
acgggacttt ccaaaatgtc gtaacaactc cgccccattg acgcaaatgg gcggtaggcg      720
tgtacggtgg gaggtctata taagcagagc tcgtttagtg aaccgtcaga tcgcctggag      780
acgccatcca cgctgttttg acctccatag aagacaccgg gaccgatcca gcctccgcgg      840
attcgaatcc cggccgggaa cggtgcattg gaacgcggat tccccgtgcc aagagtgacg      900
taagtaccgc ctatagagtc tataggccca caaaaaatgc tttcttcttt taatatactt      960
ttttgtttat cttatttcta atactttccc taatctcttt ctttcagggc aataatgata     1020
caatgtatca tgcctctttg caccattcta aagaataaca gtgataattt ctgggttaag     1080
gcaatagcaa tatttctgca tataaatatt tctgcatata aattgtaact gatgtaagag     1140
gtttcatatt gctaatagca gctacaatcc agctaccatt ctgcttttat tttatggttg     1200
ggataaggct ggattattct gagtccaagc taggcccttt tgctaatcat gttcatacct     1260
cttatcttcc tcccacagct cctgggcaac gtgctggtct gtgtgctggc ccatcacttt     1320
ggcaaagaat tgggattcga acatcgaatt cgggcacgag ggaggacaga gagcaagtca     1380
ctcccggctg cctttttcac ctctgacaga gcccagacac catgaacgca agtgaattcc     1440
gaaggagagg gaaggagatg gtggattacg tggccaacta catggaaggc attgagggac     1500
gccaggtcta ccctgacgtg gagcccgggt acctgcggcc gctgatccct gccgctgccc     1560
ctcaggagcc agacacgttt gaggacatca tcaacgacgt tgagaagata atcatgcctg     1620
gggtgacgca ctggcacagc ccctacttct tcgcctactt ccccactgcc agctcgtacc     1680
cggccatgct tgcggacatg ctgtgcgggg ccattggctg catcggcttc tcctgggcgg     1740
caagcccagc atgcacagag ctggagactg tgatgatgga ctggctcggg aagatgctgg     1800
aactaccaaa ggcattttg aatgagaaag ctggagaagg gggaggagtg atccagggaa     1860
gtgccagtga agccaccctg gtggccctgc tggccgctcg gaccaaagtg atccatcggc     1920
tgcaggcagc gtccccagag ctcacacagg ccgctatcat ggagaagctg gtggcttact     1980
catccgatca ggcacactcc tcagtggaaa gagctgggtt aattggtgga gtgaaattaa     2040
aagccatccc ctcagatggc aacttcgcca tgcgtgcgtc tgccctgcag gaagccctgg     2100
agagagacaa agcggctggc ctgattcctt tctttatggt tgccaccctg gggaccacaa     2160
catgctgctc ctttgacaat ctcttagaag tcggtcctat ctgcaacaag gaagacatat     2220
ggctgcacgt tgatgcagcc tacgcaggca gtgcattcat ctgccctgag ttccggcacc     2280
ttctgaatgg agtggagttt gcagattcat tcaactttaa tccccacaaa tggctattgg     2340
tgaattttga ctgttctgcc atgtgggtga aaaagagaac agacttaacg ggagccttta     2400
gactggaccc cacttacctg aagcacagcc atcaggattc agggcttatc actgactacc     2460
ggcattggca gataccactg ggcagaagat ttcgctcttt gaaaatgtgg tttgtattta     2520
ggatgtatgg agtcaaagga ctgcaggctt atatccgcaa gcatgtccag ctgtcccatg     2580
agtttgagtc actggtgcgc caggatcccc gctttgaaat ctgtgtggaa gtcattctgg     2640
ggcttgtctg ctttcggcta aagggttcca acaaagtgaa tgaagctctt ctgcaaagaa     2700
taaacagtgc caaaaaaatc cacttggttc catgtcacct cagggacaag tttgtcctgc     2760
gctttgccat ctgttctcgc acggtggaat ctgcccatgt gcagcgggcc tgggaacaca     2820
```

```
tcaaagagct ggcggccgac gtgctgcgag cagagaggga gtaggagtga agccagctgc    2880
aggaatcaaa aattgaagag agatatatct gaaaactgga ataagaagca ataaatatc    2940 atcctgcctt catggaactc agctgtctgt ggcttcccat gtctttctcc aaagttatcc    3000
agagggttgt gattttgtct gcttagtatc tcatcaacaa agaaatatta tttgctaatt    3060
aaaaagttaa tcttcatggc catagctttt attcattagc tgtgattttt gttgattaaa    3120
acattataga ttttcatgtt cttgcagtca tcagaagtgg taggaaagcc tcactgatat    3180
attttccagg gcaatcaatg ttcacgcaac ttgaaattat atctgtggtc ttcaaattgt    3240
cttttgtcat gtggctaaat gcctaataaa caattcaagt gaaatactaa aaaaaaaaa    3300 aaaaaaaaa gctgctcgag agatctacgg gtggcatccc tgtgacccct ccccagtgcc    3360
tctcctggcc ctggaagttg ccactccagt gccaccagc cttgtcctaa taaaattaag    3420
ttgcatcatt ttgtctgact aggtgtcctt ctataatatt atggggtgga gggggtggt    3480 atggagcaag gggcaagttg ggaagacaac ctgtagggcc tgcggggtct attgggaacc    3540
aagctggagt gcagtggcac aatcttggct cactgcaatc tccgcctcct gggttcaagc    3600
gattctcctg cctcagcctc ccgagttgtt gggattccag gcatgcatga ccaggctcag    3660 ctaattttg ttttttggt agagacgggg tttcaccata ttggccaggc tggtctccaa    3720
ctcctaatct caggtgatct acccaccttg gcctcccaaa ttgctgggat tacaggcgtg    3780
aaccactgct cccttccctg tccttctgat tttgtaggta accacgtgcg gaccgagcgg    3840
ccgcagttaa ttaagctcgc gaaggaaccc ctagtgatgg agttggccac tccctctctg    3900
cgcgctcgct cgctcactga ggccgggcga ccaaaggtcg cccgacgccc gggctttgcc    3960
cgggcggcct cagtgagcga gcgagcgcgc agctgcctgc agg                     4003
```

<210> SEQ ID NO 21
<211> LENGTH: 3499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttcctgagtt taaacttcgt cgacgatctg cggccgcacg    180
cgtggagcta gttattaata gtaatcaatt acggggtcat tagttcatag cccatatatg    240
gagttccgcg ttacataact tacggtaaat ggcccgcctg gctgaccgcc caacgacccc    300
cgcccattga cgtcaataat gacgtatgtt cccatagtaa cgtcaatagg gactttccat    360
tgacgtcaat gggtggagta tttacggtaa actgcccact tggcagtaca tcaagtgtat    420
catatgccaa gtacgccccc tattgacgtc aatgacggta aatggcccgc ctggcattat    480
gcccagtaca tgaccttatg ggactttcct acttggcagt acatctacgt attagtcatc    540
gctattacca tggtgatgcg gttttggcag tacatcaatg ggcgtggata gcggtttgac    600
tcacggggat ttccaagtct ccaccccatt gacgtcaatg ggagtttgtt ttgcaccaaa    660
atcaacggga ctttccaaaa tgtcgtaaca actccgcccc attgacgcaa atgggcggta    720
ggcgtgtacg gtgggaggtc tatataagca gagctcgttt agtgaaccgt cagatcgcct    780
ggagacgcca tccacgctgt tttgacctcc atagaagaca ccgggaccga tccagcctcc    840
```

```
gcggattcga atcccggccg ggaacggtgc attggaacgc ggattccccg tgccaagagt    900
gacgtaagta ccgcctatag agtctatagg cccacaaaaa atgctttctt cttttaatat    960
acttttttgt ttatcttatt tctaatactt tccctaatct ctttctttca gggcaataat   1020
gatacaatgt atcatgcctc tttgcaccat tctaaagaat aacagtgata atttctgggt   1080
taaggcaata gcaatatttc tgcatataaa tatttctgca tataaattgt aactgatgta   1140
agaggtttca tattgctaat agcagctaca atccagctac cattctgctt ttattttatg   1200
gttgggataa ggctggatta ttctgagtcc aagctaggcc cttttgctaa tcatgttcat   1260
acctcttatc ttcctcccac agctcctggg caacgtgctg gtctgtgtgc tggcccatca   1320
ctttggcaaa gaattgggat tcgaacatcg ccgccacca tgaacgccag cgagttcagg    1380
aggaggggca aggagatggt ggactacgtg gccaactaca tggagggcat cgagggcagg   1440
caggtgtacc ccgacgtgga gcccggctac ctgaggcccc tgatcccgc cgccgccccc   1500
caggagcccg acaccttcga ggacatcatc aacgacgtgg agaagatcat catgcccggc   1560
gtgacccact ggcacagccc ctacttcttc gcctacttcc ccaccgccag cagctacccc   1620
gccatgctgg ccgacatgct gtgcggcgcc atcggctgca tcggcttcag ctgggccgcc   1680
agccccgcct gcaccgagct ggagaccgtg atgatggact ggctgggcaa gatgctggag   1740
ctgcccaagg ccttcctgaa cgagaaggcc ggcgagggcg gcggcgtgat ccagggcagc   1800
gccagcgagg ccaccctggt ggccctgctg gccgccagga ccaaggtgat ccacaggctg   1860
caggccgcca gccccgagct gacccaggcc gccatcatgg agaagctggt ggcctacagc   1920
agcgaccagg cccacagcag cgtggagagg gccggcctga tcgcggcgt gaagctgaag   1980
gccatcccca gcgacggcaa cttcgccatg agggccagcg ccctgcagga ggccctggag   2040
agggacaagg ccgccggcct gatccccttc ttcatggtgg ccaccctggg caccaccacc   2100
tgctgcagct tcgacaacct gctggaggtg ggccccatct gcaacaagga ggacatctgg   2160
ctgcacgtgg acgccgccta cgccggcagc gccttcatct gccccgagtt caggcacctg   2220
ctgaacggcg tggagttcgc cgacagcttc aacttcaacc cccacaagtg gctgctggtg   2280
aacttcgact gcagcgccat gtgggtgaag aagaggaccg acctgaccgg cgccttcagg   2340
ctggaccccca cctacctgaa gcacagccac caggacagcg gcctgatcac cgactacagg   2400
cactggcaga tcccctggg caggaggttc aggagcctga agatgtggtt cgtgttcagg   2460
atgtacggcg tgaagggcct gcaggcctac atcaggaagc acgtgcagct gagccacgag   2520
ttcgagagcc tggtgaggca ggaccccagg ttcgagatct gcgtggaggt gatcctgggc   2580
ctggtgtgct tcaggctgaa gggcagcaac aaggtgaacg aggccctgct gcagaggatc   2640
aacagcgcca gaagatcca cctggtgccc tgccacctga ggacaagtt cgtgctgagg   2700
ttcgccatct gcagcaggac cgtggagagc gcccacgtgc agagggcctg ggagcacatc   2760
aaggagctgg ccgccgacgt gctgagggcc gagagggagt gagctgctcg agagatctac   2820
gggtggcatc cctgtgaccc ctccccagtg cctctcctgg ccctggaagt tgccactcca   2880
gtgcccacca gccttgtcct aataaaatta agttgcatca ttttgtctga ctaggtgtcc   2940
ttctataata ttatgggtg gagggggtg gtatggagca aggggcaagt tgggaagaca   3000
acctgtaggg cctgcgggt ctattgggaa ccaagctgga gtgcagtggc acaatcttgg   3060
ctcactgcaa tctccgcctc ctgggttcaa gcgattctcc tgcctcagcc tcccgagttg   3120
ttgggattcc aggcatgcat gaccaggctc agctaatttt tgttttttttg gtagagacgg   3180
```

```
ggtttcacca tattggccag gctggtctcc aactcctaat ctcaggtgat ctacccacct    3240
tggcctccca aattgctggg attacaggcg tgaaccactg ctcccttccc tgtccttctg    3300
attttgtagg taaccacgtg cggaccgagc ggccgcagtt aattaagctc gcgaaggaac    3360
ccctagtgat ggagttggcc actccctctc tgcgcgctcg ctcgctcact gaggccgggc    3420
gaccaaaggt cgcccgacgc ccgggctttg cccggcggc ctcagtgagc gagcgagcgc    3480
gcagagaggg agtggccaa                                                 3499
```

<210> SEQ ID NO 22
<211> LENGTH: 3896
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca    120
actccatcac tagggttcc tgagtttaaa cttcgtcgac gatctgcggc cgcacgcgtg     180
gagctagtta ttaatagtaa tcaattacgg ggtcattagt tcatagccca tatatggagt    240
tccgcgttac ataacttacg gtaaatggcc cgcctggctg accgcccaac gacccccgcc    300
cattgacgtc aataatgacg tatgttccca tagtaacgtc aatagggact ttccattgac    360
gtcaatgggt ggagtattta cggtaaactg cccacttggc agtacatcaa gtgtatcata    420
tgccaagtac gccccctatt gacgtcaatg acggtaaatg gcccgcctgg cattatgccc    480
agtacatgac cttatgggac tttcctactt ggcagtacat ctacgtatta gtcatcgcta    540
ttaccatggt gatgcggttt tggcagtaca tcaatgggcg tggatagcgg tttgactcac    600
ggggatttcc aagtctccac cccattgacg tcaatgggag tttgttttgc accaaaatca    660
acgggacttt ccaaaatgtc gtaacaactc cgccccattg acgcaaatgg gcggtaggcg    720
tgtacggtgg gaggtctata taagcagagc tcgtttagtg aaccgtcaga tcgcctggag    780
acgccatcca cgctgttttg acctccatag aagacaccgg gaccgatcca gcctccgcgg    840
attcgaatcc cggccgggaa cggtgcattg gaacgcggat tccccgtgcc aagagtgacg    900
taagtaccgc ctatagagtc tataggccca caaaaaatgc tttcttcttt taatatactt    960
ttttgtttat cttatttcta atactttccc taatctcttt ctttcagggc aataatgata    1020
caatgtatca tgcctctttg caccattcta agaataaca gtgataattt ctgggttaag    1080
gcaatagcaa tatttctgca tataaatatt tctgcatata aattgtaact gatgtaagag    1140
gtttcatatt gctaatagca gctacaatcc agctaccatt ctgcttttat tttatggttg    1200
ggataaggct ggattattct gagtccaagc taggcccttt tgctaatcat gttcatacct    1260
cttatcttcc tcccacagct cctgggcaac gtgctggtct gtgtgctggc ccatcacttt    1320
ggcaaagaat tgggattcga acatcggccg ccaccatgaa cgcaagtgaa ttccgaagga    1380
gagggaagga gatggtggat tacgtggcca actacatgga aggcattgag ggacgccagg    1440
tctaccctga cgtggagccc gggtacctgc ggccgctgat cctgccgct gcccctcagg    1500 agccagacac gtttgaggac atcatcaacg acgttgagaa gataatcatg cctggggtga    1560
cgcactggca cagcccctac ttcttcgcct acttccccac tgccagctcg tacccggcca    1620
tgcttgcgga catgctgtgc ggggccattg gctgcatcgg cttctcctgg gcggcaagcc    1680
```

```
cagcatgcac agagctggag actgtgatga tggactggct cgggaagatg ctggaactac    1740
caaaggcatt tttgaatgag aaagctggag aaggggagg agtgatccag ggaagtgcca    1800
gtgaagccac cctggtggcc ctgctggccg ctcggaccaa agtgatccat cggctgcagg    1860
cagcgtcccc agagctcaca caggccgcta tcatggagaa gctggtggct tactcatccg    1920
atcaggcaca ctcctcagtg gaaagagctg ggttaattgg tggagtgaaa ttaaaagcca    1980
tccccctcaga tggcaacttc gccatgcgtg cgtctgccct gcaggaagcc ctggagagag    2040
acaaagcggc tggcctgatt cctttcttta tggttgccac cctggggacc acaacatgct    2100
gctcctttga caatctctta gaagtcggtc ctatctgcaa caaggaagac atatggctgc    2160
acgttgatgc agcctacgca ggcagtgcat tcatctgccc tgagttccgg caccttctga    2220
atggagtgga gtttgcagat tcattcaact ttaatcccca caaatggcta ttggtgaatt    2280
ttgactgttc tgccatgtgg gtgaaaaaga gaacagactt aacgggagcc tttagactgg    2340
accccactta cctgaagcac agccatcagg attcagggct tatcactgac taccggcatt    2400
ggcagatacc actgggcaga agatttcgct cttttgaaaat gtggtttgta tttaggatgt    2460
atggagtcaa aggactgcag gcttatatcc gcaagcatgt ccagctgtcc catgagtttg    2520
agtcactggt gcgccaggat ccccgctttg aaatctgtgt ggaagtcatt ctggggcttg    2580
tctgctttcg gctaaagggt tccaacaaag tgaatgaagc tcttctgcaa agaataaaca    2640
gtgccaaaaa aatccacttg gttccatgtc acctcaggga caagtttgtc ctgcgctttg    2700
ccatctgttc tcgcacggtg gaatctgccc atgtgcagcg ggcctgggaa cacatcaaag    2760
agctggcggc cgacgtgctg cgagcagaga gggagtagga gtgaagccag ctgcaggaat    2820
caaaaattga agagagatat atctgaaaac tggaataaga agcaaataaa tatcatcctg    2880
ccttcatgga actcagctgt ctgtggcttc ccatgtcttt ctccaaagtt atccagaggg    2940
ttgtgatttt gtctgcttag tatctcatca acaaagaaat attatttgct aattaaaaag    3000
ttaatcttca tggccatagc ttttattcat tagctgtgat ttttgttgat taaaacatta    3060
tagattttca tgttcttgca gtcatcagaa gtggtaggaa agcctcactg atatattttc    3120
cagggcaatc aatgttcacg caacttgaaa ttatatctgt ggtcttcaaa ttgtcttttg    3180
tcatgtggct aaatgcctaa taagctgctc gagagatcta cgggtggcat ccctgtgacc    3240
cctcccagt gcctctcctg gccctggaag ttgccactcc agtgcccacc agccttgtcc    3300
taataaaatt aagttgcatc attttgtctg actaggtgtc cttctataat attatggggt    3360
ggaggggggt ggtatggagc aagggcaag ttgggaagac aacctgtagg gcctgcgggg    3420
tctattggga accaagctgg agtgcagtgg cacaatcttg gctcactgca atctccgcct    3480
cctgggttca gcgattctc ctgcctcagc ctcccgagtt gttgggattc caggcatgca    3540
tgaccaggct cagctaattt ttgtttttt ggtagagacg gggtttcacc atattggcca    3600
ggctggtctc caactcctaa tctcaggtga tctacccacc ttggcctccc aaattgctgg    3660
gattacaggc gtgaaccact gctcccttcc ctgtccttct gattttgtag gtaaccacgt    3720
gcggaccgag cggccgcagt taattaagct cgcgaaggaa cccctagtga tggagttggc    3780
cactccctct ctgcgcgctc gctcgctcac tgaggccggg cgaccaaagg tcgcccgacg    3840
cccgggcttt gcccgggcgg cctcagtgag cgagcgagcg cgcagctgcc tgcagg       3896
```

<210> SEQ ID NO 23
<211> LENGTH: 3475
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 23
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc   120
actaggggtt gagtttaaac ttcgtcgacg atctgcggcc gcacgcgtgg agctagttat   180
taatagtaat caattacggg gtcattagtt catagcccat atatggagtt ccgcgttaca   240
taacttacgg taaatggccc gcctggctga ccgcccaacg accccgccc attgacgtca   300 ataatgacgt atgttcccat agtaacgtca atagggactt tccattgacg tcaatgggtg   360
gagtatttac ggtaaactgc ccacttggca gtacatcaag tgtatcatat gccaagtacg   420
ccccctattg acgtcaatga cggtaaatgg cccgcctggc attatgccca gtacatgacc   480
ttatgggact ttcctacttg gcagtacatc tacgtattag tcatcgctat taccatggtg   540
atgcggtttt ggcagtacat caatgggcgt ggatagcggt ttgactcacg ggatttcca   600 agtctccacc ccattgacgt caatgggagt ttgttttgca ccaaaatcaa cgggactttc   660
caaaatgtcg taacaactcc gccccattga cgcaaatggg cggtaggcgt gtacggtggg   720
aggtctatat aagcagagct cgtttagtga accgtcagat cgcctggaga cgccatccac   780
gctgttttga cctccataga agacaccggg accgatccag cctccgcgga ttcgaatccc   840
ggccgggaac ggtgcattgg aacgcggatt ccccgtgcca agagtgacgt aagtaccgcc   900
tatagagtct ataggcccac aaaaaatgct ttcttctttt aatatacttt tttgtttatc   960
ttatttctaa tactttccct aatctctttc tttcagggca ataatgatac aatgtatcat  1020
gcctctttgc accattctaa agaataacag tgataatttc tgggttaagg caatagcaat  1080
atttctgcat ataaatattt ctgcatataa attgtaactg atgtaagagg tttcatattg  1140
ctaatagcag ctacaatcca gctaccattc tgcttttatt ttatggttgg ataaggctg  1200 gattattctg agtccaagct aggcctttt gctaatcatg ttcataccttc ttatcttcct  1260 cccacagctc ctgggcaacg tgctggtctg tgtgctggcc catcactttg gcaaagaatt  1320
gggattcgaa catcggccgc caccatgaac gcaagtgaat tccgaaggag agggaaggag  1380
atggtggatt acgtggccaa ctacatgaag gcattgagg gacgccaggt ctaccctgac  1440
gtggagcccg ggtacctgcg gccgctgatc cctgccgctg cccctcagga gccagacacg  1500
tttgaggaca tcatcaacga cgttgagaag ataatcatgc ctggggtgac gcactggcac  1560
agcccctact tcttcgccta cttccccact gccagctcgt acccggccat gcttgcggac  1620 atgcgtgcg gggccattgg ctgcatcggc ttctcctggg cggcaagccc agcatgcaca  1680
gagctggaga ctgtgatgat ggactggctc gggaagatgc tggaactacc aaaggcattt  1740
ttgaatgaga aagctggaga aggggagga gtgatccagg gaagtgccag tgaagccacc  1800
ctggtggccc tgctggccgc tcggaccaaa gtgatccatc ggctgcaggc agcgtcccca  1860
gagctcacac aggccgctat catggagaag ctggtggctt actcatccga tcaggcacac  1920
tcctcagtgg aaagagctgg gttaattggt ggagtgaaat taaagccat cccctcagat  1980 ggcaacttcg ccatgcgtgc gtctgccctg caggaagccc tggagagaga caaagcggct  2040
ggcctgattc ctttctttat ggttgccacc ctgggacca caacatgctg ctcctttgac  2100
aatctcttag aagtcggtcc tatctgcaac aaggaagaca tatggctgca cgttgatgca  2160
gcctacgcag gcagtgcatt catctgccct gagttccggc accttctgaa tggagtggag  2220
```

```
tttgcagatt cattcaactt taatccccac aaatggctat tggtgaattt tgactgttct  2280
gccatgtggg tgaaaaagag aacagactta acgggagcct ttagactgga ccccacttac  2340
ctgaagcaca gccatcagga ttcagggctt atcactgact accggcattg gcagatacca  2400
ctgggcagaa gatttcgctc tttgaaaatg tggtttgtat ttaggatgta tggagtcaaa  2460
ggactgcagg cttatatccg caagcatgtc cagctgtccc atgagtttga gtcactggtg  2520
cgccaggatc cccgctttga aatctgtgtg gaagtcattc tggggcttgt ctgctttcgg  2580
ctaaagggtt ccaacaaagt gaatgaagct cttctgcaaa gaataaacag tgccaaaaaa  2640
atccacttgg ttccatgtca cctcagggac aagtttgtcc tgcgctttgc catctgttct  2700
cgcacggtgg aatctgccca tgtgcagcgg gcctgggaac acatcaaaga gctggcggcc  2760
gacgtgctgc gagcagagag ggagtaggag tgagctgctc gagagatcta cgggtggcat  2820
ccctgtgacc cctccccagt gcctctcctg gccctggaag ttgccactcc agtgcccacc  2880
agccttgtcc taataaaatt aagttgcatc attttgtctg actaggtgtc cttctataat  2940
attatggggt ggaggggggt ggtatggagc aaggggcaag ttgggaagac aacctgtagg  3000
gcctgcgggg tctattggga accaagctgg agtgcagtgg cacaatcttg gctcactgca  3060
atctccgcct cctgggttca agcgattctc ctgcctcagc ctcccgagtt gttgggattc  3120
caggcatgca tgaccaggct cagctaattt ttgtttttt ggtagagacg gggtttcacc  3180
atattggcca ggctggtctc caactcctaa tctcaggtga tctacccacc ttggcctccc  3240
aaattgctgg gattacaggc gtgaaccact gctcccttcc ctgtccttct gattttgtag  3300
gtaaccacgt gcggaccgag cggccgcagt taattaagct cgcgaaaccc ctagtgatgg  3360
agttggccac tccctctctg cgcgctcgct cgctcactga ggccgggcga ccaaaggtcg  3420
cccgacgccc gggctttgcc cgggcggcct cagtgagcga gcgagcgcgc agctg       3475
```

AADC POLYNUCLEOTIDES FOR THE TREATMENT OF PARKINSON'S DISEASE

CROSS REFERENCE TO RELATED APPLICATIONS

This application is a 35 U.S.C. § 371 U.S. National Stage Entry of International Application No. PCT/US2015/059201 filed Nov. 5, 2015, which claims priority to U.S. Provisional Patent Application No. 62/075,298, entitled AADC Polynucleotides for the Treatment of Parkinson's Disease, filed Nov. 5, 2014, U.S. Provisional Patent Application No. 62/155,692, entitled AADC Polynucleotides for the Treatment of Parkinson's Disease, filed May 1, 2015, U.S. Provisional Patent Application No. 62/199,578, entitled AADC Polynucleotides for the Treatment of Parkinson's Disease, filed Jul. 31, 2015 and U.S. Provisional Patent Application No. 62/243,537, entitled AADC Polynucleotides for the Treatment of Parkinson's Disease, filed Oct. 19, 2015; the contents of each of which is herein incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created on May 5, 2017 is named 2057-1010US371_SEQLST.txt and is 178,222bytes in size.

FIELD OF THE INVENTION

The invention relates to compositions, particularly nucleic acid molecules, e.g., polynucleotides encoding AADC, for use in the treatment of Parkinson's disease. In some embodiments such AADC polynucleotides may be encoded by or within recombinant adeno-associated viruses (AAVs).

BACKGROUND OF THE INVENTION

Aromatic L-amino acid decarboxylase (AADC) is a homodimeric pyridoxal phosphate-dependent enzyme responsible for the synthesis of dopamine and serotonin. The encoded protein catalyzes the decarboxylation of L-3,4-dihydroxyphenylalanine (L-DOPA or levodopa) to dopamine; L-5-hydroxytryptophan to serotonin; and L-tryptophan to tryptamine. Defects in this gene are the cause of aromatic L-amino-acid decarboxylase deficiency (AADCD), which is an inborn error in neurotransmitter metabolism leading to combined serotonin and catecholamine deficiency that results in severe motor and autonomic dysfunctions.

Parkinson's Disease (PD) is a progressive neurodegenerative disease of the central nervous system (CNS) producing sensory and motor symptoms. Dopamine replacement (i.e., levodopa) has been the standard pharmacotherapy for motor impairment in PD. However, the benefit of dopamine therapy becomes less marked over time, due, in part, to the progressive death of dopamine-generating cells and corresponding loss of AADC activity. Furthermore, systemic administration of high-dose dopamine is complicated by side effects, such as fluctuations in motor performance, dyskinesias, and hallucinations, resulting from dopaminergic stimulation of the mesolimbic system. One strategy to restore dopaminergic function and minimize side effects is the use of gene therapy to deliver AADC directly to a targeted region of the CNS.

The adeno-associated virus (AAV) has emerged as an attractive vector for gene therapy due to its long-term gene expression, the inability to autonomously replicate without a helper virus, the ability to transduce dividing and non-dividing cells, and the lack of pathogenicity from wild-type infections (See e.g., Hadaczek et al. Mol. Ther. 18(8), 1458-1461, August 2010). AAV is a helper-dependent DNA parvovirus which belongs to the genus *Dependovirus*.

The present invention provides such improved nucleic acid constructs, e.g., polynucleotides, for use with AAV-derived vectors comprising dopa carboxylase ("DDC") gene sequence which encodes a full-length AADC protein for the purpose of gene therapy in the treatment of Parkinson's Disease.

The nucleic acid constructs described herein comprise at least a 5'-ITR and a 3'-ITR, each or both of which may be derived from an AAV, positioned about a DDC gene sequence, as well as additional components required for gene expression and clone selection.

SUMMARY OF THE INVENTION

Described herein are compositions, methods, processes, kits and devices for the design, preparation, manufacture and/or formulation of AADC polynucleotides.

In some embodiments such AADC polynucleotides may be encoded by or contained within plasmids or vectors or recombinant adeno-associated viruses (AAV).

The details of various embodiments of the invention are set forth in the description below. Other features, objects, and advantages of the invention will be apparent from the description and from the claims.

DETAILED DESCRIPTION

Compositions of the Invention

According to the present invention, AADC polynucleotides are provided which function alone or in combination with additional nucleic acid sequence(s) to encode the AADC protein. As used herein an "AADC polynucleotide" is any nucleic acid polymer which encodes an AADC protein and when present in a vector, plasmid or translatable construct, expresses such AADC protein in a cell, tissue, organ or organism.

AADC polynucleotides include precursor molecules which are processed inside the cell. AADC polynucleotides or the processed forms thereof may be encoded in a plasmid, vector, genome or other nucleic acid expression vector for delivery to a cell.

In some embodiments AADC polynucleotides are designed as components of AAV viral genomes and packaged in AAV viral particles which are processed within the cell to produce the wild type AADC protein.

As used herein, the wild type AADC protein may be any of the naturally occurring isoforms or variants from the DDC gene. Multiple alternatively spliced transcript variants encoding different isoforms of AADC have been identified. Specifically, the DDC gene produces seven transcript variants that encode six distinct isoforms. DDC transcript variants 1 and 2 both encode AADC isoform 1. In some embodiments, the AADC polynucleotides encode DDC transcript variant 2, thereby encoding a native AADC isoform 1 (NCBI Reference Sequence: NP_000781.1). This sequence is given here:

(SEQ ID NO: 1)
MNASEFRRRGKEMVDYVANYMEGIEGRQVYPDVEPGYLRPLIPAAAPQEP

DTFEDIINDVEKIIMPGVTHWHSPYFFAYFPTASSYPAMLADMLCGAIGC

IGFSWAASPACTELETVMMDWLGKMLELPKAFLNEKAGEGGGVIQGSASE

ATLVALLAARTKVIHRLQAASPELTQAAIMEKLVAYSSDQAHSSVERAGL

IGGVKLKAIPSDGNFAMRASALQEALERDKAAGLIPFFMVATLGTTTCCS

FDNLLEVGPICNKEDIWLHVDAAYAGSAFICPEFRHLLNGVEFADSFNFN

PHKWLLVNFDCSAMWVKKRTDLTGAFRLDPTYLKHSHQDSGLITDYRHWQ

IPLGRRFRSLKMWFVFRMYGVKGLQAYIRKHVQLSHEFESLVRQDPRFEI

CVEVILGLVCFRLKGSNKVNEALLQRINSAKKIHLVPCHLRDKFVLRFAI

CSRTVESAHVQRAWEHIKELAADVLRAERE

The AADC polynucleotides of the invention, may be engineered to contain modular elements and/or sequence motifs assembled to create AADC polynucleotide constructs.

AADC Polynucleotide Constructs

According to the present invention, AADC polynucleotides are provided. Such polynucleotides comprise nucleic acid polymers which comprise a region of linked nucleosides encoding one or more isoforms or variants of the AADC protein.

In some embodiments, the AADC polynucleotide comprises a codon optimized transcript encoding an AADC protein.

In some embodiments, the AADC polynucleotide comprises a sequence region encoding one or more wild type isoforms or variants of an AADC protein. Such polynucleotides may also comprise a sequence region encoding any one or more of the following: a 5' ITR, a cytomegalovirus (CMV) Enhancer, a CMV Promoter, an ie1 exon 1, an ie1 intron1, an hbBglobin intron2, an hBglobin exon 3, a 5' UTR, a 3' UTR, an hGH poly(A) signal, and/or a 3' ITR. Such sequence regions are taught herein or may be any of those known in the art.

In some embodiments, the AADC polynucleotide comprises a sequence of any of SEQ ID NOs. 2-23.

In one embodiment, the AADC polynucleotide comprises a sequence which has a percent identity to any of SEQ ID NOs: 2-23. The AADC polynucleotide may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to any of SEQ ID NOs: 2-23. The AADC polynucleotide may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to any of SEQ ID NOs: 2-23. As a non-limiting example, the AADC polynucleotide comprises a sequence which as 80% identity to any of SEQ ID NOs 6, 7, 8, 9, 17, 18, 19, 20, 21, 22, and 23. As another non-limiting example, the AADC polynucleotide comprises a sequence which as 85% identity to any of SEQ ID NOs 6, 7, 8, 9, 17, 18, 19, 20, 21, 22, and 23. As another non-limiting example, the AADC polynucleotide comprises a sequence which as 90% identity to any of SEQ ID NOs 6, 7, 8, 9, 17, 18, 19, 20, 21, 22, and 23. As another non-limiting example, the AADC polynucleotide comprises a sequence which as 95% identity to any of SEQ ID NOs 6, 7, 8, 9, 17, 18, 19, 20, 21, 22, and 23. As another non-limiting example, the AADC polynucleotide comprises a sequence which as 99% identity to any of SEQ ID NOs 6, 7, 8, 9, 17, 18, 19, 20, 21, 22, and 23.

In some embodiments the AADC coding region is 1440 nucleotides in length. Such an AADC polynucleotide may be codon optimized over all or a portion of the polynucleotide.

In some embodiments the AADC coding region is 1443 nucleotides in length. In such case, an additional codon may be present at the 3' end of the polynucleotide.

In some embodiments the AADC coding region is 1449 nucleotides in length. In such case, additional codons may be present at the 3' end of the polynucleotide.

In some embodiments, the AADC polynucleotide comprises any of SEQ ID NOs 6-9, 17-23 but lacking the 5' and/or 3' ITRs. Such a polynucleotide may be incorporated into a plasmid or vector and utilized to express the encoded AADC protein.

In one embodiment, the AADC polynucleotides may be produced in insect cells (e.g., Sf9 cells).

In one embodiment, the AADC polynucleotides may be produced using triple transfection.

In one embodiment, the AADC polynucleotide may comprise a codon optimized open reading frame of an AADC mRNA, at least one 5'ITR and at least one 3'UTR where the one or more of the 5'ITRs may be located at the 5'end of the promoter region and one or more 3' ITRs may be located at the 3' end of the poly(A) signal. The AADC mRNA may comprise a promoter region, a 5'untranslated region (UTR), a 3'UTR and a poly(A) signal. The promoter region may inclue, but is not limited to, enhancer element, a promoter element, a first exon region, a first intron region, a second intron region and a second exon region. As a non-limiting example, the enhancer element and the promoter element are derived from CMV. As another non-limiting example, the first exon region is ie1 exon 1 or fragments thereof, the first intron region is ie1 intron 1 or fragments thereof, the second intron region is hbBglobin intron 2 or fragments thereof and the second exon region is hbBglobin exon 3 or fragments thereof. As yet another non-limiting example, the poly(A) signal is derived from human growth hormone.

In one embodiment, the AADC polynucleotide is encoded in a plasmid or vector, which may be derived from an adeno-associated virus (AAV). The AAV may be a recombinant AAV virus and may comprise a capsid serotype such as, but not limited to, of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8. As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9(hu14). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8.

Promoters

A person skilled in the art may recognize that a target cell may require a specific promoter including but not limited to a promoter that is species specific, inducible, tissue-specific, or cell cycle-specific Parr et al., Nat. Med.3:1145-9 (1997); the contents of which are herein incorporated by reference in its entirety).

In one embodiment, the promoter is a promoter deemed to be efficient for the AADC polynucleotide.

In one embodiment, the promoter is a promoter deemed to be efficient for the cell being targeted.

In one embodiment, the promoter is a weak promoter which provides expression of a payload for a period of time in targeted tissues such as, but not limited to, nervous system tissues. Expression may be for a period of 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues. As another non-limiting example, the promoter is a weak promoter for sustained frataxin expression in nervous system tissue such as, but not limited to, neuronal tissue and glial tissue.

In one embodiment, the FRDA promoter is used with the AADC polynucleotides described herein.

In one embodiment, there is a region located approximately ~5 kb upstream of the first exon of the payload. As a non-limiting example, there is a 17 bp region located approximately 4.9 kb upstream of the first exon of the frataxin gene in order to allow for expression with the FRDA promoter (See e.g., Puspasari et al. *Long Range Regulation of Human FXN Gene Expression*, PLOS ONE, 2011; the contents of which is herein incorporated by reference in its entirety).

In one embodiment, the promoter may be a promoter which is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. As a non-limiting example, the promoter is a combination of a 382 nucleotide CMV-enhancer sequence and a 260 nucleotide CBA-promoter sequence.

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety) such as promoters. Promoters for which promote expression in most tissues include, but are not limited to, human elongation factor 1α-subunit (EF1α), immediate-early cytomegalovirus (CMV), chicken β-actin (CBA) and its derivative CAG, the β glucuronidase (GUSB), or ubiquitin C (UBC). Tissue-specific expression elements can be used to restrict expression to certain cell types such as, but not limited to, nervous system promoters which can be used to restrict expression to neurons, astrocytes, or oligodendrocytes. Non-limiting example of tissue-specific expression elements for neurons include neuron-specific enolase (NSE), platelet-derived growth factor (PDGF), platelet-derived growth factor B-chain (PDGF-β), the synapsin (Syn), the methyl-CpG binding protein 2 (MeCP2), CaMKII, mGluR2, NFL, NFH, nβ2, PPE, Enk and EAAT2 promoters. A non-limiting example of a tissue-specific expression elements for astrocytes include the glial fibrillary acidic protein (GFAP) and EAAT2 promoters. A non-limiting example of a tissue-specific expression element for oligodendrocytes include the myelin basic protein (MBP) promoter.

In one embodiment, a ubiquitous promoter may be used with the AADC polynucleotides described herein. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3). Yu et al. (Molecular Pain 2011, 7:63; the contents of which are herein incorporated by reference in its entirety) evaluated the expression of eGFP under the CAG, EF1α, PGK and UBC promoters in rat DRG cells and primary DRG cells using lentiviral vectors and found that UBC showed weaker expression than the other 3 promoters and there was only 10-12% glia expression seen for all promoters. Soderblom et al. (E. Neuro 2015; the contents of which are herein incorporated by reference in its entirety) the expression of eGFP in AAV8 with CMV and UBC promoters and AAV2 with the CMV promoter after injection in the motor cortex. Intranasal administration of a plasmid containing a UBC or EF1α promoter showed a sustained airway expression greater than the expression with the CMV promoter (See e.g., Gill et al., Gene Therapy 2001, Vol. 8, 1539-1546; the contents of which are herein incorporated by reference in its entirety). Husain et al. (Gene Therapy 2009; the contents of which are herein incorporated by reference in its entirety) evaluated a HβH construct with a hGUSB promoter, a HSV-1LAT promoter and a NSE promoter and found that the HβH construct showed weaker expression than NSE in mice brain. Passini and Wolfe (J. Virol. 2001, 12382-12392, the contents of which are herein incorporated by reference in its entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in its entirety) when NF-L and NF-H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650 nucleotide promoter and NFH is a 920 nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. 2007 and Raymond et al. 2004; the contents of each of which are herein incorporated by reference in their entireties).

In one embodiment, an UBC promoter may be used with the AADC polynucleotides described herein. The UBC promoter may have a size of 300-350 nucleotides. As a non-limiting example, the UBC promoter is 332 nucleotides.

In one embodiment, a GUSB promoter may be used with the AADC polynucleotides described herein. The GUSB promoter may have a size of 350-400 nucleotides. As a non-limiting example, the GUSB promoter is 378 nucleotides. As a non-limiting example, the construct may be AAV-promoter-CMV/globin intron-hFXN-RBG, where the AAV may be self-complementary and the AAV may be the DJ serotype.

In one embodiment, a NFL promoter may be used with the AADC polynucleotides described herein. The NFL promoter may have a size of 600-700 nucleotides. As a non-limiting example, the NFL promoter is 650 nucleotides. As a non-limiting example, the construct may be AAV-promoter-CMV/globin intron-hFXN-RBG, where the AAV may be self-complementary and the AAV may be the DJ serotype.

In one embodiment, a NFH promoter may be used with the AADC polynucleotides described herein. The NFH promoter may have a size of 900-950 nucleotides. As a non-limiting example, the NFH promoter is 920 nucleotides. As a non-limiting example, the construct may be AAV-promoter-CMV/globin intron-hFXN-RBG, where the AAV may be self-complementary and the AAV may be the DJ serotype.

In one embodiment, a scn8a promoter may be used with the AADC polynucleotides described herein. The scn8a promoter may have a size of 450-500 nucleotides. As a non-limiting example, the scn8a promoter is 470 nucleotides. As a non-limiting example, the construct may be AAV-promoter-CMV/globin intron-hFXN-RBG, where the AAV may be self-complementary and the AAV may be the DJ serotype.

In one embodiment, a FXN promoter may be used with the AADC polynucleotides described herein.

In one embodiment, a PGK promoter may be used with the AADC polynucleotides described herein.

In one embodiment, a CBA promote may be used with the AADC polynucleotides described herein.

In one embodiment, a CMV promoter may be used with the AADC polynucleotides described herein.

In one embodiment, a liver or a skeletal muscle promoter may be used with the AADC polynucleotides described herein. Non-limiting examples of liver promoters include hAAT and TBG. Non-limiting examples of skeletal muscle promoters include Desmin, MCK and C5-12.

In one embodiment, an enhancer element, a promoter and/or a 5'UTR intron may be used with the AADC polynucleotides described herein. The enhancer may be, but is not limited to, a CMV enhancer, the promoter may be, but is not limited to, a CMV, CBA, UBC, GUSB, NSE, Sunapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter and (9) GFAP promoter.

In one embodiment, an engineered promoter may be used with the AADC polynucleotides described herein.

Introns

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

Introduction into Cells

The AADC polynucleotides of the invention can be introduced into host cells using any of a variety of approaches. Infection with a viral vector comprising the AADC polynucleotide can be effected. Examples of suitable viral vectors include replication defective retroviral vectors, adenoviral vectors, adeno-associated vectors and lentiviral vectors.

According to the present invention, viral vectors for use in therapeutics and/or diagnostics comprise a virus that has been distilled or reduced to the minimum components necessary for transduction of a nucleic acid payload or cargo of interest.

In this manner, viral vectors are engineered as vehicles for specific delivery while lacking the deleterious replication and/or integration features found in wild-type virus.

As used herein, a "vector" is any molecule or moiety which transports, transduces or otherwise acts as a carrier of a heterologous molecule such as the polynucleotides of the invention. A "viral vector" is a vector which comprises one or more polynucleotide regions encoding or comprising payload molecule of interest, e.g., a transgene, a polynucleotide encoding a polypeptide or multi-polypeptide. Viral vectors of the present invention may be produced recombinantly and may be based on adeno-associated virus (AAV) parent or reference sequence. Serotypes which may be useful in the present invention include any of those arising from AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in its entirety, may comprise two mutations: (1) R587Q where arginine (R; arg) at amino acid 587 is changed to glutamine (Q; gln) and (2) R590T where arginine (R; arg) at amino acid 590 is changed to threonine (T; thr). As another non-limiting example, may comprise three mutations: (1) K406R where lysine (K; lys) at amino acid 406 is changed to arginine (R; arg), (2) R587Q where arginine (R; arg) at amino acid 587 is changed to glutamine (Q; gln) and (3) R590T where arginine (R; arg) at amino acid 590 is changed to threonine (T; thr).

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

Pharmaceutical Compositions

Although the descriptions of pharmaceutical compositions, e.g., those polynucleotides (including the encoding plasmids or expression vectors, such as viruses, e.g., AAV) comprising a payload, e.g., AADC encoding sequences, to be delivered, provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to the viral vector carrying the payload or to the polynucleotide payload molecule delivered by a viral vector as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

In one embodiment, the pharmaceutical composition comprises a recombinant adeno-associated virus (AAV) vector comprising an AAV capsid and an AAV vector genome. The AAV vector genome may comprise at least one AADC polynucleotide described herein, such as, but not limited to, SEQ ID NOs 6, 7, 8, 9, 17, 18, 19, 20, 21, 22, and 23 or variants having at least 95% identity thereto. The recombinant AAV vectors in the pharmaceutical composition may have at least 70% which contain an AAV vector genome.

Formulation

The AADC polynucleotides or viral vectors encoding them can be formulated using one or more excipients to: (1) increase stability; (2) increase cell transfection or transduction; (3) permit the sustained or delayed release; or (4) alter the biodistribution (e.g., target the viral vector to specific tissues or cell types).

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one payload molecule, e.g., an AADC polynucleotide. As a non-limiting example, the formulations may contain 1, 2, 3, 4 or 5 AADC polynucleotide payload molecules.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In one embodiment, the AADC polynucleotides may be formulated in a hydrogel prior to administration. Hydrogels have a degree of flexibility which is similar to natural tissue as a result of their significant water content.

In another embodiment, a hydrogel may be administered to a subject prior to the administration of an AADC polynucleotide formulation. As a non-limiting example, the site of administration of the hydrogel may be within 3 inches (e.g., within 2.9, 2.8, 2.7, 2.6, 2.5, 2.4, 2.3, 2.2., 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less than 0.1 inches) of the site of administration of the AADC polynucleotide formulation.

In one embodiment, the AADC polynucleotides may be administered in saline. As a non-limiting example, the formulation may be phosphate buffered saline (PBS) with 0.001% Pluronic acid (F-68). Additionally the formulation may be sterilized.

Inactive Ingredients

In some embodiments, AADC polynucleotide formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of viral vectors carrying AADC polynucleotides disclosed herein may include cations or anions. In one embodiment, the formulations include metal cations such as, but not limited to, Zn2+, Ca2+, Cu2+, Mg+ and combinations thereof. As a non-limiting example, formulations may include polymers and AADC polynucleotides complexed with a metal cation (See e.g., U.S. Pat. Nos. 6,265,389 and 6,555,525, each of which is herein incorporated by reference in its entirety).

Administration

The viral vectors comprising AADC polynucleotides of the present invention may be administered by any route which results in a therapeutically effective outcome. These include, but are not limited to epidural (into the dura matter), oral (by way of the mouth), transdermal, peridural, intracerebral (into the cerebrum), intracerebroventricular (into the cerebral ventricles), subcutaneous (under the skin), nasal administration (through the nose), intravenous (into a vein), intravenous bolus, intravenous drip, intraarterial (into an artery), intrathecal (into the spinal canal), endocervical, intracaudal (within the cauda equine), intracisternal (within the cisterna magna cerebellomedularis), intradiscal (within a disc), intradural (within or beneath the dura), intrameningeal (within the meninges), intrapleural (within the pleura), intraspinal (within the vertebral column), intrathecal (within the cerebrospinal fluid at any level of the cerebrospinal axis), intrathoracic (within the thorax), intrastriatal (within the striatum, caudate nucleus and/or putamen), caudal block, nerve block, or spinal. In specific embodiments, compositions may be administered in a way which allows them cross the blood-brain barrier, vascular barrier, or other epithelial barrier. In one embodiment, a formulation for a route of administration may include at least one inactive ingredient.

In one embodiment, the viral vectors comprising AADC polynucleotides of the present invention may be administered to the right putamen and/or the left putamen. The administration may be at one or more sites in the putamen such as, but not limited to, 2 sites, 3 sites, 4 sites or more than 4 sites. As a non-limiting example, the viral vectors comprising AADC polynucleotides of the present invention are delivered to 2 sites in the left putamen and 2 sites in the right putamen.

In one embodiment, the administration of the formulation of the viral vectors comprising the AADC polynucleotides of the present invention to a subject provides coverage of the putamen of a subject (e.g., the left and/or right putamen). In one aspect, the administration of the viral vectors comprising the AADC polynucleotides may provide at least 8%, 9%, 10%, 13%, 14%, 15%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% to the left and/or right putamen of a subject. As a non-limiting example, the coverage is at least 20%. As a non-limiting example, the coverage is at least 40%. In another aspect, the administration of the viral vectors comprising the AADC polynucleotides may provide at least 8%, 9%, 10%, 13%, 14%, 15%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% coverage of the surface area of the left and/or right putamen of a subject. As a non-limiting example, the total coverage is at least 20%. As a non-limiting example, the total coverage is at least 40%. In yet another aspect, the administration of the viral vectors comprising the AADC polynucleotides may provide 10-40%, 20-40%, 20-30%, 20-35%, 20-50%, 30-40%, 35-40%, 30-60%, 40-70%, 50-80% or 60-90% coverage to the left and/or right putamen of a subject or to the total surface area of the left and/or right putamen of a subject.

In one embodiment, the administration of the formulation of the viral vectors comprising the AADC polynucleotides of the present invention to a subject provides coverage of the posterior putamen of a subject (e.g., the left and/or right posterior putamen). In one aspect, the administration of the viral vectors comprising the AADC polynucleotides may provide at least 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% to the left and/or right posterior putamen of a subject. As a non-limiting example, the coverage is at least 20%. As a non-limiting example, the coverage is at least 40%. In another aspect, the administration of the viral vectors comprising the AADC polynucleotides may provide at least 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% coverage of the surface area of the left and/or right posterior putamen of a subject. As a non-limiting example, the total coverage is at least 20%. As a non-limiting example, the total coverage is at least 40%. In yet another aspect, the administration of the viral vectors comprising the AADC polynucleotides may provide 10-40%, 20-50%, 30-60%, 40-70%, 50-80% or 60-90% coverage to the left and/or right posterior putamen of a subject or to the total surface area of the left and/or right putamen of a subject.

In one embodiment, a subject may be administered the viral-vectors comprising AADC polynucleotides of the present invention safely delivered to substantia nigra pars compacta (SNpc) and ventral tegmental area (VTA) via bilateral infusions, or alternatively, intrastriatally (into the caudate nucleus and putamen), or into the subthalamic nucleus (STN).

In one embodiment, the AADC polynucleotides described herein may be administered using acute bilateral placement of catheters into each putamen. The placement may use magnetic resonance image (MRI)-guided stereotactic neurosurgical techniques known in the art or described herein. Additionally, a contrast agent such as, but not limited to a gadolinium based contrast agent (e.g., PROHANCE®) may be used in the formulation to monitor and confirm the distribution of the formulation.

In one embodiment, a subject may be administered the viral vectors comprising AADC polynucleotides of the present invention in a bilateral stereotactic CED-assisted step infusion into the putamen (e.g., the post commissural putamen).

In one embodiment, delivery of viral vector pharmaceutical compositions in accordance with the present invention to cells of the central nervous system (e.g., parenchyma) comprises a rate of delivery defined by [VG/hour=mL/hour*VG/mL] wherein VG is viral genomes, VG/mL is composition concentration, and mL/hour is rate of prolonged infusion.

In one embodiment, delivery of viral vector pharmaceutical compositions in accordance with the present invention to cells of the central nervous system (e.g., parenchyma) comprises infusion of up to 1 mL. In one embodiment, delivery of viral vector pharmaceutical compositions in accordance with the present invention to cells of the central nervous system (e.g., parenchyma) may comprise infusion of 0.001, 0.002, 0.003, 0.004, 0.005, 0.010, 0.015, 0.020, 0.025, 0.030, 0.040, 0.050, 0.060, 0.070, 0.080, 0.090, 0.1, 0.2, 0.3, 0.4, 0.5, 0.6, 0.7, 0.8, or 0.9 mL.

In one embodiment, delivery of viral vector pharmaceutical compositions in accordance with the present invention to cells of the central nervous system (e.g., parenchyma) comprises infusion of between about 1 mL to about 120 mL. In one embodiment, delivery of viral vector pharmaceutical compositions in accordance with the present invention to cells of the central nervous system (e.g., parenchyma) may comprise infusion of 0.1, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 mL. In one embodiment, delivery of AAV particles to cells of the central nervous system (e.g., parenchyma) comprises infusion of at least 3 mL. In one embodiment, delivery of AAV particles to cells of the central nervous system (e.g., parenchyma) consists of infusion of 3 mL. In one embodiment, delivery of AAV particles to cells of the central nervous system (e.g., parenchyma) comprises infusion of at least 10 mL. In one embodiment, delivery of AAV particles to cells of the central nervous system (e.g., parenchyma) consists of infusion of 10 mL.

In one embodiment, the volume of the viral vector pharmaceutical composition delivered to the cells of the central nervous system (e.g., parenchyma) of a subject is 50 ul, 100 ul, 200 ul, 300 ul, 400 ul, 500 ul, 600 ul, 700 ul, 800 ul, 900 ul, 1000 ul, 1100 ul, 1200 ul, 1300 ul, 1400 ul, 1500 ul, 1600 ul, 1700 ul, 1800 ul, 1900 ul, 2000 ul or more than 2000 ul.

In one embodiment, the volume of the viral vector pharmaceutical composition delivered to a region in both hemispheres of a subject brain is 50 ul, 100 ul, 200 ul, 300 ul, 400 ul, 500 ul, 600 ul, 700 ul, 800 ul, 900 ul, 1000 ul, 1100 ul, 1200 ul, 1300 ul, 1400 ul, 1500 ul, 1600 ul, 1700 ul, 1800 ul, 1900 ul, 2000 ul or more than 2000 ul. As a non-limiting example, the volume delivered to a region in both hemispheres is 200 ul. As another non-limiting example, the volume delivered to a region in both hemispheres is 900 ul. As yet another non-limiting example, the volume delivered to a region in both hemispheres is 1800 ul.

In one embodiment, the volume of the viral vector pharmaceutical composition delivered to the putamen in both hemispheres of a subject brain is 50 ul, 100 ul, 200 ul, 300 ul, 400 ul, 450 ul, 500 ul, 600 ul, 700 ul, 800 ul, 900 ul, 1000 ul, 1100 ul, 1200 ul, 1300 ul, 1400 ul, 1500 ul, 1600 ul, 1700 ul, 1800 ul, 1900 ul, 2000 ul or more than 2000 ul. As a non-limiting example, the volume delivered to the putamen in both hemispheres is 100 ul. As another non-limiting example, the volume delivered to the putamen in both hemispheres is 200 ul. As a non-limiting example, the volume delivered to the putamen in both hemispheres is 300 ul. As another non-limiting example, the volume delivered to the putamen in both hemispheres is 450 ul. As another non-limiting example, the volume delivered to the putamen in both hemispheres is 900 ul. As yet another non-limiting example, the volume delivered to the putamen both hemispheres is 1800 ul.

In one embodiment, the total volume delivered to a subject may be split between one or more administration sites e.g., 1, 2, 3, 4, 5 or more than 5 sites. As a non-limiting example, the total volume is split between administration to the left and right putamen. As another non-limiting example, the total volume is split between two sites of administration to each of the left and right putamen.

In one embodiment, the viral vector pharmaceutical composition is administered using a fenestrated needle. Non-limiting examples of fenestrated needles are described in U.S. Pat. Nos. 8,333,734, 7,135,010, 7,575,572, 7,699,852, 4,411,657, 6,890,319, 6,613,026, 6,726,659, 6,565,572, 6,520,949, 6,382,212, 5,848,996, 5,759,179, 5 674,267, 5,588,960, 5,484,401, 5,199,441, 5,012,818, 4,474,569, 3,766,907, 3,552,394, the contents of each of which are herein incorporated by reference in its entirety.

In one embodiment, a composition comprises AADC polynucleotides described herein and the AADC polynucleotides are components of an AAV viral genome packaged in an AAV viral particle. The percent (%) ratio of AAV viral particles comprising the AADC polynucleotide (also referred to herein and AADC particles) to the AAV viral particles without the AADC polynucleotide (also referred to herein as empty capsids) in the composition may be 0:100, 1:99, 0: 90, 15:85, 25:75, 30:70, 50:50, 70:30, 85:15, 90:10, 99:1 or 100:0. As a non-limiting example, the percent ratio of AADC particles to empty capsids is 50:50. As another non-limiting example, the percent ratio of AADC particles to empty capsids is 70:30. As another non-limiting example, the percent ratio of AADC particles to empty capsids is 85:15. As another non-limiting example, the percent ratio of AADC particles to empty capsids is 100:0.

In one embodiment, the composition described herein comprises at least 1, 5, 10, 15, 20, 25, 30, 35, 40, 45, 50, 51, 52, 53, 54, 55, 60, 65, 70, 75, 80, 81, 82, 83, 84, 85, 86, 87, 88, 89, 90, 91, 92, 93, 94, 95, 96, 97, 98, 99 or greater than 99% AADC particles. As a non-limiting example, the composition comprises at least 50% AADC particles. As another non-limiting example, the composition comprises at least 52% AADC particles. As another non-limiting example, the composition comprises at least 58% AADC particles. As another non-limiting example, the composition comprises at least 70% AADC particles. As another non-limiting example, the composition comprises at least 83% AADC particles. As another non-limiting example, the composition comprises at least 85% AADC particles. As another non-limiting example, the composition comprises at least 99% AADC particles. As another non-limiting example, the composition comprises 100% AADC particles.

In one embodiment, the composition described herein comprises 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% AADC particles. As a non-limiting example, the composition described herein comprises 50-100% AADC particles. As another non-limiting example, the composition described herein comprises 50-60% AADC particles. As another non-limiting example, the composition described herein comprises 80-99% AADC particles. As another non-limiting example, the composition described herein comprises 80-90% AADC particles. As a non-limiting example, the composition described herein comprises 80-95% AADC particles. As a non-limiting example, the composition described herein comprises 80-85% AADC particles.

In one embodiment, the composition described herein comprises less than 1, 5, 10, 15, 20, 25, 30, 35, 40, 45, 50, 51, 52, 53, 54, 55, 60, 65, 70, 75, 80, 81, 82, 83, 84, 85, 86, 87, 88, 89, 90, 91, 92, 93, 94, 95, 96, 97, 98, 99 or 100% empty particles. As a non-limiting example, the composition comprises less than 50% empty particles. As a non-limiting example, the composition comprises less than 45% empty particles. As a non-limiting example, the composition comprises less than 40% empty particles. As a non-limiting example, the composition comprises less than 35% empty particles. As a non-limiting example, the composition comprises less than 30% empty particles. As a non-limiting example, the composition comprises less than 25% empty particles. As a non-limiting example, the composition comprises less than 20% empty particles. As a non-limiting example, the composition comprises less than 15% empty particles. As a non-limiting example, the composition comprises less than 10% empty particles. As a non-limiting example, the composition comprises less than 5% empty particles. As a non-limiting example, the composition comprises less than 1% empty particles.

In the composition described herein comprises 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% empty particles. As a non-limiting example, the composition described herein comprises 30-40% empty particles. As another non-limiting example, the composition described herein comprises 30-50% empty particles. As another non-limiting example, the composition described herein comprises 30-60% empty particles. As another non-limiting example, the composition described herein comprises 30-70% empty particles. As a non-limiting example, the composition described herein comprises 30-80% empty particles. As a non-limiting example, the composition described herein comprises 30-90% empty particles.

In one embodiment, the AADC polynucleotides described herein may be administered to a subject who is also undergoing levodopa therapy. As a non-limiting example, the subject may have a positive response to levodopa therapy and at least one symptom of PD is reduced. As another non-limiting example, the subject may have a response to levodopa therapy where the symptoms of PD experienced by the subject are stable. As yet another non-limiting example, the subject may have a negative response to levodopa therapy where the symptoms of PD experienced by the subject are increasing.

In one embodiment, the dose of levodopa administered to the subject prior to the AADC polynucleotides is 1, 2, 3, 4, 5, 6, 7, 8, 9, 10, 11, 12, 13, 14, 15, 16, 17, 18, 19, 20, 21, 22, 23, 24, 25 or more than 25 mg/kg. As a non-limiting example, the dose is 3 mg/kg. As another non-limiting example, the dose is 10 mg/kg. As yet another non-limiting example, the dose is 20 mg/kg. The subject's response (e.g., behavioral response) to levodopa may be assessed prior to administration of the AADC polynucleotides. Additionally, the subject may be administered levodopa again after the administration of the AADC polynucleotides (e.g., 1 week, 2, weeks, 3 weeks, 1 month, 2 months, 3 months, 4 months, 5 months, 6 months, 7 months, 8 months, 9 months, 10 months, 11 months, 1 year or more than 1 year after the administration of AADC polynucleotides). The behavioral response can be re-assessed and compared to the initial response to determine the effects of the AADC polynucleotides. The subject may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% behavioral improvement.

In one embodiment, Levodopa may be administered multiple times after the administration of the AADC polynucleotides. Levodopa may be administered on a repeating schedule (e.g., every 5 days, weekly, every 10 days, every 15 days, every 30 days, monthly, bimonthly, every 3 months, every 4 months, every 5 months, every 6 months, every 7 months, every 8 months, every 9 months, every 10 months, every 11 months or yearly) or as symptoms arise. As a non-limiting example, 3 years post administration of AADC polynucleotides a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive. As a non-limiting example, 6 years post administration of AADC polynucleotides a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive. As a non-limiting example, 9 years post administration of AADC polynucleotides a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive.

In one embodiment, a subject who may be administered the AADC polynucleotides described herein have a documented response to levodopa therapy but have medically refractory fluctuations and are considered good surgical candidates. The determination if a subject is a good surgical candidate may be made by the physician treating the subject for PD or the physician administering the AADC polynucleotides who takes into consideration the overall risk to benefit ratio for the patient for the surgical intervention required for delivery of the AADC polynucleotides.

In one embodiment, the ratio of distribution volume in the parenchyma of an area of a subject to the infusion volume of an area of a subject may be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 or more than 6.0. As a non-limiting example, the ratio of distribution volume in the parenchyma to infusion volume was 1.6 in the caudate nucleus. As a non-limiting example, the ratio of distribution volume in the parenchyma to infusion volume was 3.1 in the putamen. As a non-limiting example, the distribution of the AADC polynucleotides in the putamen may be 2-3 times the volume infused.

Dosing

The present invention provides methods comprising administering viral vectors and their AADC polynucleotide payload or complexes in accordance with the invention to a subject in need thereof. Viral vector pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific polynucleotide payload employed; the duration of the treatment; drugs used in combination or coincidental with the specific compound employed; and like factors well known in the medical arts.

In certain embodiments, viral vector pharmaceutical compositions in accordance with the present invention may be administered at AADC polynucleotide dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired AADC polynucleotide dosage may be delivered three times in a single day, two times in a single day, once in a single day or in a period of 24 hours the dosage may be delivered once, twice, three times or more than three times. In certain embodiments, the desired AADC polynucleotide dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total dose into two or more doses, e.g., two or more administrations of the single unit dose. As used herein, a "single unit dose" is a dose of any polynucleotide therapeutic administered in one dose/at one time/single route/single point of contact, i.e., single administration event. As used herein, a "total daily dose" is an amount given or prescribed in 24 hr period. It may be administered as a single unit dose. In one embodiment, the viral vectors comprising the AADC polynucleotides of the present invention are administered to a subject in split doses. They may be formulated in buffer only or in a formulation described herein.

In one embodiment, delivery of viral vector pharmaceutical compositions in accordance with the present invention to cells of the central nervous system (e.g., parenchyma) may comprise a total concentration between about $1\times10^6$ VG/mL and about $1\times10^{16}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7'10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.8\times10^{11}$, $2\times10^{11}$, $3\times10^{11}$, $4\times10^{11}$, $5\times10^{11}$, $5.5\times10^{11}$, $6\times10^{11}$, $7\times10^{11}$, $8\times10^{11}$, $9\times10^{11}$, $0.8\times10^{12}$, $0.83\times10^{12}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5 \times 10^{13}$, $6 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/mL. In one embodiment, the concentration of the viral vector in the composition is $1 \times 10^{13}$ VG/mL. In one embodiment, the concentration of the viral vector in the composition is $3 \times 10^{12}$ VG/mL. In one embodiment, the concentration of the viral vector in the composition is $1.1 \times 10^{12}$ VG/mL. In one embodiment, the concentration of the viral vector in the composition is $3.7 \times 10^{12}$ VG/mL. In one embodiment, the concentration of the viral vector in the composition is $8 \times 10^{11}$ VG/mL. In one embodiment, the concentration of the viral vector in the composition is $2.6 \times 10^{12}$ VG/mL. In one embodiment, the concentration of the viral vector in the composition is $4.9 \times 10^{12}$ VG/mL. In one embodiment, the concentration of the viral vector in the composition is $0.8 \times 10^{12}$ VG/mL. In one embodiment, the concentration of the viral vector in the composition is $0.83 \times 10^{12}$ VG/mL. In one embodiment, the concentration of the viral vector in the composition is the maximum final dose which can be contained in a vial.

In one embodiment, delivery of viral vector pharmaceutical compositions in accordance with the present invention to cells of the central nervous system (e.g., parenchyma) may comprise a total concentration per subject between about $1 \times 10^6$ VG and about $1 \times 10^{16}$ VG. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $1.5 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $1.3 \times 10^{11}$, $2 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3 \times 10^{11}$, $4 \times 10^{11}$, $5 \times 10^{11}$, $5.4 \times 10^{11}$, $6 \times 10^{11}$, $7 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8 \times 10^{11}$, $9 \times 10^{11}$, $9.4 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.3 \times 10^{12}$, $2.4 \times 10^{12}$, $3 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $8.1 \times 10^{12}$, $8.2 \times 10^{12}$, $8.3 \times 10^{12}$, $8.4 \times 10^{12}$, $8.5 \times 10^{12}$, $8.6 \times 10^{12}$, $8.7 \times 10^{12}$, $8.8 \times 10^{12}$, $8.9 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/subject. In one embodiment, the concentration of the viral vector in the composition is $1 \times 10^{13}$ VG/subject. In one embodiment, the concentration of the viral vector in the composition is $3 \times 10^{12}$ VG/subject. As a non-limiting example, the composition administered to the subject has a concentration of about $3 \times 10^{11}$ VG/subject. As a non-limiting example, the composition administered to the subject has a concentration of about $9 \times 10^{11}$ VG/subject. In one embodiment, the concentration of the viral vector in the composition is $2.3 \times 10^{11}$ VG/subject. In one embodiment, the concentration of the viral vector in the composition is $7.2 \times 10^{11}$ VG/subject. In one embodiment, the concentration of the viral vector in the composition is $7.5 \times 10^{11}$ VG/subject. In one embodiment, the concentration of the viral vector in the composition is $1.4 \times 10^{12}$ VG/subject. In one embodiment, the concentration of the viral vector in the composition is $4.8 \times 10^{12}$ VG/subject. In one embodiment, the concentration of the viral vector in the composition is $8.8 \times 10^{12}$ VG/subject. In one embodiment, the concentration of the viral vector in the composition is $2.3 \times 10^{12}$ VG/subject.

In one embodiment, the effectiveness of the dose, route of administration and/or volume of administration may be evaluated using various methods described herein such as, but not limited to, PET imaging, L-DOPA challenge test (e.g., see Forsayeth et al. 2006, Mol. Ther. 14(4): 571-577), UPDRS scores and patient diaries. As a non-limiting example, a subject may have decreased dyskinesia or periods of decreased dyskinesia after administration of the AADC polynucleotide composition. As another non-limiting example, a subject may have a decrease in Parkinson's Disease related symptoms including limited mobility and dyskinesia. As yet another non-limiting example, a subject may show improvement in off time and motor fluctuations. The improvement may be at least 10%, at least 20%, at least 30%, at least 40%, at least 50%, at least 60%, at least 70%, at least 80%, at least 90% or greater than 90%. The improvement may last for minutes (e.g., 1, 2, 3, 4, 5, 6, 7, 8, 9, 10, 15, 20, 25, 30, 35, 40, 45, 50, 55 or more than 55), hours (e.g., 1, 2, 3, 4, 5, 6, 7, 8, 9, 10, 11, 12, 13, 14, 15, 16, 17, 18, 19, 20, 21, 22, 23 or more than 24), days (e.g., 1, 2, 3, 4, 5, 6 or more than 7), weeks (1, 2, 3, 4, 5, 6, 7 or more than 7), months (1, 2, 3, 4, 5, 6, 7, 8, 9, 10, 11 or more than 11) or years (e.g., 1, 2, 3, 4, 5, 6, 7, 8, 9 or more than 9).

In one embodiment, the selection of subjects for administration of the viral vectors described herein and/or the effectiveness of the dose, route of administration and/or volume of administration may be evaluated using imaging of the perivascular spaces (PVS) which are also known as Virchow-Robin spaces. PVS surround the arterioles and venules as they perforate brain parenchyma and are filled with cerebrospinal fluid (CSF)/interstitial fluid. PVS are common in the midbrain, BG, and centrum semiovale. While not wishing to be bound by theory, PVS may play a role in the normal clearance of metabolites and have been associated with worse cognition and several disease states including Parkinson's disease. PVS are usually normal in size but they can increase in size in a number of disease states. Potter et al. (Cerebrovasc Dis. 2015 January; 39(4): 224-231; the contents of which are herein incorporated by reference in its entirety) developed a grading method where they studied a full range of PVS and rated basal ganglia, centrum semiovale and midbrain PVS. They used the frequency and range of PVS used by Mac and Lullich et al. (J Neurol Neurosurg Psychiatry. 2004 November; 75(11): 1519-23; the contents of which are herein incorporated by reference in its entirety) and Potter et al. gave 5 ratings to basal ganglia and centrum semiovale PVS: 0 (none), 1 (1-10), 2 (11-20), 3 (21-40) and 4 (>40) and 2 ratings to midbrain PVS: 0 (non visible) or 1 (visible). The user guide for the rating system by Potter et al. can be found at: www.sbirc.ed.ac.uk/documents/epvs-rating-scale-user-guide.pdf.

In one embodiment, the selection of subjects for administration of the viral vectors described herein and/or the effectiveness of the dose, route of administration and/or volume of administration may be evaluated using positron emission tomography (PET) measurements of neuroimaging biomarkers such as, but not limited to [$^{18}$F]FDOPA. Neuroimaging biomarkers such as [$^{18}$F]FDOPA may be used to identify affected individuals and/or may be used to detect a nigrostriatal defect prior to the onset of clinical manifestations. Further, PET-based criteria may be used to categorize subjects based on their nigrostriatal neuronal integrity (e.g., abnormal, normal or uncertain nigrostriatal neuronal integrity) (Rachette et al. Am J Med Genet B Neuropsychiatr Genet. 2006 Apr. 5; 141B(3): 245-249; the contents of which are herein incorporated by reference in its entirety).

In one embodiment, a subject who may be administered a dose of the AADC polynucleotides described herein may have advanced PD and still respond to levodopa therapy but the subject also experiences medically refractory motor complications (e.g., sever motor fluctuations and/or dyskinesias that occur during levodopa and other dopaminergic therapies despite adjustments in and optimization of medication). The subject may be healthy enough to undergo a neurosurgical procedure which may be determined by methods known in the art. As a non-limiting example, the subject may meet the selection criteria for deep brain stimulation (DBS). The subject may have idiopathic PD, younger than 69 years of age, have pronounced responses to levodopa, have medication-refractory symptoms (e.g., motor fluctuation and/or dyskinesia) and/or have little or no cognitive dysfunction.

In one embodiment, a subject who may be administered a dose of the AADC polynucleotides described herein may also suffer from dementia or cognitive impairment.

In one embodiment, a subject who may be administered a dose of the AADC polynucleotides described herein may have been previously treated with the same or similar therapeutic. In another embodiment, a subject may have been treated with a therapeutic which has been shown to reduce the symptoms of Parkinson's Disease.

In one embodiment, a subject who may be administered a dose of the AADC polynucleotides described herein may have failed to derive adequate benefit from standard medical therapy. As a non-limiting example, the subject may not have responded to treatment. As another non-limiting example, a subject may have residual disability despite treatment.

In one embodiment, a subject who may be administered a dose of the AADC polynucleotides described herein may undergo testing to evaluate the levels of neurotransmitter analytes to determine the effectiveness of the dose. As a non-limiting example, CSF neurotransmitters, plasma AADC activity and/or urine VLA may be analyzed.

In one embodiment, a subject who may be administered a dose of the AADC polynucleotide described herein may be videotaped or recorded in order to monitor the progress of the subject during the course of treatment.

Combinations

The viral vectors comprising the AADC polynucleotide may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

Delivery

In one embodiment, the viral vector comprising an AADC polynucleotide may be administered or delivered using the methods for the delivery of AAV virions described in European Patent Application No. EP1857552, the contents of which are herein incorporated by reference in its entirety.

In one embodiment, the viral vector comprising an AADC polynucleotide may be administered or delivered using the methods for delivering proteins using AAV vectors described in European Patent Application No. EP2678433, the contents of which are herein incorporated by reference in its entirety.

In one embodiment, the viral vector comprising an AADC polynucleotide may be administered or delivered using the methods for delivering DNA molecules using AAV vectors described in U.S. Pat. No. 5,858,351, the contents of which are herein incorporated by reference in its entirety.

In one embodiment, the viral vector comprising an AADC polynucleotide may be administered or delivered using the methods for delivering DNA to the bloodstream described in U.S. Pat. No. 6,211,163, the contents of which are herein incorporated by reference in its entirety.

In one embodiment, the viral vector comprising an AADC polynucleotide may be administered or delivered using the methods for delivering AAV virions described in U.S. Pat. No. 6,325,998, the contents of which are herein incorporated by reference in its entirety.

In one embodiment, the viral vector comprising an AADC polynucleotide may be administered or delivered using the methods for delivering a payload to the central nervous system described in U.S. Pat. No. 7,588,757, the contents of which are herein incorporated by reference in its entirety.

In one embodiment, the viral vector comprising an AADC polynucleotide may be administered or delivered using the methods for delivering a payload described in U.S. Pat. No. 8,283,151, the contents of which are herein incorporated by reference in its entirety.

In one embodiment, the viral vector comprising an AADC polynucleotide may be administered or delivered using the methods for delivering a payload using a glutamic acid decarboxylase (GAD) delivery vector described in International Patent Publication No. WO2001089583, the contents of which are herein incorporated by reference in its entirety.

In one embodiment, the viral vector comprising an AADC polynucleotide may be administered or delivered using the methods for delivering a payload to neural cells described in International Patent Publication No. WO2012057363, the contents of which are herein incorporated by reference in its entirety.

The pharmaceutical compositions of viral vectors described herein may be characterized by one or more of bioavailability, therapeutic window and/or volume of distribution.

Bioavailability

Viral vectors comprising an AADC polynucleotide of the present invention, when formulated into compositions with delivery/formulation agents or vehicles as described herein, may exhibit increased bioavailability as compared to compositions lacking delivery agents as described herein. As used herein, the term "bioavailability" refers to the systemic availability of a given amount of a particular agent administered to a subject. Bioavailability may be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound may be calculated using methods known to those of ordinary skill in the art and as described in G. S. Banker, Modern Pharmaceutics, Drugs and the Pharmaceutical Sciences, v. 72, Marcel Dekker, New York, Inc., 1996, the contents of which are herein incorporated by reference in their entirety.

$C_{max}$ values are maximum concentrations of compounds achieved in serum or plasma of a subject following administration of compounds to the subject. $C_{max}$ values of particular compounds may be measured using methods known to those of ordinary skill in the art. As used herein, the phrases "increasing bioavailability" or "improving the pharmacokinetics," refer to actions that may increase the systemic availability of a viral vector of the present invention (as measured by AUC, $C_{max}$, or $C_{min}$) in a subject. In some embodiments, such actions may comprise co-administration with one or more delivery agents as described herein. In some embodiments, the bioavailability of viral vectors may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Therapeutic window

Viral vectors comprising an AADC polynucleotide of the present invention, when formulated with one or more delivery agents as described herein, may exhibit increases in the therapeutic window of compound and/or composition administration as compared to the therapeutic window of viral vectors administered without one or more delivery agents as described herein. As used herein, the term "therapeutic window" refers to the range of plasma concentrations, or the range of levels of therapeutically active substance at the site of action, with a high probability of eliciting a therapeutic effect. In some embodiments, therapeutic windows of viral vectors when administered in a formulation may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Volume of Distribution

Viral vectors comprising an AADC polynucleotide of the present invention, when formulated with one or more delivery agents as described herein, may exhibit an improved volume of distribution ($V_{dist}$), e.g., reduced or targeted, relative to formulations lacking one or more delivery agents as described herein. $V_{dist}$ relates the amount of an agent in the body to the concentration of the same agent in the blood or plasma. As used herein, the term "volume of distribution" refers to the fluid volume that would be required to contain the total amount of an agent in the body at the same concentration as in the blood or plasma: $V_{dist}$ equals the amount of an agent in the body/concentration of the agent in blood or plasma. For example, for a 10 mg dose of a given agent and a plasma concentration of 10 mg/L, the volume of distribution would be 1 liter. The volume of distribution reflects the extent to which an agent is present in the extravascular tissue. Large volumes of distribution reflect the tendency of agents to bind to the tissue components as compared with plasma proteins. In clinical settings, $V_{dist}$ may be used to determine loading doses to achieve steady state concentrations. In some embodiments, volumes of distribution of viral vector compositions of the present invention when co-administered with one or more delivery agents as described herein may decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Kits and Devices

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

Any of the AADC vectors, AADC constructs, AADC polynucleotides, or AADC polypeptides of the present invention may be comprised in a kit. In some embodiments, kits may further include reagents and/or instructions for creating and/or synthesizing compounds and/or compositions of the present invention. In some embodiments, kits may also include one or more buffers. In some embodiments, kits of the invention may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and preferably, suitably aliquoted. Where there are more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present invention may also typically include means for containing compounds and/or compositions of the present invention, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly preferred. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the invention. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In some embodiments, AADC compounds and/or AADC compositions of the present invention may be combined with, coated onto or embedded in a device. Devices may include, but are not limited to stents, pumps, and/or other implantable therapeutic device. Additionally AADC compounds and/or AADC compositions may be delivered to a subject while the subject is using a compression device such as, but not limited to, a compression device to reduce the chances of deep vein thrombosis (DVT) in a subject.

The present invention provides for devices which may incorporate viral vectors that encode one or more AADC polynucleotide payload molecules. These devices contain in a stable formulation the viral vectors which may be immediately delivered to a subject in need thereof, such as a human patient.

Devices for administration may be employed to deliver the viral vectors comprising an AADC polynucleotide of the present invention according to single, multi- or split-dosing regimens taught herein.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

In some embodiments, AADC compounds and/or AADC compositions of the present invention may be delivered using a device such as, but not limited to, a stent, a tube, a catheter, a pipe, a straw, needle and/or a duct. Methods of using these devices are described herein and are known in the art.

In one embodiment, the AADC polynucleotides of the present invention may be administered to a subject using delivery systems which integrate image guided therapy and integrate imaging such as, but not limited to, laser, MRg-FUS, endoscopic and robotic surgery devices.

In one embodiment, the AADC polynucleotides of the present invention may be administered to a subject using the CLEARPOINT® neuro intervention system by MRI Interventions, Inc. The CLEARPOINT® neuro intervention system may be used alone or in combination with any of the other administration methods and devices described herein. The CLEARPOINT® neuro intervention system helps to provide stereotactic guidance in the placement and operation of instruments or devices during the planning and operation of neurological procedures.

In one embodiment, the AADC polynucleotides of the present invention may be administered to a subject using the NEUROMATE® stereotactic robot system by Renishaw PLC. The NEUROMATE® system may be used alone or in combination with any of the other administration methods and devices described herein. As a non-limiting example, the NEUROMATE® system may be used with head holders, CT image localizers, frame attachments, remote controls and software.

In one embodiment, the AADC polynucleotides of the present invention may be administered to a subject using the Elekta MICRODRIVE™ device by Elekta AB. The MICRODRIVE™ device may be used alone or in combination with any of the other administration methods and devices described herein. As a non-limiting example, the MICRODRIVE™ device may be used to position electrodes (e.g., for micro electrode recording (MER), macro stimulation and deep brain stimulation (DBS) electrode implantation), implantation of catheters, tubes or DBS electrodes using cross-hair and A-P holders to verify position, biopsies, injections and aspirations, brain lesioning, endoscope guidance and GAMMA KNIFE® radiosurgery.

In one embodiment, the AADC polynucleotides of the present invention may be administered to a subject using the AXIIIS® stereotactic miniframe by MONTERIS® Medical, Inc. The AXIIIS® stereotactic miniframe may be used alone or in combination with any of the other administration methods and devices described herein. The AXIIIS® stereotactic miniframe is a trajectory alignment device which may be used for laser coagulation, biopsies, catheter placement, electrode implant, endoscopy, and clot evacuation. The miniframe allows for 360 degree interface and provides access to multiple intracranial targets with a simple adjustment. Further, the miniframe is compatible with MRI.

In one embodiment, the AADC polynucleotides of the present invention may be administered to a subject using the INTEGRA™ CRW® system by Integra LifeSciences Corporation. The INTEGRA™ CRW® system may be used alone or in combination with any of the other administration methods and devices described herein. The CRW® system may be used for various applications such as, but not limited to, stereotactic surgery, microsurgery, catheterization and biopsy. The CRW® system is designed to provide accuracy to those who use the system (e.g., thumb lock screws, Vernier scaling, double bolt fixation, and a solid frame).

In one embodiment, the AADC polynucleotides of the present invention may be administered to a subject using the EPOCH® solution system by Stereotaxis, Inc. which may include the NIOBE® ES magnetic navigation system, the VDRIVE® robotic navigation system and/or the ODYSSEY® information solution (all by Stereotaxis, Inc.). The EPOCH® solution system may be used alone or in combination with any of the other administration methods and devices described herein. As a non-limiting example, the NIOBE® ES magnetic navigation system may be used to accurately contact a subject. As another non-limiting example the NIOBE® ES magnetic system may be used with the VDRIVE® robotic navigation system to provide precise movement and stability.

In one embodiment, the AADC polynucleotides of the present invention may be administered to a subject using a NeuroStation workstation which uses frameless stereotactic methods to provide image-guidance for applications such as, but not limited to, surgical planning, biopsies, craniotomies, endoscopy, intra-operative ultrasound and radiation therapy.

In one embodiment, the AADC polynucleotides of the present invention may be administered to a subject using a robotic stereotaxis system such as, but not limited to the device described in U.S. Pat. No. 5,078,140, the contents of which are herein incorporated by reference in its entirety. The robotic arm of the device may be used to precisely orient the surgical tools or other implements used to conduct a procedure.

In one embodiment, the AADC polynucleotides of the present invention may be administered to a subject using an automatic delivery system such as, but not limited to, the device described in U.S. Pat. No. 5,865,744, the contents of which are herein incorporated by reference in its entirety. Based on the images gathered by the delivery system, the computer adjusts the administration of the needle to be the appropriate depth for the particular subject.

In one embodiment, the AADC polynucleotides of the present invention may be administered to a subject who is simultaneously using during administration, and/or uses for a period of time before and/or after administration a compression device such as, but not limited to, a compression device which reduces the chances of deep vein thrombosis (DVT) in a subject. The compression device may be used for at least 5 minutes, 15 minutes, 30 minutes, 45 minutes, 1 hour, 2 hours, 3 hours, 4 hours, 5 hours, 6 hours, 7 hours, 8 hours, or more than 8 hours before a subject is administered the AADC polynucleotides. The compression device may be used for at least 5 minutes, 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 2 weeks, 3 weeks or a month after the AADC polynucleotides are administered. As a non-limiting example, the compression device is used simultaneously during the procedure of the delivery of the AADC polynucleotides. As another non-limiting example, the compression device is used before the administration of the AADC polynucleotides. As another non-limiting example, the compression device is used after administration of the AADC polynucleotides. As another non-limiting example, the compression device is used before, during and after administration of the AADC polynucleotides.

Non-limiting examples, of compression devices include ActiveCare+S.F.T. intermittent compression device, ActiveCare+S.F.T pneumatic compression device, DVTlite's Venowave, KCI system compression pump, Aircast VenaFlow system, SCD Express Compression System or Bio Compression Systems, Inc. pneumatic compression therapy equipment (e.g., the pump may be selected from Model SC-2004, Model SC-2004-FC, Model SC-3004, Model SC-3004-FC, Model SC-2008, Model SC-2008-DL, Model SC-3008-T, the BioCryo system, Model IC-BAP-DL or multi-flo DVT combo IC 1545-DL and the garment used with the pump may be a 4 chamber, 8 chamber, BioCryo, Multi-Flo or BioArterial garment).

CNS Diseases

The polynucleotides of the present invention may be used in the treatment, prophylaxis or amelioration of any disease or disorder characterized by aberrant or undesired target expression. In one embodiment, the invention relates to compositions, particularly nucleic acid molecules, e.g., polynucleotides encoding AADC, for use in the treatment of Parkinson's disease.

In some embodiments, the polynucleotides of the invention may be used in the treatment, prophylaxis or amelioration of any disease or disorder characterized by aberrant or undesired target expression wherein the payload, i.e. AADC, is swapped for an alternate payload.

The present disclosure provides a method for treating a disease, disorder and/or condition in a mammalian subject, including a human subject, comprising administering to the subject any of the viral particles e.g., AAV, AAV polynucleotides or AAV genomes described herein (i.e., viral genomes or "VG") or administering to the subject a particle comprising said AAV polynucleotide or AAV genome, or administering to the subject any of the described compositions, including pharmaceutical compositions.

In one embodiment, the disease, disorder and/or condition is a neurological disease, disorder and/or condition. The CNS diseases may be diseases that affect any component of the brain (including the cerebral hemispheres, diencephalon, brain stem, and cerebellum) or the spinal cord.

In some embodiments, viral particles of the present invention, through delivery of a functional payload that is a therapeutic product that can modulate the level or function of a gene product in the CNS, may be used to treat a neurodegenerative diseases and/or diseases or disorders that are characteristic with neurodegeneration, neuromuscular diseases, lysosomal diseases, trauma, bone marrow injuries, pain (including neuropathic pain), cancers of the nervous system, demyelinating diseases, autoimmune diseases of the nervous system, neurotoxic syndromes, sleeping disorders, genetic brain disorders and developmental CNS disorders. A functional payload may alleviate or reduce symptoms that result from abnormal level and/or function of a gene product (e.g., an absence or defect in a protein) in a subject in need thereof or that otherwise confers a benefit to a CNS disorder in a subject in need thereof.

As non-limiting examples, therapeutic products delivered by viral particles of the present invention may include, but are not limited to, growth and trophic factors, cytokines, hormones, neurotransmitters, enzymes, anti-apoptotic factors, angiogenic factors, and any protein known to be mutated in pathological disorders such as the "survival of motor neuron" protein (SMN); antisense RNA or RNAi targeting messenger RNAs coding for proteins having a therapeutic interest in any of CNS diseases discussed herein; or microRNAs that function in gene silencing and post-transcriptionally regulation of gene expression in the CNS (e.g., brain specific Mir-128a, See Adlakha and Saini, Molecular cancer, 2014, 13:33). For example, an RNAi targeting the superoxide dismutase enzyme may be packaged by viral particles of the present invention, for the treatment of ALS.

The growth and trophic factors may include, but are not limited to brain-derived growth factor (BDNF), epidermal growth factor (EGF), basic Fibroblast growth factor (bFGF), Ciliary neurotrophic factor (CNTF), corticotropin-releasing factor (CRF), Glial cell line derived growth factor (GDNF), Insulin-like growth factor-1 (IGF-1), nerve growth factor (NGF), neurotrophin-3 (NT-3), neurotrophin-4 (NT-4), and vascular endothelial growth factor (VEGF). Cytokines may include interleukin-10 (IL-10), interleukin-6, Interleukin-8, chemokine CXCL12 (SDF-1), TGF-beta, and Growth and differentiation factor (GDF-1/10).

In some embodiments, the neurological disorders may be neurodegenerative disorders including, but not limited to, Alzheimer's Diseases (AD); Amyotrophic lateral sclerosis (ALS); Creutzfeldt-Jakob Disease (CJD); Huntingtin's disease (HD); Friedreich's ataxia (FA); Parkinson Disease (PD); Multiple System Atrophy (MSA); Spinal Muscular Atrophy (SMA), Multiple Sclerosis (MS); Primary progressive aphasia; Progressive supranuclear palsy (PSP); Dementia; Brain Cancer, Degenerative Nerve Diseases, Encephalitis, Epilepsy, Genetic Brain Disorders that cause neurodegeneration, Retinitis pigmentosa (RP), Head and Brain Malformations, Hydrocephalus, Stroke, Prion disease, Infantile neuronal ceroid lipofuscinosis (INCL) (a neurodegenerative disease of children caused by a deficiency in the lysosomal enzyme palmitoyl protein thioesterase-1 (PPT1)), and others.

In some embodiments, viral particles of the present invention may be used to treat diseases that are associated with impairments of the growth and development of the CNS, i.e., neurodevelopmental disorders. In some aspects, such neurodevelopmental disorders may be caused by genetic mutations, including but not limited to, Fragile X syndrome (caused by mutations in FMR1 gene), Down syndrome (caused by trisomy of chromosome 21), Rett syndrome, Williams syndrome, Angelman syndrome, Smith-Magenis syndrome, ATR-X syndrome, Barth syndrome, Immune dysfunction and/or infectious diseases during infancy such as Sydenham's chorea, Schizophrenia Congenital toxoplasmosis, Congenital rubella syndrome, Metabolic disorders such as diabetes mellitus and phenylketonuria; nutritional defects and/or brain trauma, Autism and autism spectrum.

In some embodiments, viral particles of the present invention, may be used to treat a tumor in the CNS, including but not limited to, acoustic neuroma, Astrocytoma (Grades I, II, III and IV), Chordoma, CNS Lymphoma, Craniopharyngioma, Gliomas (e.g., brain stem glioma, ependymoma, optical nerve glioma, subependymoma), Medulloblastoma, Meningioma, Metastatic brain tumors, Oligodendroglioma, Pituitary Tumors, Primitive neuroectodermal (PNET), and Schwannoma.

In some embodiments, the neurological disorders may be functional neurological disorders with motor and/or sensory symptoms which have neurological origin in the CNS. As non-limiting examples, functional neurological disorders may be chronic pain, seizures, speech problems, involuntary movements, and sleep disturbances.

In some embodiments, the neurological disorders may be white matter disorders (a group of diseases that affects nerve fibers in the CNS) including but not limited to, Pelizaeus-Merzbacher disease, Hypomyelination with atrophy of basal ganglia and cerebellum, Aicardi-Goutieres syndrome, Megalencephalic leukoencephalopathy with subcortical cysts, Congenital muscular dystrophies, Myotonic dystrophy, Wilson disease, Lowe syndrome, Sjögren-Larsson syndrome, PIBD or Tay syndrome, Cockayne's disease, erebrotendinous xanthomatosis, Zellweger syndrome, Neonatal adrenoleukodystrophy, Infantile Refsum disease, Zellweger-like syndrome, Pseudo-Zellweger syndrome, Pseudo-neonatal adrenoleukodystrophy, Bifunctional protein deficiency, X-linked adrenoleukodystrophy and adrenomyeloneuropathy and Refsum disease.

In some embodiments, the neurological disorders may be lysosomal storage disorders (LSDs) caused by the inability of cells in the CNS to break down metabolic end products, including but not limited to Niemann-Pick disease (a LSD resulting from inherited deficiency in acid sphingomyelinase (ASM); Metachromatic leukodystrophy (MLD) (a LSD characterized by accumulation of sulfatides in glial cells and neurons, the result of an inherited deficiency of arylsulfatase A (ARSA)); Globoid-cell leukodystrophy (GLD) (a LSD caused by mutations in galactosylceramidase); Fabry disease (a LSD caused by mutations in the alpha-galactosidase A (GLA) gene); Gaucher disease (caused by mutations in the beta-glucocerebrosidase (GBA) gene); GM1/GM2 gangliosidosis; Mucopolysaccharidoses disorder; Pompe disease; and Neuronal ceroid lipofuscinosis.

In one embodiment, the neurological disease, disorder and/or condition is Parkinson's disease. In one embodiment the polynucleotide used to treat Parkinson's disease comprises any one of SEQ ID NOs 2-23, such as, but not limited to SEQ ID NOs: 6-9 and 17-23, wherein the payload is replaced by AADC or any other payload known in the art for treating Parkinson's disease. As a non-limiting example, the condition is early stage Parkinson's disease. As another non-limiting example, the condition is late stage Parkinson's disease.

In one embodiment, the subject is a human patient who has a minimum motor score of about 30 to a maximum score of about 100, about 10 to a maximum score of about 100, about 20 to a maximum score of about 100 in the Unified Parkinson's Disease Rating Scale.

In one embodiment, the subject has been diagnosed with Parkinson's disease within the past 5 years prior to treatment with the compositions described herein. As a non-limiting example, the subject may have been diagnosed with Parkinson's disease within a week, 2 weeks, 3 weeks, 4 weeks, 5 weeks, 6 weeks, 7 weeks, 8 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 1 year, 2 years, 3 years, 4 years or less than 5 years prior to treatment with the compositions described herein.

In one embodiment, the subject has been diagnosed with Parkinson's disease between 5 and 10 years prior to treatment with the compositions described herein. As a non-limiting example, the subject may have been diagnosed with Parkinson's disease 5, 5.5., 6, 6.5, 7, 7.5, 8, 8.5, 9, 9.5 or 10 years prior to treatment with the compositions described herein.

In one embodiment, the subject has been diagnosed with Parkinson's disease more than 10 years prior to treatment with the compositions described herein. As a non-limiting example, the subject may have been diagnosed with Parkinson's disease 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24 or more than 24 years prior to treatment with the compositions described herein.

In one embodiment, a subject has seen a change in motor symptoms such as tremors and movements prior to administration of the composition described herein. Non-limiting examples of tremors include, unilateral or bilateral mild tremors, bilateral or midline moderate tremors or intractable tremors. Non-limiting examples of movements include mild bradykinesia, moderate bradykinesia, severe bradykinesia and morning akinesia.

In one embodiment, a subject may have changes in balance such as, but not limited to, impaired balance, impaired righting reflexes, significant balance disorder or falling.

In one embodiment, a subject may have a reduced quality of life. As a non-limiting example, the subject may have a moderate impact on their quality of life such as experiencing some limitations to activities of daily living. As another non-limiting example, the subject may have a quality of life which has been diminished by illness.

In one embodiment, a subject has seen a change in non-motor symptoms prior to administration of the composition described herein. As a non-limiting example, the subject may have mild to moderate cognitive impairment prior to administration to the composition described herein. As another non-limiting example, the subject may have significant cognitive impairment such as dementia which may also include behavioral disturbances such as hallucinations.

In one embodiment, a subject may have a satisfactory response with limited fluctuations on one or more dopaminergic medications prior to administration of the compositions described herein.

In one embodiment, a subject may have motor fluctuations causing mild to moderate disability on one or more dopaminergic medications prior to administration of the compositions described herein.

In one embodiment, a subject may have medically refractory motor fluctuations consisting of "wearing off" and/or levodopa-induced dyskinesias causing significant disability prior to administration of the compositions described herein.

In one embodiment, a subject may have mild symptoms associated with Parkinson's disease such as, but not limited to, no cognitive impairment, diagnosed within the past 5 years, satisfactory response with limited fluctuations on one or more dopaminergic medications, unilateral or bilateral mild tremors, little to no impact on the quality of life, and/or no balance impairment.

In one embodiment, a subject may have moderate symptoms associated with Parkinson's disease such as, but not limited to, mild to moderate cognitive impairment, first signs of impaired balance and righting reflexes, motor fluctuations causing mild-moderate disability on one or more dopaminergic medications, diagnosed within the past 5 to 10 years, bilateral or midline moderate tremors, moderate bradykinesia and/or subject experiencing some limitations to activities of daily living.

In one embodiment, a subject may have advanced symptoms associated with Parkinson's disease such as, but not limited to, being diagnosed with Parkinson's more than 10 years, medium refractory motor fluctuations wearing off and/or levodopa-induced dyskinesia causing significant disability, intractable tremors, significant balance disorder and/or falling, significant cognitive impairment (such as dementia with or without behavioral disturbances), sever bradykinesia, quality of life markedly diminished by illness and/or morning akinesia.

In one embodiment, a subject has been referred to a movement disorder specialist (MDS) but has not undergone deep brain stimulation.

In one embodiment, a subject is using DUOPA™ in combination with the compositions described herein. As a non-limiting example, the subject may have success with using DUOPA™ alone. As a non-limiting example, the subject may not have any success or limited success using DUOPA™ alone.

In another embodiment, the neurological disease, disorder and/or condition is Friedreich's Ataxia. In one embodiment the polynucleotide used to treat Friedreich's Ataxia comprises any one of SEQ ID NOs 2-23, such as, but not limited to SEQ ID NOs: 6-9 and 17-23, wherein the payload is replaced by Frataxin or any other payload known in the art for treating Friedreich's Ataxia.

In another embodiment, the neurological disease, disorder and/or condition is Amyotrophic lateral sclerosis (ALS). In one embodiment the polynucleotide used to treat ALS comprises any one of SEQ ID NOs 2-23, such as, but not limited to SEQ ID NOs: 6-9 and 17-23, wherein the payload is replaced by an shRNA, miRNA, siRNA, RNAi for SOD1 or any other payload known in the art for treating ALS.

In another embodiment, the neurological disease, disorder and/or condition is Huntington's disease. In one embodiment the polynucleotide used to treat Huntington's disease comprises any one of SEQ ID NOs 2-23, such as, but not limited to SEQ ID NOs: 6-9 and 17-23, wherein the payload is replaced by an shRNA, miRNA, siRNA, RNAi for Htt or any other payload known in the art for treating Huntington's disease.

In another embodiment, the neurological disease, disorder or condition is spinal muscular atrophy (SMA). In one embodiment the polynucleotide used to treat SMA comprises any one of SEQ ID NOs 2-23, such as, but not limited to SEQ ID NOs: 6-9 and 17-23, wherein the payload is replaced by SMN or any other payload known in the art for treating SMA.

Circadian Rhythm and Sleep-Wake Cycles

Circadian rhythms are physical, mental and behavioral changes that tend to follow a 24 hour cycle. Circadian rhythms can influence sleep-wake cycles, hormone release, body temperature and other bodily functions. Changes in the circadian rhythm can cause conditions and/or disorder such as, but not limited to sleep disorders (e.g., insomnia), depression, bipolar disorder, seasonal affective disorder, obesity and diabetes.

In one embodiment, the AADC polynucleotides described herein may be used to treat insomnia.

The sleep-wake cycle comprises periods of sleep and periods of wake. Generally, in a 24 hour period the total hours of sleep are less than the total hours of wakefulness. As a non-limiting example, the sleep-wake cycle comprises 7-9 hours of sleep and 15-17 hours of wakefulness. As a non-limiting example, the sleep-wake cycle comprises 8 hours of sleep and 16 hours of wakefulness. As a non-limiting example, the sleep-wake cycle comprises 8-10 hours of sleep and 14-16 hours of wakefulness.

In one embodiment, the sleep-wake cycle of a subject is improved by administered to the subject the AADC polynucleotides described herein.

In one embodiment, the sleep-wake cycle of a subject is regulated by administering to the subject the AADC polynucleotides described herein. As a non-limiting example, the regulation may be the correction of more periods of sleep occurring at night and less periods of sleep occurring In one embodiment, the sleep-wake cycle of a subject administered the AADC polynucleotides described herein improves as compared to the sleep-wake cycle of the subject prior to administration of the AADC polynucleotides. As a non-limiting example, the subject has an increased period of sleep and a decreased period of wakefulness. As another non-limiting example, the subject has a decreased period of sleep and an increased period of wakefulness.

In one embodiment, the sleep-wake cycle of a subject administered the AADC polynucleotides described herein is regulated as compared to the sleep-wake cycle of the subject prior to administration of the AADC polynucleotides. As a non-limiting example, the length of the periods of sleep and the periods of wakefulness may be about the same (e.g., +/−1 hour) for at least 2 days. As another non-limiting example, the length of the periods of sleep and the periods of wakefulness if a 24 hours period may be within 10 minutes, 15 minutes, 20 minutes, 25 minutes, 30 minutes, 35 minutes, 40 minutes, 45 minutes, 50 minutes, 55 minutes, 1 hour, 1.5 hours, or 2 hours of the previous 24 hour period.

In one embodiment, the amount of rapid eye movement (REM) sleep a subject experiences in a 24 hour period is altered after the subject is administered the AADC polynucleotides described herein. REM sleep is generally considered an active period of sleep marked by intense brain activity where brain waves are fast and desynchronized. An adult, on average, spends about 20-25% of their total daily sleep period in REM sleep. As a non-limiting example, the amount of REM sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of REM sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of REM sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of REM sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of non-REM (NREM) sleep a subject experiences in a 24 hour period is altered after the subject is administered the AADC polynucleotides described herein. NREM sleep is generally characterized by a reduction in physiological activity since as the brain waves, measured by EEG, get slower and have greater amplitude. NREM has four stages: Stage 1 is the time of drowsiness or transition from being awake to falling asleep where the brain waves and muscle activity begin to slow; Stage 2 is a period of light sleep during which eye movements stop and brain waves become slower with occasional bursts of rapid waves (sometimes called sleep spindles); Stage 3 and Stage 4 (collectively referred to as slow wave sleep) are characterized by the presence of slow brain waves (delta waves) interspersed with smaller faster waves where there are no eye movements. An adult, on average, spends about 75-80% of their total daily sleep period in NREM sleep with about half of their total daily sleep time in NREM stage 2 sleep.

In one embodiment, the amount of NREM sleep a subject experiences is altered after the subject is administered the AADC polynucleotides described herein. As a non-limiting example, the amount of NREM sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of NREM Stage 1 sleep a subject experiences is altered after the subject is administered the AADC polynucleotides described herein. As a non-limiting example, the amount of NREM Stage 1 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 1 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM Stage 1 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 1 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of NREM Stage 2 sleep a subject experiences is altered after the subject is administered the AADC polynucleotides described herein. As a non-limiting example, the amount of NREM Stage 2 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 2 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM Stage 2 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 2 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of NREM Stage 3 and 4 sleep a subject experiences is altered after the subject is administered the AADC polynucleotides described herein. As a non-limiting example, the amount of NREM Stage 3 and 4 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 3 and 4 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM Stage 3 and 4 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 3 and 4 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, periods of NREM and REM cycles are more consistent in a subject after the subject is administered the AADC polynucleotides described herein. Generally NREM and REM cycles alternate every 90 to 110 minutes four to six times per night.

Definitions

At various places in the present specification, substituents of compounds of the present disclosure are disclosed in groups or in ranges. It is specifically intended that the present disclosure include each and every individual subcombination of the members of such groups and ranges.

About: As used herein, the term "about" means +/−10% of the recited value.

Activity: As used herein, the term "activity" refers to the condition in which things are happening or being done. Compositions described herein may have activity and this activity may involve one or more biological events.

Adeno-associated virus: The term "adeno-associated virus" or "AAV" as used herein refers to members of the dependovirus genus comprising any particle, sequence, gene, protein, or component derived therefrom. The term "AAV particle" as used herein comprises a capsid and a polynucleotide. The AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Administered in combination: As used herein, the term "administered in combination" or "combined administration" means that two or more agents (e.g., AAV) are administered to a subject at the same time or within an interval such that there may be an overlap of an effect of each agent on the patient and/or the subject is at some point in time simultaneously exposed to both. In some embodiments, they are administered within about 60, 30, 15, 10, 5, or 1 minutes of one another or within about 24 hours, 12 hours, 6 hours, 3 hours of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biologically active: As used herein, the phrase "biologically active" refers to a characteristic of any substance (e.g., AAV) that has activity in a biological system and/or organism. For instance, a substance that, when administered to an organism, has a biological effect on that organism, is considered to be biologically active. In particular embodiments, a polynucleotide of the present invention may be considered biologically active if even a portion of the polynucleotides is biologically active or mimics an activity considered biologically relevant.

Biological system: As used herein, the term "biological system" refers to a group of organs, tissues, cells, intracellular components, proteins, nucleic acids, molecules (including, but not limited to biomolecules) that function together to perform a certain biological task within cellular membranes, cellular compartments, cells, tissues, organs, organ systems, multicellular organisms, or any biological entity. In some embodiments, biological systems are cell signaling pathways comprising intracellular and/or extracellular cell signaling biomolecules. In some embodiments, biological systems comprise growth factor signaling events within the extracellular/cellular matrix and/or cellular niches.

Biomolecule: As used herein, the term "biomolecule" is any natural molecule which is amino acid-based, nucleic acid-based, carbohydrate-based or lipid-based, and the like.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pairs in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form a hydrogen bond with a nucleotide unit of a second polynucleotide strand. Less than perfect complementarity refers to the situation in which some, but not all, nucleotide units of two strands can form hydrogen bonds with each other. For example, for two 20-mers, if only two base pairs on each strand can form hydrogen bonds with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide, a polynucleotide or polypeptide or may apply to a portion, region or feature thereof.

In one embodiment, conserved sequences are not contiguous. Those skilled in the art are able to appreciate how to achieve alignment when gaps in contiguous alignment are present between sequences, and to align corresponding residues not withstanding insertions or deletions present.

In one embodiment, conserved sequences are not contiguous. Those skilled in the art are able to appreciate how to achieve alignment when gaps in contiguous alignment are present between sequences, and to align corresponding residues not withstanding insertions or deletions present.

Delivery: As used herein, "delivery" refers to the act or manner of delivering a compound such as a parvovirus, e.g. an AAV and/or AAV compound, substance, entity, moiety, cargo or payload to a target. Such target may be a cell, tissue, organ, organism, or system (whether biological or production).

Delivery Agent: As used herein, "delivery agent" refers to any agent or substance which facilitates, at least in part, the in vivo and/or in vitro delivery of a polynucleotide and/or one or more substances (including, but not limited to a compounds and/or compositions of the present invention, e.g., viral particles or expression vectors) to targeted cells.

Destabilized: As used herein, the term "destable," "destabilize," or "destabilizing region" means a region or molecule that is less stable than a starting, reference, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance immunological detection, and the like. Detectable labels may include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Dosing regimen: As used herein, a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, upon single or multiple dose administration to a subject cell, in curing, alleviating, relieving or improving one or more symptoms of a disorder, clinical results, and, as such, an "effective amount" depends upon the context in which it is being applied. For example, in the context of administering an agent that treats Parkinson's Disease, an effective amount of an agent is, for example, an amount sufficient to achieve treatment, as defined herein, of Parkinson's Disease, as compared to the response obtained without administration of the agent.

Encapsulate: As used herein, the term "encapsulate" means to enclose, surround or encase.

Engineered: As used herein, embodiments are "engineered" when they are designed to have a feature or property, whether structural or chemical, that varies from a starting point, wild-type or native molecule. Thus, engineered agents or entities are those whose design and/or production include an act of the hand of man.

Epitope: As used herein, an "epitope" refers to a surface or region on a molecule that is capable of interacting with a biomolecule. For example a protein may contain one or more amino acids, e.g., an epitope, which interacts with an antibody, e.g., a biomolecule. In some embodiments, when referring to a protein or protein module, an epitope may comprise a linear stretch of amino acids or a three dimensional structure formed by folded amino acid chains.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein;

(4) folding of a polypeptide or protein; and (5) post-translational modification of a polypeptide or protein.

Feature: As used herein, a "feature" refers to a characteristic, a property, or a distinctive element.

Formulation: As used herein, a "formulation" includes at least one polynucleotide and/or compound and/or composition of the present disclosure (e.g., a vector, AAV particle, etc.) and a delivery agent.

Fragment: A "fragment," as used herein, refers to a contiguous portion of a whole. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. In some embodiments, fragments of an antibody include portions of an antibody subjected to enzymatic digestion or synthesized as such.

Functional: As used herein, a "functional" biological molecule is a biological molecule and/or entity with a structure and in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is typically determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids. In many embodiments, homologous protein may show a large overall degree of homology and a high degree of homology over at least one short stretch of at least 3, 4, 5, 6, 7, 8, 9, 10, 11, 12, 13, 14, 15, 16, 17, 18, 19, 20, 25, 30, 35, 40, 45, 50 or more amino acids. In many embodiments, homologous proteins share one or more characteristic sequence elements. As used herein, the term "characteristic sequence element" refers to a motif present in related proteins. In some embodiments, the presence of such motifs correlates with a particular activity (such as biological activity).

Identity: As used herein, the term "identity" refers to the overall relatedness between polymeric molecules, e.g., between oligonucleotide and/or polynucleotide molecules (e.g. DNA molecules and/or RNA molecules) and/or between polypeptide molecules. Calculation of the percent identity of two polynucleotide sequences, for example, may be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference in its entirety. For example, the percent identity between two nucleotide sequences can be determined, for example using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference in its entirety. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product may be RNA transcribed from the gene (e.g. mRNA) or a polypeptide translated from mRNA transcribed from the gene. Typically a reduction in the level of mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art. In some embodiments, isolation of a substance or entity includes disruption of chemical associations and/or bonds. In some embodiments, isolation includes only the separation from components with which the isolated substance or entity was previously combined and does not include such disruption.

Modified: As used herein, the term "modified" refers to a changed state or structure of a molecule or entity of the invention as compared with a parent or reference molecule or entity. Molecules may be modified in many ways including chemically, structurally, and functionally. In some embodiments, compounds and/or compositions of the present disclosure are modified by the introduction of non-natural amino acids, or non-natural nucleotides.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids). In embodiments wherein mutations comprise the addition and/or substitution of amino acids and/or nucleotides, such additions and/or substitutions may comprise 1 or more amino acid and/or nucleotide residues and may include modified amino acids and/or nucleotides.

Naturally occurring: As used herein, "naturally occurring" means existing in nature without artificial aid or involvement of the hand of man Non-human vertebrate: As used herein, a "non-human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid: As used herein, the term "nucleic acid", "polynucleotide" and "oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

Off-target: As used herein, "off target" refers to any unintended effect on any one or more target, gene and/or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained professional for a particular disease or condition, such as for example Parkinson's Disease.

Payload: As used herein, "payload" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid.

Payload construct: As used herein, "payload construct" is one or more polynucleotide regions encoding or comprising a payload that is flanked on one or both sides by an inverted terminal repeat (ITR) sequence. The payload construct is a template that is replicated in a viral production cell to produce a viral genome.

Payload construct vector: As used herein, "payload construct vector" is a vector encoding or comprising a payload construct, and regulatory regions for replication and expression in bacterial cells.

Payload construct expression vector: As used herein, a "payload construct expression vector" is a vector encoding or comprising a payload construct and which further comprises one or more polynucleotide regions encoding or comprising components for viral expression in a viral replication cell.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers to any ingredient other than the compounds and/or active agents (e.g. as described herein) present in pharmaceutical compositions and having the properties of being substantially nontoxic and non-inflammatory in a subject such as a patient. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspension or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein. As used herein, "pharmaceutically acceptable salts" refers to derivatives or forms of the disclosed compounds wherein the parent compound is modified by converting an existing acid or base moiety to its salt form (e.g., as generated by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. In some embodiments a pharmaceutically acceptable salt of the present disclosure can be synthesized salt prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

Pharmaceutically acceptable solvate: The term "pharmaceutically acceptable solvate," as used herein, refers to a crystalline form of a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition, such as for example Parkinson's Disease.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand, replicate or increase or cause to grow, expand, replicate or increase. "Proliferative" means having the ability to proliferate. "Anti-proliferative" means having properties counter to or in opposition to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest: As used herein, the terms "proteins of interest" or "desired proteins" include those provided herein and fragments, mutants, variants, and alterations thereof Purified: As used herein, "purify," "purified," "purification" means to make substantially pure or clear from unwanted components, material defilement, admixture or imperfection. "Purified" refers to the state of being pure. "Purification" refers to the process of making pure.

Region: As used herein, the term "region" refers to a zone or general area. In some embodiments, when referring to a protein or protein module, a region may comprise a linear sequence of amino acids along the protein or protein module or may comprise a three dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group. C-termini refer to the end of a protein comprising an amino acid with a free carboxyl group. N- and/or C-terminal regions may therefore comprise the N- and/or C-termini as well as surrounding amino acids. In some embodiments, N- and/or C-terminal regions comprise from about 3 amino acid to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. In some embodiments, C-terminal regions may comprise any length of amino acids, which include the C-terminus, but do not comprise the N-terminus.

In some embodiments, when referring to a polynucleotide, a region may comprise a linear sequence of nucleic acids along the polynucleotide or may comprise a three dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and 3' termini. 5' termini refer to the end of a polynucleotide comprising a nucleic acid with a free phosphate group. 3' termini refer to the end of a polynucleotide comprising a nucleic acid with a free hydroxyl group. 5' and 3' regions may therefore comprise the 5' and 3' termini as well as surrounding nucleic acids. In some embodiments, 5' and 3' terminal regions comprise from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In some embodiments, 5' regions may comprise any length of nucleic acids that includes the 5' terminus, but does not include the 3' terminus. In some embodiments, 3' regions may comprise any length of nucleic acids, which include the 3' terminus, but does not comprise the 5' terminus.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interference: As used herein, the term "RNA interference" or "RNAi" refers to a sequence specific regulatory mechanism mediated by RNA molecules which results in the inhibition or interference or "silencing" of the expression of a corresponding protein-coding gene.

Sample: As used herein, the term "sample" refers to an aliquot, subset or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. In some embodiments, a sample is or comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Self-complementary viral particle: As used herein, a "self-complementary viral particle" is a particle comprised of at least two components, a protein capsid and a polynucleotide sequence encoding a self-complementary genome enclosed within the capsid.

Sense strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the siRNA strand.

Signal Sequences: As used herein, the phrase "signal sequences" refers to a sequence which can direct the transport or localization.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Small/short interfering RNA: As used herein, the term "small/short interfering RNA" or "siRNA" refers to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, the subject may be an infant, neonate, or a child under the age of 12 years old. In some embodiments, the subject may be in utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term typically means within about 2 seconds.

Suffering from: An individual who is "suffering from" a disease, disorder, and/or condition has been diagnosed with or displays one or more symptoms of a disease, disorder, and/or condition such as for example Parkinson's Disease.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeting: As used herein, "targeting" means the process of design and selection of nucleic acid sequence that will hybridize to a target nucleic acid and induce a desired effect.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition such as for example Parkinson's Disease. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transfection: As used herein, the term "transfection" refers to methods to introduce exogenous nucleic acids into a cell. Methods of transfection include, but are not limited to, chemical methods, physical treatments and cationic lipids or mixtures. P Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition such as for example Parkinson's Disease.

Unmodified: As used herein, "unmodified" refers to any substance, compound or molecule prior to being changed in any way. Unmodified may, but does not always, refer to the wild type or native form of a biomolecule or entity. Molecules or entities may undergo a series of modifications whereby each modified substance, compound, molecule or entity may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly and may be based on and/or may comprise adeno-associated virus (AAV) parent or reference sequence. Such parent or reference AAV sequences may serve as an original, second, third or subsequent sequence for engineering vectors. In non-limiting examples, such parent or reference AAV sequences may comprise any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral construct vector: As used herein, a "viral construct vector" is a vector which comprises one or more polynucleotide regions encoding or comprising Rep and or Cap protein.

Viral construct expression vector: As used herein, a "viral construct expression vector" is a vector which comprises one or more polynucleotide regions encoding or comprising Rep and or Cap that further comprises one or more polynucleotide regions encoding or comprising components for viral expression in a viral replication cell.

Viral genome: As used herein, a "viral genome" is a polynucleotide encoding at least one inverted terminal repeat (ITR), at least one regulatory sequence, and at least one payload. The viral genome is derived by replication of a payload construct from the payload construct expression vector. A viral genome encodes at least one copy of the payload construct.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Design of AADC Polynucleotides

AADC polynucleotides are designed to comprise at a minimum a nucleic acid sequence encoding an AADC protein.

Once designed, the sequence is engineered or synthesized or inserted in a plasmid or vector and administered to a cell or organism. Suitable plasmids or vectors are any which transduce or transfect the target cell.

Adeno-associated viral vectors (AAV), viral particles or entire viruses may be used.

Administration results in the processing of the AADC polynucleotide to generate the AADC protein which alters the etiology of the disease, in this case Parkinson's Disease.

In one non-limiting example, plasmids containing an AADC polynucleotide of the invention are given in Table 1. These AADC polynucleotides in the table are contained in a Fastback plasmid and have a CMV promoter and encode AADC. In some embodiments the open reading frame of the AADC protein mRNA is codon optimized (e.g., codop).

TABLE 1

AADC polynucleotide-containing plasmids/vectors.

| Construct | SEQ ID NO |
|---|---|
| pFB CMV hAADC-1 | 2 |
| pFB CMV hAADC-2 | 3 |
| pFB CMV hAADC-3 | 4 |
| pFB CMV hAADC-4 | 5 |

Example 2

AADC Polynucleotides: ITR to ITR

AADC polynucleotides suitable for use in an AAV viral vector include those in Table 2.

Given in Table 2 are the ITR to ITR sequences from Table 1.

TABLE 2

ITR to ITR AADC polynucleotides

| Construct | SEQ ID NO |
|---|---|
| pFB CMV hAADC-1 (ITR to ITR) | 6 |
| pFB CMV hAADC-2 (ITR to ITR) | 7 |
| pFB CMV hAADC-3 (ITR to ITR) | 8 |
| pFB CMV hAADC-4 (ITR to ITR) | 9 |

Example 3

Relative to the ITR to ITR Parent Sequence

AADC polynucleotides are designed according to Table 3 and Table 4. The start and stop positions given are relative to the ITR to ITR AADC polynucleotides described in Table 2.

TABLE 3

Component modules or sequence regions of AADC polynucleotides

| | pFB CMV hAADC-1 (ITR to ITR) | | pFB CMV hAADC-2 (ITR to ITR) | | pFB CMV hAADC-3 (ITR to ITR) | | pFB CMV hAADC-4 (ITR to ITR) | |
|---|---|---|---|---|---|---|---|---|
| | Start | Stop | Start | Stop | Start | Stop | Start | Stop |
| 5' ITR | 1 | 130 | 1 | 130 | 1 | 130 | 1 | 130 |
| CMV Enhancer | 263 | 566 | 263 | 566 | 263 | 566 | 296 | 599 |
| CMV Promoter | 567 | 769 | 567 | 769 | 567 | 769 | 600 | 802 |
| ie1 exon 1 | 784 | 917 | 784 | 917 | 784 | 917 | 817 | 950 |

TABLE 3-continued

Component modules or sequence regions of AADC polynucleotides

| | pFB CMV hAADC-1 (ITR to ITR) | | pFB CMV hAADC-2 (ITR to ITR) | | pFB CMV hAADC-3 (ITR to ITR) | | pFB CMV hAADC-4 (ITR to ITR) | |
|---|---|---|---|---|---|---|---|---|
| | Start | Stop | Start | Stop | Start | Stop | Start | Stop |
| ie1 intron1 | 918 | 949 | 918 | 949 | 918 | 949 | 951 | 982 |
| hbBglobin intron2 | 950 | 1296 | 950 | 1296 | 950 | 1296 | 983 | 1329 |
| hBglobin exon 3 | 1297 | 1349 | 1297 | 1349 | 1297 | 1349 | 1330 | 1382 |
| 5' UTR | — | — | — | — | — | — | 1398 | 1468 |
| hAADC | 1374 | 2822 | — | — | 1374 | 2822 | 1473 | 2921 |
| hAADC codop | — | — | 1374 | 2816 | — | — | — | — |
| 3' UTR | — | — | — | — | 2823 | 3221 | 2922 | 3361 |
| hGH poly(A) signal | 2841 | 3317 | 2835 | 3311 | 3240 | 3716 | 3380 | 3856 |
| 3' ITR | 3417 | 3535 | 3416 | 3534 | 3822 | 3940 | 3961 | 4079 |

TABLE 4

Component modules or sequence regions of AADC polynucleotides

| | hAADC_1k | | hAADC_2k | | hAADC_3k | | hAADC_4 | |
|---|---|---|---|---|---|---|---|---|
| | Start | Stop | Start | Stop | Start | Stop | Start | Stop |
| 5' ITR | 1 | 141 | 1 | 141 | 1 | 141 | 1 | 141 |
| CMV Enhancer | 245 | 548 | 245 | 548 | 245 | 548 | 245 | 548 |
| CMV Promoter | 549 | 751 | 549 | 751 | 549 | 751 | 549 | 751 |
| ie1 exon 1 | 766 | 899 | 766 | 899 | 766 | 899 | 766 | 899 |
| ie1 intron1 | 900 | 931 | 900 | 931 | 900 | 931 | 900 | 931 |
| hbBglobin intron2 | 932 | 1278 | 932 | 1278 | 932 | 1278 | 932 | 1278 |
| hBglobin exon 3 | 1279 | 1331 | 1279 | 1331 | 1279 | 1331 | 1279 | 1331 |
| 5' UTR | — | — | — | — | — | — | 1347 | 3310 |
| hAADC | 1356 | 2804 | 1356 | 2804 | — | — | 1422 | 2864 |
| hAADC codop | — | — | — | — | 1356 | 2798 | — | — |
| 3' UTR | — | — | — | — | — | — | 2865 | 3310 |
| hGH poly(A) signal | 2823 | 3299 | 2823 | 3299 | 2817 | 3293 | 3329 | 3805 |
| 3' ITR | 3357 | 3497 | 3357 | 3497 | 3351 | 3491 | 3863 | 4003 |

TABLE 5

Component modules or sequence regions of AADC polynucleotides

| | hAADC_5k | | hAADC_6k | | hAADC_9k | |
|---|---|---|---|---|---|---|
| | Start | Stop | Start | Stop | Start | Stop |
| 5' ITR | 1 | 145 | 1 | 141 | 1 | 130 |
| CMV Enhancer | 249 | 552 | 245 | 548 | 234 | 537 |
| CMV Promoter | 553 | 755 | 549 | 751 | 538 | 740 |
| ie1 exon 1 | 770 | 903 | 766 | 899 | 755 | 888 |
| ie1 intron1 | 904 | 935 | 900 | 931 | 889 | 920 |
| hbBglobin intron2 | 936 | 1282 | 932 | 1278 | 921 | 1267 |
| hBglobin exon 3 | 1283 | 1335 | 1279 | 1331 | 1268 | 1320 |
| 5' UTR | — | — | — | — | — | — |
| hAADC | — | — | 1356 | 2798 | 1345 | 2793 |
| hAADC codop | 1360 | 2802 | — | — | — | — |
| 3' UTR | — | — | 2799 | 3203 | — | — |
| hGH poly(A) signal | 2821 | 3297 | 3222 | 3698 | 2812 | 3288 |
| 3' ITR | 3355 | 3499 | 3756 | 3896 | 3346 | 3475 |

Example 4

Design of AADC Polynucleotides

AADC polynucleotides are designed to comprise at a minimum a nucleic acid sequence encoding an AADC protein.

Once designed, the sequence is engineered or synthesized or inserted in a plasmid or vector and administered to a cell or organism. Suitable plasmids or vectors are any which transduce or transfect the target cell.

Adeno-associated viral vectors (AAV), viral particles or entire viruses may be used.

Administration results in the processing of the AADC polynucleotide to generate the AADC protein which alters the etiology of the disease, in this case Parkinson's Disease.

In one non-limiting example, plasmids containing an AADC polynucleotide of the invention are given in Table 6. These AADC polynucleotides in the table are contained in a Fastback plasmid and have a CMV promoter and encode AADC. In some embodiments the open reading frame of the AADC protein mRNA is codon optimized (e.g., codop).

TABLE 6

AADC polynucleotide-containing plasmids/vectors.

| Construct | SEQ ID NO |
|---|---|
| phAADC_1k | 10 |
| phAADC_2k | 11 |
| phAADC_3k | 12 |
| phAADC_4 | 13 |
| phAADC_5k | 14 |
| phAADC_6k | 15 |
| phAADC_9k | 16 |

Given in Table 7 are the ITR to ITR sequences from Table 6.

TABLE 7

ITR to ITR AADC polynucleotides

| Construct | SEQ ID NO |
|---|---|
| phAADC_1k (ITR to ITR) | 17 |
| phAADC_2k (ITR to ITR) | 18 |

TABLE 7-continued

ITR to ITR AADC polynucleotides

| Construct | SEQ ID NO |
|---|---|
| phAADC_3k (ITR to ITR) | 19 |
| phAADC_4 (ITR to ITR) | 20 |
| phAADC_5k (ITR to ITR) | 21 |
| phAADC_6k (ITR to ITR) | 22 |
| phAADC_9k (ITR to ITR) | 23 |

Example 5

Administration of AADC polynucleotide compositions to patients for gene therapy

AADC polynucleotide-containing recombinant AAV vector compositions are infused into the substantia nigra, and in particular, the substantia nigra pars compacta (SNpc) and ventral tegmental area (VTA) of patients having Parkinson's Disease and identified as qualified for treatment according to methods known in the art.

One method of administration contemplated for use in the methods described herein is real-time convection-enhanced delivery (RCD) of AADC polynucleotide-containing AAV vector compositions by co-infusion of gadoteridol (a magnetic resonance (MR) contrast agent) and T1 or T2 magnetic resonance imaging (MRD, which can predict areas of subsequent AADC gene expression. As described in Richardson, et al., 2011, the accuracy of cannula placement and initial infusate distribution may be safely determined by saline infusion without significantly altering the subsequent distribution of the tracer agent (Richardson, et al., 2011, *Neurosurgery,* 69(1):154-163). T2 RCD provides detection of intraparenchymal convection-enhanced delivery in the uninjured brain and may predict subsequent distribution of a transgene after viral vector infusion. Subjects undergo saline infusion/T2 acquisition, immediately followed by gadoteridol infusion/T1 acquisition in the putamen and brainstem. Distribution volumes and spatial patterns are analyzed. Gadoteridol and AAV-encoded AADC are co-infused under alternating T2/T1 acquisition in the thalamus, and hyperintense areas are compared with areas of subsequent transgene expression. Ratios of distribution volume to infusion volume are expected to be similar between saline and gadoteridol RCD. Spatial overlap should correlate well between T2 and T1 images. The second infusate will follow a spatiotemporal pattern similar to that of the first, filling the target area before developing extra-target distribution. Areas of AADC expression should correlate well with areas of both T1 and T2 hyperintensity observed during RCD (Richardson, et al., 2011, *Neurosurgery,* 69(1):154-163).

Convection-enhanced delivery (CED) of macromolecules directly into the brain parenchyma has been known for over two decades. CED is a term that denotes the use of a pressure gradient to generate bulk flow within the brain parenchyma, i.e. convection of macromolecules within the interstitial fluid driven by infusing a solution through a cannula placed directly in the targeted structure. This method allows therapeutic agents to be homogenously distributed through large volumes of brain tissue by bypassing the blood brain barrier and surpassing simple diffusion (Richardson, et al., 2011, *Stereotact. Funct. Neurosurg.* 89:141-151).

Salegio, et al. recently demonstrated the distribution of nanoparticles of different sizes, including micelles (~15 nm in size), AAV (~20-25 nm) and liposomes (~65 nm), within the CNS of rodents and NHPs (Salegio et al., 2014, *Frontiers in Neuroanatomy,* vol. 8, article 9: pp. 1-8). Simple injections cannot engage the perivascular system, and specialized infusion cannulae are required, enabling constant pressures to be exerted at the tip of the cannula such that the interstitial hydrostatic pressure is exceeded and infusate can flow out into the tissue. Simple needles generate significant reflux; thus, reflux-resistant cannulas have been developed to counter this tendency. The advent of platforms for MRI-guided convection-enhanced infusions further refined understanding of the mechanics of perivascular flow, and it was demonstrated that perivascular distribution of liposomes was linear with respect to time, the slope of the curve was increased in myelinated regions, and cessation of infusion prevented further expansion in the volume of distribution. (Richardson, et al., 2011, *Stereotact. Funct. Neurosurg.* 89:141-151; Salegio et al., 2014, *Frontiers in Neuroanatomy,* vol. 8, article 9: pp. 1-8).

Intraparenchymal rAAV injections are known to result in robust but relatively local transduction. Such local delivery methods are advantageous when attempting gene therapy for neurological disorders that result from neuropathology that is localized to a specific anatomical region or anatomical circuitry such as in the case of Parkinson's disease. However, in treatments requiring more widespread CNS transduction, intraparenchymal injections are impractical. Treatment of neurological disorders attributable to inborn errors of metabolism and/or single-gene defects, or those that affect motor neurons of the spinal cord can require transduction of large proportions of the brain or spinal cord, respectively. Development of less invasive trans-BBB delivery methods for vectors is an extremely important endeavor. Numerous attempts to use molecules that are known to interact with various active transport mechanisms (probably receptor-mediated) to convey proteins across the BBB have been reported with varying results. Given the large number of AAV serotypes available, one or more serotypes may bind a cell-entry receptor capable of transporting the AAV capsid across the BBB (Manfredsson, et al., 2009, "AAV9: a potential blood-brain barrier buster." Molecular Therapy 17(3):403-405).

Vector and Stereotaxic Infusion

A stereotactic approach may be used to surgically deliver the AADC polynucleotides. Although individuals with AADC deficiency lack epinephrine and norepinephrine, these patients should maintain stable blood pressure and heart rates during the surgery. There should be no notable intracerebral hemorrhages in the postoperative computed tomography (CT) or MRI scans. The needle tracts, as shown on the MRI scans, should show accurate injection into the substantia nigra pars compacta (SNpc) and ventral tegmental area (VTA). The patients will be discharged from the hospital about one week after the surgery (Hwu, W. L., et al., 2012. Gene therapy for aromatic L-amino acid decarboxylase deficiency. *Sci. Transl. Med. Vol.* 4, 134ra61).

Subjects of treatment receive the AAV-vector composition vector, safely delivered to substantia nigra pars compacta (SNpc) and ventral tegmental area (VTA) via bilateral infusions, or alternatively, intrastriatally (into the caudate nucleus and putamen), or into the subthalamic nucleus (STN), for example optionally using the FDA-approved SMARTFLOW® neuroventricular cannula (SurgiVision, Inc.) specifically designed for clinical application, with or without the aid of the CLEARPOINT® system to help the treating neurosurgeon(s) target and observe the delivery of the therapeutic agent in the brain (See, for example, San Sebastian, et al., 2014, *Mol. Ther. Methods Clin. Dev.* 3: 14049; See, for example, Feng and Maguire-Zeiss, 2010, *CNS Drugs* 24(3):177-192).

For example, during the surgery, two target points are determined in the substantia nigra pars compacta (SNpc) and ventral tegmental area (VTA) that are sufficiently separated from each other in dorsolateral directions and identified on a magnetic resonance image. One burr hole is trepanned in each side of the cranial bone, through which the vector is injected into the two target points via the two-track insertion route. The AAV-vector-containing solution is prepared to a concentration of $1.5 \times 10^{12}$ vector genome/ml, and 50 µl per point of the solution is injected at 1 µl/min; each patient receives $3 \times 10^{11}$ vector genome of the AAV-vector construct.

Neutralizing antibody titers against AAV2 are determined by measuring β-galactosidase activities in HEK293 cells transduced with $5 \times 10^3$ vector genome/cell of AAV2 vectors expressing β-galactosidase in various dilutions of sera.

PET

The AADC expression level in the substantia nigra are assessed on PET imaging with FMT six days before surgery and at one- and six-months after gene transfer. All patients cease taking dopaminergic medications 18 hours before PET and take 2.5 mg/kg of carbidopa orally one hour before FMT injection. Subsequently, 0.12 mCi/kg of FMT in saline is infused into an antecubital vein, and a 90-minute dynamic acquisition sequence is obtained. The PET and magnetic resonance imaging data are co-registered with a fusion processing program (Syntegra; Philips, Amsterdam, The Netherlands) to produce the fusion images. Radioactivities within volumes of interest drawn in the nigrostriatal pathway are calculated between 80 and 90 minutes after tracer injection. A change in nigrostriatal pathway FMT uptake from baseline to 24 weeks is assessed using the substantia nigra to striatal ratio of radioactivities.

Statistical Analysis

Values at baseline and 6 months after gene transfer are compared using Student's t-test (paired analyses). A two-sided P value <0.05 is taken to indicate significant differences. Two-way analysis of variance with Bonferroni correction of P values is used for the short-duration response to levodopa. (See, for example, Muramatsu, et al., 2010, "A phase I study of aromatic L-amino acid decarboxylase gene therapy for Parkinson's disease."*Mol. Ther.* 18:1731-1735).

Safety and tolerability of bilateral administration of AAV-vector compositions using real-time image-guided infusion into the brains of Parkinson's Disease subjects may be monitored for up to or after 9 months post-surgery. Broad coverage of targeted areas (substantia nigra pars compacta (SNpc) and ventral tegmental area (VTA)) and widespread AADC protein distribution in the striatum should be achieved without inducing any adverse effects.

Changes in growth and motor skills: The patients should gain weight and exhibit improvement in their motor scores after gene transfer, within a year, post-treatment. Weight will be measured at 3 to 6 months after gene transfer. All patients initially should have raw scores of zero on the Alberta Infant Motor Scale (AIMS) and very low raw scores for the Peabody Developmental Motor Scale, Second Edition (PDMS-II). After the gene transfer, all of the patients should show continuous increases in their raw scores on these two scales, which indicates that their motor functions have improved. The Comprehensive Developmental Inventory for Infants and Toddlers (CDIIT) covers both cognition and motor development. All of the patients should show low raw CDIIT scores before gene transfer, and the subsequent increase in scores demonstrate improvement in both motor and cognitive functions.

Subjective Improvements after Gene Transfer

To document the symptoms that are more difficult to quantify, spouses, guardians or caretakers of the patients are asked to fill out a questionnaire at the end of the study. The symptoms of the oculogyric crises should lessen, and eye deviations and sleep disruptions, for example, are some mild symptoms of the oculogyric crises that may remain after gene therapy. Subjects may experience increased emotional stability, and/or some improvements in sweating and hyperthermia (a common manifestation of body temperature instability in hot weather). There should be no detectable abnormality in heart rate variability as assessed by 24-hour Holter monitoring either before or after gene transfer. Before gene therapy, patients that were bedridden and showed little spontaneous movement may exhibit less severe ptosis (drooping of the upper eyelid) one to two weeks after the gene transfer. According to previous studies, dyskinesia may occur one month after gene transfer, but upon observation of a decrease in dyskinesia, motor development should start (Hwu, W. L., et al., 2012. Gene therapy for aromatic L-amino acid decarboxylase deficiency. *Sci. Transl. Med.* Vol. 4, 134ra61). Subjects may exhibit increased head control after three months, sitting with support after six to nine months, sitting up from the prone position after thirteen months, and holding toys and standing with support sixteen months after the gene transfer, for example. Anti-AAV2 antibodies should be negative in the patients before gene therapy, and the titers may increase slightly after gene transfer.

PET Scans and CSF Analyses

PET scans and CSF analyses are completed for the treated patients. Six months after gene transfer, PET scans should reveal that uptake of 6-[18F] fluorodopa (FDOPA) increase from baseline in the combined (right and left) treatment sites. The CSF analysis should reveal increases in the levels of homovanillic acid (HVA, a metabolite of dopamine) and 5-hydroxyindoleacetic acid (HIAA, a metabolite of serotonin). However, the levels of L-DOPA and 3-O-methyldopa may remain elevated (Hwu, W. L., et al., 2012. Gene therapy for aromatic L-amino acid decarboxylase deficiency. *Sci. Transl. Med.* Vol. 4, 134ra61).

Example 6

Administration of AADC Polynucleotides

AADC polynucleotide-containing recombinant AAV vector compositions are infused into the putamen of patients having Parkinson's Disease using the administration methods described in Example 5. The dose, number of patients and volume are outlined in Table 8.

TABLE 8

Study Design

| Study No. | Number of Patients | Dose | Volume |
|---|---|---|---|
| 1 | 6 | $3 \times 10^{11}$ vg | 100 ul peration putamen |
| 2 | 6 | $9 \times 10^{11}$ vg | 300 ul peration putamen |
| 3 | 10 | $2.3 \times 10^{11}$ vg | 100 ul peration putamen |
| 4 | 10 | $7.5 \times 10^{11}$ vg | 100 ul peration putamen |
| 5 | 5 | $7.5 \times 10^{11}$ vg | 450 ul peration putamen |
| 6 | Up to 20 | $1.4 \times 10^{12}$ vg | Up to 900 ul peration putamen |

TABLE 8-continued

Study Design

| Study No. | Number of Patients | Dose | Volume | |
|---|---|---|---|---|
| 7 | Up to 20 | $4.8 \times 10^{12}$ vg | Up to 900 ul | peration putamen |
| 8 | Up to 20 | $8.8 \times 10^{12}$ vg | Up to 900 ul | peration putamen |

During the course of the study the safety and tolerability of the infusion of the AADC polynucleotide-containing recombinant adeno-associated virus (AAV) vector compositions in human patients diagnosed with Parkinson's Disease is evaluated. Patients are evaluated preoperatively and monthly postoperatively for six months, using multiple measures, including the Global Systonia Scale (GDS) (see Comella, et al., 2003, *Movement Disorders,* 18(3):303-312), L-DOPA challenge test, UPDRS scores, motor state diaries, and laboratory tests. Using diaries that separate the day into half-hour segments, the caregivers of the patients will record their mobility during the four days before admission and for another four days at six months after admission to the study site. The patient caregivers are trained to rate subject's condition as sleeping, immobile, mobile without troublesome dyskinesias, or mobile with troublesome dyskinesias. The total number of hours spent in each of these categories is calculated, and the differences between the baseline and the six-month scores are compared between the groups. The short-duration response to levodopa is evaluated at baseline and 6 months after gene transfer; subjects take 100 mg of levodopa orally with 25 mg benserazide after 20 hours without dopaminergic medication. Motor symptoms based on GDS and plasma levodopa concentrations are assessed at baseline and 30 minutes, 1, 2, 3, and 4 hours after levodopa intake (See, for example, Muramatsu, et al., 2010, "A phase I study of aromatic L-amino acid decarboxylase gene therapy for Parkinson's disease."*Mol. Ther.* 18:1731-1735).

Example 7

In Vivo Administration of AADC Polynucleotides

Two AADC polynucleotide-containing recombinant AAV vector compositions (plasmid SEQ ID NO: 10 and 12; ITR to ITR SEQ ID NO: 17 and 19), a control and a standard were administered to rats (n=5) by bilateral intrastriation (10 ul/side) at a dose level of $2 \times 10^{12}$ vg/ml. The expression of AADC in rat striatum was determined by ELISA after 4 and 8 weeks. Variation was seen between the animals and the hemispheres due to variable delivery between the infusion sites. Both constructs expressed AADC, but the phAADC_3k construct (plasmid SEQ ID NO: 12; ITR to ITR SEQ ID NO: 19) showed up to 200% increase of expression as compared to the standard construct.

Example 8

Dose Response Study of AADC Polynucleotides

Compositions of AADC polynucleotide-containing recombinant AAV vectors (plasmid SEQ ID NO: 10; ITR to ITR SEQ ID NO: 17) at five different dose levels ranging from $1 \times 10^{11}$ vg/ml to $1 \times 10^{13}$ vg/ml and a control are administered to 6-OHDA lesioned rats. The behavioral response to low-dose levodopa administration is quantified before and after (week 3 and 4) delivery of the composition. 5 weeks after dosing, necropsy is conducted and the AADC enzymatic activity is measured in ex vivo striatal tissue assay and the distribution of AADC in the brain is determined by immunohistochemical (IHC) staining.

Example 9

Effect of Empty Particles on Intrastriatal Transduction

Adult rats (n=6) were administered varying ratios of full:empty vector particles at: 0% full, 50% full, 85% full or 99% full. AADC polynucleotide-containing recombinant AAV vector (plasmid SEQ ID NO: 10; ITR to ITR SEQ ID NO: 17) at a constant dose and volume (5 ul and $1 \times 10$ vg) was administered intrastriatally. The rats were evaluated 4 weeks after administration. The low vector dose resulted in limited AADC vector expression. The volume of distribution for the particles is shown in Table 9 (ELISA) and the striatal levels of AADC expression is shown in Table 10 (Histology).

TABLE 9

Volume of Distribution

| % Ratio of full AAV2-AADC particle to empty capsids | Approximate Volume of Distribution (mm$^3$) |
|---|---|
| 50:50 | 2 |
| 70:30 | 2.4 |
| 85:15 | 2.5 |
| 100:0 | 3 |

TABLE 10

Striatal Levels

| % full of AAV2-AADC particles | AADC pg/ug protein |
|---|---|
| 0 | 0.4 |
| 52 | 1.1 |
| 58 | 1.7 |
| 83 | 2 |
| >99 | 2.1 |

Distribution was comparable for all groups. Relatively low vector dose resulted in limited AADC expression. There was also a trend to lower AADC expression levels with >30% empty particles.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

We claim:

1. An adeno-associated virus (AAV) vector genome comprising, in order:
   a) a 5' inverted terminal repeat (ITR), wherein said 5' ITR is 141 nucleotides in length;
   b) a cytomegalovirus (CMV) sequence region comprising from 5' to 3' a CMV enhancer or a fragment thereof of at least 250 nucleotides, and a CMV promoter or a fragment thereof of at least 150 nucleotides, wherein said CMV sequence region is at least 500 nucleotides;
   c) an immediate early 1 (IE1) sequence region comprising IE1 exon1 or a fragment thereof of at least 50 nucleotides, and IE1 intron 1 or a fragment thereof of at least 20 nucleotides;
   d) a human beta globin (HB) sequence region comprising HB intron 2 or a fragment thereof of at least 250 nucleotides, and HB exon 3 or a fragment thereof of at least 40 nucleotides;
   e) an Aromatic L-amino acid decarboxylase (AADC) sequence region, said AADC sequence region comprising a nucleotide sequence encoding SEQ ID NO: 1;
   f) a poly(A) signal sequence region comprising a human growth hormone (hGH) poly(A) signal or a fragment thereof of at least 200 nucleotides; and
   g) a 3' ITR, wherein said 3' ITR is 141 nucleotides in length;
wherein the AAV vector genome comprises a nucleotide sequence selected from the group consisting of SEQ ID NO: 17 and variants having at least 95% identity thereto.

2. The AAV vector genome of claim 1, wherein the 5' ITR and the 3' ITR are derived from AAV2.

3. The AAV vector genome of claim 1, wherein the CMV sequence region is 507 nucleotides in length.

4. The AAV vector genome of claim 1, wherein the IE1 sequence region is 166 nucleotides in length.

5. The AAV vector genome of claim 1, wherein the HB sequence region is about 400 nucleotides in length.

6. The AAV vector genome of claim 1, wherein the poly(A) signal sequence region is 477 nucleotides in length.

7. The AAV vector genome of claim 1, wherein the CMV sequence region is 507 nucleotides in length, the IE1 sequence region is 166 nucleotides in length, the HB sequence region is 400 nucleotides in length, and the poly (A) signal region is 477 nucleotides in length.

8. A recombinant AAV virus comprising the AAV vector genome of claim 1.

9. The recombinant AAV virus of claim 8, comprising a capsid serotype selected from the group consisting of AAV2, AAV1, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8.

10. The recombinant AAV virus of claim 9, wherein the capsid serotype is AAV2.

11. A pharmaceutical composition comprising the recombinant AAV virus of claim 9.

12. The pharmaceutical composition of claim 11, wherein at least 70% of the recombinant AAV vectors in the pharmaceutical composition contain an AAV vector genome.

13. The AAV vector genome of claim 1, wherein the 5' ITR consists of a nucleotide sequence selected from the group consisting of nucleotides 1-141 of SEQ ID NO: 17 and variants having at least 95% identity thereto.

14. The AAV vector genome of claim 1, wherein the 3' ITR consists of a nucleotide sequence selected from the group consisting of nucleotides 3357-3497 of SEQ ID NO: 17 and variants having at least 95% identity thereto.

\* \* \* \* \*